(12) United States Patent
Wrasidlo et al.

(10) Patent No.: US 8,372,971 B2
(45) Date of Patent: Feb. 12, 2013

(54) HETEROCYCLIC COMPOUNDS AND METHODS OF USE

(75) Inventors: Wolfgang Wrasidlo, La Jolla, CA (US); Elena Dneprovskaia, San Diego, CA (US)

(73) Assignee: TargeGen, Inc., Bridgewater, NJ (US)

( * ) Notice: Subject to any disclaimer, the term of this patent is extended or adjusted under 35 U.S.C. 154(b) by 0 days.

(21) Appl. No.: 13/243,924

(22) Filed: Sep. 23, 2011

(65) Prior Publication Data

US 2012/0220584 A1  Aug. 30, 2012

Related U.S. Application Data

(63) Continuation of application No. 12/684,312, filed on Jan. 8, 2010, now Pat. No. 8,084,618, which is a continuation of application No. 11/212,064, filed on Aug. 24, 2005, now Pat. No. 7,652,051.

(60) Provisional application No. 60/696,168, filed on Jul. 1, 2005, provisional application No. 60/604,298, filed on Aug. 25, 2004.

(51) Int. Cl.
| | |
|---|---|
| C07D 401/12 | (2006.01) |
| C07D 401/14 | (2006.01) |
| C07D 403/12 | (2006.01) |
| C07D 403/14 | (2006.01) |
| C07D 413/12 | (2006.01) |
| C07D 413/14 | (2006.01) |
| C07D 417/12 | (2006.01) |
| C07D 417/14 | (2006.01) |
| A61K 31/53 | (2006.01) |
| A61P 19/02 | (2006.01) |
| A61P 35/00 | (2006.01) |

(52) U.S. Cl. ...................................... 544/183; 514/243
(58) Field of Classification Search .................. 544/183; 514/243
See application file for complete search history.

(56) References Cited

U.S. PATENT DOCUMENTS

| | | | |
|---|---|---|---|
| 2,001,051 A | 5/1935 | Bruno | |
| 2,002,165 A | 5/1935 | Winslow | |
| 2,003,060 A | 5/1935 | Thomas | |
| 2,003,065 A | 5/1935 | Boyce | |
| 2,003,149 A | 5/1935 | Johnson | |
| 2,003,166 A | 5/1935 | Zancan | |
| 2,003,187 A | 5/1935 | Good | |
| 2,003,199 A | 5/1935 | Johnson et al. | |
| 2,004,092 A | 6/1935 | Chaney | |
| 2,004,102 A | 6/1935 | Dickey | |
| 2,004,138 A | 6/1935 | Story et al. | |
| 2,667,486 A | 1/1954 | Cain | |
| 4,057,530 A | 11/1977 | Pigerol et al. | |
| 4,160,833 A | 7/1979 | Diel | |
| 4,309,211 A | 1/1982 | Serban et al. | |
| 5,062,685 A | 11/1991 | Cain et al. | |
| 5,214,059 A | 5/1993 | Tegeler et al. | |
| 5,231,097 A | 7/1993 | Klausener et al. | |
| 5,332,745 A | 7/1994 | Carter et al. | |
| 5,482,951 A | 1/1996 | Ozaki et al. | |
| 5,527,763 A | 6/1996 | Miyazaki et al. | |
| 5,530,000 A | 6/1996 | Sanfilippo et al. | |
| 5,597,826 A | 1/1997 | Howard et al. | |
| 5,597,901 A | 1/1997 | Stern | |
| 5,665,724 A | 9/1997 | Sanfilippo et al. | |
| 5,763,441 A | 6/1998 | App et al. | |
| 5,776,502 A | 7/1998 | Foulkes et al. | |
| 5,827,850 A | 10/1998 | Brown et al. | |
| 5,830,880 A | 11/1998 | Sedlacek et al. | |
| 5,849,738 A | 12/1998 | Lee et al. | |
| 5,935,383 A | 8/1999 | Sun et al. | |
| 5,965,761 A | 10/1999 | Buchecker et al. | |
| 5,972,580 A | 10/1999 | Fukui et al. | |
| 6,048,675 A | 4/2000 | Hirano et al. | |
| 6,070,126 A | 5/2000 | Kokolus et al. | |
| 6,093,838 A | 7/2000 | Vasudevan et al. | |
| 6,121,434 A | 9/2000 | Peyman et al. | |
| 6,127,382 A | 10/2000 | Beard et al. | |
| 6,136,779 A | 10/2000 | Foulkes et al. | |
| 6,136,971 A | 10/2000 | Harrington et al. | |
| 6,153,752 A | 11/2000 | Bauer et al. | |
| 6,194,191 B1 | 2/2001 | Zhang et al. | |
| 6,204,260 B1 | 3/2001 | Bruns, Jr. et al. | |
| 6,235,736 B1 | 5/2001 | Ina et al. | |
| 6,245,916 B1 | 6/2001 | Fauchere et al. | |
| 6,277,502 B1 | 8/2001 | Buchecker et al. | |
| 6,288,082 B1 | 9/2001 | Wissner et al. | |
| 6,297,258 B1 | 10/2001 | Wissner et al. | |
| 6,326,487 B1 | 12/2001 | Peyman et al. | |
| 6,348,312 B1 | 2/2002 | Peyman et al. | |
| 6,378,526 B1 | 4/2002 | Bowman et al. | |
| 6,399,773 B1 | 6/2002 | Liu et al. | |
| 6,471,968 B1 | 10/2002 | Baker, Jr. et al. | |
| 6,489,328 B2 | 12/2002 | Snow et al. | |
| 6,506,769 B2 | 1/2003 | Snow et al. | |
| 6,531,491 B1 | 3/2003 | Kania et al. | |
| 6,596,749 B2 | 7/2003 | Fauchere et al. | |

(Continued)

FOREIGN PATENT DOCUMENTS

| | | |
|---|---|---|
| AU | 38554/93 A1 | 11/1993 |
| CA | 2375982 A1 | 2/2001 |

(Continued)

OTHER PUBLICATIONS

Allgayer, H. et al. (Jan. 15, 2002). "Activation of Src Kinase in Primary Colorectal Carcinoma: An Indicator of Poor Clinical Prognosis," *Cancer* 94(2):344-351.

Arbiser, J. L. (Oct. 2007). "Why Targeted Therapy Hasn't Worked in Advanced Cancer," *J. Clin. Invest.* 117(10):2762-2765.

Assmus, B. et al. (May 16, 2003). "HMG-CoA Reductase Inhibitors Reduce Senescence and Increase Proliferation of Endothelial Progenitor Cells Via Regulation of Cell Cycle Regulatory Genes," *Circ. Res.* 92(9):1049-1055.

Bailey, W. C. et al. (2007). "Pharmacologic Therapy: Novel Approaches for Chronic Obstructive Pulmonary Disease," *Proc. Am. Thorac. Soc.* 4:543-548.

(Continued)

*Primary Examiner* — Venkataraman Balasubramanian
(74) *Attorney, Agent, or Firm* — Morrison & Foerster LLP

(57) ABSTRACT

Heterocyclic compounds derived from benzotriazine, triazines, triazoles and oxadiazoles are disclosed. The methods of synthesis and of use of such heterocyclic compounds are also provided.

22 Claims, 1 Drawing Sheet

U.S. PATENT DOCUMENTS

| | | | |
|---|---|---|---|
| 6,605,615 | B2 | 8/2003 | Medina et al. |
| 6,613,773 | B2 | 9/2003 | Clough et al. |
| 6,635,626 | B1 | 10/2003 | Barrish et al. |
| 6,685,938 | B1 | 2/2004 | Cheresh et al. |
| 6,689,778 | B2 | 2/2004 | Bemis et al. |
| 6,777,412 | B2 | 8/2004 | Clough et al. |
| 6,794,378 | B2 | 9/2004 | Iino et al. |
| 6,838,464 | B2 | 1/2005 | Pease et al. |
| 7,008,954 | B1 | 3/2006 | Arimura et al. |
| 7,067,522 | B2 | 6/2006 | Pease et al. |
| 7,087,597 | B1 | 8/2006 | Miwa et al. |
| 7,087,625 | B2 | 8/2006 | Schumacher et al. |
| 7,115,597 | B2 | 10/2006 | Bilodeau et al. |
| 7,208,493 | B2 * | 4/2007 | Wrasidlo et al. ............. 514/249 |
| 7,230,101 | B1 | 6/2007 | Murthi et al. |
| 7,402,696 | B2 | 7/2008 | Suzuki et al. |
| 7,435,823 | B2 | 10/2008 | Potashman et al. |
| 7,456,176 | B2 * | 11/2008 | Noronha et al. ............. 514/243 |
| 7,528,143 | B2 | 5/2009 | Noronha et al. |
| 7,652,051 | B2 * | 1/2010 | Wrasidlo et al. ............. 514/383 |
| 7,691,858 | B2 | 4/2010 | Doukas et al. |
| 7,700,631 | B2 | 4/2010 | Schumacher et al. |
| 7,816,365 | B2 | 10/2010 | Schiemann et al. |
| 7,825,246 | B2 | 11/2010 | Noronha et al. |
| 8,030,487 | B2 | 10/2011 | Noronha et al. |
| 8,084,618 | B2 * | 12/2011 | Wrasidlo et al. ............. 548/131 |
| 8,133,900 | B2 | 3/2012 | Hood et al. |
| 8,138,199 | B2 | 3/2012 | Noronha et al. |
| 2001/0051620 | A1 | 12/2001 | Berger et al. |
| 2002/0165244 | A1 | 11/2002 | Zhou et al. |
| 2003/0060626 | A1 | 3/2003 | Clough et al. |
| 2003/0065180 | A1 | 4/2003 | Tsou et al. |
| 2003/0134838 | A1 | 7/2003 | Bornemann et al. |
| 2003/0149061 | A1 | 8/2003 | Nishihara et al. |
| 2003/0166932 | A1 | 9/2003 | Beard et al. |
| 2003/0187026 | A1 | 10/2003 | Li et al. |
| 2003/0199511 | A1 | 10/2003 | Li et al. |
| 2004/0092746 | A1 | 5/2004 | Clough et al. |
| 2004/0102630 | A1 | 5/2004 | Brumby et al. |
| 2004/0106615 | A1 | 6/2004 | Cochran et al. |
| 2004/0138257 | A1 | 7/2004 | Bouchard et al. |
| 2005/0234083 | A1 | 10/2005 | Chamberlain et al. |
| 2005/0239852 | A1 | 10/2005 | Ciufolini et al. |
| 2005/0282814 | A1 | 12/2005 | Wrasidlo et al. |
| 2006/0131762 | A1 | 6/2006 | Meudt et al. |
| 2006/0131835 | A1 | 6/2006 | Simpson |
| 2006/0247250 | A1 | 11/2006 | Cao et al. |
| 2006/0292203 | A1 | 12/2006 | Dellamary et al. |
| 2007/0032493 | A1 | 2/2007 | Foley et al. |
| 2007/0072682 | A1 | 3/2007 | Crawford et al. |
| 2007/0149508 | A1 | 6/2007 | Noronha et al. |
| 2007/0161645 | A1 | 7/2007 | Noronha et al. |
| 2007/0208019 | A1 | 9/2007 | Wrasidlo et al. |
| 2007/0259876 | A1 | 11/2007 | Doukas et al. |
| 2009/0275569 | A1 | 11/2009 | Gong et al. |
| 2010/0278811 | A1 | 11/2010 | Wrasidlo et al. |
| 2010/0330030 | A1 | 12/2010 | Wrasidlo et al. |
| 2011/0166149 | A1 | 7/2011 | Dellamary et al. |
| 2011/0212077 | A1 | 9/2011 | Noronha et al. |
| 2011/0243999 | A1 | 10/2011 | Dellamary et al. |
| 2011/0269721 | A1 | 11/2011 | Hood |
| 2011/0294796 | A1 | 12/2011 | Gong et al. |

FOREIGN PATENT DOCUMENTS

| | | |
|---|---|---|
| CN | 1202827 A | 12/1998 |
| DE | 3205638 A1 | 8/1983 |
| DE | 10024622 A1 | 11/2001 |
| EP | 0 059 524 A1 | 9/1982 |
| EP | 0 444 769 A1 | 9/1991 |
| EP | 1 282 628 B1 | 2/2004 |
| EP | 1 170 353 B1 | 11/2005 |
| FR | 2 275 461 A1 | 1/1976 |
| GB | 1 149 640 A | 4/1969 |
| GB | 1 423 585 A | 2/1976 |
| JP | 02-064553 A | 3/1990 |
| JP | 03-127790 A | 5/1991 |
| JP | 03-240066 A | 10/1991 |
| JP | 07-041461 A | 2/1995 |
| JP | 07-082183 A | 3/1995 |
| JP | 09-508642 A | 9/1997 |
| JP | 09-274290 A | 10/1997 |
| JP | 10-153838 A | 6/1998 |
| JP | 10-207019 A | 8/1998 |
| JP | 10-213820 A | 8/1998 |
| JP | 10-260512 A | 9/1998 |
| JP | 10-310583 A | 11/1998 |
| JP | 2001-089412 A | 4/2001 |
| JP | 2001-247411 A | 9/2001 |
| JP | 2002-221770 A | 8/2002 |
| WO | WO-91/18887 A1 | 12/1991 |
| WO | WO-92/001675 A2 | 2/1992 |
| WO | WO-92/001675 A3 | 2/1992 |
| WO | WO-94/15622 A1 | 7/1994 |
| WO | WO-95/21613 A1 | 8/1995 |
| WO | WO-97/09315 A1 | 3/1997 |
| WO | WO 97/11699 A1 | 4/1997 |
| WO | WO-97/21711 A1 | 6/1997 |
| WO | WO-97/24122 A1 | 7/1997 |
| WO | WO-98/24974 A1 | 6/1998 |
| WO | WO-98/28282 A2 | 7/1998 |
| WO | WO-98/28282 A3 | 7/1998 |
| WO | WO-99/09016 A1 | 2/1999 |
| WO | WO-99/24404 A1 | 5/1999 |
| WO | WO-99/32454 A1 | 7/1999 |
| WO | WO-99/41253 A1 | 8/1999 |
| WO | WO-00/18740 A1 | 4/2000 |
| WO | WO-00/18761 A1 | 4/2000 |
| WO | WO-00/39101 A1 | 7/2000 |
| WO | WO-00/39108 A1 | 7/2000 |
| WO | WO-00/39129 A1 | 7/2000 |
| WO | WO-00/46203 A2 | 8/2000 |
| WO | WO-00/46203 A3 | 8/2000 |
| WO | WO-00/62778 A1 | 10/2000 |
| WO | WO-00/66583 A1 | 11/2000 |
| WO | WO-00/71536 A1 | 11/2000 |
| WO | WO-01/07027 A2 | 2/2001 |
| WO | WO-01/07027 A3 | 2/2001 |
| WO | WO-01/07401 A1 | 2/2001 |
| WO | WO-01/12227 A1 | 2/2001 |
| WO | WO-01/17995 A1 | 3/2001 |
| WO | WO-01/19825 A1 | 3/2001 |
| WO | WO-01/21597 A1 | 3/2001 |
| WO | WO-01/27105 A1 | 4/2001 |
| WO | WO-01/32628 A1 | 5/2001 |
| WO | WO-01/44194 A2 | 6/2001 |
| WO | WO-01/44194 A3 | 6/2001 |
| WO | WO-01/47892 A1 | 7/2001 |
| WO | WO-01/53266 A1 | 7/2001 |
| WO | WO-01/55116 A2 | 8/2001 |
| WO | WO-01/55116 A3 | 8/2001 |
| WO | WO-01/62233 A2 | 8/2001 |
| WO | WO-01/62233 A3 | 9/2001 |
| WO | WO-01/64646 A2 | 9/2001 |
| WO | WO-01/64646 A3 | 9/2001 |
| WO | WO-01/64655 A1 | 9/2001 |
| WO | WO-01/64674 A1 | 9/2001 |
| WO | WO-01/68186 A2 | 9/2001 |
| WO | WO-01/68186 A3 | 9/2001 |
| WO | WO-01/70668 A2 | 9/2001 |
| WO | WO-01/70668 A3 | 9/2001 |
| WO | WO-01/72758 A1 | 10/2001 |
| WO | WO-01/76582 A1 | 10/2001 |
| WO | WO-02/12227 A2 | 2/2002 |
| WO | WO-02/12227 A3 | 2/2002 |
| WO | WO-02/22608 A1 | 3/2002 |
| WO | WO-02/30358 A2 | 4/2002 |
| WO | WO-02/30358 A3 | 4/2002 |
| WO | WO-02/36570 A1 | 5/2002 |
| WO | WO-02/42272 A2 | 5/2002 |
| WO | WO-02/44166 A1 | 6/2002 |
| WO | WO-02/53101 A2 | 7/2002 |
| WO | WO-02/53101 A3 | 7/2002 |
| WO | WO-02/53160 A1 | 7/2002 |
| WO | WO-02/53160 A3 | 8/2002 |
| WO | WO-02/64096 A2 | 8/2002 |
| WO | WO-02/64211 A1 | 8/2002 |

| | | |
|---|---|---|
| WO | WO-02/68409 A1 | 9/2002 |
| WO | WO-02/76438 A1 | 10/2002 |
| WO | WO-02/76438 A2 | 10/2002 |
| WO | WO-02/079197 A1 | 10/2002 |
| WO | WO-02/90347 A1 | 11/2002 |
| WO | WO-02/92087 A1 | 11/2002 |
| WO | WO-02/94766 A1 | 11/2002 |
| WO | WO-02/096905 A1 | 12/2002 |
| WO | WO-02/97116 A2 | 12/2002 |
| WO | WO-02/97116 A3 | 12/2002 |
| WO | WO-03/004018 A1 | 1/2003 |
| WO | WO-03/016306 A1 | 2/2003 |
| WO | WO-03/024448 A2 | 3/2003 |
| WO | WO-03/024448 A3 | 3/2003 |
| WO | WO-03/030909 A1 | 4/2003 |
| WO | WO-03/032994 A2 | 4/2003 |
| WO | WO-03/032994 A3 | 4/2003 |
| WO | WO-03/033503 A2 | 4/2003 |
| WO | WO-03/033503 A3 | 4/2003 |
| WO | WO-03/033504 A1 | 4/2003 |
| WO | WO-03/033505 A1 | 4/2003 |
| WO | WO-03/037869 A1 | 5/2003 |
| WO | WO-03/037891 A1 | 5/2003 |
| WO | WO-03/045921 A1 | 6/2003 |
| WO | WO-03/050090 A1 | 6/2003 |
| WO | WO-03/051366 A2 | 6/2003 |
| WO | WO-03/051366 A3 | 6/2003 |
| WO | WO-03/057165 A2 | 7/2003 |
| WO | WO-03/057165 A3 | 7/2003 |
| WO | WO-03/066575 A1 | 8/2003 |
| WO | WO-03/066601 A1 | 8/2003 |
| WO | WO-03/074515 A1 | 9/2003 |
| WO | WO-03/078404 A1 | 9/2003 |
| WO | WO-03/082272 A1 | 10/2003 |
| WO | WO-03/099771 A2 | 12/2003 |
| WO | WO-03/099771 A3 | 12/2003 |
| WO | WO-2004/000833 A1 | 12/2003 |
| WO | WO-2004/005283 A1 | 1/2004 |
| WO | WO-2004/014382 A1 | 2/2004 |
| WO | WO-2004/018433 A1 | 3/2004 |
| WO | WO-2004/024663 A1 | 3/2004 |
| WO | WO-2004/030635 A2 | 4/2004 |
| WO | WO-2004/030635 A3 | 4/2004 |
| WO | WO-2004/032709 A2 | 4/2004 |
| WO | WO-2004/032709 A3 | 4/2004 |
| WO | WO-2004/032882 A2 | 4/2004 |
| WO | WO-2004/032882 A3 | 4/2004 |
| WO | WO-2004/037176 A2 | 5/2004 |
| WO | WO-2004/037176 A3 | 5/2004 |
| WO | WO-2004/037814 A1 | 5/2004 |
| WO | WO-2004/039780 A1 | 5/2004 |
| WO | WO-2004/052373 A1 | 6/2004 |
| WO | WO-2004/054186 A1 | 6/2004 |
| WO | WO-2004/056786 A2 | 7/2004 |
| WO | WO-2004/056786 A3 | 7/2004 |
| WO | WO-2004/058254 A1 | 7/2004 |
| WO | WO-2004/058782 A1 | 7/2004 |
| WO | WO-2004/060305 A2 | 7/2004 |
| WO | WO-2004/060305 A3 | 7/2004 |
| WO | WO-2004/060376 A1 | 7/2004 |
| WO | WO-2004/069812 A1 | 8/2004 |
| WO | WO-2004/071426 A2 | 8/2004 |
| WO | WO-2004/071426 A3 | 8/2004 |
| WO | WO-2004/074261 A1 | 9/2004 |
| WO | WO-2004/074262 A1 | 9/2004 |
| WO | WO-2004/074266 A1 | 9/2004 |
| WO | WO-2004/097504 A1 | 11/2004 |
| WO | WO-2005/016894 A1 | 2/2005 |
| WO | WO-2005/026130 A1 | 3/2005 |
| WO | WO-2005/030140 A2 | 4/2005 |
| WO | WO-2005/030140 A3 | 4/2005 |
| WO | WO-2005/035541 A1 | 4/2005 |
| WO | WO-2005/054246 A2 | 6/2005 |
| WO | WO-2005/054246 A3 | 6/2005 |
| WO | WO 2005/070891 A2 | 8/2005 |
| WO | WO-2005/070891 A3 | 8/2005 |
| WO | WO-2005/096784 A2 | 10/2005 |
| WO | WO-2005/096784 A3 | 10/2005 |
| WO | WO-2005/108370 A1 | 11/2005 |
| WO | WO-2006/024034 A1 | 3/2006 |
| WO | WO-2006/081172 A2 | 8/2006 |
| WO | WO-2006/081172 A3 | 8/2006 |
| WO | WO-2006/101977 A2 | 9/2006 |
| WO | WO-2006/101977 A3 | 9/2006 |
| WO | WO-2006/128129 A2 | 11/2006 |
| WO | WO-2006/128129 A3 | 11/2006 |
| WO | WO-2006/131835 A2 | 12/2006 |
| WO | WO-2006/131835 A3 | 12/2006 |
| WO | WO-2006/133411 A1 | 12/2006 |
| WO | WO-2007/008541 A2 | 1/2007 |
| WO | WO-2007/008541 A3 | 1/2007 |
| WO | WO-2007/021937 A2 | 2/2007 |
| WO | WO-2007/021937 A3 | 2/2007 |
| WO | WO-2007/032028 A1 | 3/2007 |
| WO | WO-2007/053452 A1 | 5/2007 |
| WO | WO-2007/056023 A2 | 5/2007 |
| WO | WO-2007/056023 A3 | 5/2007 |
| WO | WO-2007/056075 A2 | 5/2007 |
| WO | WO-2007/056075 A3 | 5/2007 |
| WO | WO-2007/127366 A2 | 11/2007 |
| WO | WO-2007/127366 A3 | 11/2007 |
| WO | WO-2008/008234 A1 | 1/2008 |
| WO | WO-2009/026345 A1 | 2/2009 |
| WO | WO-2009/026346 A1 | 2/2009 |
| WO | WO-2009/046416 A1 | 4/2009 |
| WO | WO-2009/049028 A1 | 4/2009 |
| WO | WO-2009/055674 A1 | 4/2009 |
| WO | WO-2009/100305 A1 | 8/2009 |
| WO | WO-2010/017122 A2 | 2/2010 |
| WO | WO-2010/017122 A3 | 2/2010 |

OTHER PUBLICATIONS

Banker, G. S. et al. (1996). *Modern Pharmaceutics*, 3rd edition, Marcel Dekker Inc., New York, pp. 451, 596.

Barber, D. F. et al. (Sep. 2005, e-pub: Aug. 28, 2005). "PI3Kγ Inhibition Blocks Glomerulonephritis and Extends Lifespan in a Mouse Model of Systemic Lupus," *Nat. Med.* 11(9):933-935.

Bell, R. M. et al. (Feb. 2003). "Bradykinin Limits Infarction When Administered as an Adjunct to Reperfusion in Mouse Heart: the Role of PI3K, Akt and eNOS," *J. Mol. & Cellul. Cardiol.* 35(2):185-193.

Bénistant, C. et al. (Jul. 5, 2000). "Deregulation of Cytoplasmic Tyrosine Kinase cSRC in the Absence of a Truncating Mutation at Codon 531 in Human Bladder Carcinoma," *Biochem. Biophys. Res. Commun.* 273(2):425-430.

Berti, F. et al. (Nov. 1990). "Production and Biologic Interactions of Prostacyclin and Platelet-Activating Factor in Acute Myocardial Ischemia in the Perfused Rabbit Heart," *J. Cardiovasc. Pharmacol.* 16(5):727-732.

Bolen, J. B. et al. (1991). "Expression and Interactions of the Src Family of Tyrosine Protein Kinases in T Lymphocytes," *Adv. Cancer Res.* 57:103-149.

Bolli, R. et al. (Jul. 23, 2004). "Myocardial Protection at a Crossroads: The Need for Translation Into Clinical Therapy," *Cir. Res.* 95:125-134.

Bonniaud, P. et al. (2005). "Progressive Transforming Growth Factor β1-Induced Lung Fibrosis is Blocked by an Orally Active ALK5 Kinase Inhibitor," *Am. J. Respir. Crit. Care Med.* 171:889-898.

Boyer, B. et al. (Oct. 15, 2000). "Induction and Regulation of Epithelial-Mesenchymal Transitions," *Biochem. Pharmacol.* 60(8):1091-1099.

Boyer, B. et al. (Apr. 4, 2002). "Src Kinase Contributes to the Metastatic Spread of Carcinoma Cells," *Oncogene* 21(15):2347-2356.

Brugge, J. S. et al. (Sep. 22, 1977). "Identification of a Transformation-Specific Antigen Induced by Avian Sarcoma Virus," *Nature* 269(5626):346-348.

Bunnett, J. F. et al. (1951). "Aromatic Nucleophilic Substitution Reactions," *Chemical Reviews* 49:273-412.

Bussolino, F. et al. (Oct. 1, 1987). "Human Endothelial Cells Are Target for Platelet-Activating Factor. I. Platelet-Activating Factor Induces Changes in Cytoskeleton Structures," *J. Immunol.* 139(7):2439-2446.

Cain, C. K. et al. (Mar. 1949). "Pteridines. IV. Derivatives of 2,4-Diamino-6,7- Diphenylpteridine," *J. Am. Chem. Soc.* 71(3):892-896.

Camps, M. et al. (Sep. 2005, e-pub. Aug. 28, 2005). "Blockade of P13Ky Suppresses Joint Inflammation and Damage in Mouse Models of Rheumatoid Arthritis," *Nat. Med.*11(9):936-943.

Cartwright, C. A. et al. (Jan. 1990). "Activation of pp60$^{c-src}$Protein Kinase is an Early Event in Colonic Carcinogenesis," *Proc. Natl. Acad. Sci.*USA 87(2):558-562.

Chawla, G. et al. (Jan.-Mar. 2004). "Challenges in Polymorphism of Pharmaceuticals", *CRIPS*5(1)12-15.

Cohen, P. et al. (Aug. 1999). "The Development and Therapeutic Potential of Protein Kinase Inhibitors," *Curr. Opin. Chem. Bio.* 3(4):459-465.

Collett, M. S. et al. (Apr. 1978). "Protein Kinase Activity Associated With the Avian Sarcoma Virus src Gene Product," *Proc. Natl. Acad. Sci.*USA 75(4):2021-2024.

Condliffe, A. M. et al. (Aug. 15, 2005, e-pub. May 5, 2005). "Sequential Activation of Class IB and Class IA P13K is Important for the Primed Respiratory Burst of Human But Not Murine Neutrophils," *Blood*106(4):1432-1440.

De La Peña, L. et al. (Jun. 2006). "Inhibition of Akt by the Alkylphospholipid Perifosine Does Not Enhance the Radiosensitivity of Human Glioma Cells,"*Mol. Cancer Ther.*596):1504-1510.

Dermer, G. B. (Mar. 12, 1994). "Another Anniversary on the War of Cancer," *Bio/Technology*12:320.

Dörwald, F. Z. (2005). "Organic Synthesis: General Remarks," *Side Reactions in Organic Synthesis*,A Guide to Successful Synthesis Design, Wiley-VCH, Weinheim, p. IX of preface pp. 1-6.

Doukas, J. et al. (Dec. 26, 2006, e-pub. Dec. 15, 2006). "Phosphoinositide 3-Kinase γ/δ Inhibition Limits Infarct Size After Myocardial Ischemia/Reperfusion Injury," *Proc. Natl. Acad. Sci.* USA 103(52):19866-19871.

Doukas, J. et al. (Mar. 2009, e-pub. Dec. 4, 2008). "Aerosolized Phosphoinositide 3- Kinase γ/δ Inhibitor TG100-115 [5[3,4-Diamino-6-(3-Hydroxyphenyl)Pteridin-7-yl]Phenol] as a Therapeutic Candidate for Asthma and Chronic Obstructive Pulmonary Disease," *J. PharmacoL Exp. Ther.*328(3):758-765.

Doukas, J. et al. (2009). "Aerosolized Phosphoinositide 3-Kinase Gamma/Delta Inhibitor TG100-115 [3[2,4-Diamino-6-(3-Hydroxyphenyl)Pteridin-7-yl]Phenol] as a Therapeutic Candidate for Asthma and Chronic Obstructive Pulmonary Disease," *J. PharmacoL Exp. Ther.*328(3):758-765, ACS on STN, caplus an 2009:272611, 2 pages.

Duncan, R. L. et al. (Feb. 1973). "Synthesis of Indolo and Benzimidazoquinazolines and Benzodiazepines," *J. Heterocycl. Chem.*10(1):65-70.

Ebrahim, S. et al. (Mar.-Apr. 2005). "Applications of Liposomes in Ophthalmology," *Surv. Ophthalmol.*50(2):167-182.

Emedicinehealth, (Nov. 19, 2007). "Acute Respiratory Distress Syndrome," located at <http://www.emedicinehealth.com/acute_respiratory_distress_syndrome/page2_em.htm>, last visited on Nov. 19, 2007, 2 pages.

Fabbro, D. et al. (Feb.-Mar. 2002). "Protein Kinases as Targets for Anticancer Agents: From Inhibitors to Useful Drugs," *Pharmacol. Ther.*93(2-3):79-98.

Fincham, V. J. et al. (Jan. 2, 1998). "The Catalytic Activity of Src is Dispensable for Translocation to Focal Adhesions But Controls the Turnover of These Structures During Cell Motility," *EMBO J.*17(1):81-92.

Freshney, R. I. et al. (1983). "Chapter 1:Introduction," in *Culture of Animal Cells*, A Manual of Basic Technique, Alan R. Liss, Inc., New York, pp. 1-6.

Fröhlich, L. G. et al. (1999, E-pub Sep. 18, 1999). "Inhibition of Neuronal Nitric Oxide Synthase by 4-Amino Pteridine Derivatives: Structure-Activity Relationship of Antagonists of (6R)-5,6,7,8,-Tetrahydrobiopterin Cofactor," *J. Med. Chem.*42(20):4108-4121.

Gazit, A. et al. (May 24, 1996). "Tyrphostins. 5. Potent Inhibitors of Platelet-Derived Growth Factor Receptor Tyrosine Kinase: Structure-Activity Relationships in Quinoxalines, Quinolines, and Indole Tyrphostins," *J. Med. Chem.*39(11):2170-2177.

Ghosh, D. et. al. (Sep. 1967). "2,4-Bis(Arylamino)-5-Methylpyrimidines as Antimicrobial Agents," *J. Med. Chem.*10(5): 974-975.

Golub, T. R. et al. (Oct. 15, 1999). "Molecular Classification of Cancer: Class Directory and Class Prediction by Gene Expression Monitoring," *Science*286(5439):531-537.

Granelli-Piperno, A. (Apr. 1992). "SRC-Related Proto-Oncogenes and Transcription Factors in Primary Human T Cells: Modulation by Cyclosporine A and FK506," *J. Autoimmun.*5(Suppl. A):145-158.

Hanke, J. H. et al. (Jan. 12, 1996). "Discovery of a Novel, Potent, and Src Family-Selective Tyrosine Kinase Inhibitor: Study of Lck- and FynT-Dependent T Cell Activation," *J. Bio. Chem.*271(2):695-701.

Innovaro Pharmalicensing (2012). "Treatment of Vascular Leakage and Related Syndromes by Administering Metalloproteinase Inhibitors," article located at http://pharmalicensing.com/public/outlicensing/view/8022/treatment-of-vascular-leakage-and-related-symdromes-by-administering-metalloproteinase-inhibitors, last visited Mar. 9, 2012, 2 pages.

ITO, K. et al. (Apr. 2007, e-pub.: Oct. 4, 2006). "Therapeutic Potential of Phosphatidylinositol 3-Kinase Inhibitors in Inflammatory Respiratory Disease," *J. Pharm. Exp. Ther.*321(1):1-8.

Jacobson, J. R. et al. (Jun. 2005, e-pub.: Jan. 21, 2005). "Simvastatin Attenuates Vascular Leak and Inflammation in Murine Inflammatory Lung Injury," *Am. J. Physiol. Lung. Cell. Mol. Physiol.* 288(6):L1026-L1032.

Jacquet, R. et al. (2004). "Liquid Chromatography Analysis of Monosubstituted Sulfobutyl Ether-β-Cyclodextrin Isomers on Porous Graphitic Carbon," *J. Sep. Sol.*27:1221-1228.

Kiang, A. K. et al. (1956). "The Action of Acyl Cyanides on 2- and 1, 2-Substituted Indoles. Part II. Derivatives of 2-o-Aminophenylindole," *J. Am. Chem. Soc.*2(14):1319-1324.

Kijlstra, A. et al. (Feb. 2005). "Immunological Factors in the Pathogenesis and Treatment of Age-Related Macular Degeneration," *Ocul. Immunol. Inflamm.*13(1):3-11.

Klein, R. J. et al. (Apr. 15, 2005, e-pub. Mar. 20, 2010). "Complement Factor H Polymorphism in Age-Related Macular Degeneration," *Science*308(5720):385-389.

Klutchko, S. R. et al. (Aug. 13, 1998, e-pub. Jul. 24, 1998). "2-Substituted Aminopyrido [2,3-*d*] pyrimidin-7 (81-*H*)—ones. Structure-Activity Relationships Against Selected Tyrosine Kinases and in Vitro and in Vivo Anticancer Activity," *J. Med. Chem.*41(17):3276-3292.

Kobayashi, N. et al. (May 1, 1993). "Functional Coupling of the src-Family Protein Tyrosine Kinases p59$^{b\prime\prime}$and p53/56$^{b\prime\prime}$with the Interleukin 2 Receptor: Implications for Redundancy and Pleiotropism in Cytokine Signal Transduction," *Proc. Natl. Acad. Sci.*USA 90(9):4201-4205.

Krause, D. S. et al. (Jul. 14, 2005). "Tyrosine Kinases as Targets for Cancer Therapy," *N. Eng. J. Med.*353(2):172-187.

Laffargue, M. et al. (Mar. 2002). "Phosphoinositide 3-Kinase γis an Essential Amplifier of Mast Cell Function," *Immunity*16(3):441-451.

Lee, C.-H. et al. (2001). "Discovery of 4-Amino-5-(3-Bromophenyl)-7-(6-Morpholino-Pyridin-3- yl)Pyrido[2,3-*d*]Pyrimidine, an Orally Active, Non-Nucleoside Adenosine Kinase Inhibitor," *J. Med. Chem.*44(13):2133-2138.

Liu, K. et al. (Apr. 11, 2008). "Epidermal Growth Factor Receptor Signaling to Erk1/2 and STATs Control the Intensity of the Epithelial Inflammatory Responses to Rhinovirus Infection," *J. Biol. Chem.* 283(15):9977-9985.

Lowe, C. et al. (May 15, 1993). "Osteopetrosis in Src-Deficient Mice is Due to an Autonomous Defect of Osteoclasts," *Proc. Natl. Acad. Sci.*USA 90(10):4485-4489.

Madhusudan, S. et al. (2004). "Tyrosine Kinase Inhibitors in Cancer Therapy," *Clin. Biochem.*37:618-635.

Mainardes, R. M. et al. (2005). "Colloidal Carriers for Ophthalmic Drug Delivery," *Curr. Drug. Targets*6(3):363-371.

Mass, R. D. (Mar. 1, 2004). "The HER Receptor Family: A Rich Target for Therapeutic Development," *Int. J. Radiat Oncol. Bio. Phys.*58(3):932-940.

Mayoclinic, (Jul. 5, 2006). "Stroke," article located at <http://www.mayoclinic.com/health/stroke/DS00150/dsection=7>, last visited on Nov. 19, 2007, 4 pages.

Medscape, (Sep. 5, 2006). "VEGF Manipulation Ameliorates Murine Asthma Symptoms," by David Douglas, located at <http://www.medscape.com/viewarticle/544205_print>, last visited on Nov. 19, 2007, one page.

Milhoan, K. A. et al. (Sep. 1992). "Hypoxia Induces Endothelial Cells to Increase Their Adherence for Neutrophils: Role of PAF," *Am. J. Physiol* 263(3 Pt 2):H956-H962.

Montrucchio, G. et al. (Oct. 2000). "Role of Platelet-Activating Factor in Cardiovascular Pathophysiology," *Physiol Rev.*80(4):1669-1699.

Mullins, R. F. et al. (May 2000). "Drusen Associated with Aging and Age-Related Macular Degeneration Contain Proteins Common to Extracellular Deposits Associated with Atherosclerosis, Elastosis, Amyloidosis, and Dense Deposit Disease," *FASEB J.*14:835-846.

New Mexico Department of Health, (Apr. 30, 2002). "Interleukin-2," located at <http://www.aidsinfonet.org> Project of the New Mexico Aids Education and Training Center, Fact Sheet Number 622, one page.

Newman, A. W. et al. (Oct. 19, 2003). "Solid-State Analysis of the Active Pharmaceutical Ingredient in Drug Products," *Drug Discovery Today*8(19):898-905.

Nienaber, J. J. et al. (Oct. 2003). "Inhibition of Receptor-Localized PI3K Preserves Cardiac β-Adrenergic Receptor Function and Ameliorates Pressure Overload Heart Failure," *J. Clin. Invest.* 112(7):1067-1079.

O'Shea, J. J. et al. (Mar. 1, 1991). "Expression of v-src in a Murine T-Cell Hybridoma Results in Constitutive of T-Cell Receptor Phosphorylation and Interleukin 2 Production," *Proc. Natl. Acad. Sci.*USA 88(5):1741-1745.

Palanki, M. S. S. et al. (2007). "Discovery of 3,3'-(2,4-Diaminopteridine-6,7-diyl) diphenol as an Isozyme-Selective Inhibitor of PI3K for the Treatment of Ischemia Reperfusion Injury Associated With Myocardial Infarction," *J. Med. Chem.*50(18):4279-4294, corresponding to STN caplus 2007:866646, one page.

Palanki, M. S. S. et al. (2007). "Discovery of 3,3'-(2,4-Diaminopteridine-6,7-diyl) diphenol as an Isozyme-Selective Inhibitor of PI3K for the Treatment of Ischemia Reperfusion Injury Associated with Myocardial Infarction," *J. Med. Chem.*50(18):4279-4294.

Patrucco, E. et al. (Aug. 6, 2004). "PI3Kγ Modulates the Cardiac Response to Chronic Pressure Overload by Distinct Kinase-Dependent and -Independent Effects," *Cell*118(3):375387.

Plé, P. A. et al. (Feb. 12, 2004). "Discovery of a New Class of Anilinoquinazoline Inhibitors with High Affinity and Specificity for the Tyrosine Kinase Domain of c-Src," *J. Med. Chem.*47(4):871-887.

Powell, T. J. et al. (Nov. 1999). "Growth Inhibition of Psoriatic Keratinocytes by Quinazoline Tyrosine Kinase Inhibitors," *Br. J. Dermatol.*141(5):802-810.

Purchio, A. F. et al. (Mar. 1978). "Identification of a Polypeptide Encoded by the Avian Sarcoma Virus src Gene," *Proc. Natl. Acad. Sci.*USA 75(3):1567-1571.

Puri, K. D. et al. (May 1, 2004, e-pub. Jan. 29, 2004). "Mechanisms and Implications of Phosphoinositide 3-Kinase δin Promoting Neutrophil Trafficking Into Inflamed Tissue," *Blood*103(9):3448-3456.

Radi, M. et al. (Feb. 1, 2008, e-pub. Dec. 4, 2007). "Discovery and SAR of 1,3,4,Thiadiazole Derivatives as Potent Abl Tyrosine Kinase Inhibitors and Cytodifferentiating Agents," *Bioorg Med. Chem. Lett.* 18(3):1207-1211.

Reissig, D. et al. (Apr. 2001). "Elevated Activity and Expression of Src Family Kinases in Human Breast Carcinoma Tissue Versus Matched Non-Tumor Tissue," *J. Cancer Res. Clin. Oncol.* 127(4):226-230.

Rosen, N. et al. (Oct. 15, 1986). "Analysis of pp60$^{c-src}$ Protein Kinase Activity in Human Tumor Cell Lines and Tissues," *J. Biol. Chem.* 261(29):13754-13759.

Sakurai, Y. et al. (1952). "367. Studies on Cancerocidal Substances. I. Effect of Pterins on the Yoshida Sarcoma," *Yakugaku Zasshi*72(10):1294-1296.

Schoenwald, R. D. et al. (Nov. 1983). "Corneal Penetration Behavior of β-Blocking Agents I: Physicochemical Factors," *J. Pharm. Sci.* 72(11):1266-1272.

Schroeder, M. C. et al. (Jun. 7, 2001). "Soluble 2-Substituted Aminopyrido [2,3-*d*] pyrimidin-7-yl Ureas. Structure-Activity Relationships against Selected Tyrosine Kinases and Exploration of in Vitro and in Vivo Anticancer Activity," *J. Med. Chem.*44(12):1915-1926.

Shah, N. P. et al. (Jul. 16, 2004). "Overriding Imatinib Resistance with a Novel ABL Kinase Inhibitor," *Science*305(5682):399-401.

Simone, J. V. (1996). "Introduction," in Chapter 154, in *Cecil Textbook of Medicine*, Philadelphia, W.B. Saunders Co., J. C. Bennett,eds., 20$^{th}$edition, vol. 1, Part XIV entitled. "Oncology," pp. 1004-1010.

Summy, J. M. et al. (Dec. 2003). "Src Family Kinases in Tumor Progression and Metastasis," *Cancer Metastasis Rev.* 22(4):337-358.

Taghavi-Moghadam, S. et al. (Sep. 29, 1997). "A New, General and Regioselective Method for the Synthesis of 2,6-Disubstituted 4-Aminopteridines," *Tetrahedron Letters*38(39):6835-6836.

Talamonti, M. S. et al. (Jan. 1993). "Increase in Activity and Level of pp60$^{c-src}$in Progressive Stages of Human Colorectal Cancer," *J. Clin. Investig.* 91(1):53-60.

Tanaka, N. et al. (Jun. 7, 1993). "A Novel Human Tyrosine Kinase Gene Inducible in T Cells by Interleukin 2," *FEBS Lett.* 324(1):1-5.

Torigoe, T. et al. (1992). "Regulation of SRC-Family Protein Tyrosine Kinases by Interleukins, IL-2, and IL-3," *Leukemia*6(Suppl. 3):945-975.

Ulrich, J. (2004). "Crystal Engineering," in *Kirk-Othmer Encyclopedia of Chemical Technology*, 5$^{th}$Edition, Wiley-Interscience,A John Wiley & Sons, Inc. Publication, vol. 8, definition of "Pseudopolymorphs,", pp. 68-70.

Vippagunta, S. R. et al. (May 16, 2001). "Crystalline Solids," *Adv. Drug Deliv. Rev.*48(1):3- 26.

Weber, T. (Nov. 11, 2002). "Molecular Approaches to Study Cellular Roadblocks to Transfection and Transduction (Non-Viral Vectors and AAV-Based Vectors for Gene Therapy," located at <http://www.mssm.edu/genetherapy/weber.htm>, pp. 1-8.

Weis, S. et al. (Mar. 2004). "Src Blockade Stabilizes a Flk/Cadherin Complex, Reducing Edema and Tissue Injury Following Myocardial Infarction," *J. Clin. Investig.* 113(6):885-894.

Wermuth, C. G. (1996). "Molecular Variations Based on Isosteric Replacements," in *The Practice of Medicinal Chemistry*, Chapter 13, Publisher Technomiucs, Inc., U.S. Edition published by Academic Press Limited, vol. 1, p. vi, pp. 203-204,210-215.

West, A. R. (1988). "Chapter 10 — Solid Solutions," in *Solid State Chemistry and Its Applications*, John Wiley & Sons, New York, pp. 358 & 365.

Wikipedia, (Nov. 14, 2007). "Acute Respiratory Distress Syndrome," located at <http://en.wikipedia.org/wiki/Acute_respiratory_distress_syndrome>, last visited on Nov. 19, 2007, 11 pages.

Wikipedia, (Apr. 30, 2008). "Myocardial Infarction," located at <http://en.wikipedia.org/wiki/Myocardial_Infarction>, last visited on May 1, 2008, 49 pages.

Wikipedia (Oct. 31, 2010). "Wortmannin" located at <http://en.wikipedia.org/wiki/Wortmannin>, last visited on Mar. 16, 2011, 2 pages.

Wills, B. A. et al. (Sep. 1, 2005). "Comparison of Three Fluid Solutions for Resuscitation in Dengue Shock Syndrome," *The New England Journal of Medicine*353(9):877-889.

Yamamoto, T. et al. (1991). "Role of src-Like Protooncogenes in Lymphocytes Prolifration," in *Multistage Carcinogenesis, Proceedings of the 22$^{nd}$ International Symposium of the Princess Takamatsu Cancer Research Fund,*Tokyo, C. C. Harris et al. (eds), Japan Scientfic Societies Press, Tokyo, CRC Press, vol. 22, pp. 293-305.

Yukawa, E. et al. (Dec. 1989). "MNDO (Modified Neglect of Diatomic Overlap) Study of the Nucleophilic Substitution Reactions of Chloropyrimidines," *Chem. Pharm. Bull. (Tokyo)*37(11):2892-2896.

Yum, H.-K. et al. (Dec. 1, 2001). "Involvement of Phosphoinositide 3-Kinases in Neutrophil Activation and the Development of Acute Lung Injury," *J. Immunol.*167(11):6601-6608.

Non Final Office Action mailed on Jun. 5, 2006, for U.S. Appl. No. 10/679,209, filed on Oct. 2, 2003, for Wrasidlo et al., 7 pages.

Notice of Allowance mailed on Oct. 4, 2006, for U.S. Appl. No. 10/679,209, filed on Oct. 2, 2003, for Wrasidlo et al., with PTO Form 892, 9 pages.

Non Final Office Action mailed on Jun. 1, 2009, for U.S. Appl. No. 11/653,190, filed on Jan. 11, 2007, for Wrasidlo et al., 14 pages.

Final Office Action mailed on Apr. 30, 2009, for U.S. Appl. No. 11/105,845, filed on Apr. 13, 2005, for Wrasidlo et al., 5 pages.

Final Office Action mailed on Nov. 7, 2008, for U.S. Appl. No. 11/105,845, filed on Apr. 13, 2005, for Wrasidlo et al., 9 pages.
Final Office Action mailed on May 5, 2008, for U.S. Appl. No. 11/105,845, filed on Apr. 13, 2005, for Wrasidlo et al., 8 pages.
Non Final Office Action mailed on Nov. 26, 2007, for U.S. Appl. No. 11/105,845, filed on Apr. 13, 2005, for Wrasidlo et al., 15 pages.
Non Final Office Action mailed on Jul. 28, 2011, for U.S. Appl. No. 12/780,401, filed on May 14, 2010, 11 pages.
Final Office Action mailed on Mar. 7, 2012, for U.S. Appl. No. 12/780,401, filed on May 14, 2010, 7pages.
Non Final Office Action mailed on Sep. 20, 2007, for U.S. Appl. No. 11/102,405, filed on Apr. 7, 2005, 20 pages total.
Non Final Office Action mailed on Mar. 24, 2008, for U.S. Appl. No. 11/102,405, filed on Apr. 7, 2005, 12 pages total.
Non Final Office Action mailed on Jun. 28, 2010, for U.S. Appl. No. 12/207,019, filed on Sep. 9, 2008, 22 pages.
Non Final Office Action mailed on Nov. 28, 2011, for U.S.Appl. No. 12/980,235, filed on Dec. 28, 2010, 25 pages.
Non Final Office Action mailed on Jan. 6, 2009, for U.S.Appl. No. 11/212,064, filed on Aug. 24, 2005, 26 pages.
Non Final Office Action mailed on Jul. 23, 2008, for U.S. Appl. No. 11/377,234, filed on Mar. 15, 2006, 23 pages.
Non Final Office Action mailed on Jan. 12, 2009, for U.S. Appl. No. 11/377,234, filed on Mar. 15, 2006, 6 pages.
International Search Report mailed on Jul. 2, 2004, for PCT Patent Application No. PCT/US2003/031721, filed on Oct. 2, 2003, published on Apr. 15, 2004, as WO 2004/030635, 2 pages.
International Preliminary Report on Patentability mailed on Dec. 3, 2004, for PCT Patent Application No. PCT/US2003/031721, filed on Oct. 2, 2003, published on Apr. 15, 2004, as WO 2004/030635, 3 pages.
Supplementary European Search Report mailed on Mar. 17, 2008, for European Patent Application No. 03774610.4, filed on Oct. 2, 2003, published as EP 1 549 614 on Jul. 6, 2005, 5 pages.
European Examination Report mailed on Nov. 24, 2009, for European Patent Application No. 03774610.4, filed on Oct. 2, 2003, published on Jul. 6, 2005, as EP 1 549 614, 8 pages.
Supplementary European Search Report mailed on Jun. 18, 2009, for European Patent Application No. 08014818.2, filed on Oct. 2, 2003, published on Mar. 25, 2009, as EP 2 039 683, 3 pages.
European Written Opinion mailed on Jun. 18, 2009, for European Patent Application No. 08014818.2, filed on Oct. 2, 2003, published on Mar. 25, 2009, as EP 2 039 683, 2 pages.
European Office Action mailed on Oct. 4, 2010, for European patent Application No. 08014818.2, filed on Oct. 2, 2003, published on Mar. 25, 2009, as EP 2 039 683, 7 pages.
International Search Report mailed on Sep. 2, 2008, for PCT Patent Application No. PCT/US2005/012057, filed on Apr. 7, 2005, published on Oct. 20, 2005, as PCT Publication No. WO 2005/096784, 2 pages total.
Written Opinion mailed on Sep. 2, 2008, for PCT Patent Application No. PCT/US2005/012057, filed on Apr. 7, 2005, published on Oct. 20, 2005, as PCT Publication No. WO 2005/096784, 4 pages total.
Supplementary European Search Report mailed on Jan. 18, 2010, for European Patent Application No. 07562774.7, filed on Apr. 7, 2005, published on Jul. 25, 2007, as European Publication No. 1 809 614, 3 pages total.
European Examination Report mailed on May 3, 2010, for European Patent Application No. 07562774.7, filed on Apr. 7, 2005, published on Jul. 25, 2007, as European Publication No. 1 809 614, 4 pages total.
International Search Report mailed on Jan. 27, 2006, for PCT Patent Application No. PCT/US2005/030614, filed on Aug. 24, 2005, published on Mar. 2, 2006 as PCT Publication No. WO 2006/024034, one page.
Written Opinion mailed on Jan. 27, 2006, for PCT Patent Application No. PCT/US2005/030614, filed on Aug. 24, 2005, published on Mar. 2, 2006 as PCT Publication No. WO 2006/024034, 5 pages.
European Search Report and European Written Opinion mailed on Aug. 5, 2009, for European Patent Application No. 05792421.9, filed on Aug. 24, 2005, published on Jun. 27, 2007, as European Publication No. 1 799 656, 5 pages.
International Search Report mailed on Sep. 21, 2006, for PCT Patent Application No. PCT/US2006/009518, filed on Mar. 15, 2006, published on Sep. 28, 2006, as WO 2006/101977, 2 pages.
Written Opinion mailed on Sep. 21, 2006, for PCT Patent Application No. PCT/US2006/009518, filed on Mar. 15, 2006, published on Sep. 28, 2006, as WO 2006/101977, 4 pages.
International Search Report mailed on Sep. 18, 2006, for PCT Patent Application No. PCT/US2006/022480, filed on Jun. 7, 2006, published on Dec. 14, 2006, as WO 2006/133411, one page.
Written Opinion mailed on Sep. 18, 2006, for PCT Patent Application No. PCT/US2006/022480, filed on Jun. 7, 2006, published on Dec. 14, 2006, as WO 2006/133411, 3 pages.
International Search Report mailed on Jul. 8, 2009, for PCT Patent Application No. PCT/US2009/033353, filed on Feb. 6, 2009, published on Aug. 13, 2009, as WO 2009/100305, 2 pages.
Written Opinion mailed on Jul. 8, 2009, for PCT Patent Application No. PCT/US2009/033353, filed on Feb. 6, 2009, published on Aug. 13, 2009, as WO 2009/100305, 5 page.
U.S. Appl. No. 12/846,702, filed on Jul. 29, 2010, for Noronha et al.
U.S. Appl.No. 13/220,394, filed on Aug. 29, 2011, for Noronha et al.
U.S. Appl. No. 13/243,924, filed on Sep. 23, 2011, for Wrasidlo et al.
U.S. Appl. No. 13/357,500, filed on Jan. 24, 2012, for Noronha et al.
Final Office Action mailed on Jun. 22, 2012, for U.S. Appl. No. 12/980,235, filed on Dec. 28, 2010, 7 pages.
Extended European Search Report mailed on Nov. 12, 2012 for European Patent Application No. 1118890.5, filed on Mar. 19, 2007, 5 pages.

* cited by examiner

HETEROCYCLIC COMPOUNDS AND METHODS OF USE

CROSS-REFERENCE TO RELATED APPLICATIONS

This application is a continuation application of U.S. patent application Ser. No. 12/684,312 filed Jan. 8, 2010, which is a continuation application of U.S. patent application Ser. No. 11/212,064 filed Aug. 24, 2005, which claims the benefit of priority under 35 U.S.C. §119(e) of U.S. Provisional Patent Application Nos. 60/604,298 filed Aug. 25, 2004, and 60/696,168 filed Jul. 1, 2005, the disclosures of which are incorporated herein by reference in their entirety.

FIELD OF THE INVENTION

The present invention relates generally to the use of compounds to treat a variety of disorders, diseases and pathologic conditions and more specifically to the use of various heterocyclic compounds for therapeutic purposes.

BACKGROUND

Kinases are a large family of cellular proteins involved in signal transduction of cascades which control cell growth and death, survival, migration, differentiation, gene expression, metabolism, protein synthesis and cell cycle regulation. A common mechanism by which these signals are transmitted is reversible phosphorylation, which induces conformational changes is these enzymes and alters their structure and function. The entire kinase genome discovered so far incorporates over 500 individual proteins and their isoforms. Different branches of this genomic tree have been characterized into groups specific for phosphorylating either serine/threonine residues or tyrosines. Some kinases exhibit dual specificity, capable of substrate phosphorylation of tyrosine as well as serine/threonines. Further differentiation can be made in terms of their location in cells. Transmembrane receptor protein kinases exhibit an extracellular domain, capable of ligand binding. These ligand binding mechanisms trigger activation of the kinase catalytic domain which initiates a cascade of signals that controls intracellular functions. Examples of a receptor protein kinase are growth factors such as EGF, FGF, PDGF and IGF. Nonreceptor protein kinases can be found in many compartments of a cell from inner-cell surface membranes to the cell nucleus. One example of a nonreceptor protein kinase is the mitogen activated protein kinase (MAPK) which regulates a pathway, which is important in cell signaling initiated on the exterior cell surfaces via growth factors, for example, VEGF, or hormones, and extending to the cell nucleus by activating transcription factors. These nuclear factors in turn control gene expression in the regulation of cell cycle progression and ultimately cell proliferation, and differentiation.

The MAPK cell signaling pathway is important for drug targeting as this path impinges on nearly all functional hallmarks of cancer cells such as immortalization, growth factor independent proliferation, insensitivity to growth inhibitory signals, metastasis, blood vessel attraction, evasion of apoptosis, and other functional hallmarks. Inappropriate activation though mutation of this molecule is associated with nearly 30% of all human cancers. In general, the inhibition of disregulated kinases such as Ras, PI3K and Raf is an important approach to discover novel treatments for cancer and other diseases. One approach is the discovery of small molecules capable of binding either to the kinase catalytic domain or a regulatory domain in order to modulate the function of protein kinases. Important in this respect is to discover molecules which inhibit a specific signaling path with a high degree of selectivity and a potency within a practical therapeutic window. While significant progress has been made in developing various compounds for the treatment of cancer and inflammatory diseases, there remains a need for specific chemical structures capable of modulating protein kinases, whose disregulated function has been implicated in these diseases.

SUMMARY OF THE INVENTION

The present invention provides compounds which affect the MAPK pathway. The compounds of the invention are useful as pharmaceutical compositions, for example where modulation of the MAPK pathway is indicated for the treatment of various human diseases, such as cancer.

According to one embodiment of the invention, compounds having the structure (A) are provided, or an N-oxide, N,N'-dioxide, N,N',N"-trioxide, or a pharmaceutically acceptable salt thereof:

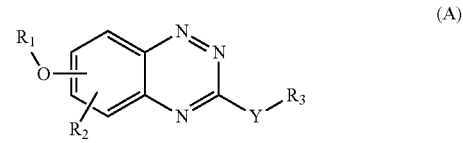

wherein Y can be absent or can be one of the following moieties:

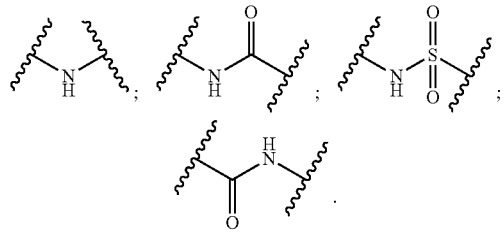

According to another embodiment of the invention, compounds having the structure (B) are provided, or an N-oxide, N,N'-dioxide, N,N',N"-trioxide, or a pharmaceutically acceptable salt thereof:

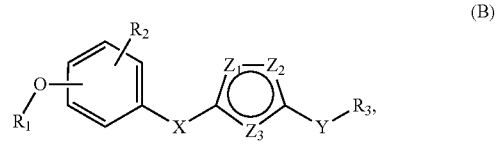

wherein X can be absent or can be NH, and Y can be absent or can be one of the following moieties:

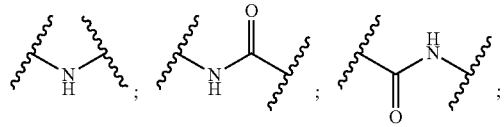

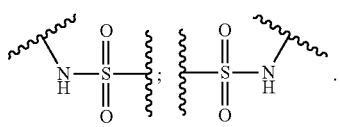

In compounds having structure (B), each of $Z_1$, $Z_2$ and $Z_3$ can be, independently, N, N=CH, CH, O, S or N—$R^4$, wherein $R^4$ is hydrogen or lower alkyl, with the further proviso that at least one of $Z_1$, $Z_2$ and $Z_3$ is not CH.

In compounds having structure (A), the substitutent $R_1$ can be an aryl, a substituted aryl, a heterocycle, a heteroaryl, a substituted heterocycle, and a substituted heteroaryl. For example, $R_1$ can be one of $C_6$-$C_{12}$ aryl; $C_3$-$C_{12}$ heteroaryl having 1-3 heteroatoms such as N, S and O; substituted $C_3$-$C_{10}$ cycloalkyl having 0-3 heteroatoms such as N, S, and O; substituted $C_6$-$C_{12}$ aryl; substituted $C_3$-$C_{12}$ heteroaryl having 1-3 heteroatoms such as N, S and O; $C_7$-$C_{24}$ aralkyl; $C_7$-$C_{24}$ alkylaryl; substituted $C_7$-$C_{24}$ aralkyl; and substituted $C_7$-$C_{24}$ alkaryl.

In compounds having structure (B), the substitutent $R_1$ can be, independently of the substitutent $R_1$ present in the structure (A), an unsubstituted or a substituted $C_3$-$C_{12}$ heteroaryl having 1-3 heteroatoms such as N, S or O. The substituent $R_1$ that can be present in compounds having structure (B), can include a substituted pyridyl group. The substituents in the substituted pyridyl group can include an amido moiety, an aminoalkyl group (e.g., aminomethyl), or a carboxyl group, or a carboxylate group. The amido moiety attached to the pyridyl group can be in turn also substituted by attaching to the nitrogen in the amido moiety a substitutent selected from an alkyl (e.g., methyl), an alkylaminoalkyl (e.g., diethylamino alkyl), a pyridyl, an alkyl pyrrolidine, an alkyl morpholine, and an alkyl piperazine groups.

Some examples of the substitutent $R_1$ that can be present in compounds having either structure (A) or structure (B), can be selected from one of the following moieties:

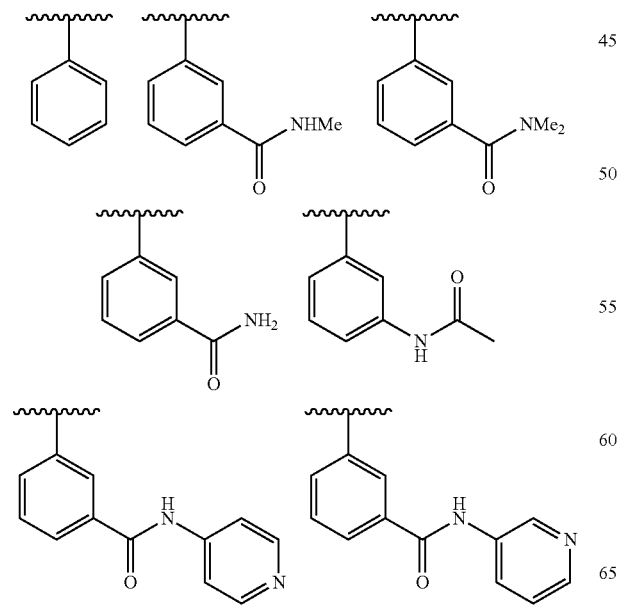

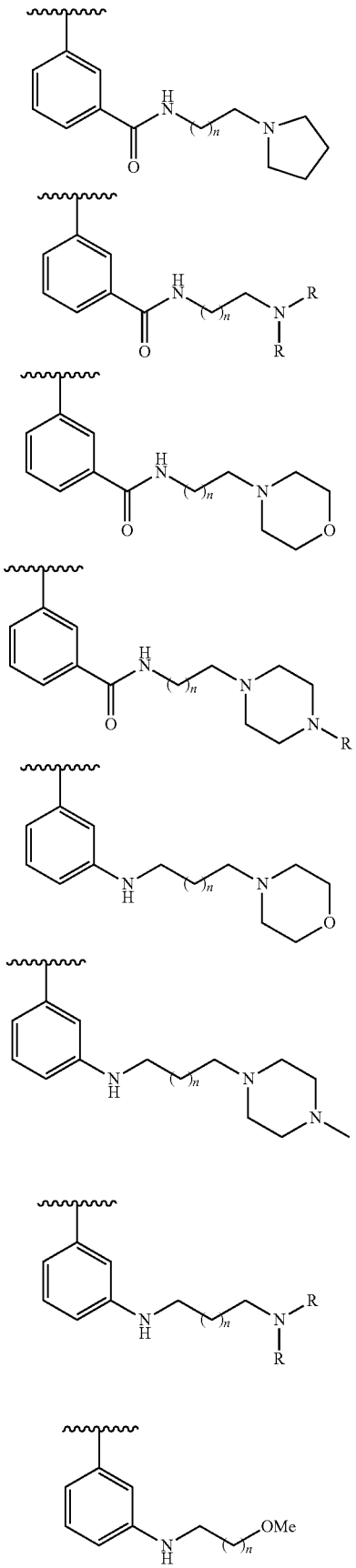

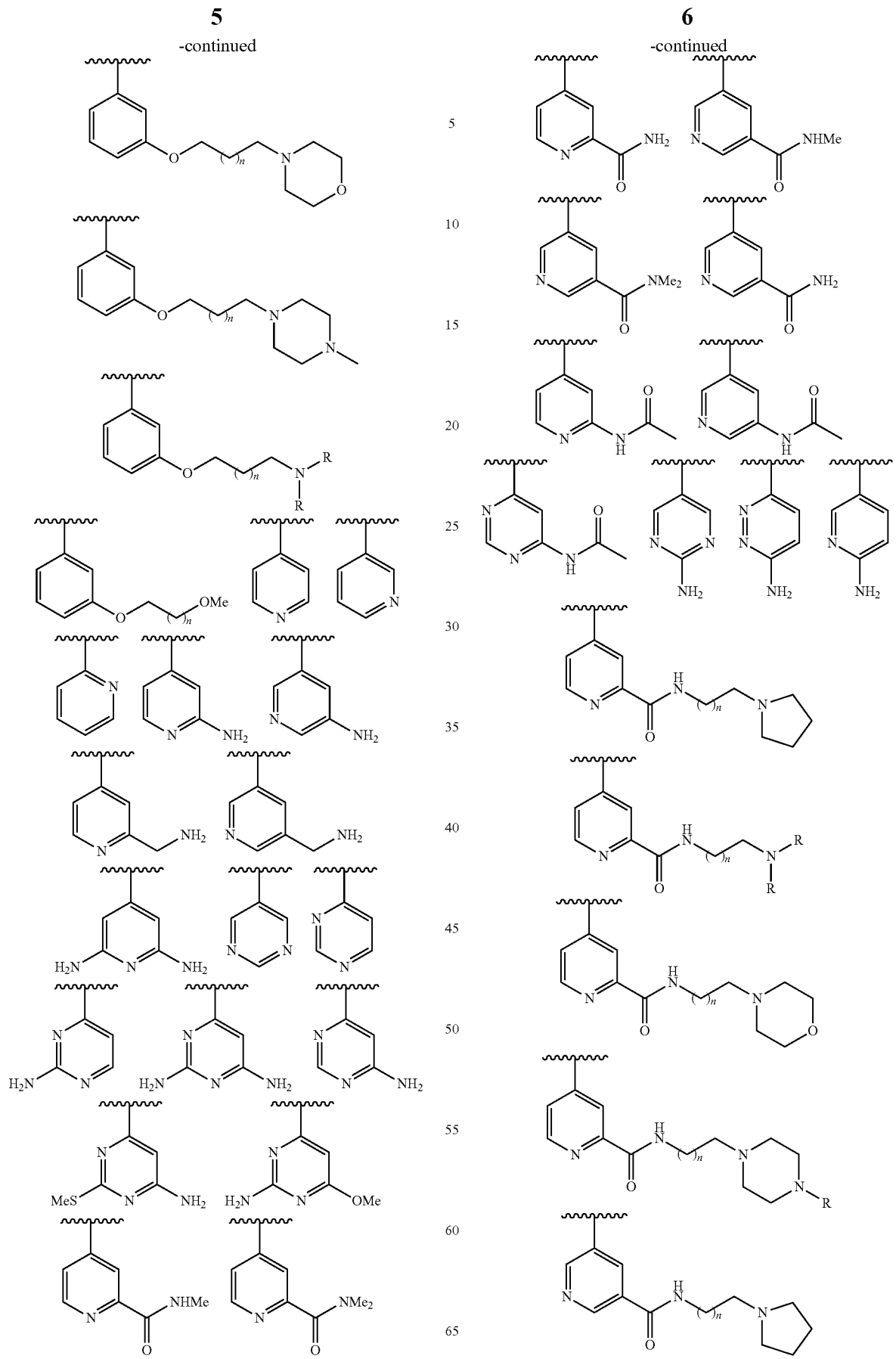

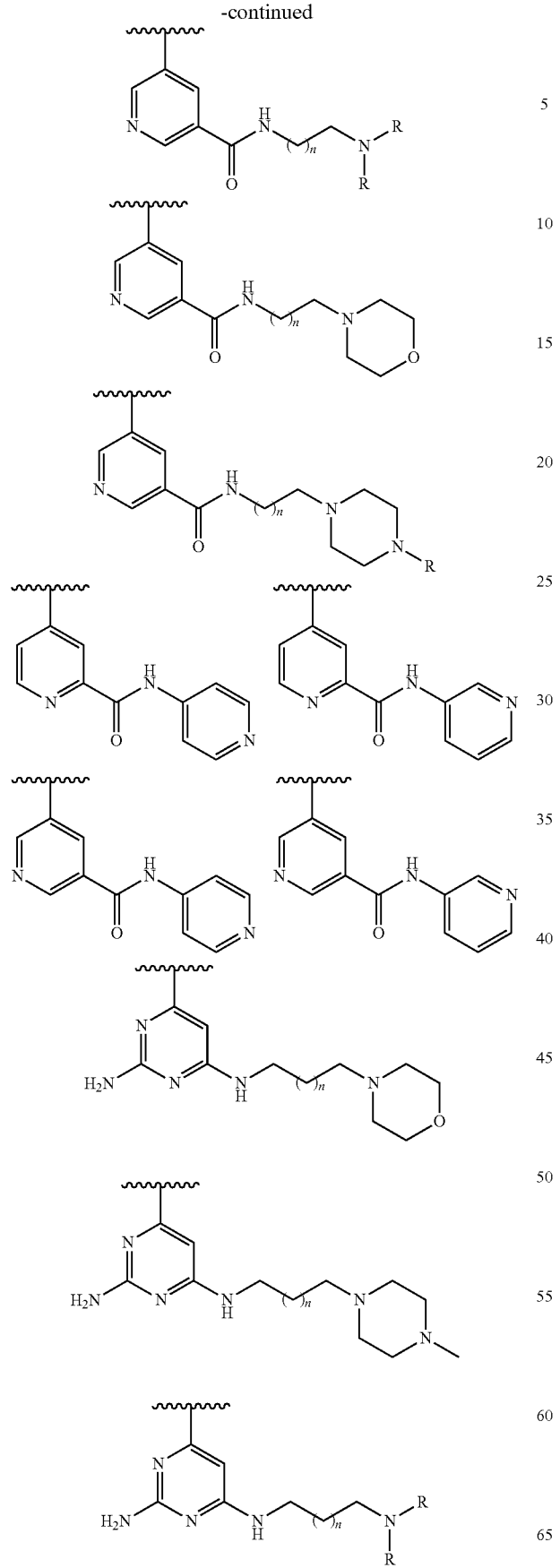
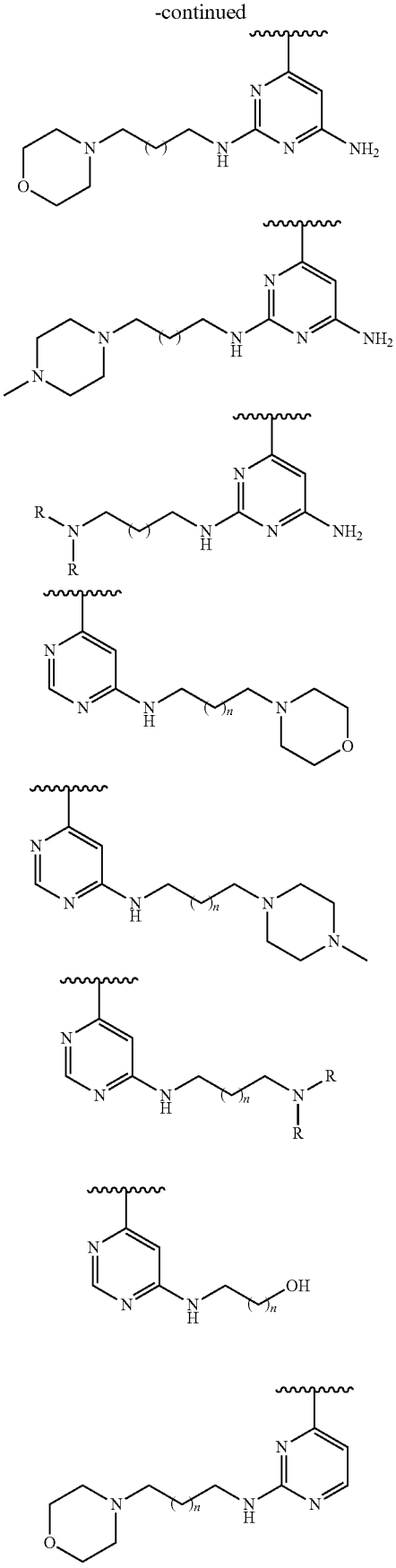

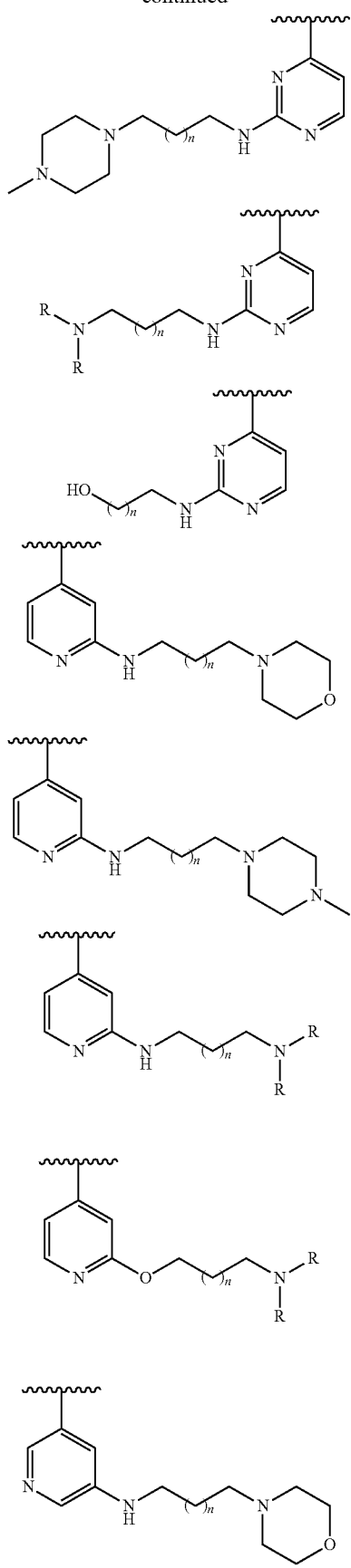
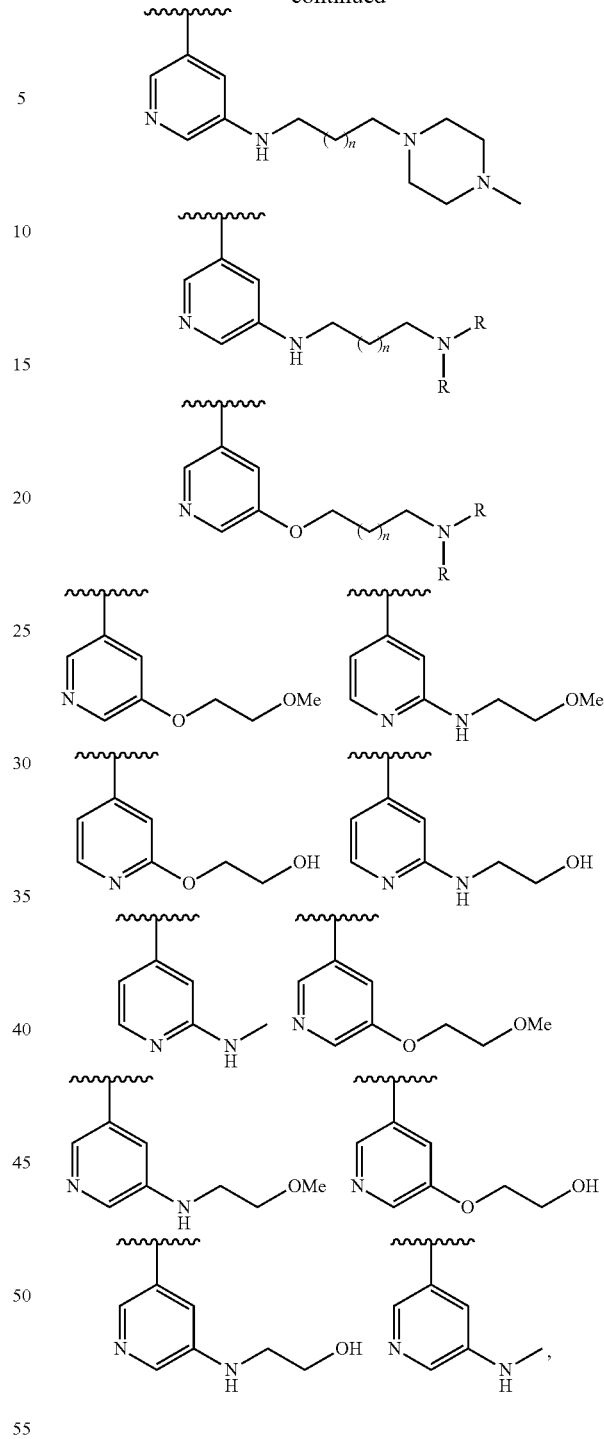

where n can be an integer selected from a group consisting of 0, 1, 2, and 3.

In compounds having structure (A) or (B), $R_2$ can be, independently, any one of hydrogen, halogen, $C_1$-$C_{18}$ alkyl (e.g., methyl), —OH, —$NO_2$, —CN, $C_1$-$C_{18}$ alkoxy (e.g., methoxy), —$NHSO_2R^5$, —$SO_2NHR^5$, —$NHCOR^5$, —$NH_2$, —$NR^5R^6$, —$S(O)R^5$, —$S(O)_2R^5$, —$CO_2R^5$, —$CONR^5R^6$, and where $R^5$ and $R^6$ are independently selected from hydrogen, a $C_1$-$C_{12}$ alkyl and a substituted $C_1$-$C_{12}$ alkyl.

In compounds having structure (A), the substituent $R_3$ can be an aryl, a substituted aryl, a heterocycle, a heteroaryl, a substituted heterocycle, and a substituted heteroaryl. For example, $R_3$ can be one of $C_6$-$C_{12}$ aryl; $C_3$-$C_{12}$ heteroaryl having 1-3 heteroatoms such as N, S and O; substituted $C_3$-$C_{10}$ cycloalkyl having 0-3 heteroatoms such as N, S, and O; substituted $C_6$-$C_{12}$ aryl; substituted $C_3$-$C_{12}$ heteroaryl having 1-3 heteroatoms such as N, S and O; $C_7$-$C_{24}$ aralkyl; $C_7$-$C_{24}$ alkylaryl; substituted $C_7$-$C_{24}$ aralkyl; and substituted $C_7$-$C_{24}$ alkaryl.

In compounds having structure (B), the substitutent $R_3$ can be, independently of the substitutent $R_3$ present in the structure (A), hydrogen, a $C_1$-$C_{18}$ alkyl, a substituted $C_1$-$C_{18}$ alkyl, a $C_1$-$C_{12}$ cycloalkyl, a substituted $C_1$-$C_{12}$ cycloalkyl, a substituted $C_3$-$C_{10}$ cycloalkyl having 0-3 heteroatoms such as N, S, or O, an aryl such as a $C_6$-$C_{12}$ aryl, a substituted aryl such as a substituted $C_6$-$C_{12}$ aryl, a heterocycle, a substituted heterocycle, a heteroaryl such as a $C_3$-$C_{12}$ heteroaryl having 1-3 heteroatoms such as N, S or O, a substituted heteroaryl such as substituted $C_3$-$C_{12}$ heteroaryl having 1-3 heteroatoms such as N, S or O, a $C_7$-$C_{24}$ aralkyl, a substituted $C_7$-$C_{24}$ aralkyl, a $C_7$-$C_{24}$ alkylaryl, and a substituted $C_7$-$C_{24}$ alkaryl. Some particular examples of the substituent $R_3$ than can be used include tert-butyl phenyl, trifluoromethoxyphenyl, methoxyphenyl, dimethylaminophenyl, aminophenyl, trifluoroethoxyphenyl, trifluoromethoxychlorophenyl, trifluoromethoxybromophenyl, trifluoroethoxychlorophenyl, chlorophenyl, dichlorophenyl, trifluoromethyl phenyl, trifluoromethylchlorophenyl, chlorotoluyl, N-phenylacetamide, N,N-alkyl-benzamide, isopropoxyphenyl, alkoxyphenyl, dialkoxyphenyl, or acetylphenyl.

To summarize, some examples of the substituent $R_3$ that can be present in compounds having either structure (A) or structure (B), can be selected from one of the following moieties:

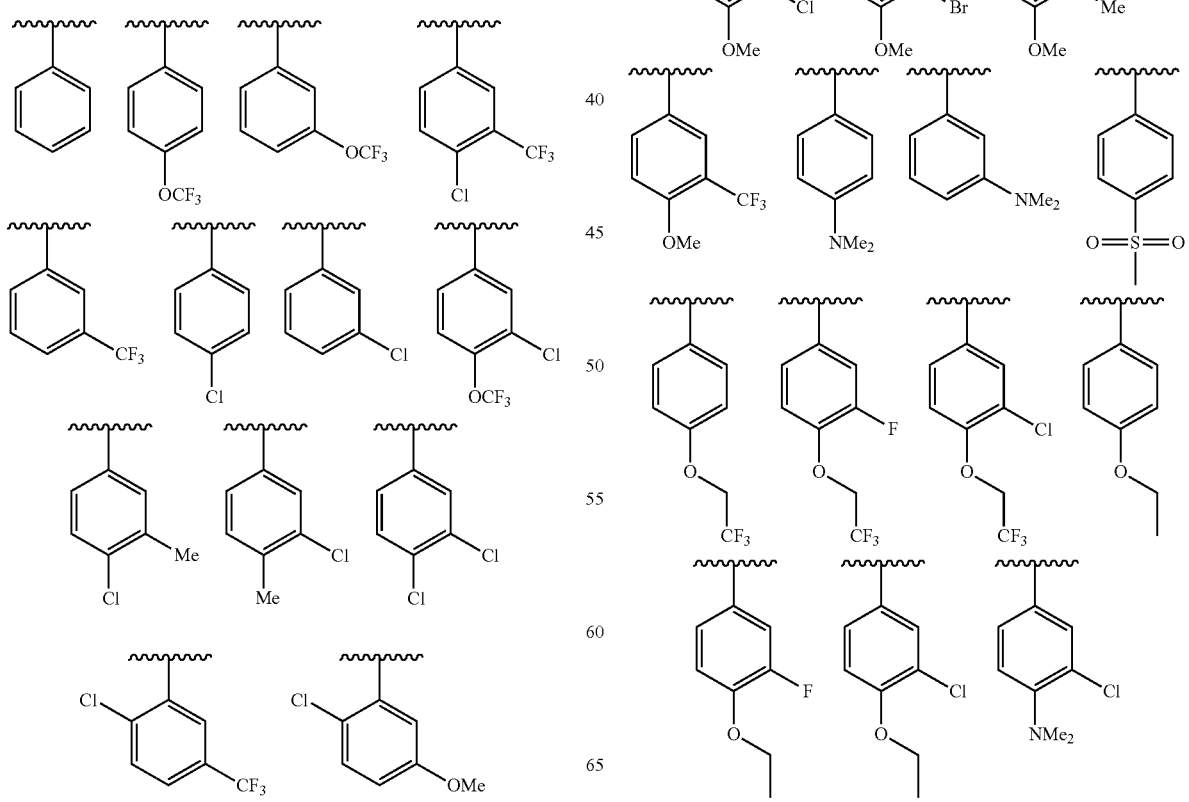
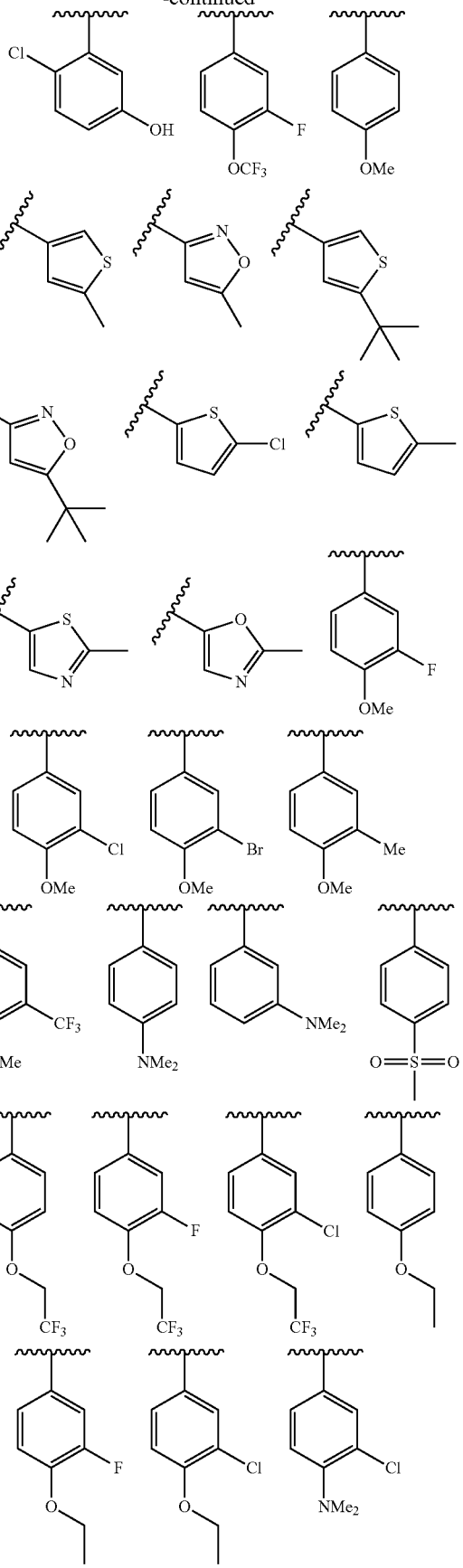

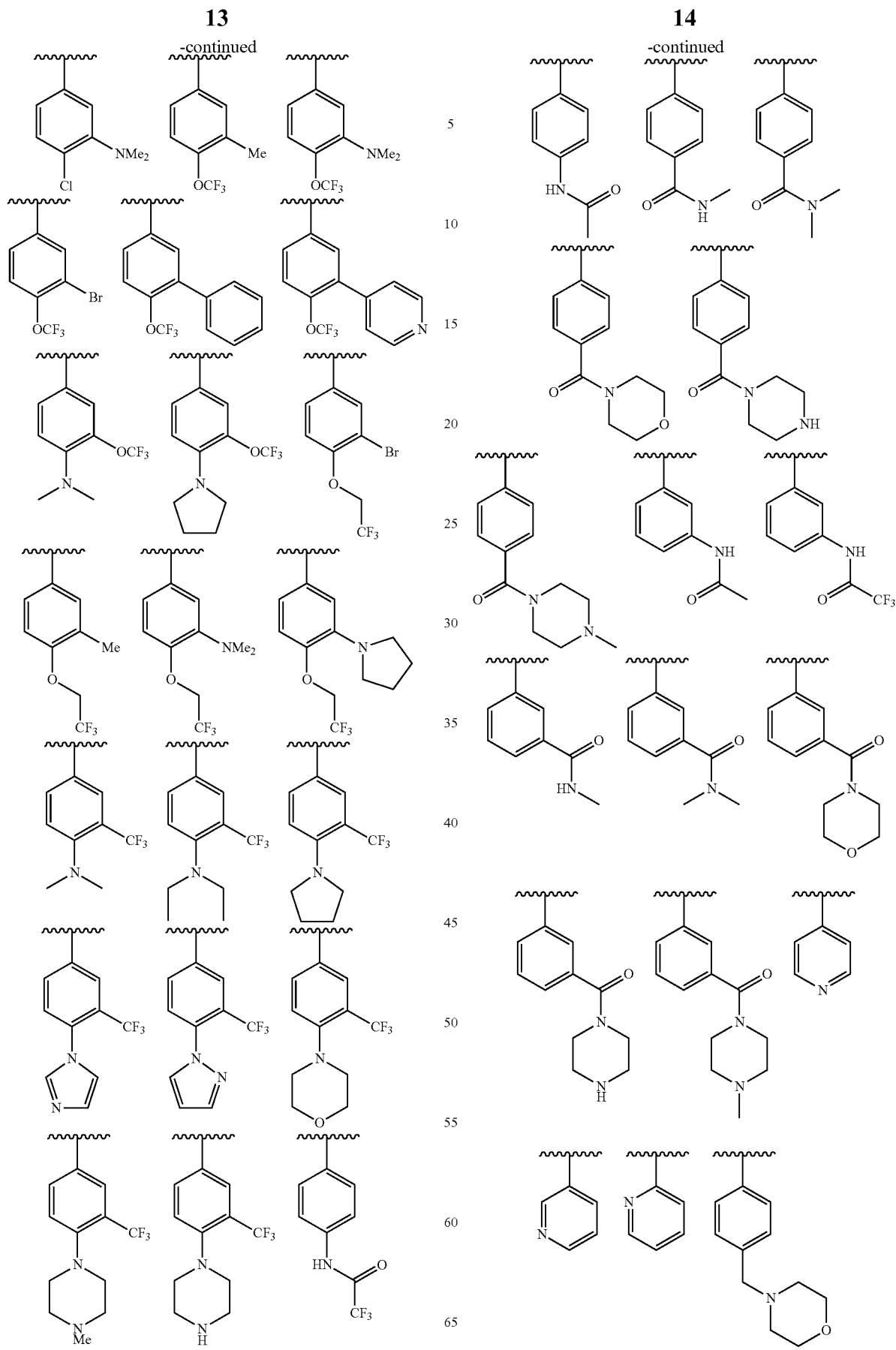

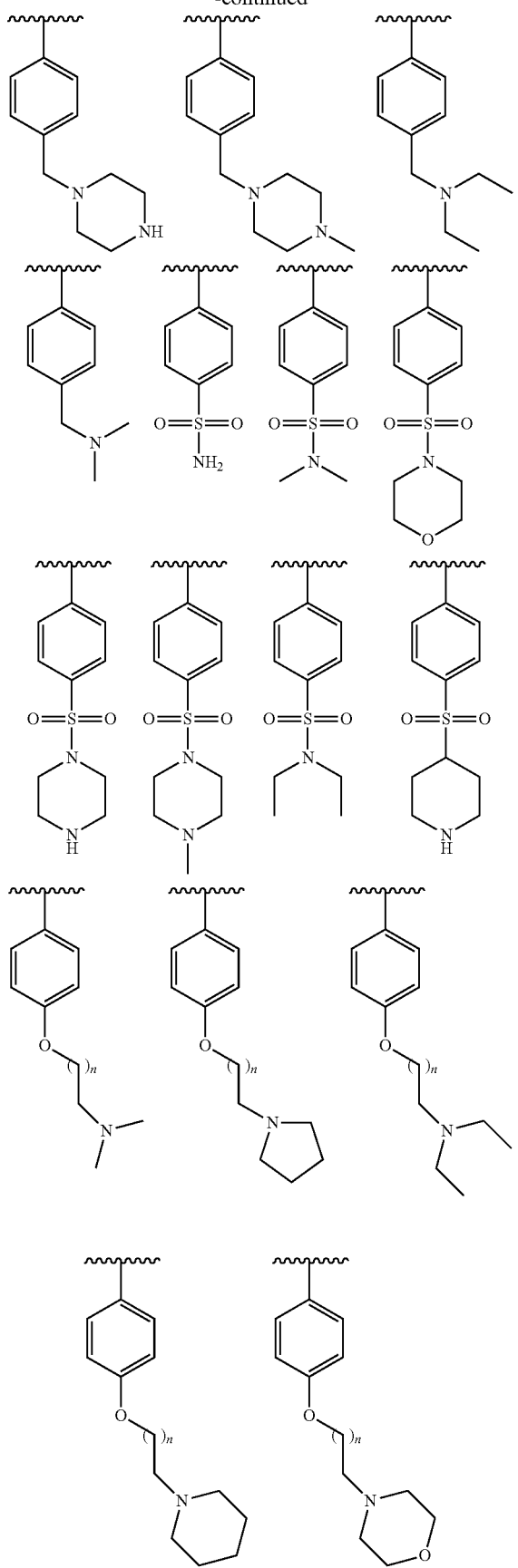
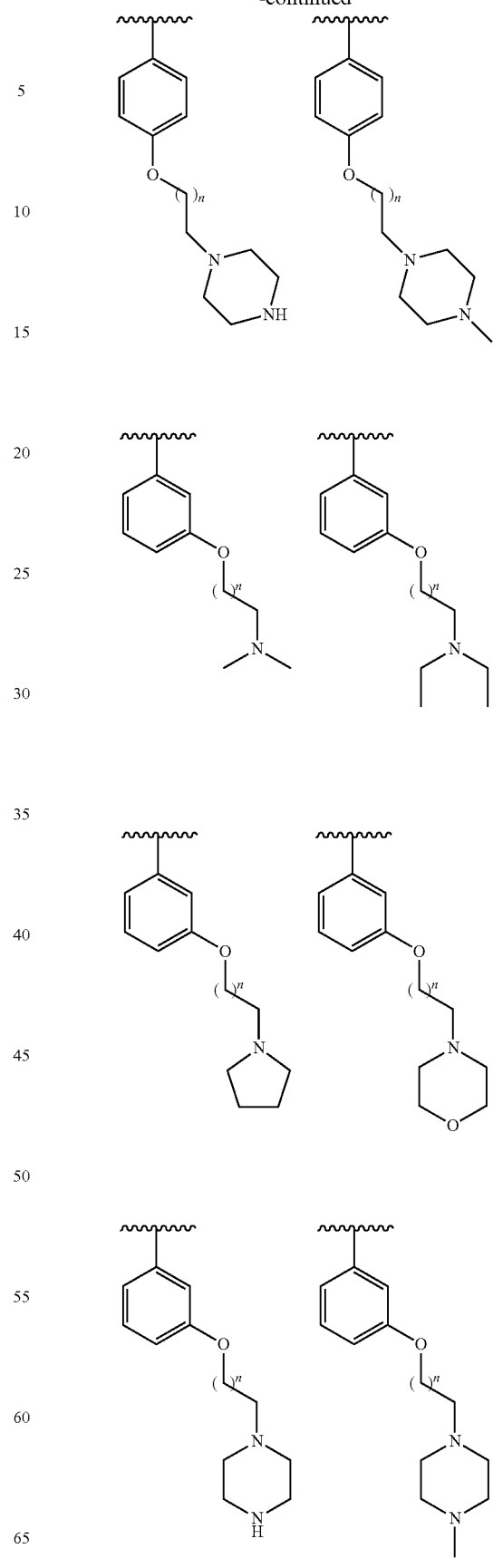

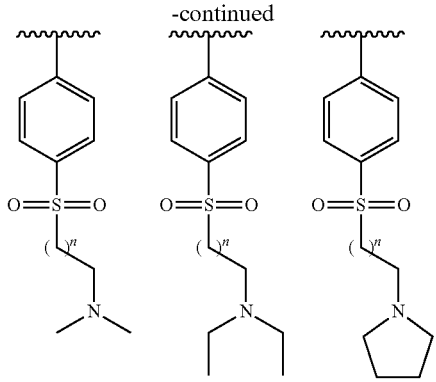
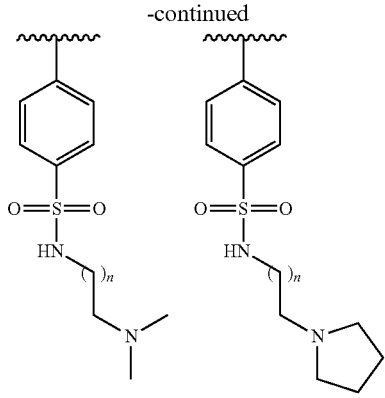
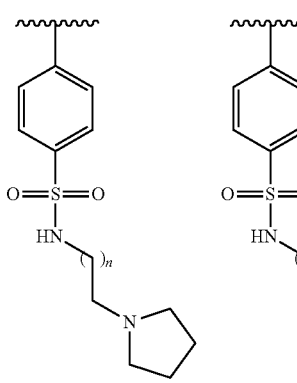
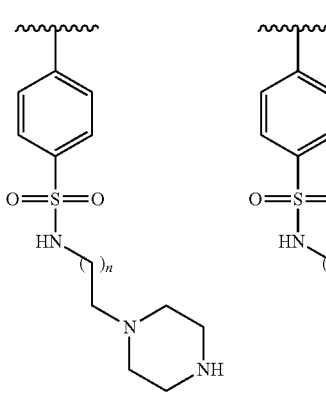
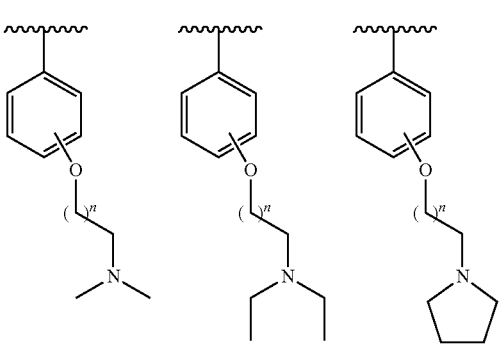

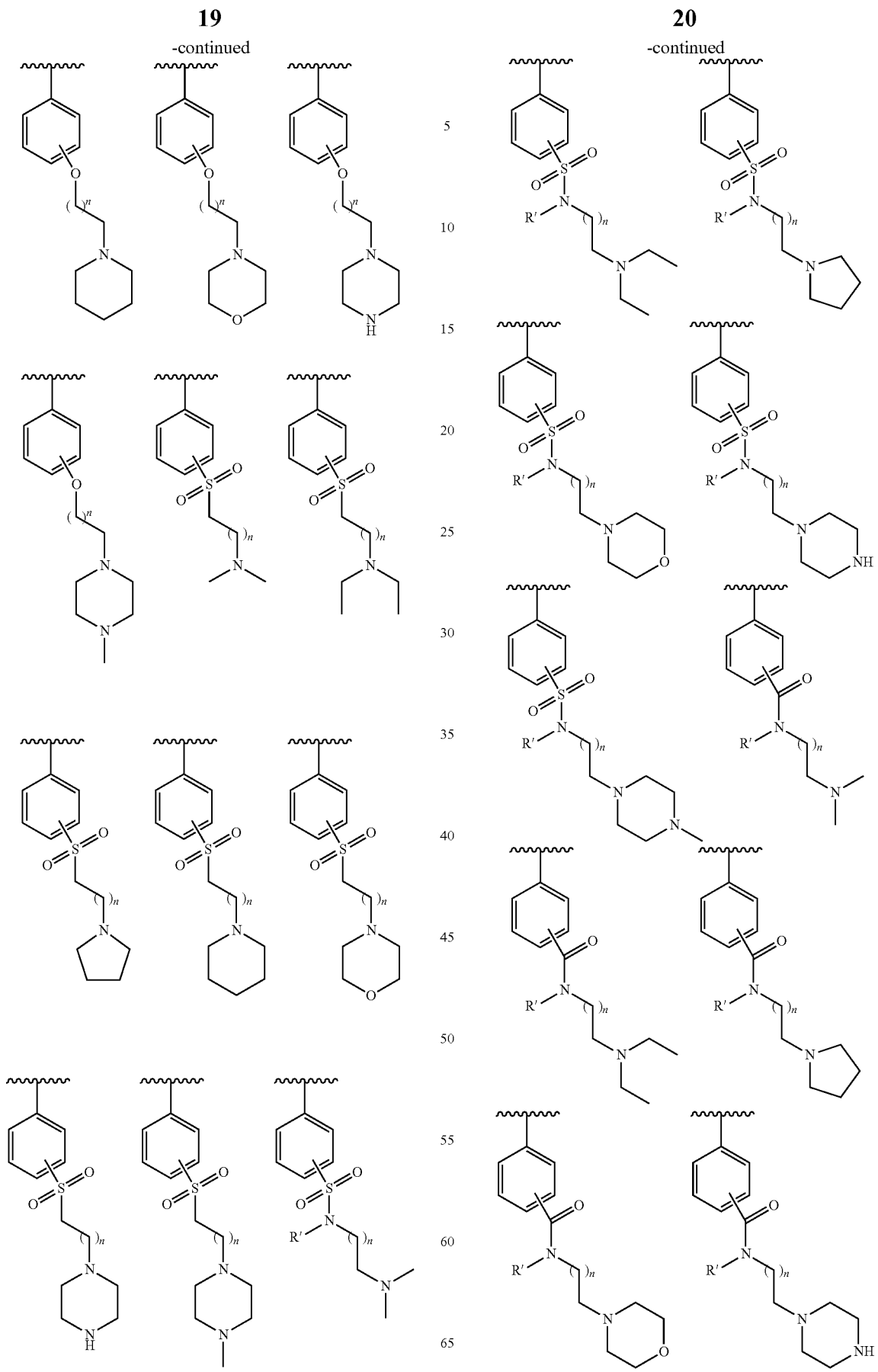

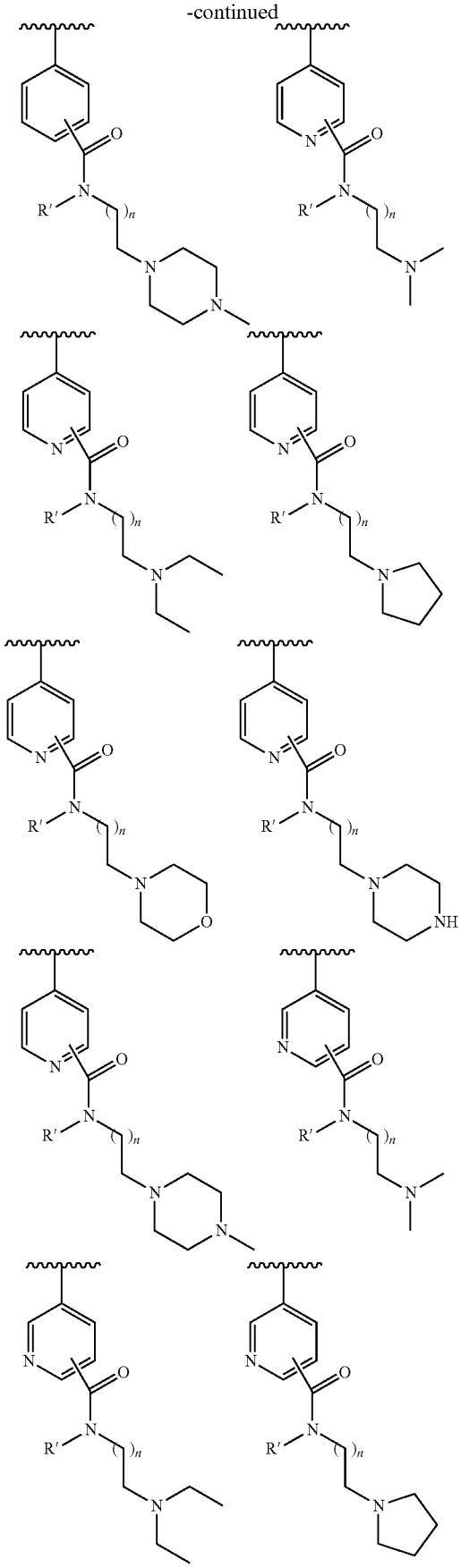

According to another embodiment of the invention, compounds that are derivatives of benzotriazine are provided, the compounds including a benzotriazine moiety having at least a first substituent attached to the benzene ring of benzotriazine and a second substituent attached to the triazine ring of the benzotriazine, where the first substituent includes a substituted pyridyl group, and the second substituent includes a secondary amino group, a substituted amide group, or a substituted sulfonylamino group.

According to yet another embodiment of the invention, compounds including a benzene-derived moiety bridged to a heterocyclic moiety are provided, where the benzene-derived moiety includes a molecule of benzene substituted with either a sulfonyl group or a pyridyl group connected to the benzene molecule via an oxygen link, and the heterocyclic moiety includes triazole, oxadiazole, oxazole, pyrazol, imidazole, thiadiazole and triazine.

According to yet another embodiment, articles of manufacture are provided, the articles including packaging material and a pharmaceutical composition contained within the packaging material, wherein the packaging material includes a label which indicates that the pharmaceutical composition can be used for treatment of disorders associated with cancer. The pharmaceutical composition can include at least one compound set forth in Structures (A) and (B) or any combination thereof.

According to another embodiment, a method for treating a disorder including administering to a subject in need thereof an effective amount of a compound, wherein the compound is set forth in Structures (A) and (B) or any combination thereof.

In one aspect, the disorder is cancer, eye disease, inflammation, psoriasis, or a viral infection, for example. More particularly, the cancer is an alimentary/gastrointestinal tract cancer, colon cancer, liver cancer, skin cancer, breast cancer, ovarian cancer, prostate cancer, lymphoma, leukemia, kidney cancer, lung cancer, muscle cancer, bone cancer, bladder cancer or brain cancer.

According to yet another embodiment, a pharmaceutical composition is provided, at least one compound set forth in structures (A) and (B) or any combination thereof, in a pharmaceutically acceptable carrier.

DETAILED DESCRIPTION OF THE INVENTION

Figure 1:
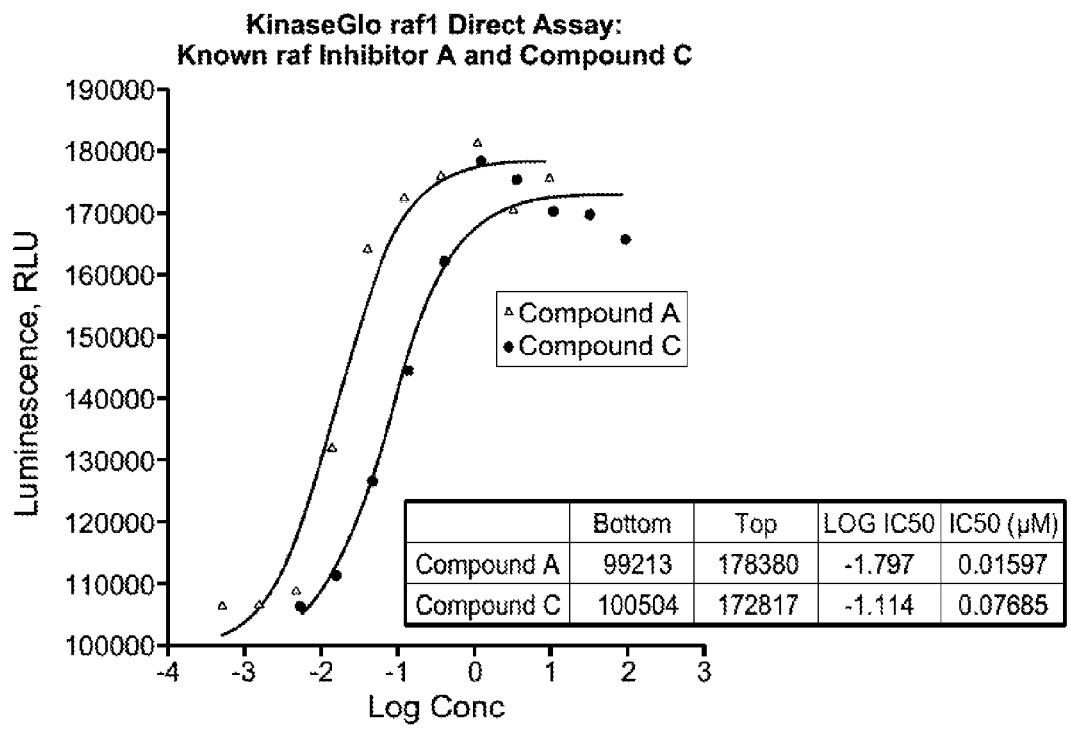
FIG. 1 shows the results of the Raf1 direct assay of invention compounds
Figure 2:
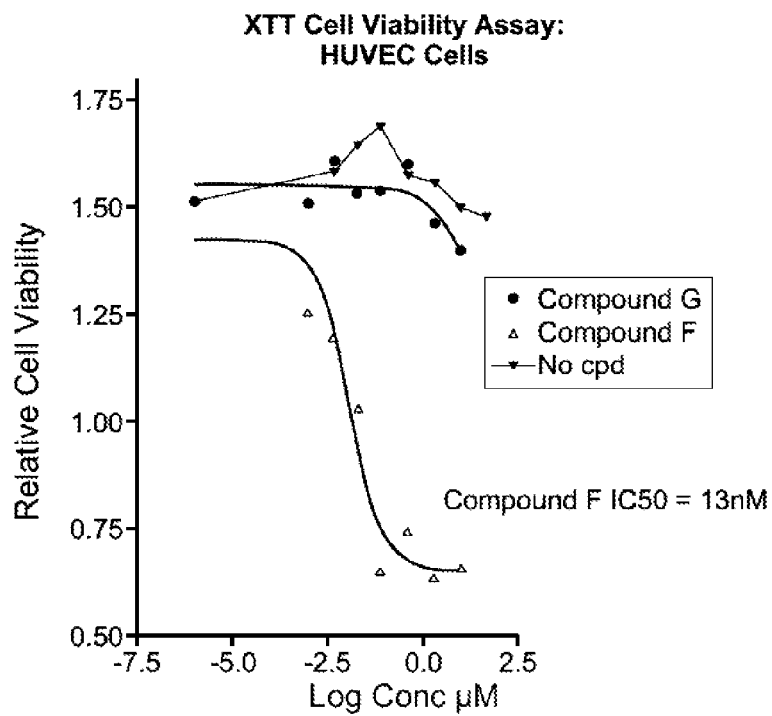
FIG. 2 shows the results of XTT cell viability assay of invention compounds

The present invention is directed to heterocyclic compounds, such as heterocyclic compounds derived from benzotriazine, triazines, triazoles, oxadiazoles, imidazoles and thiadiazole and to use of the heterocyclic compounds for therapeutic purposes.

The following terminology and definitions apply as used in the present application, generally in conformity with the terminology recommended by the International Union of Pure and Applied Chemistry (IUPAC).

The term "heterocyclic," when used to describe an aromatic ring, means that the aromatic ring contains at least one heteroatom. The abbreviation "Het" is sometimes used to signify a heterocyclic structure.

The term "heteroatom" is defined to include any atom other than carbon, for example, N, O, or S.

The term "aromatic" or "aryl" is defined to include a cyclically conjugated molecular entity with a stability, due to delocalization, significantly greater than that of a hypothetical localized structure, such as the Kekulé structure.

The term "heterocyclic," when not used to describe an aromatic ring, is defined to include cyclic (i.e., ring-containing) groups other than aromatic groups, the cyclic group being formed by between 3 and about 14 carbon atoms and at least one heteroatom described above.

The term "substituted heterocyclic" is defined to include both aromatic and non-aromatic structures to heterocyclic groups further bearing one or more substituents described above.

The term "alkyl" is defined to include a monovalent straight or branched chain hydrocarbon group having from one to about 12 carbon atoms, for example, methyl, ethyl, n-propyl, iso-propyl, n-butyl, iso-butyl, tert-butyl, n-pentyl (also known as n-amyl), n-hexyl, and the like. The abbreviations "Me" and "Et" stand for the methyl and ethyl groups, respectively.

The term "aralkyl" refers to an aryl or heteroaryl group, as defined herein, attached through a C1-C6 alkyl linker. Examples of "aralkyl" include, but are not limited to, benzyl, phenylpropyl, 2-pyridylmethyl, 3-isoxazolylmethyl, 2-imidazolylethyl.

The term "methoxy" is defined as the group —OCH$_3$.

The term "halogen" is defined to include an atom of fluorine, chlorine, bromine or iodine.

The term "carboxyl" or "carboxyl group" is defined as an acid moiety having the structure —COOH.

The term "amino" or "amino group" is defined to include moieties —NRR', where each of R and R' is hydrogen ("primary amino"), or one of them is an organic radical ("secondary amino"), or each is an organic radical ("tertiary amino").

The term "aminoalkyl" or "aminoalkyl group" is defined to include moieties —R—N(R'R"), wherein R is an organic radical and each of R' and R" is hydrogen or an organic radical. If at least one of R' and R" is an organic radical, the moiety is defined as "alkylaminoalkyl" or "alkylaminoalkyl group."

The term "sulfonyl" or "sulfonyl group" is defined to include moieties that comprise structure (S), in which R is an organic radical:

(S)

The term "sulfonylamino" or "sulfonylamino group" is defined to include moieties that comprise structure (SA), in which R is an organic radical:

(Sa)

The term "amide," or "amido," or "amide group," or "amido group" is defined to include moieties containing at least one acyl group >C=O attached to nitrogen. The term "substituted amide" is defined to include moieties containing a structure RNH—CO—, in which R is an organic radical.

The term "phenyl" is defined to include moieties having structure (Ph):

(Ph)

The term "toluoyl" is defined to include moieties having structure (Tl):

(Tl)

The term "heteroaryl" is defined to include aromatic rings, where the ring structure is formed by between 3 and about 14 carbon atoms and by at least one heteroatom described above, and the term "substituted heteroaryl" refers to heteroaryl groups further bearing one or more substituents described above.

The term "triazine" is defined to include moieties containing the aromatic 6-member heterocycle having three atoms of nitrogen in the ring. Two examples of such heterocycle are shown as the following structures (Tr):

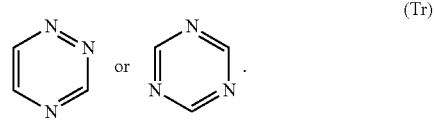 [SMILES: c1cnncn1 ; c1ncncn1]

(Tr)

The term "benzotriazine" is defined to include moieties containing a heterocyclic structure in which the triazine ring is fused with the benzene ring, as shown by structure (BTr):

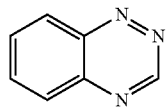

(BTr)

The terms "N-oxide," "N,N'-dioxide," and "N,N',N''-trioxide" are defined to include nitrogen-containing heterocyclic moieties in which at least one nitrogen atom is associated with oxygen to form the structures N→O. The heterocyclic moiety can be any nitrogen-containing heterocycle, for example, benzotriazine, triazine, pyridine, pyrimidine, etc. Where the heterocyclic structure is benzotriazine, for example, some N-oxides or dioxides can be described as the following structures:

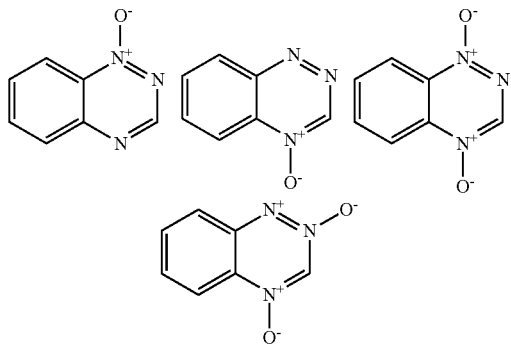

The term "pteridine" is defined to include moieties containing a heterocyclic structure having two fused 6-member rings, each ring containing two atoms of nitrogen, as shown by structure (PTr):

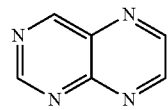

(PTr)

The term "pyridazine" is defined to include moieties containing the aromatic 6-member heterocycle having two atoms of nitrogen in the ring in ortho position, as shown by the structure (PAz):

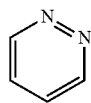

(PAz)

The term "pyrimidine" is defined to include moieties containing the aromatic 6-member heterocycle having two atoms of nitrogen in the ring in meta position, as shown by the structure (PRm):

(PRm)

The term "thiadiazole" is defined to include moieties containing the aromatic 5-member thiophene-based heterocycle, having two atoms of nitrogen and one atom of sulfur, as shown by the structure (TDa):

(TDa)

The term "pyridyl" is defined to include moieties containing a radical derived from pyridine. One structure of pyridyl is shown as the structure (Py):

(Py)

The term "alkyl pyrrolidine" is defined to include moieties containing a radical derived from pyrrolidine (a 5-member saturated heterocycle having one nitrogen atom), where an alkylene group R is attached to the nitrogen atom of the pyrrolidine ring. One structure of alkyl pyrrolidine is shown as the structure (APy):

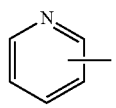

(APy)

The term "alkyl morpholine" is defined to include moieties containing a radical derived from morholine, (a 6-member saturated heterocycle having one nitrogen atom and one oxygen atom), where an alkylene group R is attached to the nitrogen atom of the morpholine ring. One structure of alkyl morpholine is shown as the structure (AMr):

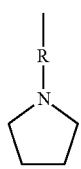

(AMr)

The term "alkyl piperazine" is defined to include moieties containing a radical derived from piperazine (a 6-member saturated heterocycle having two nitrogen atoms), where an alkylene group R is attached to one nitrogen atom of the piperazine ring. One structure of alkyl piperazine is shown as the structure (APi):

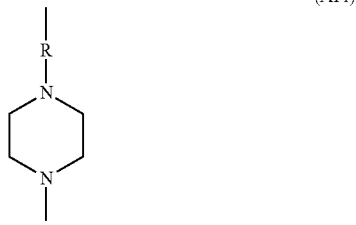

(APi)

The term "isoxazole" is defined to include moieties containing the aromatic 5-member heterocycle, having one atoms of nitrogen and one atom of oxygen, as shown by the structure (ISo):

(Iso)

The term "hydrophobic" is defined as a group or structure free of strongly polar groups such as —OH, —COOH, —NH$_2$, —NH—CO—, halogens, or the like.

The term "kinase" is defined to include any enzyme that catalyzes the addition of phosphate groups to a protein residue; for example, serine and threonine kinases catalyze the addition of phosphate groups to serine and threonine residues.

The term "therapeutically effective amount" is defined as the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

The term "pharmaceutically acceptable" is defined as a carrier, whether diluent or excipient, that is compatible with the other ingredients of the formulation and not deleterious to the recipient thereof.

The terms "administration of a compound" or "administering a compound" is defined to include an act of providing a compound of the invention or pharmaceutical composition to the subject in need of treatment.

According to embodiments of the present invention, two types of heterocyclic compounds are provided for treatment of various diseases, disorders, and pathologies, including cancer. The heterocyclic compounds of the invention can inhibit the activity of a kinase, such as any kinase in the MAPK signaling pathway.

According to an embodiment of the invention, a first type of compounds is provided for treatment of various diseases, disorders, and pathologies, including cancer. The first type of compounds can include derivatives of benzotriazine. The derivatives of benzotriazine that can be used can comprise the compounds that include a benzotriazine moiety having at least one substituent attached to the benzene ring of benzotriazine and a at least one substituent attached to the triazine ring of the benzotriazine, and an N-oxide, N,N'-dioxide, N,N', N"-trioxide, or pharmaceutically acceptable salts thereof.

A substituent attached to the benzene ring of benzotriazine can include a substituted pyridyl group. The substituents in the substituted pyridyl group can include an amido moiety, an aminoalkyl group (e.g., aminomethyl), or a carboxyl group, or a carboxylate group. The amido moiety attached to the pyridyl group can be in turn also substituted by attaching to the nitrogen in the amido moiety a substituent selected from an alkyl (e.g., methyl), an alkylaminoalkyl (e.g., diethylamino alkyl), a pyridyl, an alkyl pyrrolidine, an alkyl morpholine, and an alkyl piperazine groups.

Optionally, the benzene ring of the compounds of the first type can contain a second substituent located in any available position of the ring, for example, methyl, halogen or methoxy. Some particular examples of benzene-ring containing moieties that can be used include tert-butyl phenyl, trifluoromethoxyphenyl, methoxyphenyl, dimethylamino, dimethylaminophenyl, aminophenyl, trifluoroethoxyphenyl, trifluoromethoxychlorophenyl, trifluoromethoxybromophenyl, trifluoroethoxychlorophenyl, chlorophenyl, dichlorophenyl, trifluoromethyl phenyl, trifluoromethylchloro phenyl, chlorotoluyl, N-phenylacetamide, N,N-alkylbenzamide, isopropoxyphenyl, alkoxyphenyl, dialkoxyphenyl, acetylphenyl.

A substituent attached to the triazine ring of benzotriazine in the compounds of the first type can include a secondary amino group, a substituted amide group, or a substituted sulfonylamino group; each of these groups can further contain a moiety derived from benzene, thiophene, or isoxazole. If the substituent attached to the triazine ring of benzotriazine in the compounds of the first type is a secondary amino group, the moiety derived from benzene, thiophene, or isoxazole can be attached to the nitrogen of the secondary amino group. If the substituent in the triazine ring is a substituted amide group or the substituted sulfonylamino group, the moiety derived from benzene, thiophene, or isoxazole can be attached via the acyl group or the sulfonyl group, respectively. Moieties derived from benzene, thiophene, or isoxazole can further include alkyls, e.g., t-butyl phenyl, chlorophenyl, dichlorophenyl, trifluoromethyl phenyl, trifluoromethylchloro phenyl; and chlorotoluyl.

Compounds of the first type can be described as compounds having the general structure (A), and an N-oxide, N,N'-dioxide, N,N',N"-trioxide, or a pharmaceutically acceptable salt thereof. The general structure (A) is as follows:

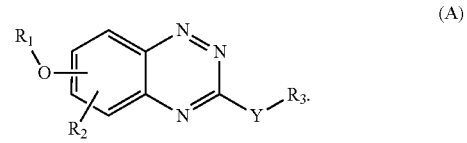

(A)

wherein Y can be absent or can be one of the following moieties:

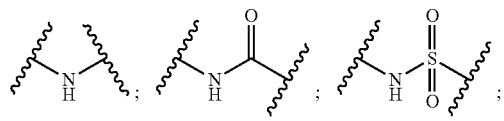

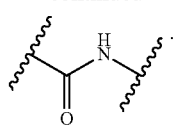

In structure (A), $R_1$ can be an aryl, a substituted aryl, a heterocycle, a heteroaryl, a substituted heterocycle, and a substituted heteroaryl, such as $C_6$-$C_{12}$ aryl; $C_3$-$C_{12}$ heteroaryl having 1-3 heteroatoms such as N, S and O; substituted $C_3$-$C_{10}$ cycloalkyl having 0-3 heteroatoms such as N, S, and O; substituted $C_6$-$C_{12}$ aryl; substituted $C_3$-$C_{12}$ heteroaryl having 1-3 heteroatoms such as N, S and O; $C_7$-$C_{24}$ aralkyl; $C_7$-$C_{24}$ alkylaryl; substituted $C_7$-$C_{24}$ aralkyl; and substituted $C_7$-$C_{24}$ alkaryl. In particular, $R_1$ can be any one of the following moieties:

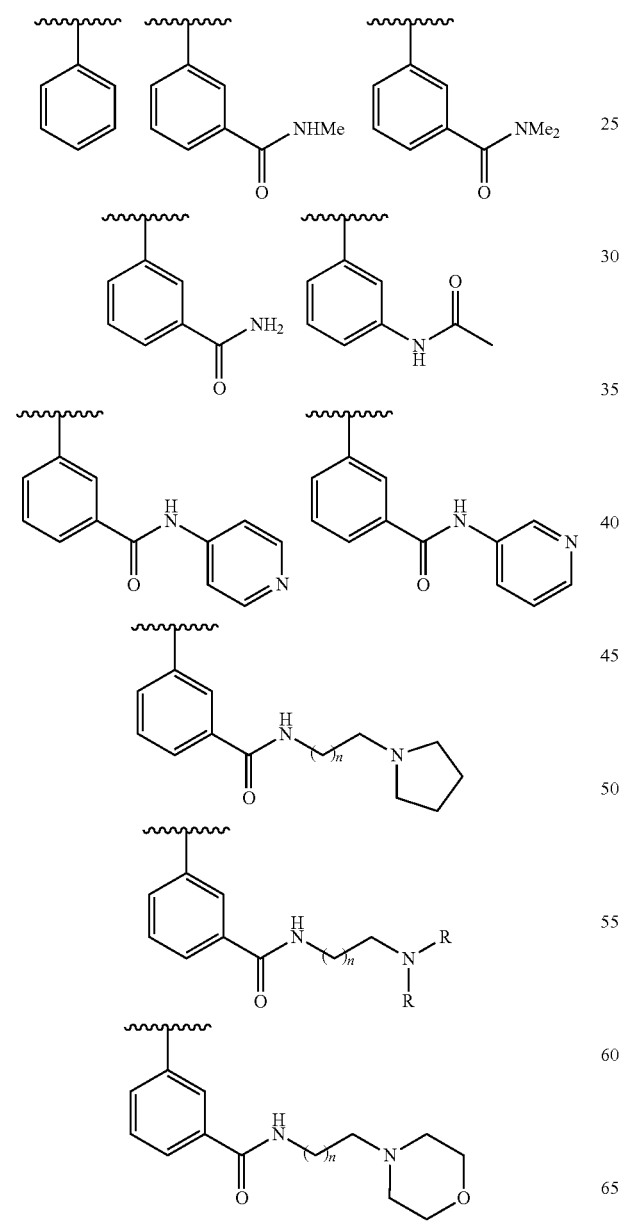

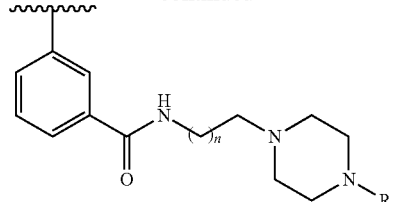
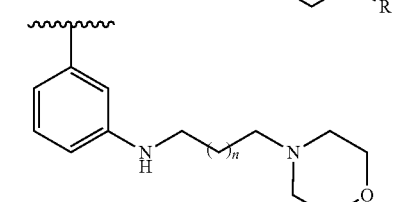
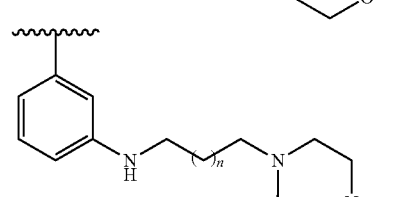
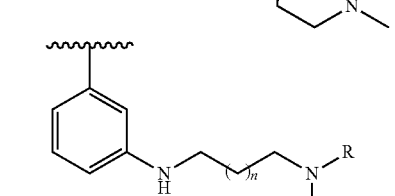
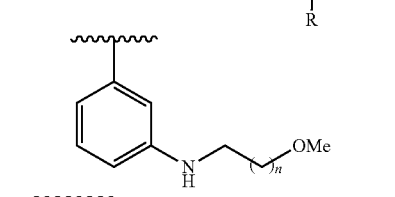
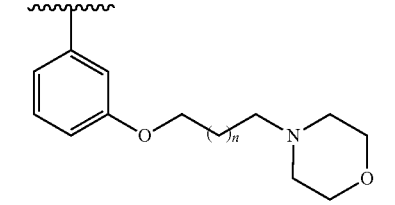
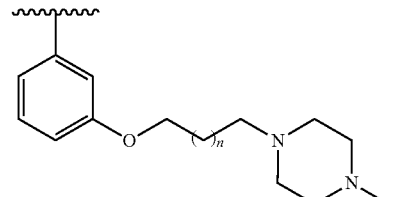
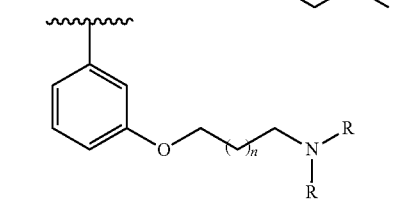
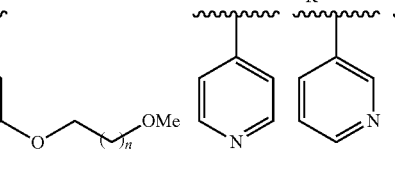

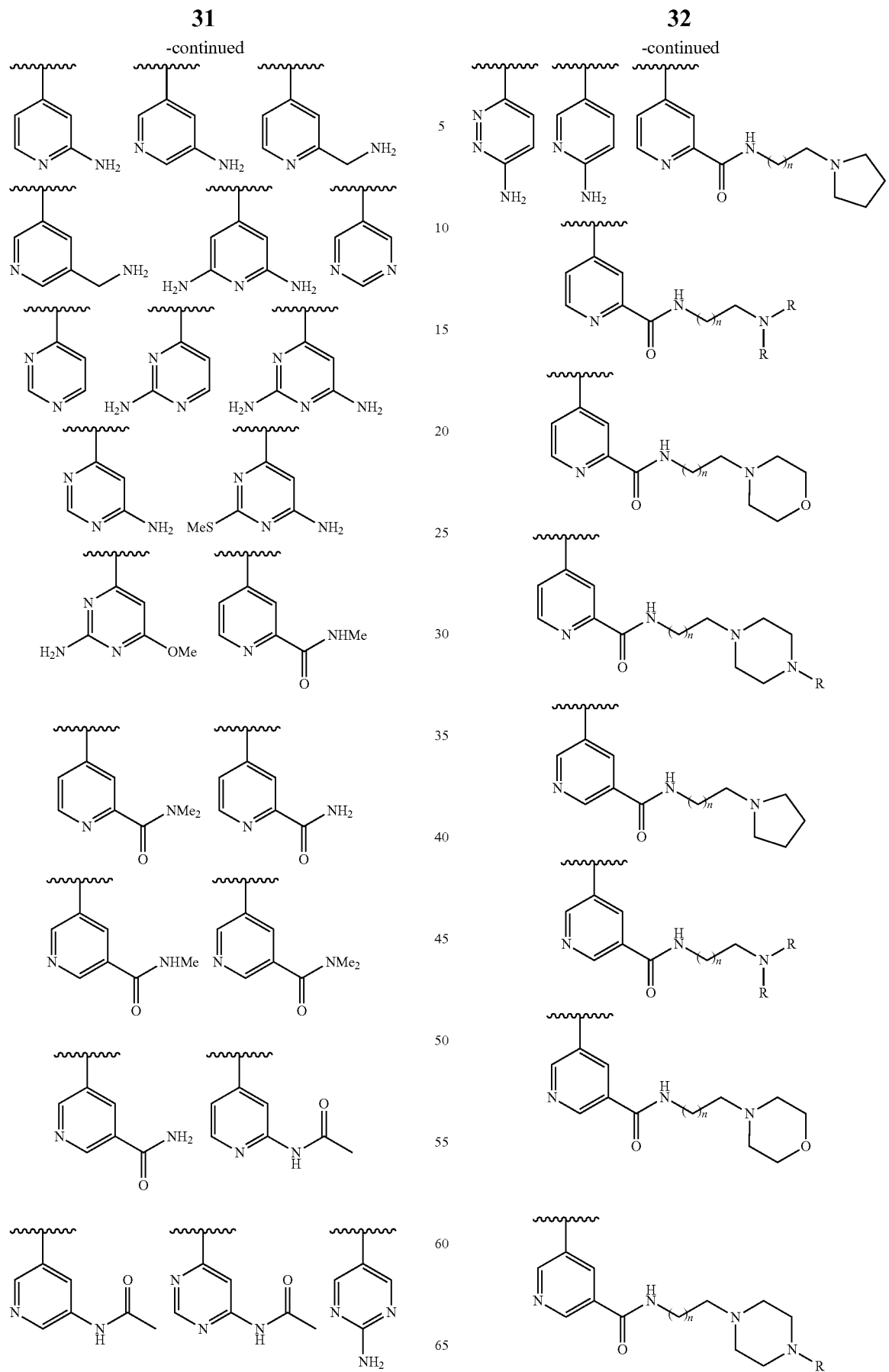

-continued
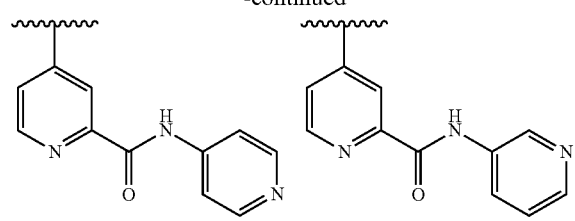
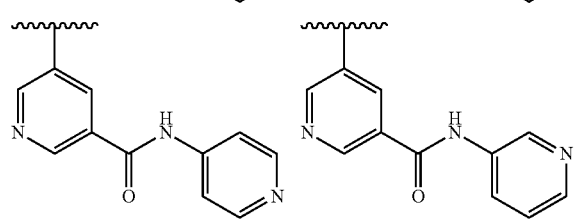
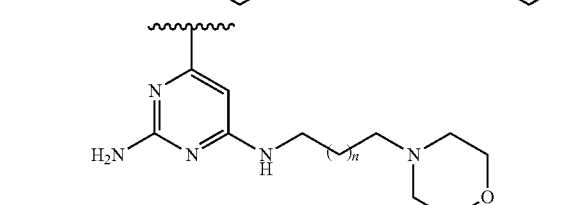
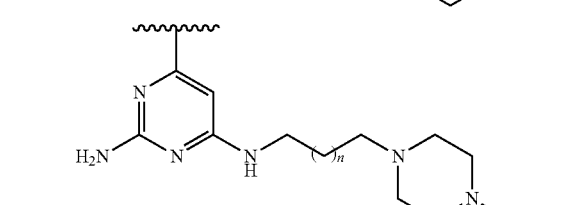
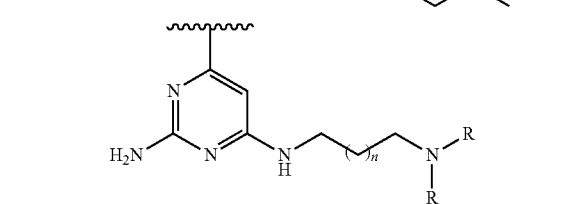
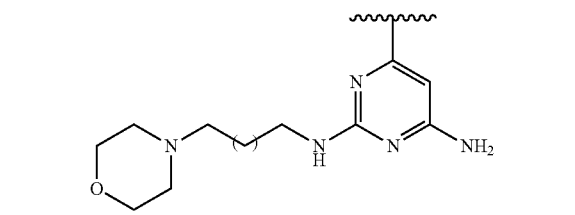
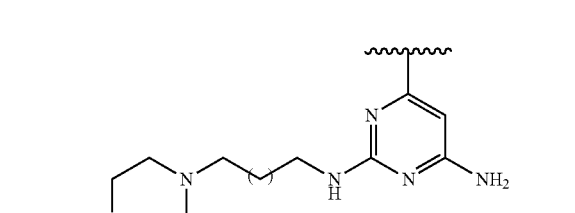
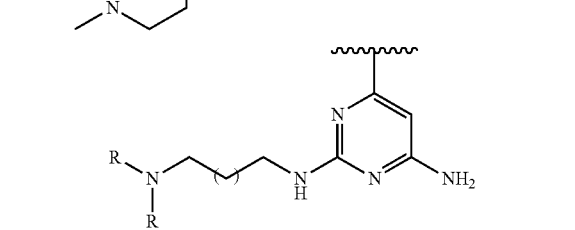
-continued
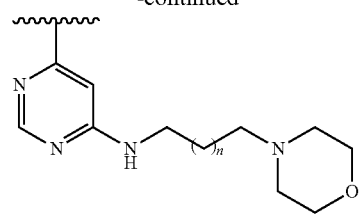
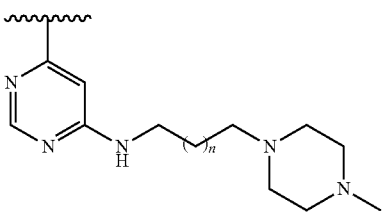
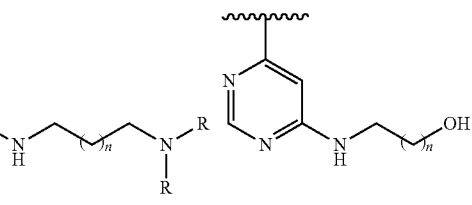
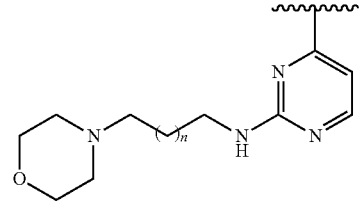
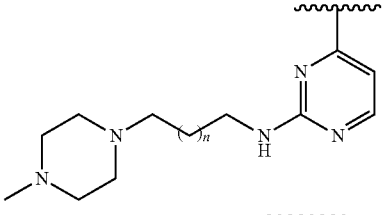
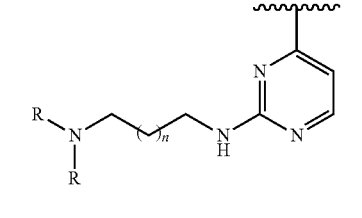
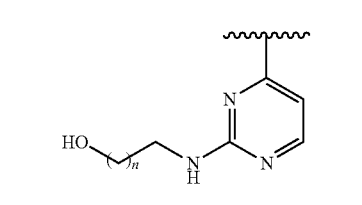
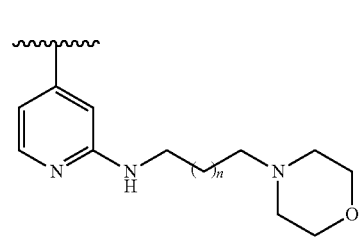

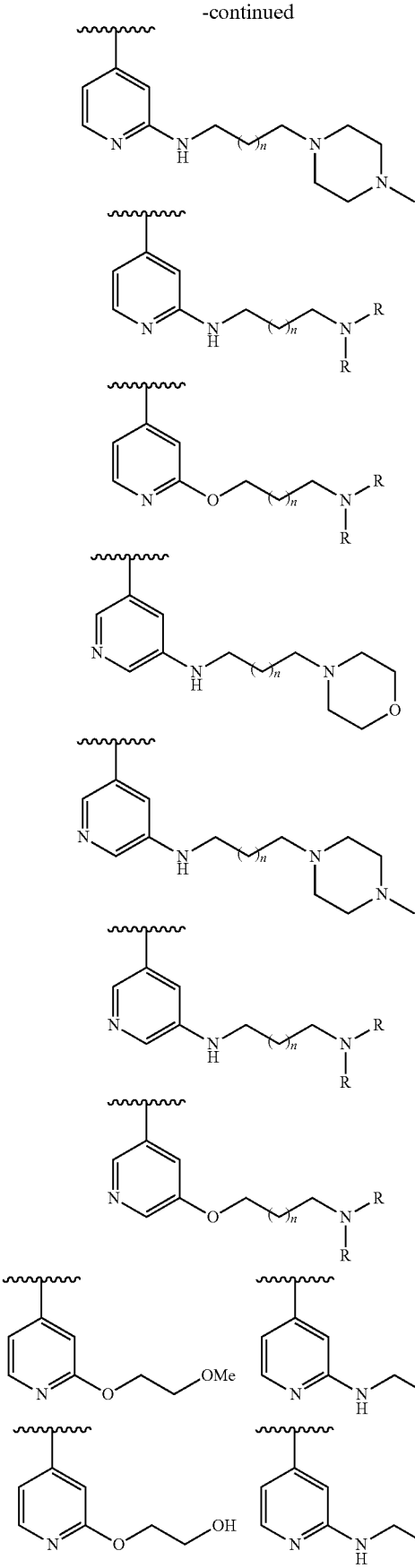
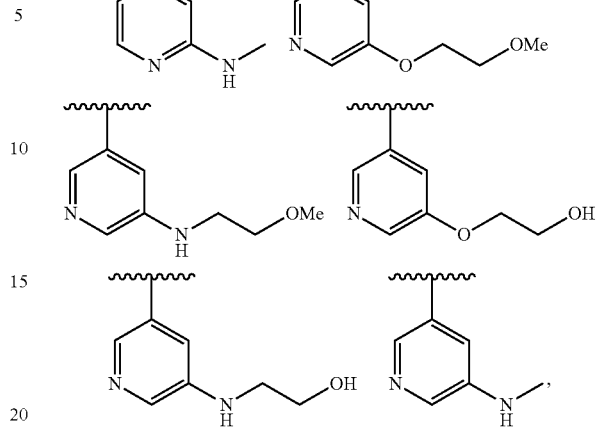

where n can be an integer selected from a group consisting of 0, 1, 2, and 3.

In structure (A), the substituent $R_2$ can be any one of hydrogen, halogen, $C_1$-$C_{18}$ alkyl (e.g., methyl), —OH, —$NO_2$, —CN, $C_1$-$C_{18}$ alkoxy (e.g., methoxy), —$NHSO_2R^5$, —$SO_2NHR^5$, —$NHCOR^5$, —$NH_2$, —$NR^5R^6$, —$S(O)R^5$, —$S(O)_2R^5$, —$CO_2R^5$, —$CONR^5R^6$, and where $R^5$ and $R^6$ are independently selected from hydrogen, a $C_1$-$C_{12}$ alkyl and a substituted $C_1$-$C_{12}$ alkyl.

In structure (A), group $R_3$ can be an aryl, a substituted aryl, a heterocycle, a heteroaryl, a substituted heterocycle, and a substituted heteroaryl. For example, $R_3$ can be one of $C_6$-$C_{12}$ aryl; $C_3$-$C_{12}$ heteroaryl having 1-3 heteroatoms such as N, S and O; substituted $C_3$-$C_{10}$ cycloalkyl having 0-3 heteroatoms such as N, S, and O; substituted $C_6$-$C_{12}$, aryl; substituted $C_3$-$C_{12}$ heteroaryl having 1-3 heteroatoms such as N, S and O; $C_7$-$C_{24}$ aralkyl; $C_7$-$C_{24}$ alkylaryl; substituted $C_7$-$C_{24}$ aralkyl; and substituted $C_7$-$C_{24}$ alkaryl. In particular, the substitutent $R_3$ can be one of the following:

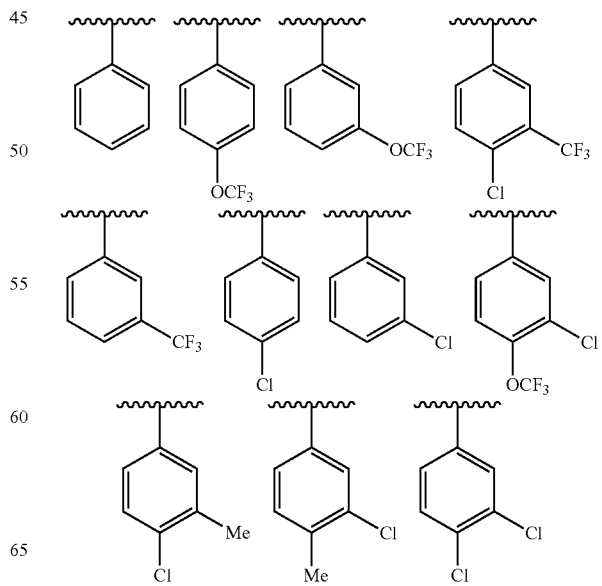

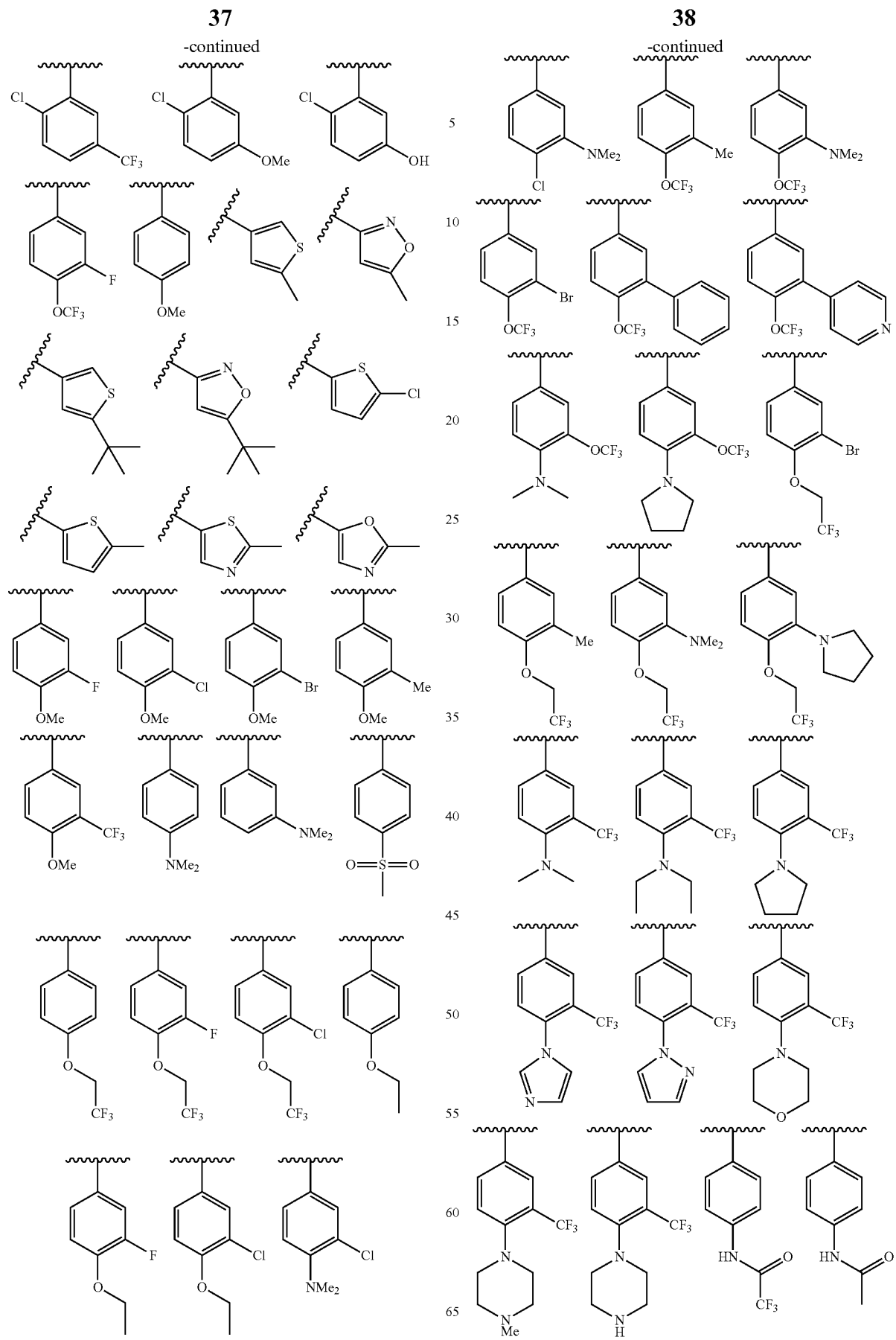

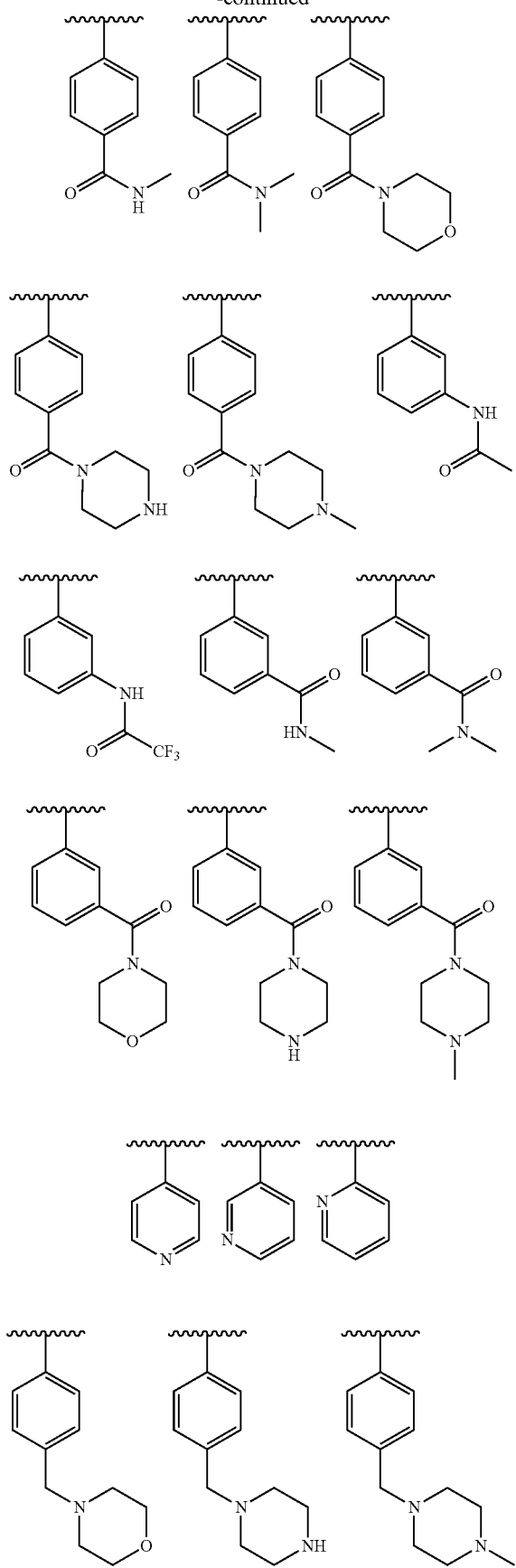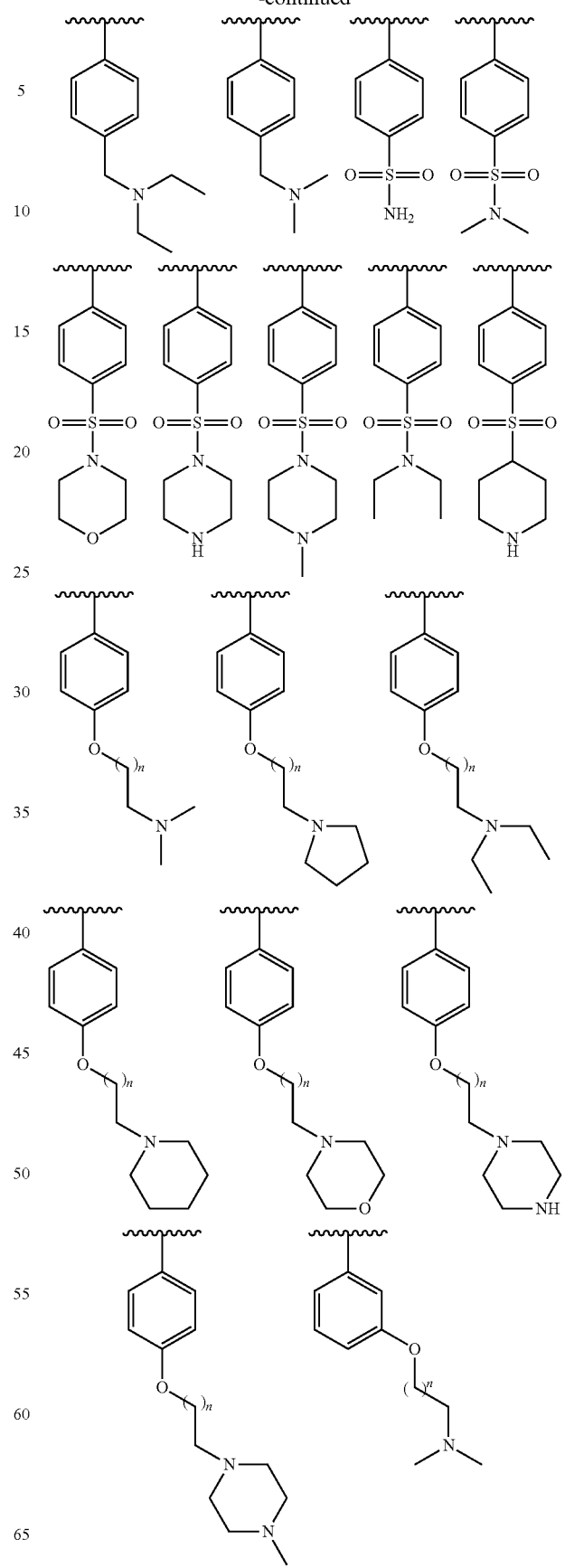

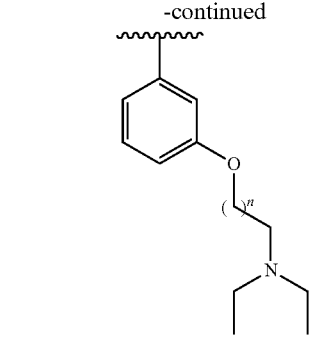
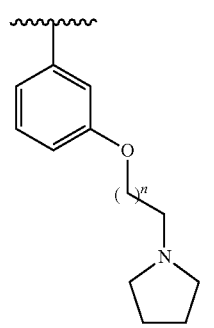
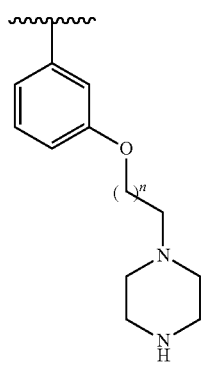
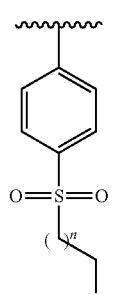
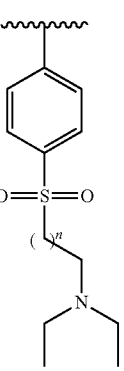
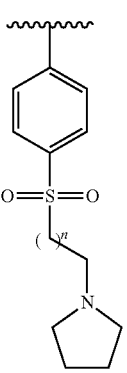
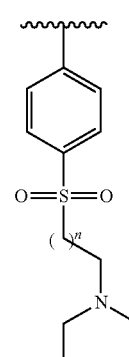
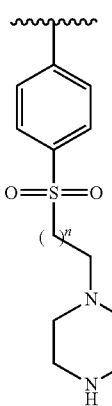
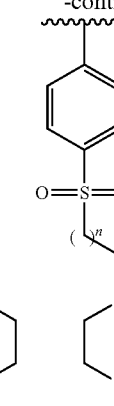
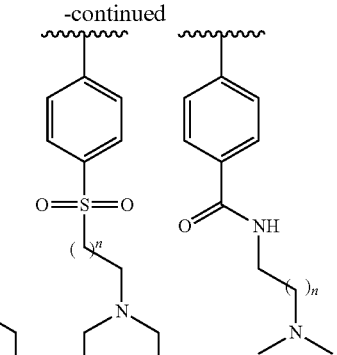
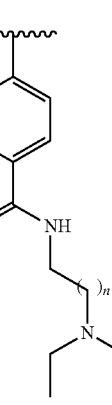
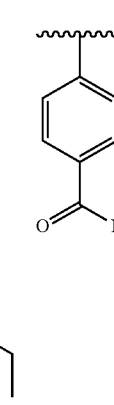
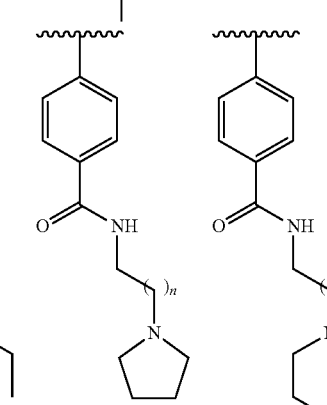
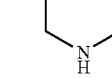
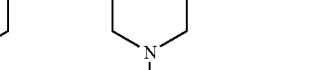
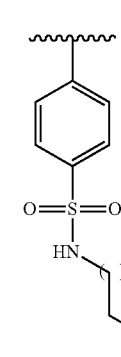
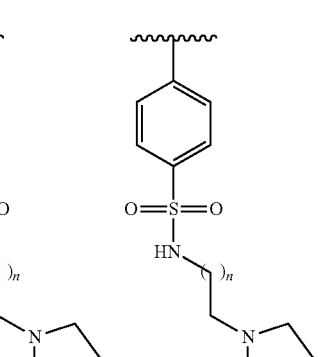

-continued
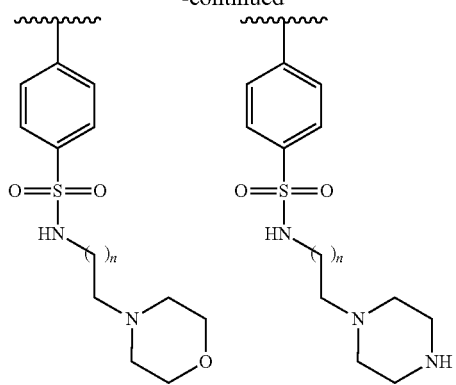
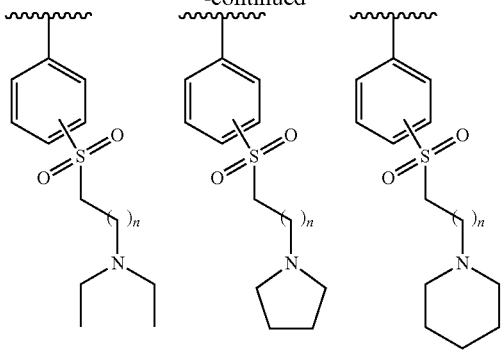
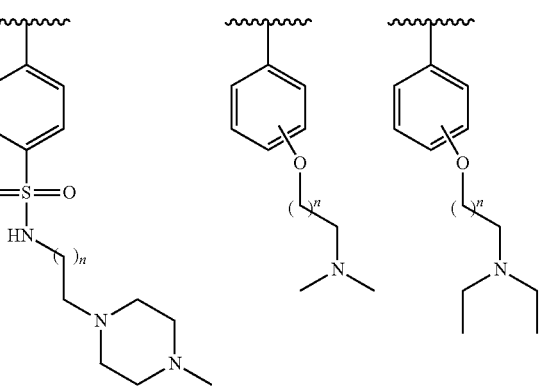
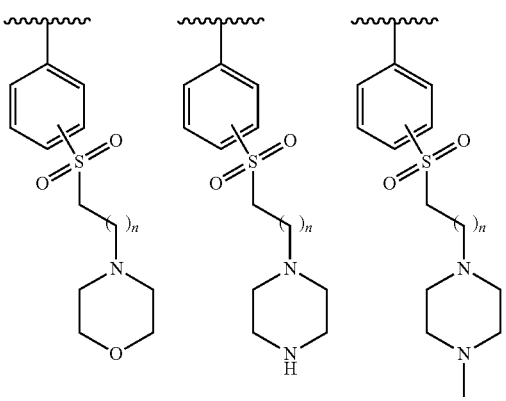
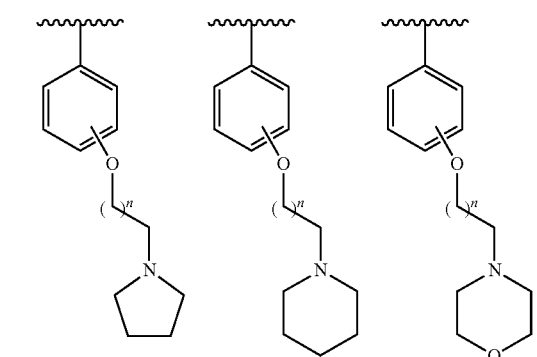
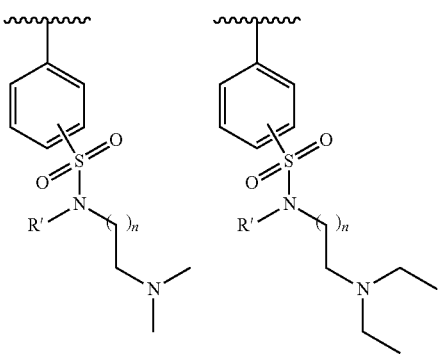
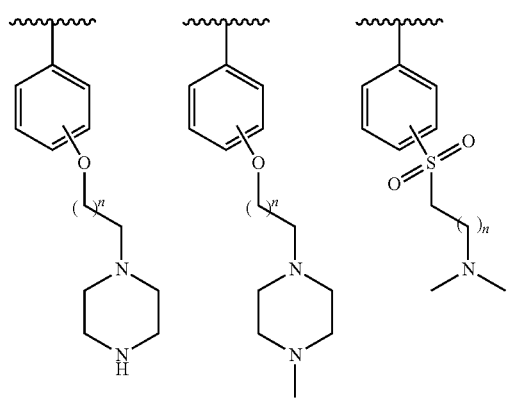
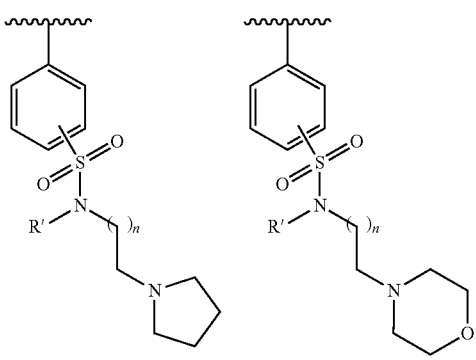

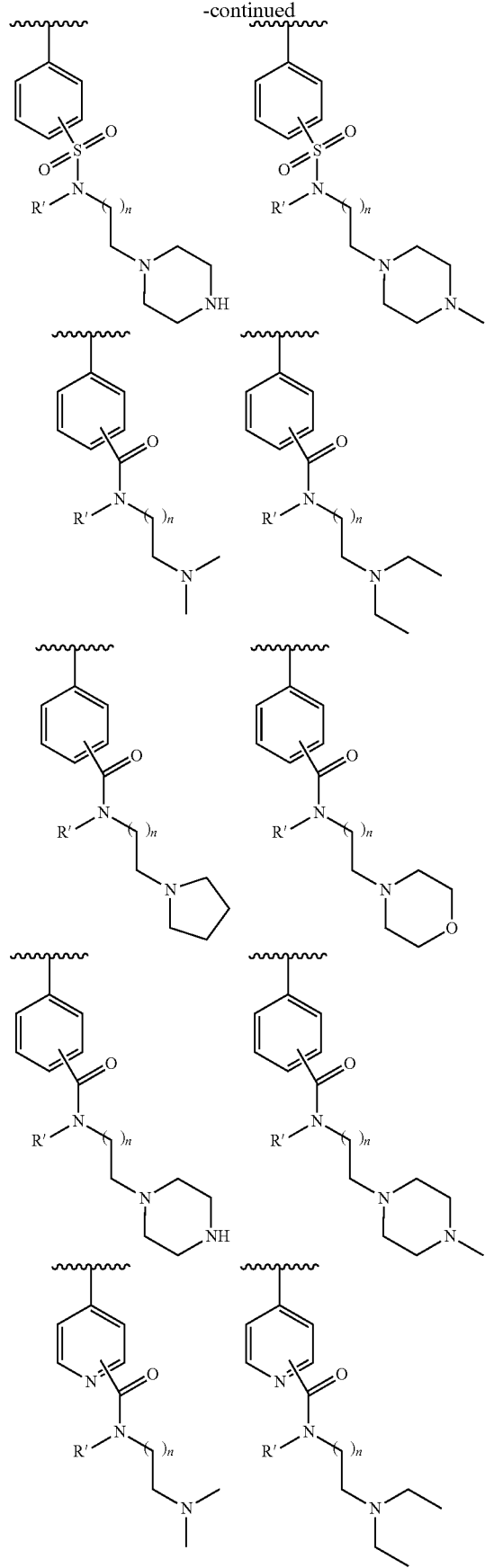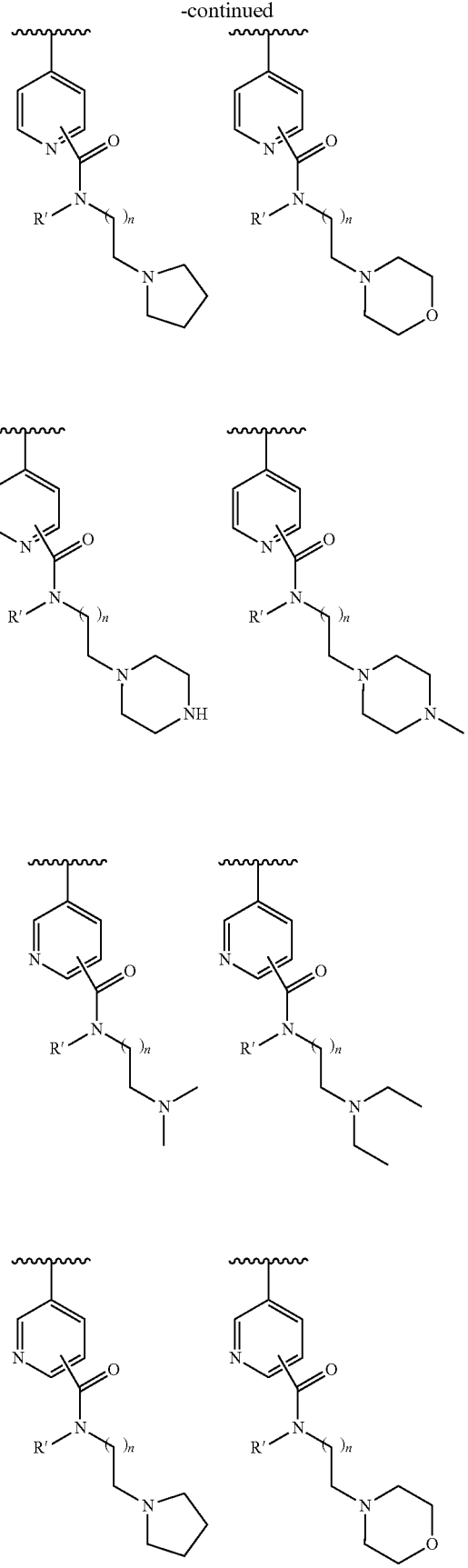

-continued

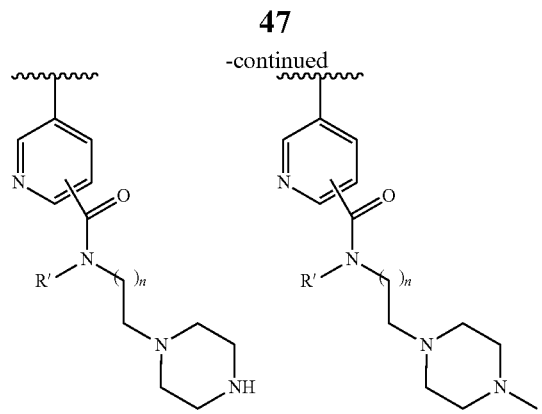

Some general examples of compounds described by the general structure (A) include a compound having the general structure (I), a compound having the general structure (II), a compound having the general structure (III) or a compound having the general structure (IV):

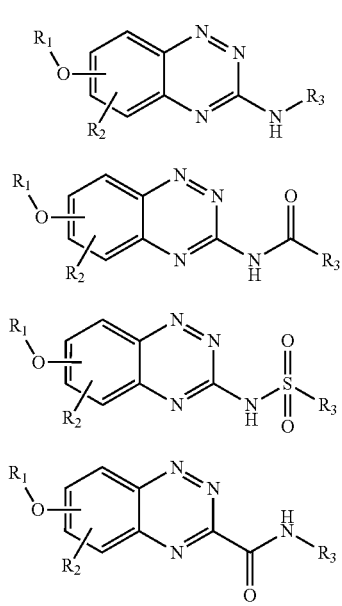

Some non-limiting examples of particular compounds described by the general structure (A) that can be used include compounds having formulae (1)-(33):

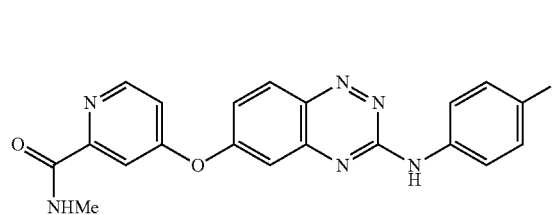

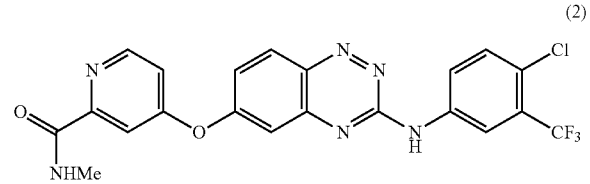

-continued

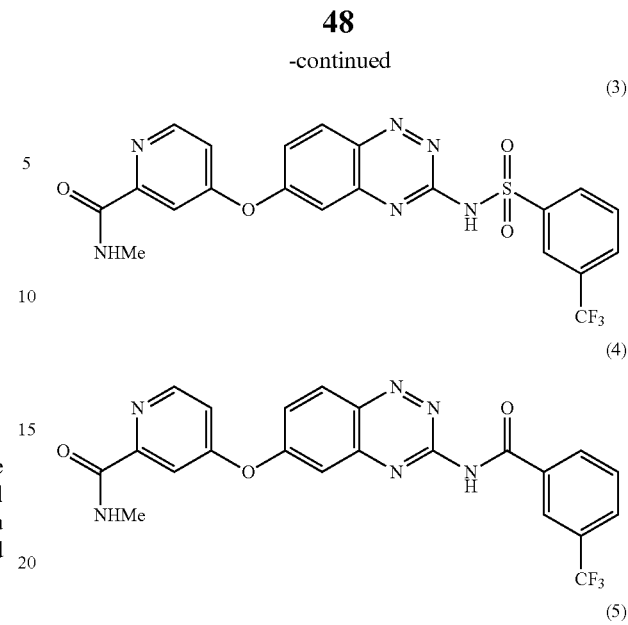

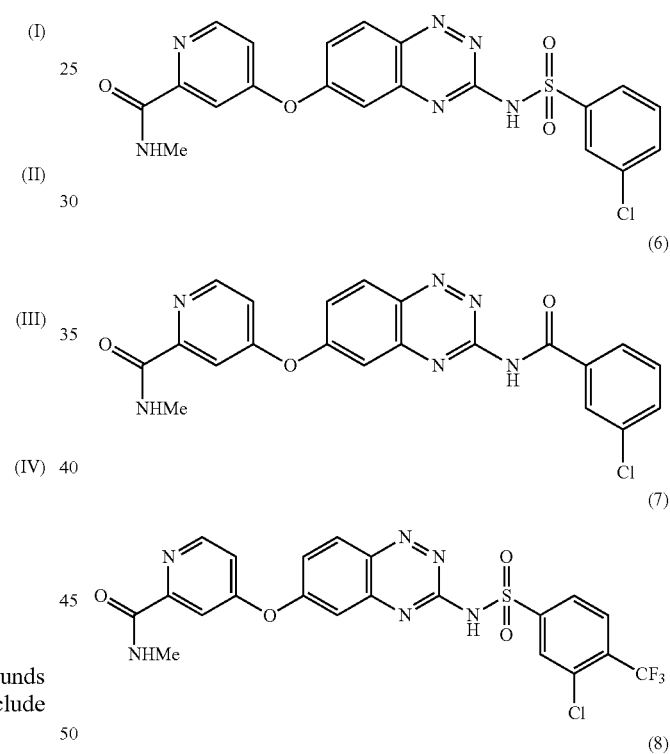

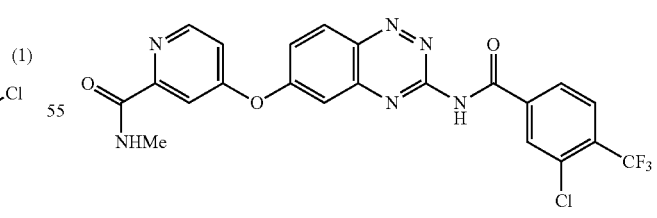

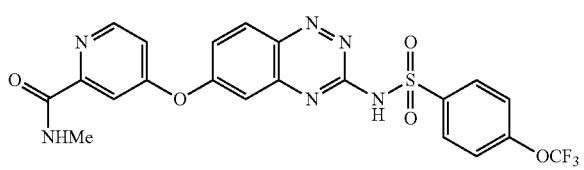

(10)
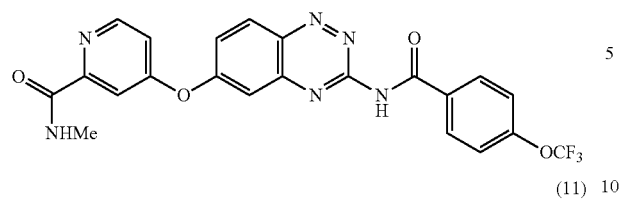
(11)
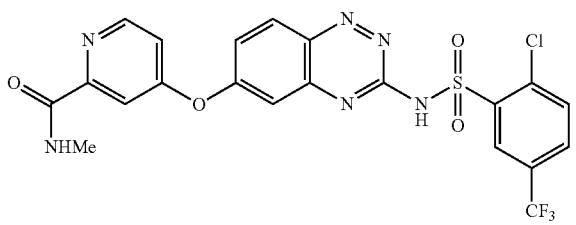
(12)
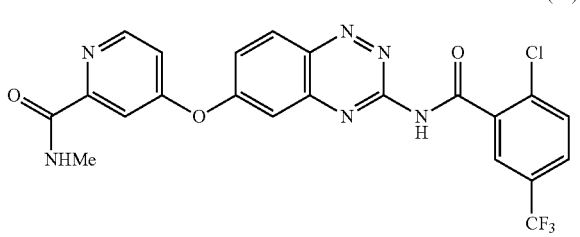
(13)
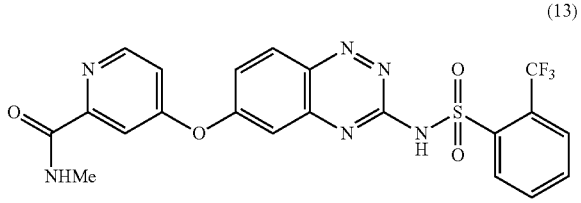
(14)
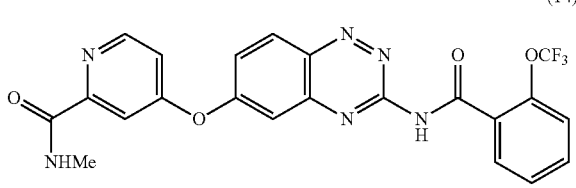
(15)
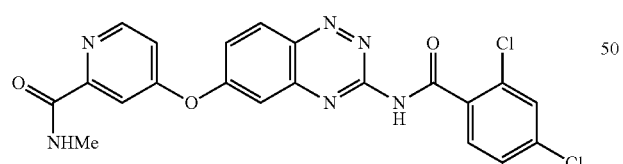
(16)
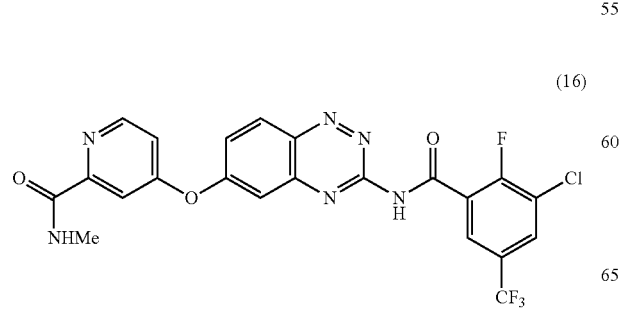
(17)
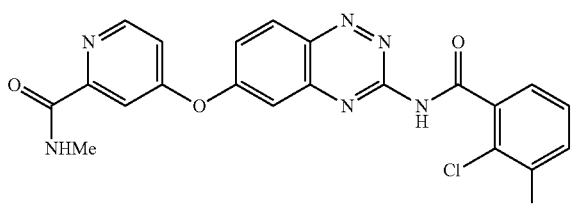
(18)
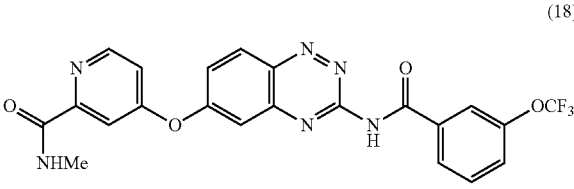
(19)
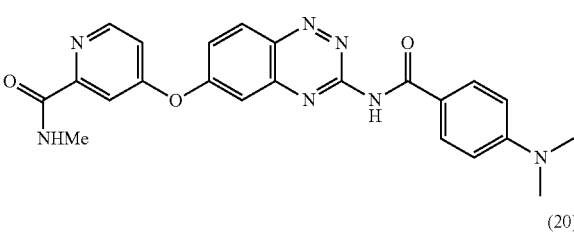
(20)
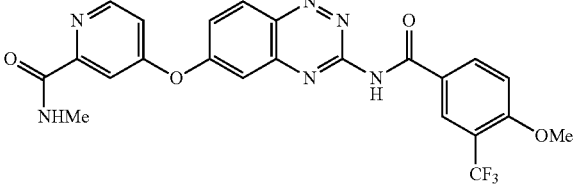
(21)
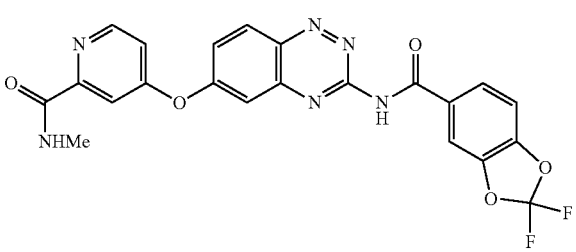
(22)
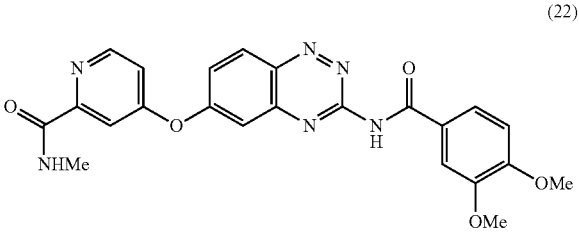
(23)
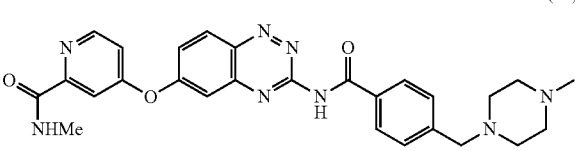

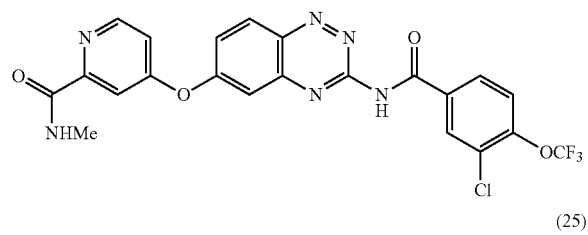
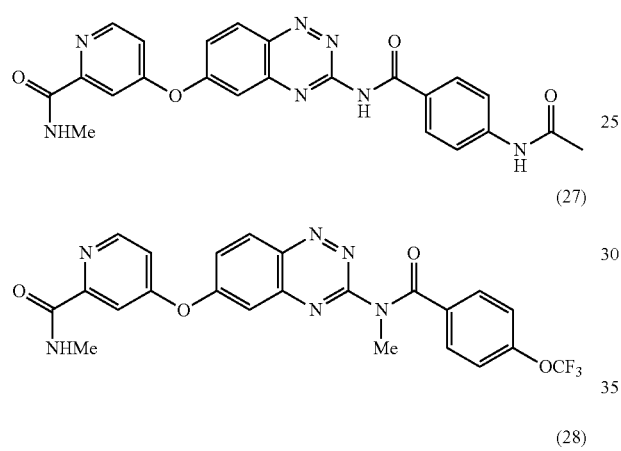
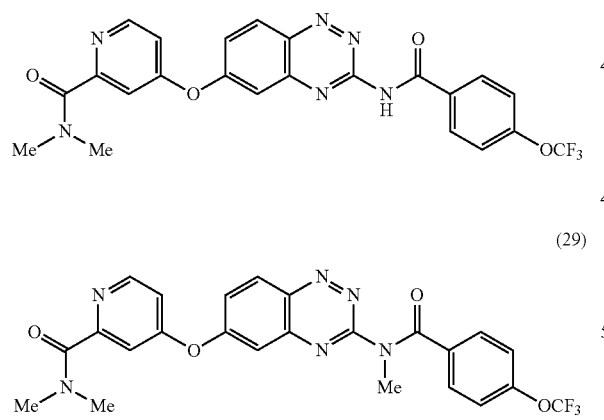
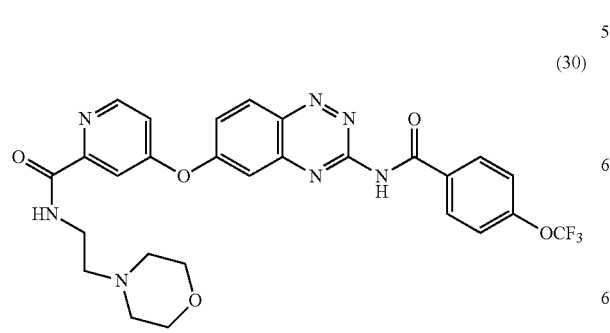
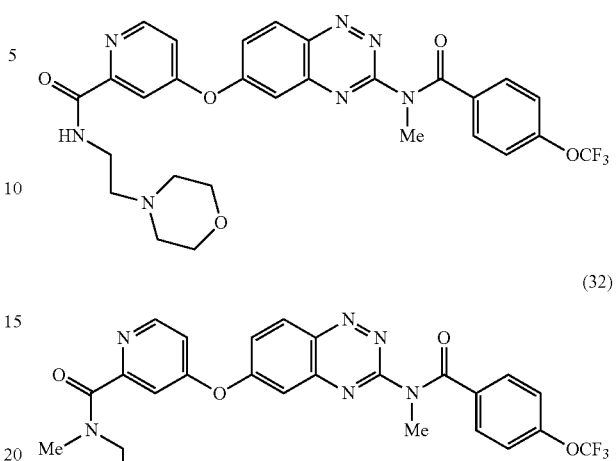
The benzotriazine derivatives described above and illustrated by the general structure (A) can be prepared as shown by Scheme I:
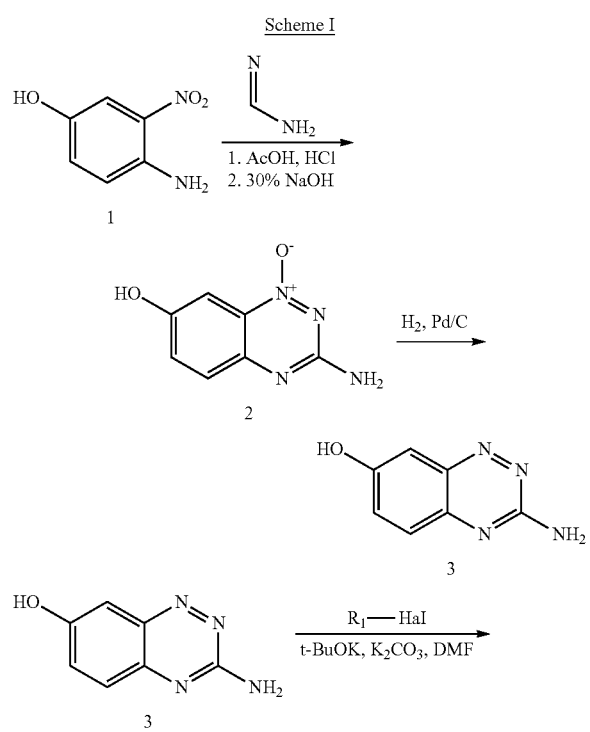

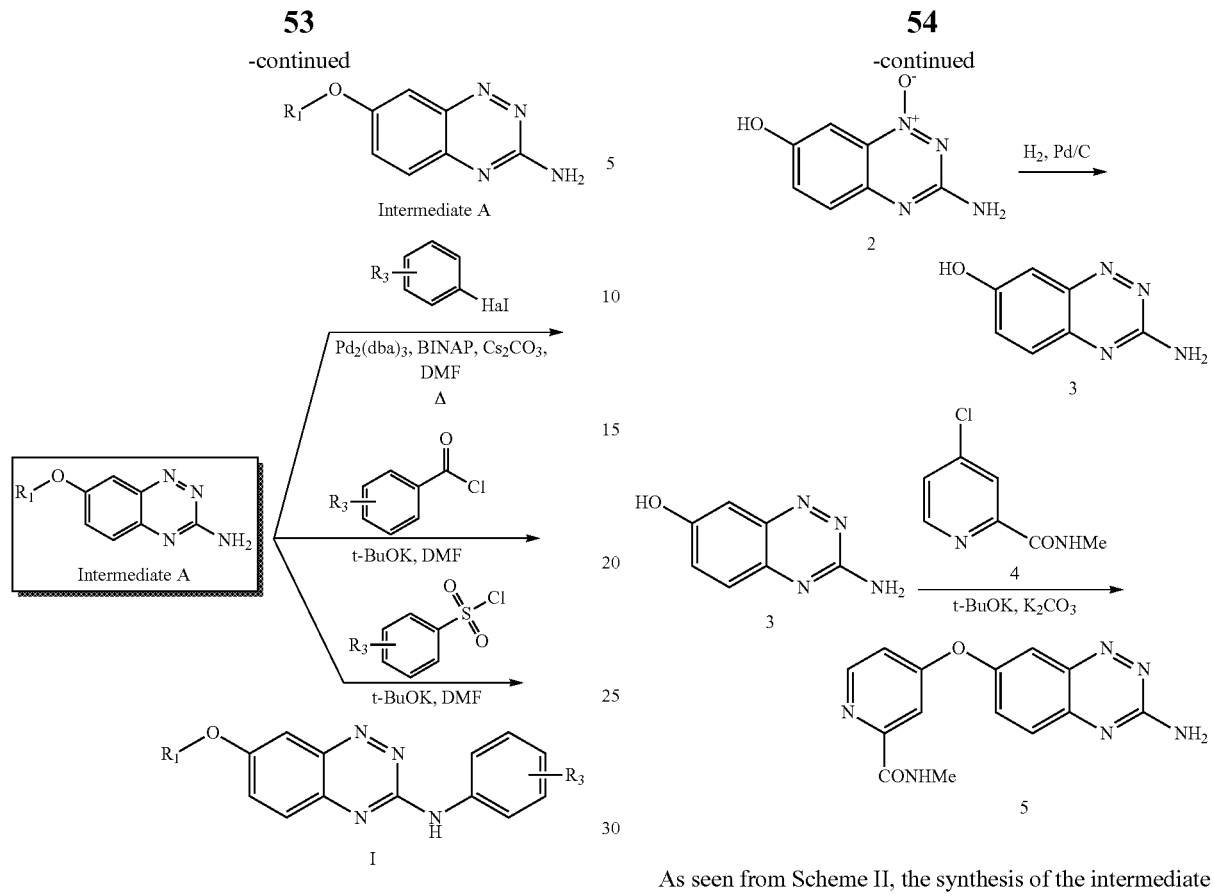

To prepare the intermediate A, where $R_1$ is, for example, 2-pyridine carboxamide, the synthetic route shown by Scheme II can be used:

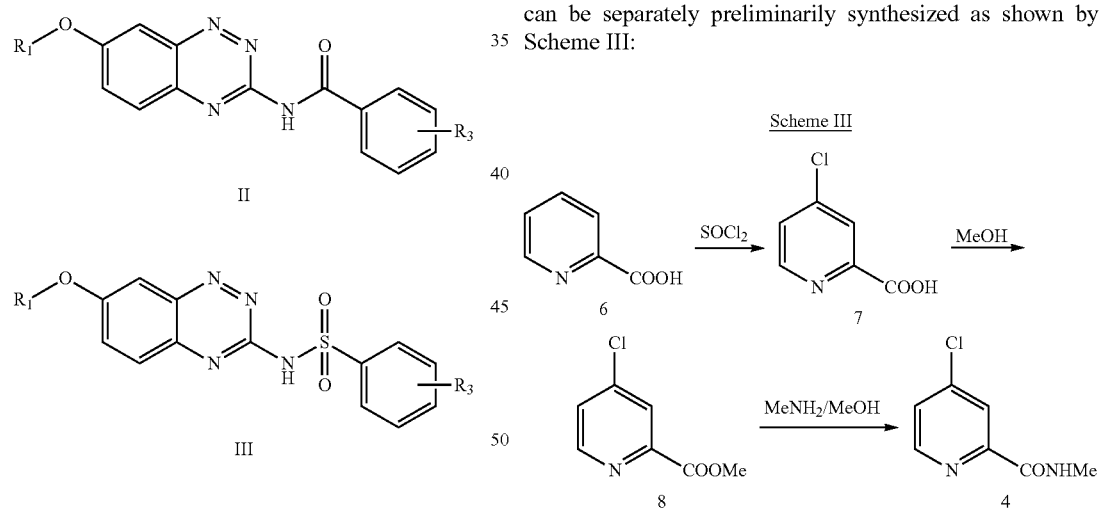

As seen from Scheme II, the synthesis of the intermediate A requires using 4-chloro-2-pyridinecarboxamide 4, which can be separately preliminarily synthesized as shown by Scheme III:

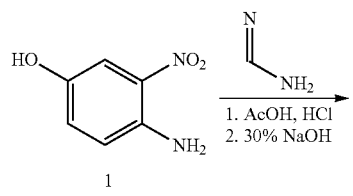

The benzotriazine derivatives described in the formula (IV) and illustrated by the general structure (A) can be prepared as shown by Scheme IV:

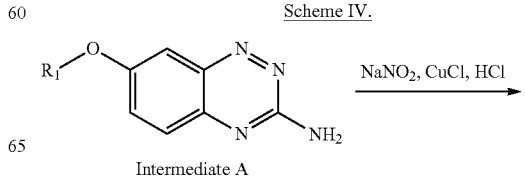

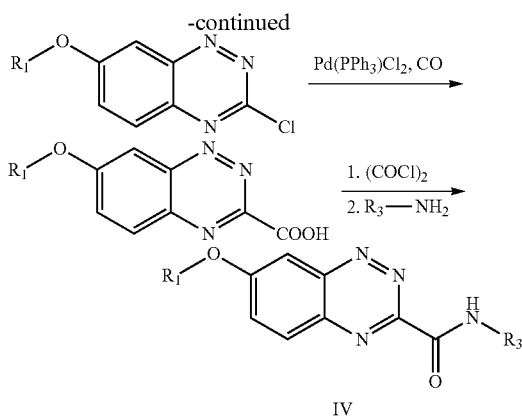

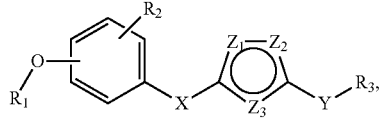

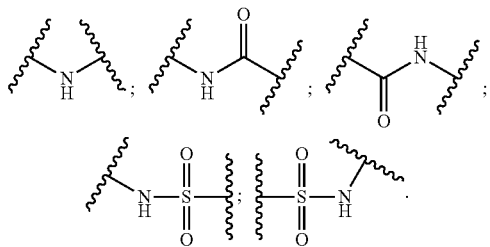

IV

According to an embodiment of the invention, a second type of compounds is provided for treatment of various diseases, disorders, and pathologies, including cancer. The second type of compounds can include a benzene derived moiety bridged to a heterocyclic moiety, or pharmaceutically acceptable salts thereof. The bridge between the benzene-derived moiety and the heterocyclic moiety can include a single bond or a nitrogen atom. If the heterocyclic moiety contains at least one nitrogen, the second type of compounds can be an N-oxide, or N,N'-dioxide, or N,N',N''-trioxide.

Whether the compound can be an N-oxide, or N,N'-dioxide, or N,N',N''-trioxide, depends on the number of nitrogen atoms contained in the heterocyclic moiety. For example, if the heterocyclic moiety has only one nitrogen, the second type of compounds can be an N-oxide. If the heterocyclic moiety has two atoms of nitrogen, the second type of compounds can be an N-oxide or N,N'-dioxide. If the heterocyclic moiety has three atoms of nitrogen, the second type of compounds can be any of an N-oxide, an N,N'-dioxide, an N,N',N''-trioxide.

The benzene-derived moiety can include a substituent such as a pyridyl group connected to the benzene molecule via an oxygen link, or a sulfonyl group. The pyridyl group connected to the benzene molecule can be further substituted. The substituents in the pyridyl group can include the same moieties as described above for the first type of compounds of the present invention. The sulfonyl group connected to the benzene molecule can be also further substituted. The substituents in the sulfonyl group can include the substituted pyridyl group described above for the first type of compounds of the present invention.

Optionally, the benzene-derived moiety of the compounds of the second type can contain a second substituent, e.g., methyl, halogen or methoxy, which can be located in any position of the benzene ring. Some exemplary benzene-derived moieties that can be included in the second type of compounds can include tert-butyl phenyl, trifluoromethoxyphenyl, methoxyphenyl, dimethylamino, dimethylaminophenyl, aminophenyl, trifluoroethoxyphenyl, trifluoromethoxychlorophenyl, trifluoromethoxybromophenyl, trifluoroethoxychlorophenyl, chlorophenyl, dichlorophenyl, trifluoromethyl phenyl, trifluoromethylchloro phenyl, chlorotoluyl, N-phenylacetamide, N,N-alkyl-benzamide, isopropoxyphenyl, alkoxyphenyl, dialkoxyphenyl, acetylphenyl.

The compounds of the second type include heterocyclic compounds having the general structure (B), or an N-oxide, or N,N'-dioxide, N,N',N''-trioxide, or a pharmaceutically acceptable salt thereof, and can inhibit the activity of a kinase, such as any kinase in the MAPK signaling pathway. The general structure (B) can be represented as follows:

(B)

In structure (B), each of $Z_1$, $Z_2$ and $Z_3$ can be, independently, N, CH, N=CH, O, S or N—$R^4$, wherein $R^4$ is hydrogen or lower alkyl, with the further proviso that at least one of $Z_1$, $Z_2$ and $Z_3$ is not CH; X can be absent or be NH; Y can be absent or can be one of the following moieties:

Further, in structure (B), the substituents $R_1$, $R_2$, and $R_3$ can be as follows:

$R_1$ can be an unsubstituted or a substituted $C_3$-$C_{12}$ heteroaryl having 1-3 heteroatoms such as N, S or O;

$R_2$ can be any one of hydrogen, halogen, $C_1$-$C_{18}$ alkyl (e.g., methyl), —OH, —$NO_2$, —CN, $C_1$-$C_{18}$ alkoxy (e.g., methoxy), —$NHSO_2R^5$, —$SO_2NHR^5$, —$NHCOR^5$, —$NH_2$, —$NR^5R^6$, —$S(O)R^5$, —$S(O)_2R^5$, —$CO_2R^5$, —$CONR^5R^6$, and where $R^5$ and $R^6$ are independently selected from hydrogen, a $C_1$-$C_{18}$ alkyl and a substituted $C_1$-$C_{12}$ alkyl; and $R_3$ can be hydrogen, a $C_1$-$C_{18}$ alkyl, a substituted $C_1$-$C_{12}$ alkyl, a $C_1$-$C_{12}$ cycloalkyl, a substituted $C_1$-$C_{12}$ cycloalkyl, a substituted $C_3$-$C_{10}$ cycloalkyl having 0-3 heteroatoms such as N, S, or O, an aryl such as a $C_6$-$C_{12}$ aryl, a substituted aryl such as a substituted $C_6$-$C_{12}$ aryl, a heterocycle, a substituted heterocycle, a heteroaryl such as a $C_3$-$C_{12}$ heteroaryl having 1-3 heteroatoms such as N, S or O, a substituted heteroaryl such as substituted $C_3$-$C_{12}$ heteroaryl having 1-3 heteroatoms such as N, S or O, a $C_7$-$C_{24}$ aralkyl, a substituted $C_7$-$C_{24}$ aralkyl, a $C_7$-$C_{24}$ alkylaryl, and a substituted $C_7$-$C_{24}$ alkaryl.

The substituent $R_1$ can include a substituted pyridyl or a substituted pyrimidyl group. The substituents in the substituted pyridyl or substituted pyrimidyl group can include an amido moiety, an aminoalkyl group (e.g., aminomethyl), or a carboxyl group, or a carboxylate group. The amido moiety attached to the pyridyl/pyrimidyl group can be in turn also substituted by attaching to the nitrogen in the amido moiety a substitutent selected from an alkyl (e.g., methyl), an alkylaminoalkyl (e.g., diethylamino alkyl), a pyridyl, an alkyl pyrrolidine, an alkyl morpholine, and an alkyl piperazine groups.

Particular, non-limiting examples of $R_1$ that can be used in compounds having the structure (B) include any of the following moieties:

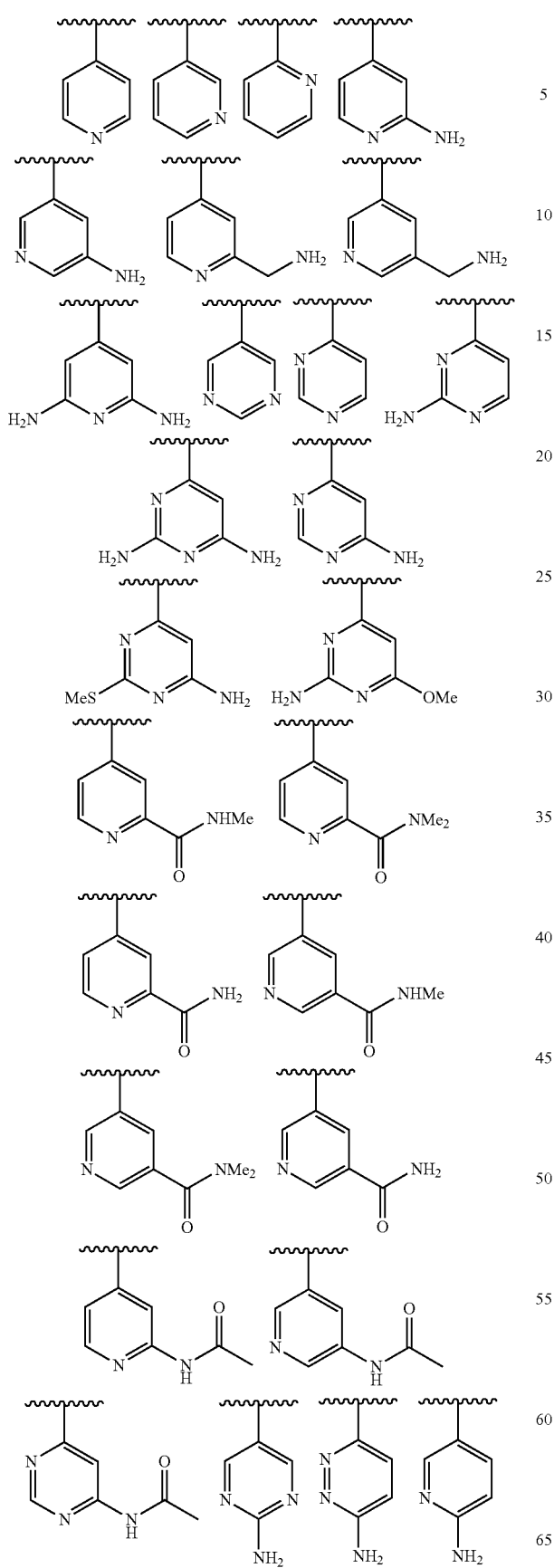
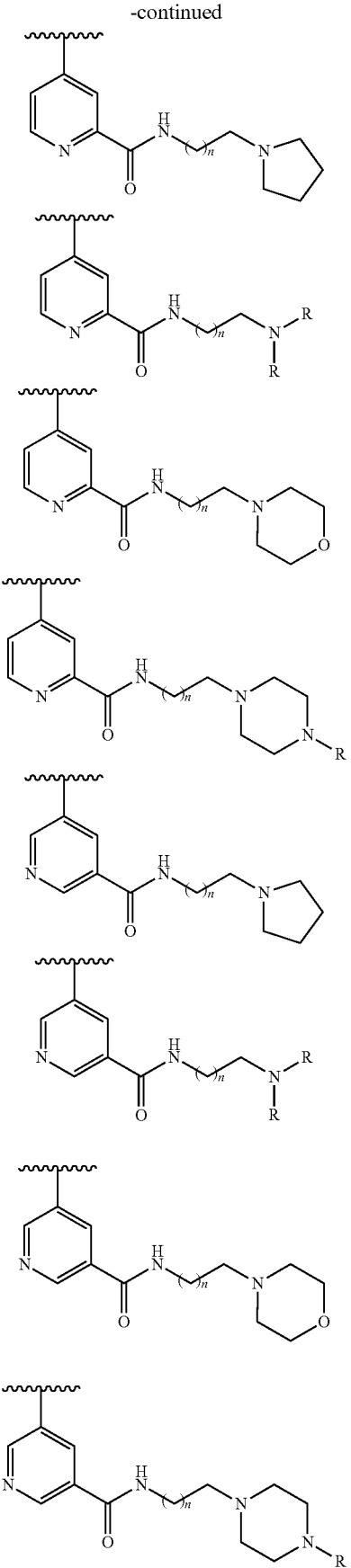

-continued
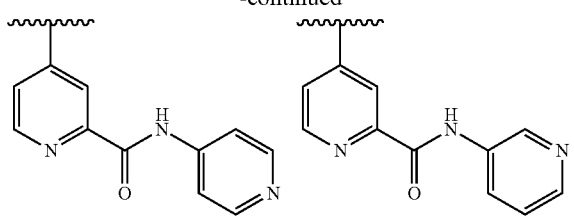
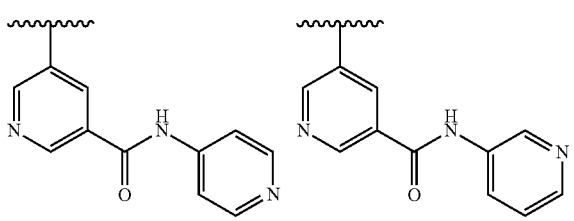
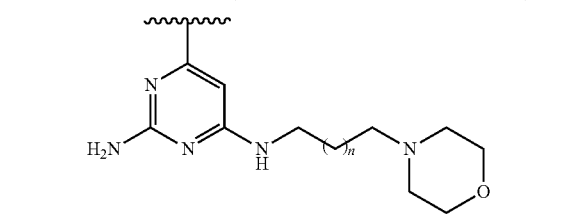
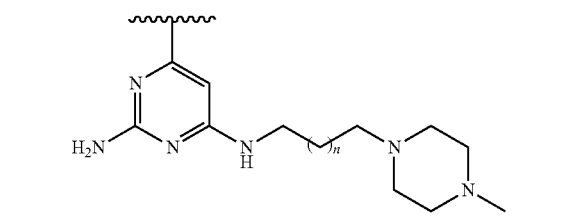
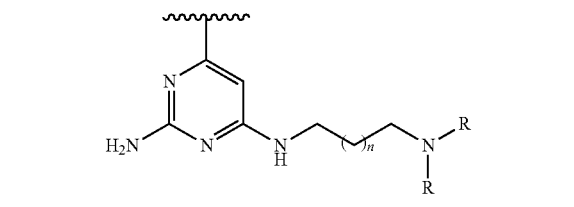
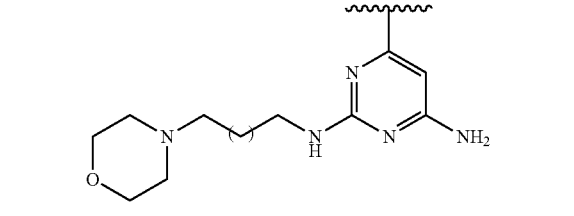
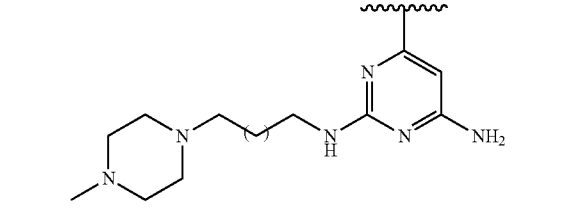
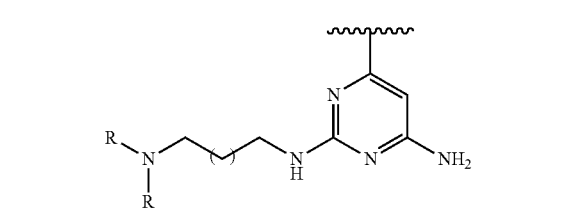
-continued
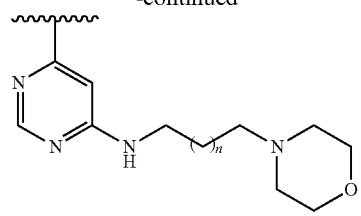
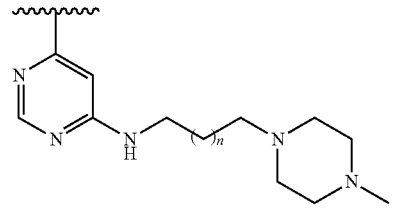
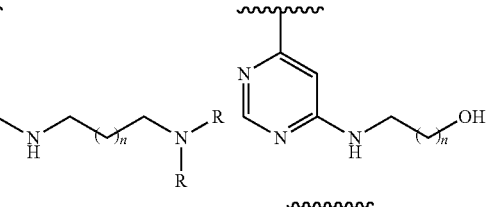
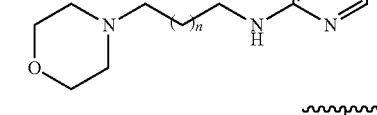
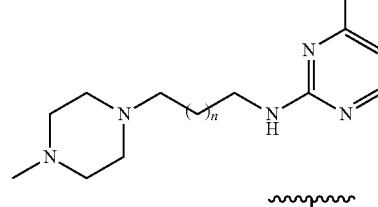
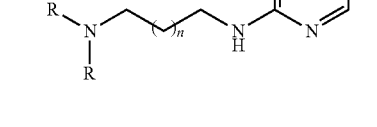
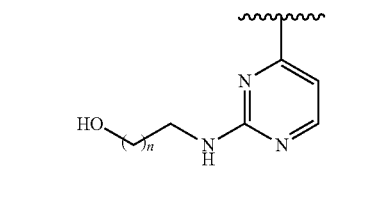
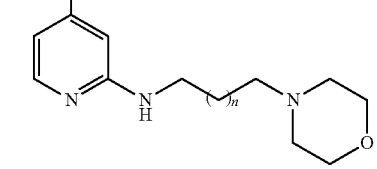

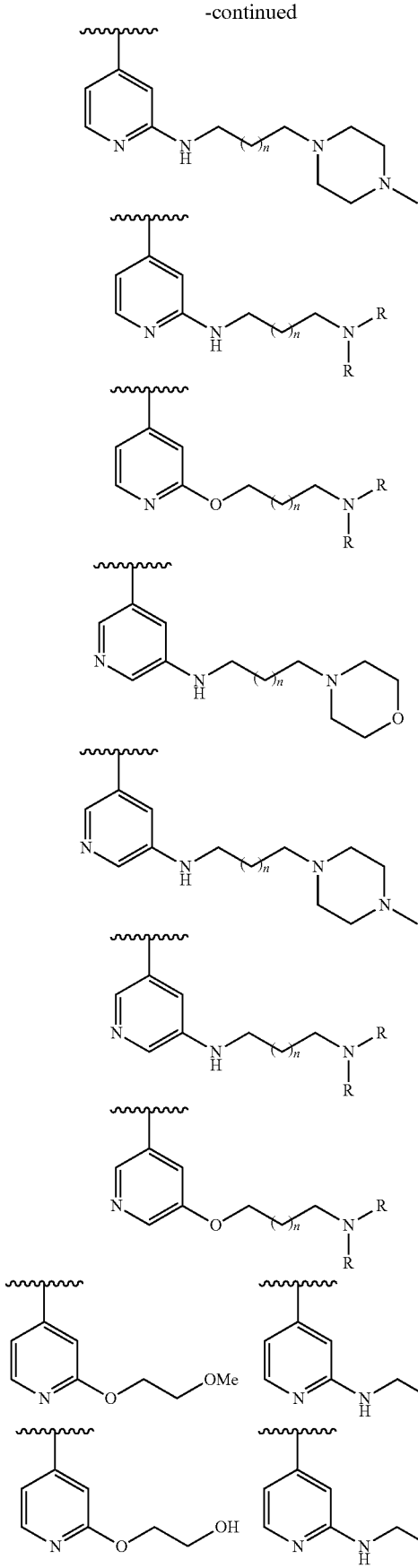

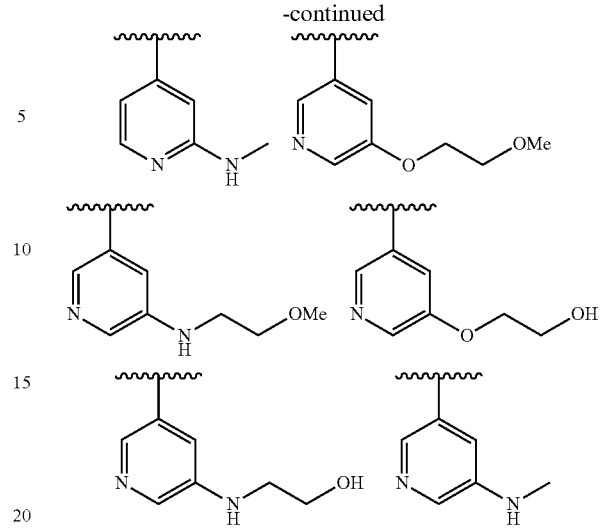

where n can be an integer selected from a group consisting of 0, 2, and 3.

Some particular non-limiting examples of the substituent $R_3$ that can be used in compounds having the structure (B) include tert-butyl phenyl, trifluoromethoxyphenyl, methoxyphenyl, dimethylaminophenyl, aminophenyl, trifluoroethoxyphenyl, trifluoromethoxychlorophenyl, trifluoromethoxybromophenyl, trifluoroethoxychlorophenyl, chlorophenyl, dichlorophenyl, trifluoromethyl phenyl, trifluoromethylchlorophenyl, chlorotoluyl, N-phenylacetamide, N,N-alkyl-benzamide, isopropoxyphenyl, alkoxyphenyl, dialkoxyphenyl, and acetylphenyl. These and yet other moieties that can be used as the substituent $R_3$ can be illustrated as follows:

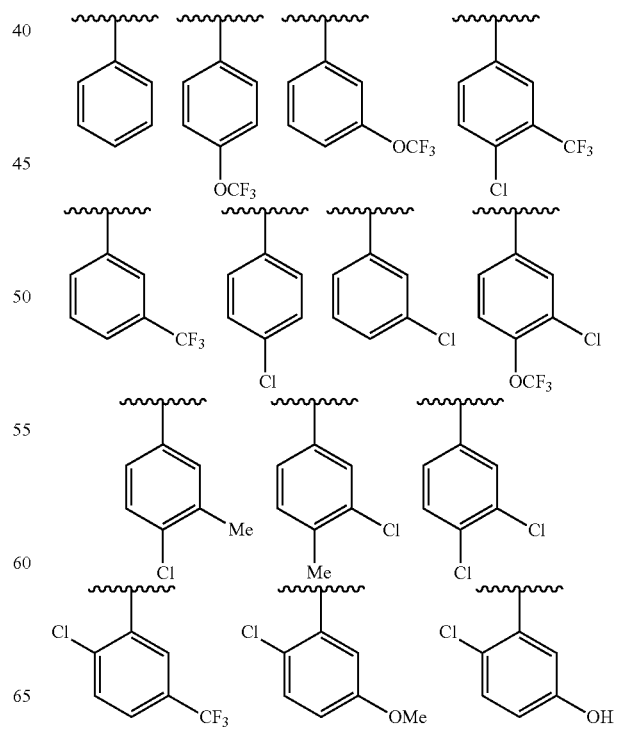

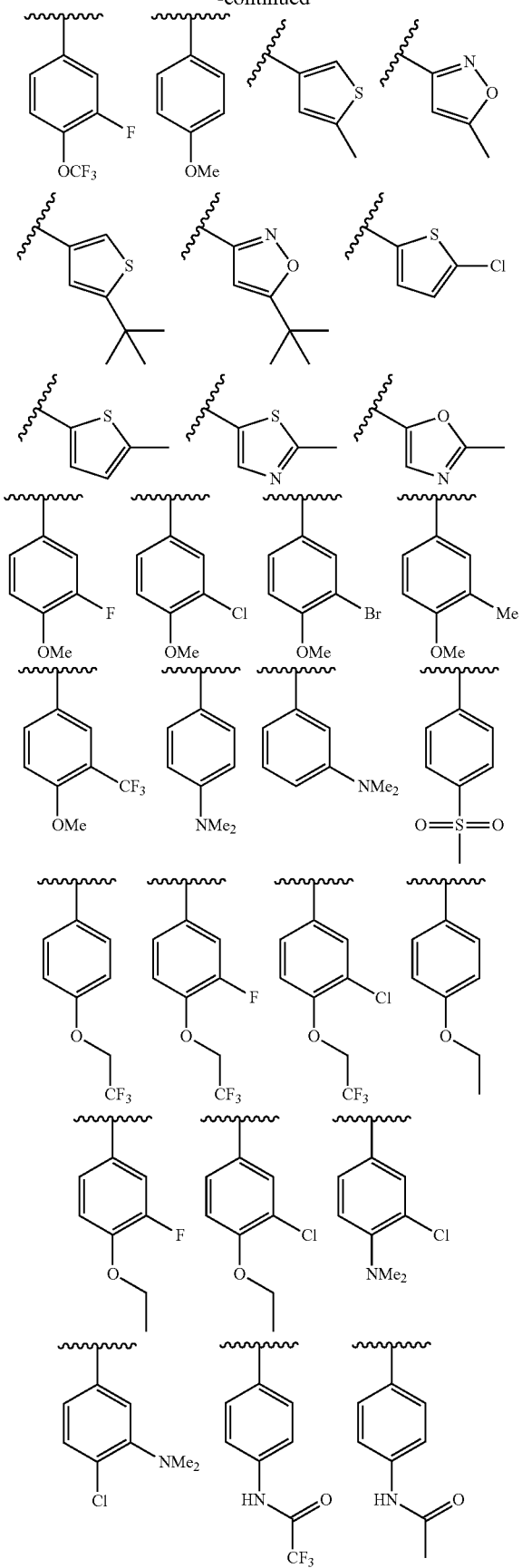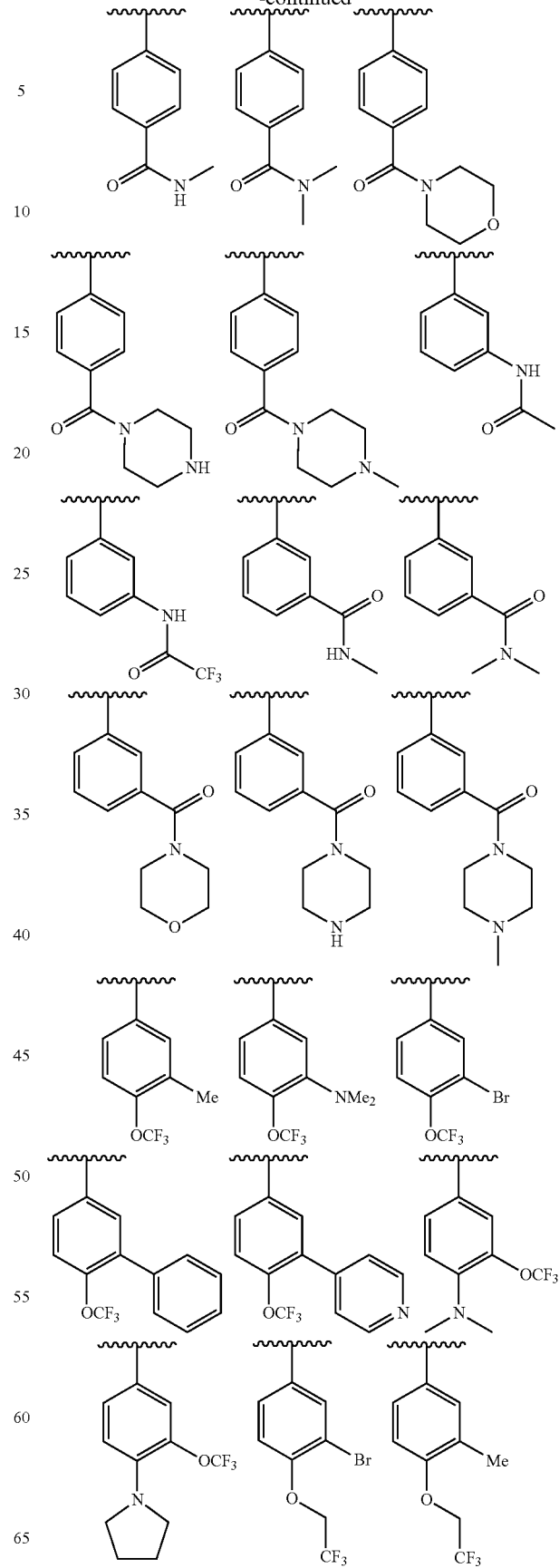

65
-continued
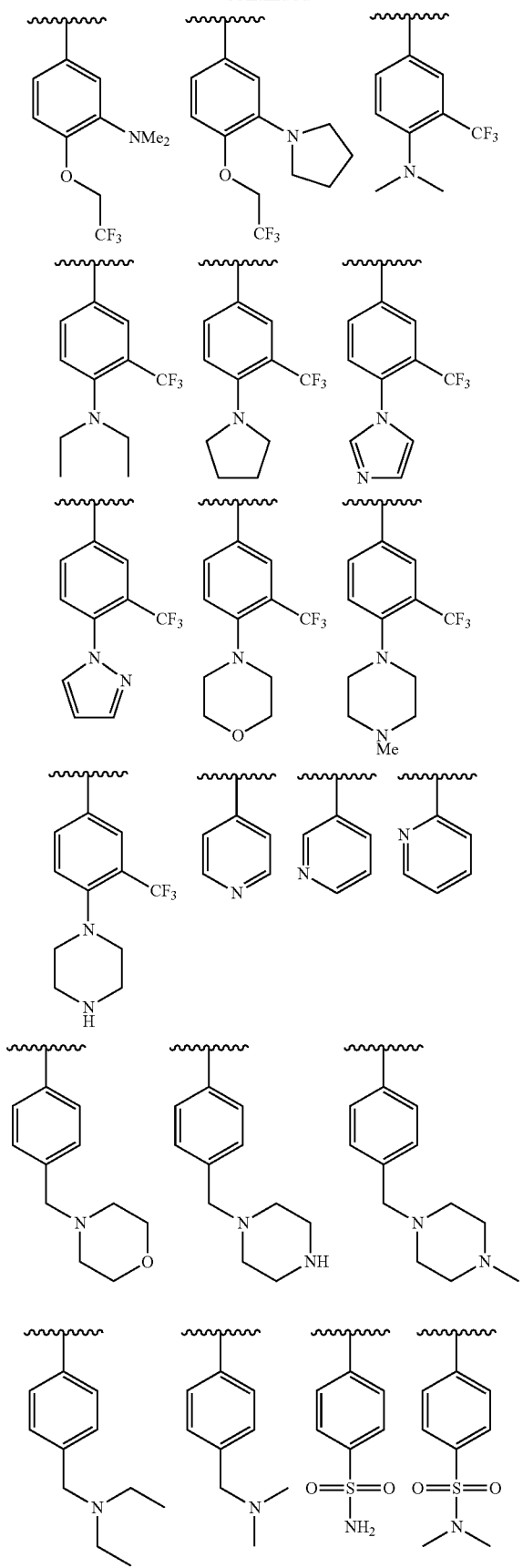
66
-continued
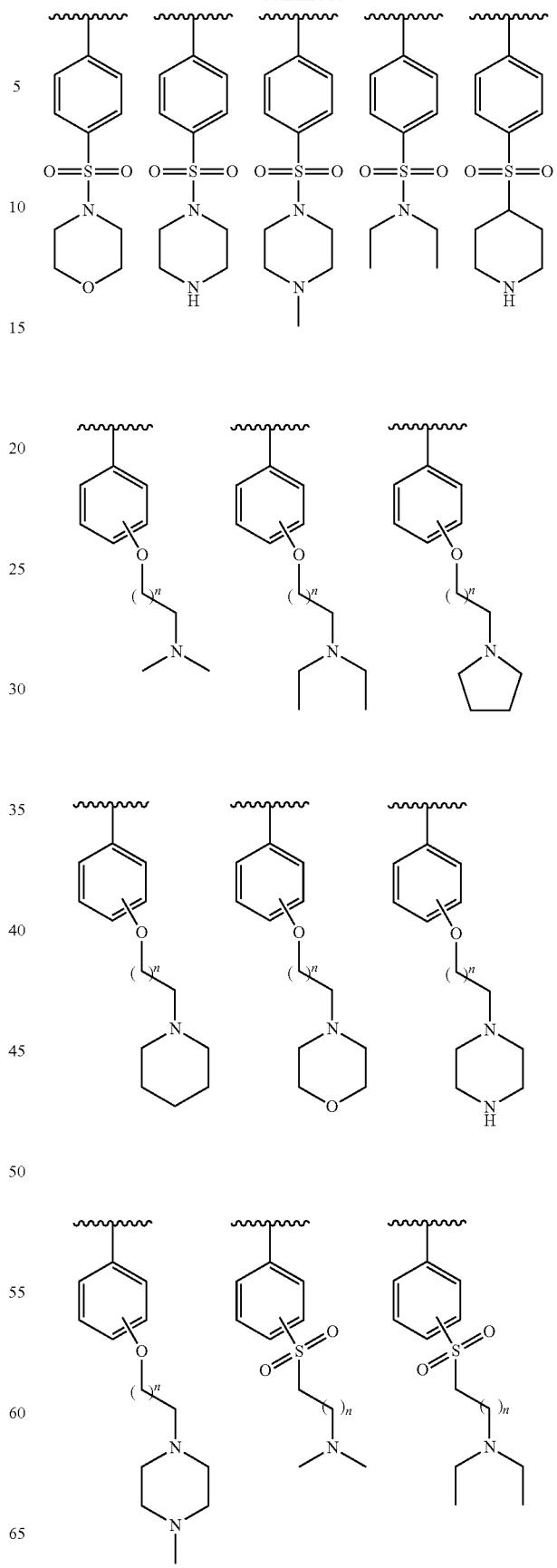

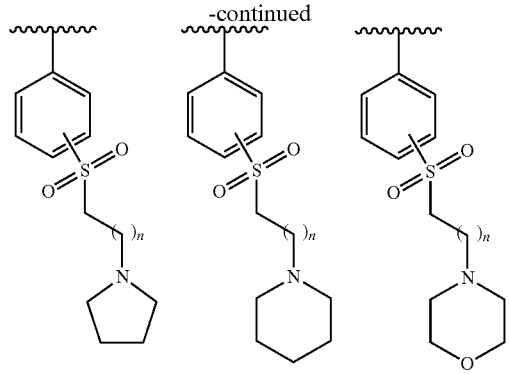
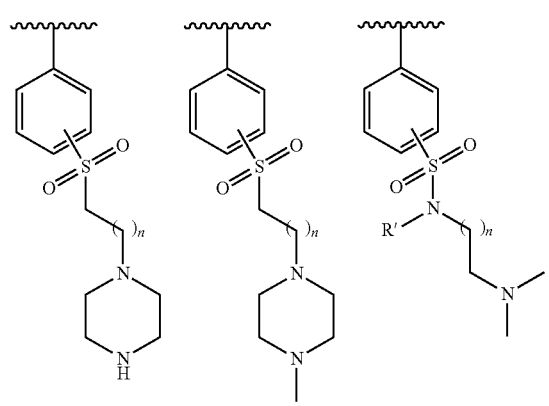
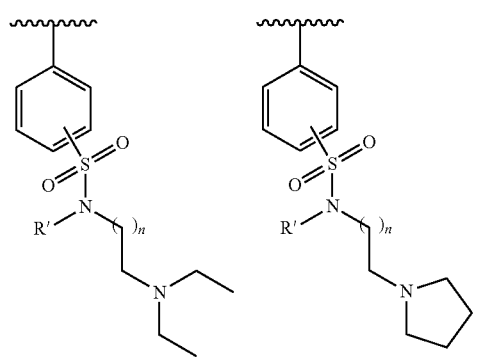
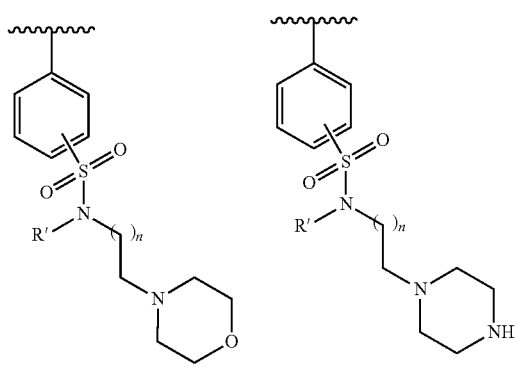
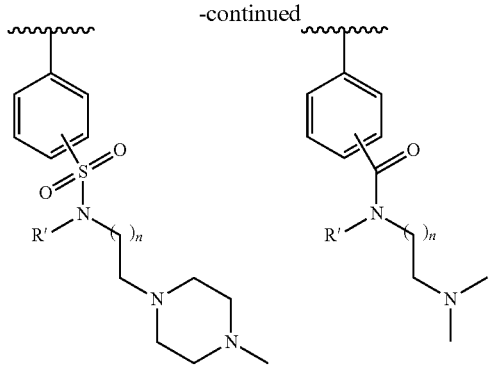
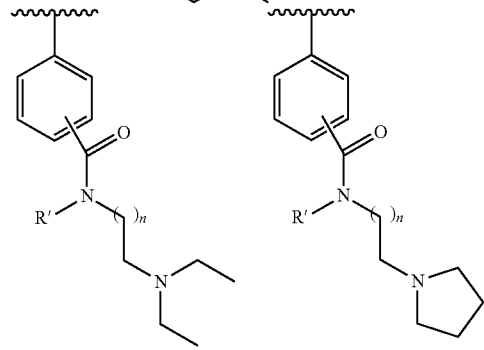
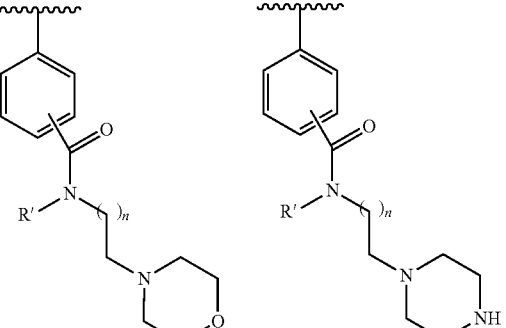
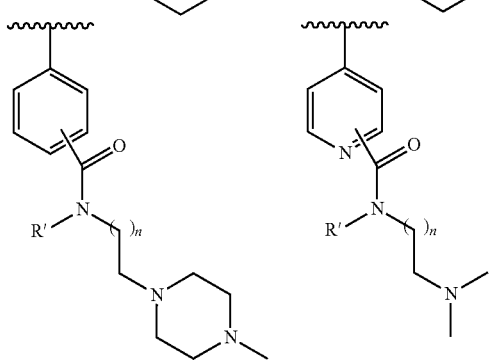
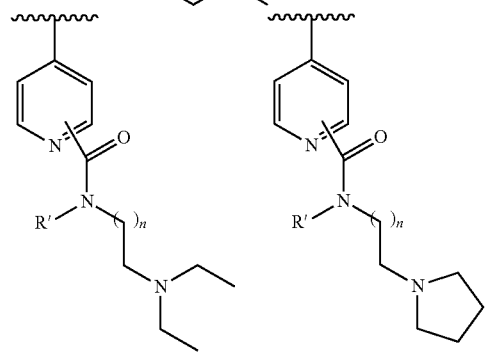

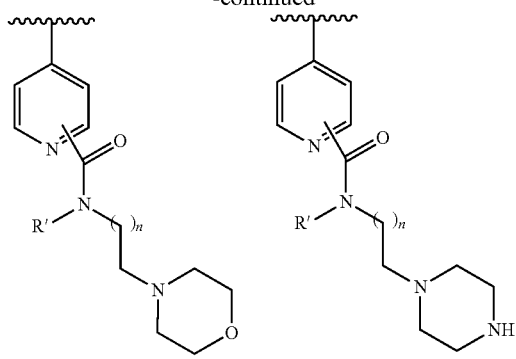
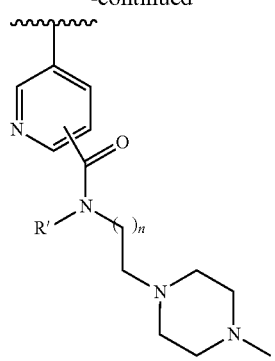
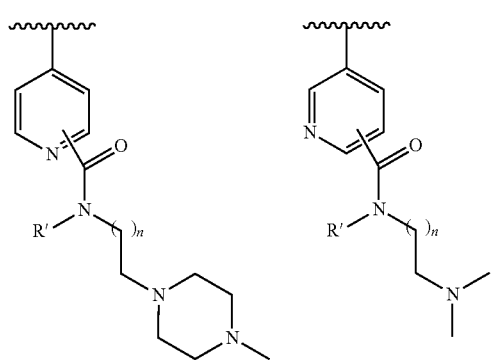
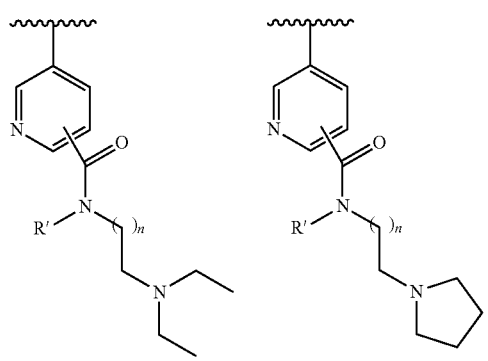
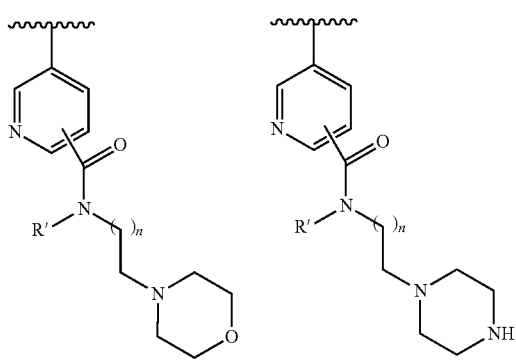
where n can be an integer selected from a group consisting of 0, 1, 2, and 3, and R' is hydrogen, a $C_1$-$C_{18}$ alkyl, or a substituted $C_1$-$C_{18}$ alkyl.
Some general examples of compounds described by the general structure (B) include a compound having the general structures (V)-(XXVIII):
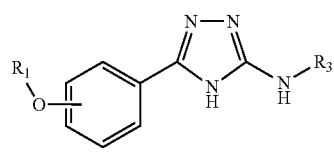
V
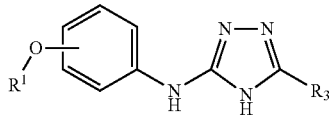
VI
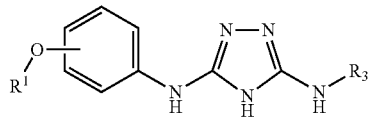
VII
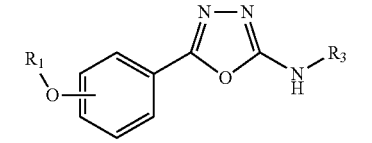
VIII
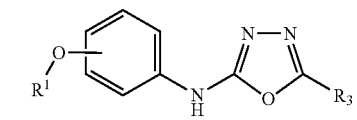
IX
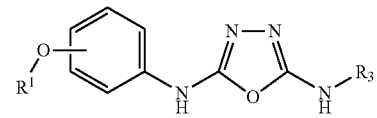
X
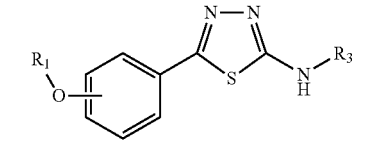
XI

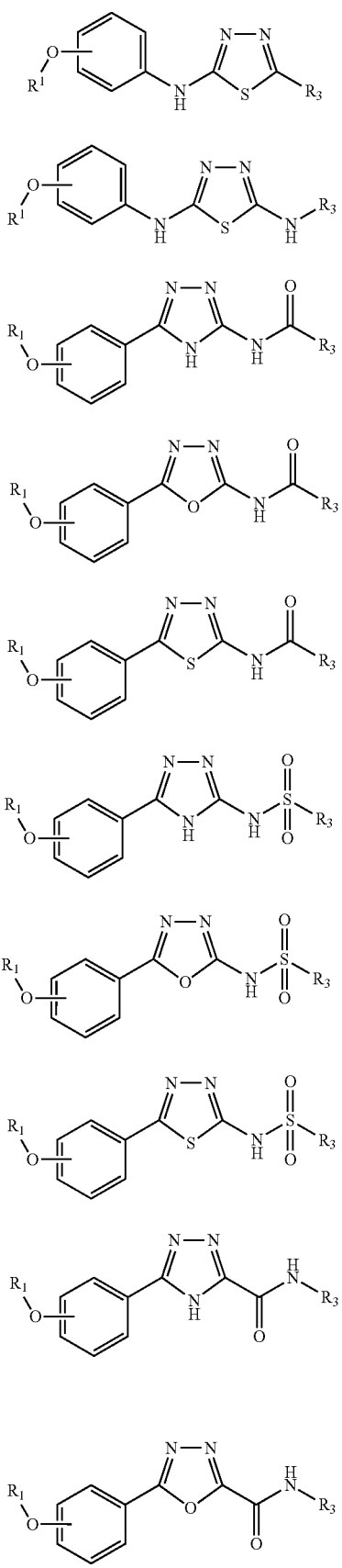
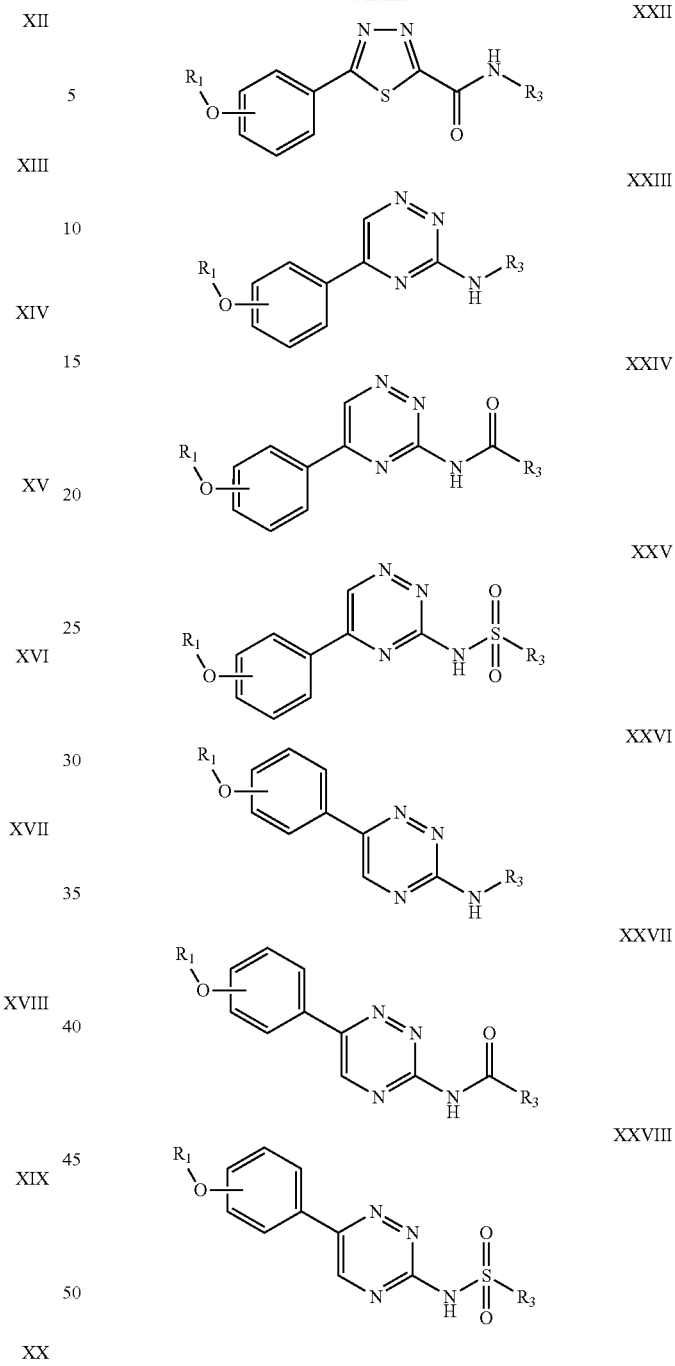
In the case of 1,2,4-triazoles, there exist three tautomeric structures, as shown below:
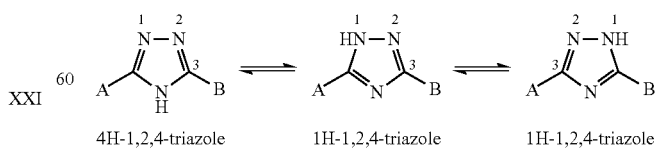
Which tautomeric structure is prevailing depends on the substituents on the triazole moiety and on the reaction conditions. As known to those having ordinary skill in the art, typically, 1H-1,2,4-triazole is the most common tautomeric form, especially if an amino substituent is attached to the ring. Even though all three tautomeric structures can be present, all the generic structures and all the examples having 1,2,4-triazole moiety are shown herein in one tautomeric form, such as 4H-1,2,4-triazole, for simplicity and for the comparison with its direct analogues, such as examples containing 1,3,4-oxadiazole moiety. Using only 4H-tautomeric form to draw the structures for the sake of simplicity, does not imply that the compounds of the examples (30)-(74) shown below exist in that particular tautomeric form.

Some examples of particular compounds described by the general structure (B) include compounds having formulae (34)-(83):

(34)

(35)

(36)

(37)

(38)

(39)

(40)

(41)

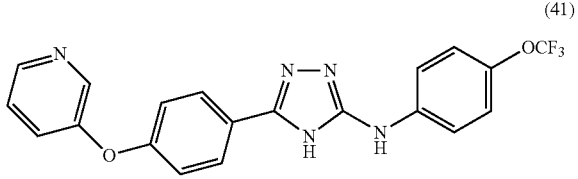

(42)

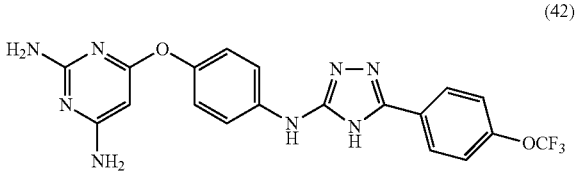

(43)

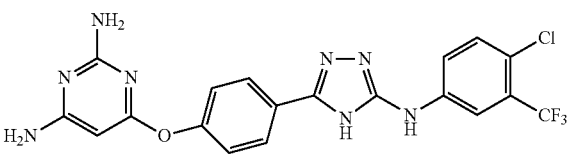

(44)

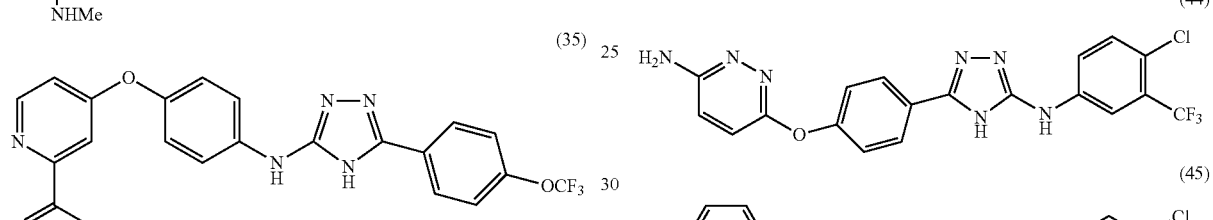

(45)

(46)

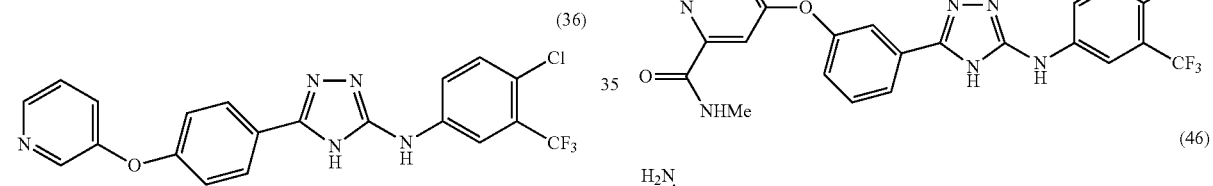

(47)

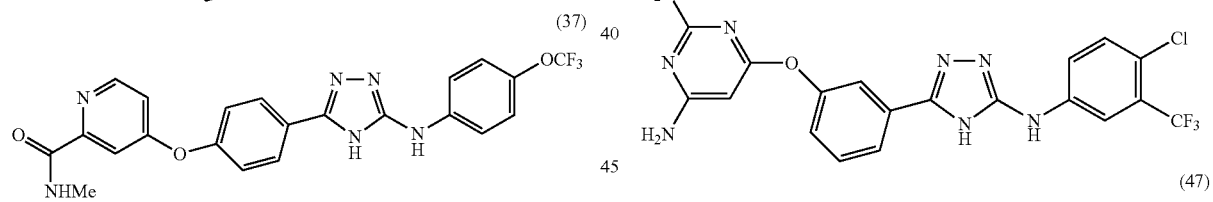

(48)

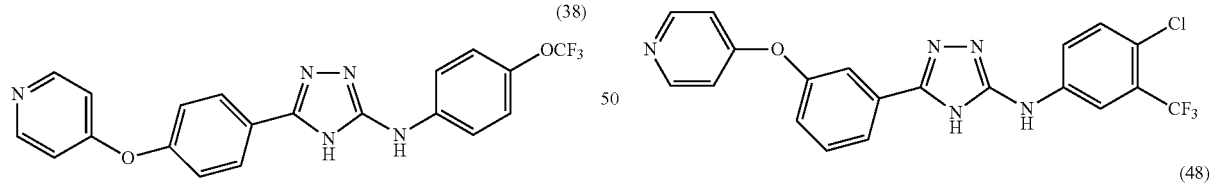

(49)

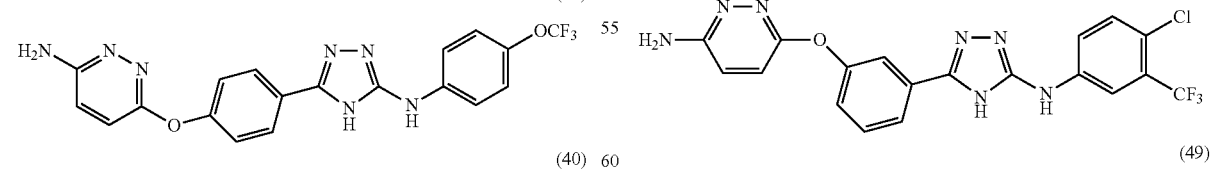

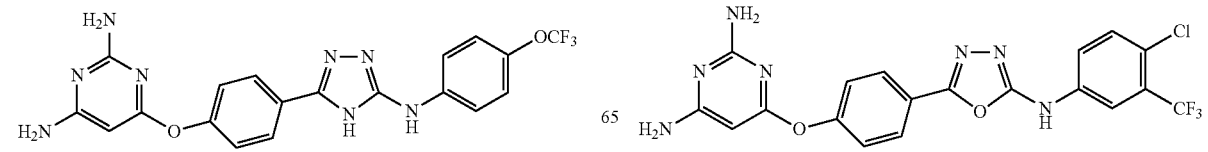

(50) 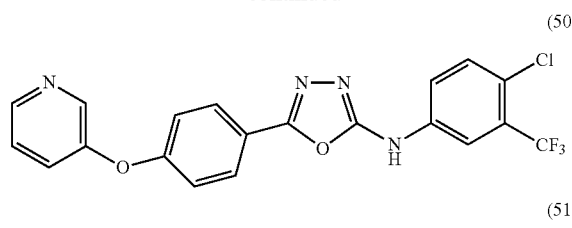
(51) 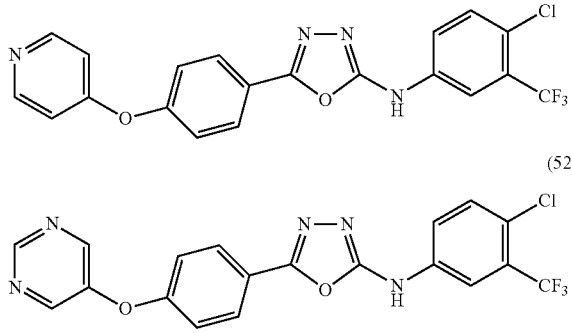
(52)
(53) 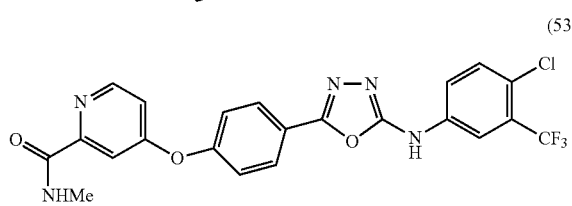
(54) 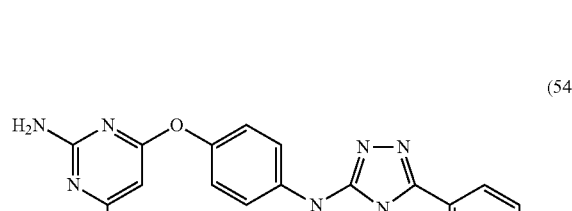
(55) 
(56) 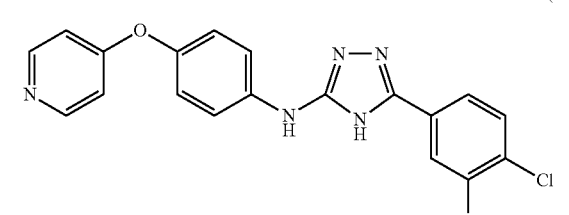
(57) 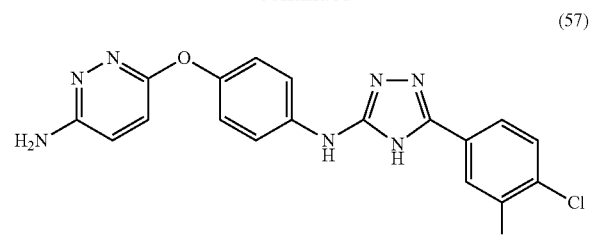
(58) 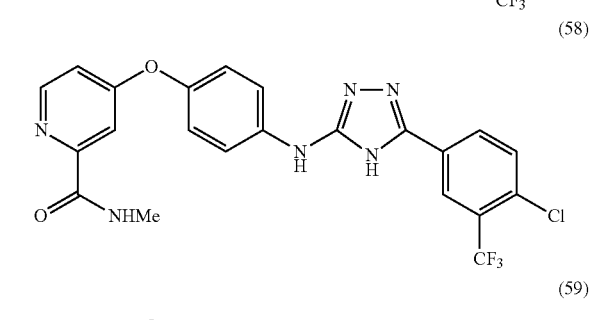
(59)
(60) 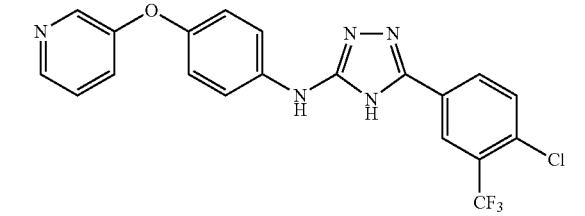
(61) 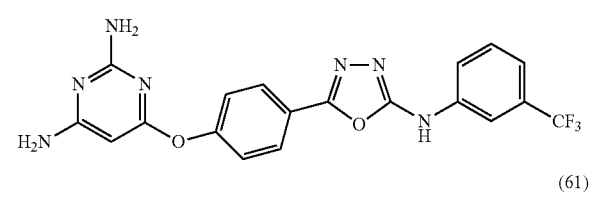
(62) 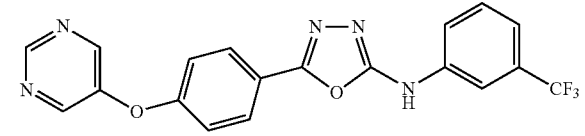
(63) 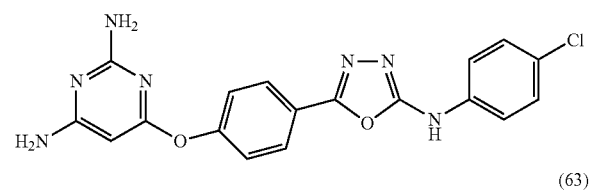
(64) 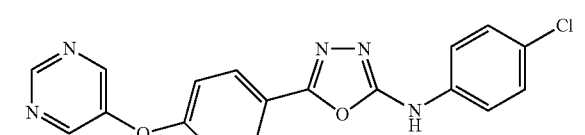

(65)
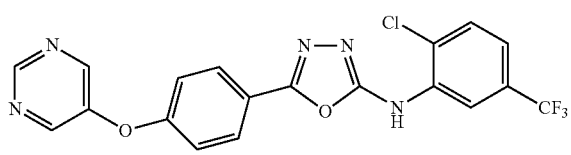
(66)
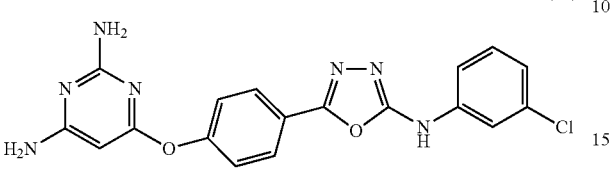
(67)
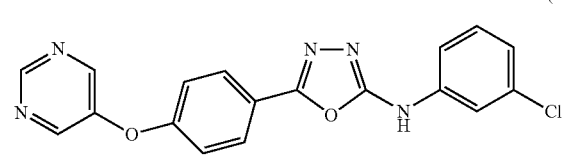
(68)
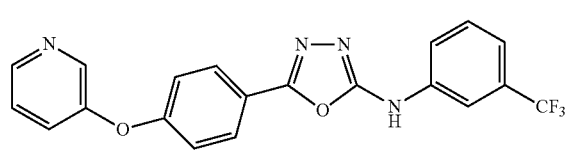
(69)
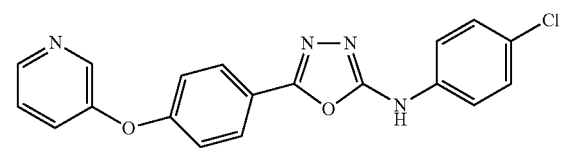
(70)
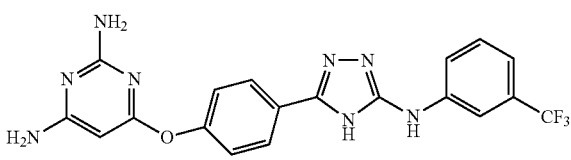
(71)
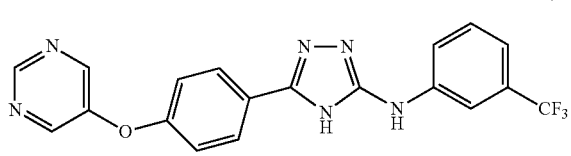
(72)
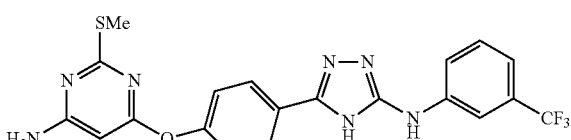
(73)
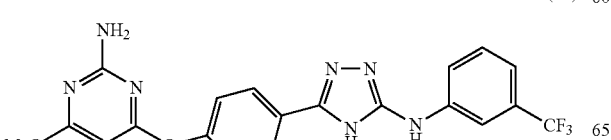
(74)
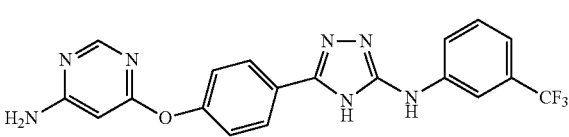
(75)
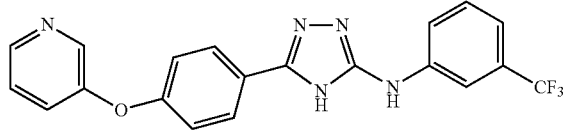
(76)
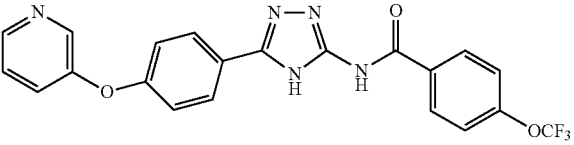
(77)
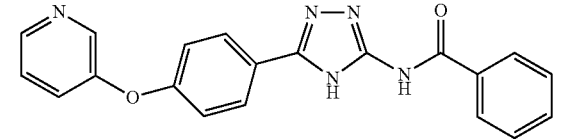
(78)
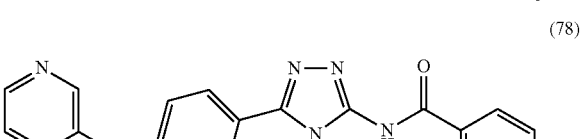
(79)
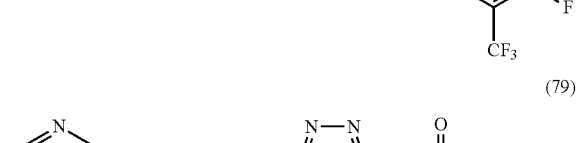
(80)
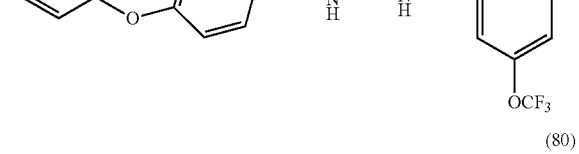
(81)
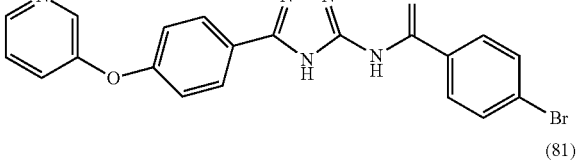

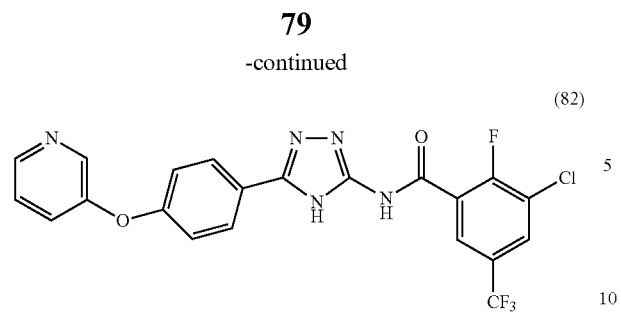
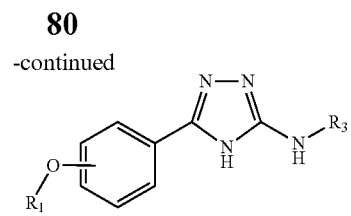
Appropriately substituted 1,2,4-triazoles of the type (V) described above and illustrated by the general structure (B) can be synthesized using one of several reaction schemes, for example as shown in Schemes V, VI and VII below. The appropriate method can be chosen based on the required substitution, availability of the starting materials and the ease of synthesis.
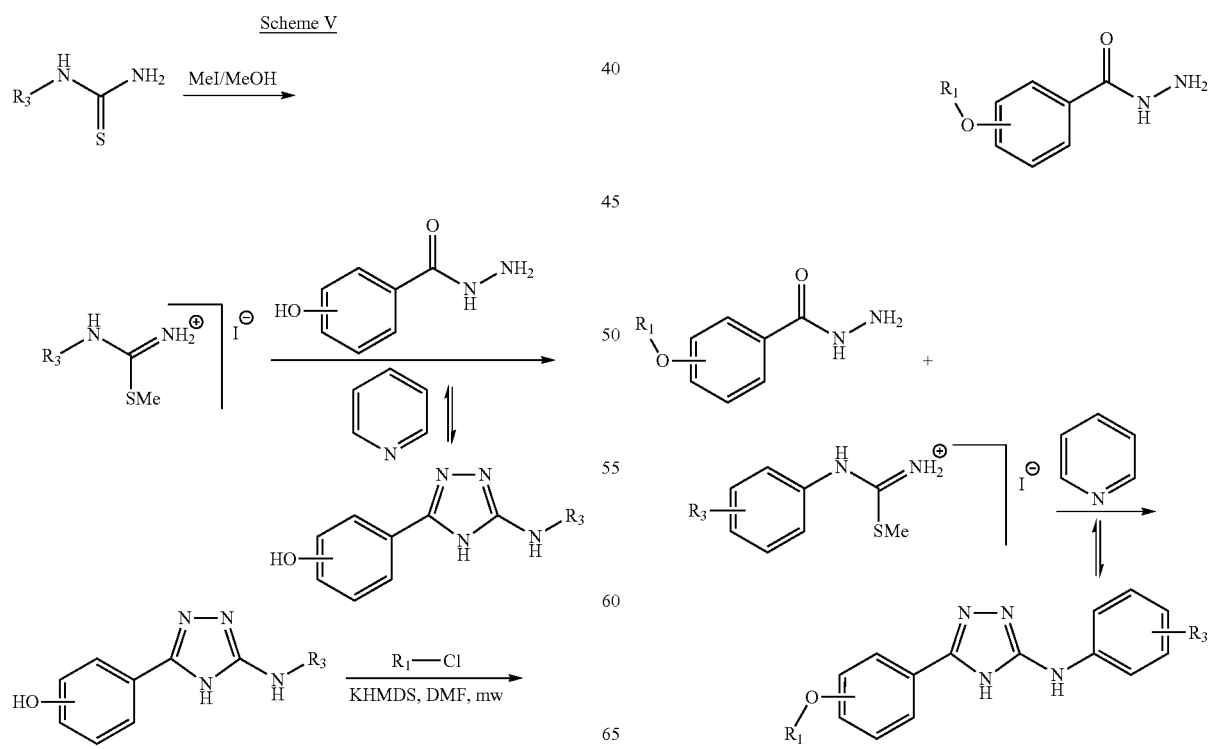

Scheme VII
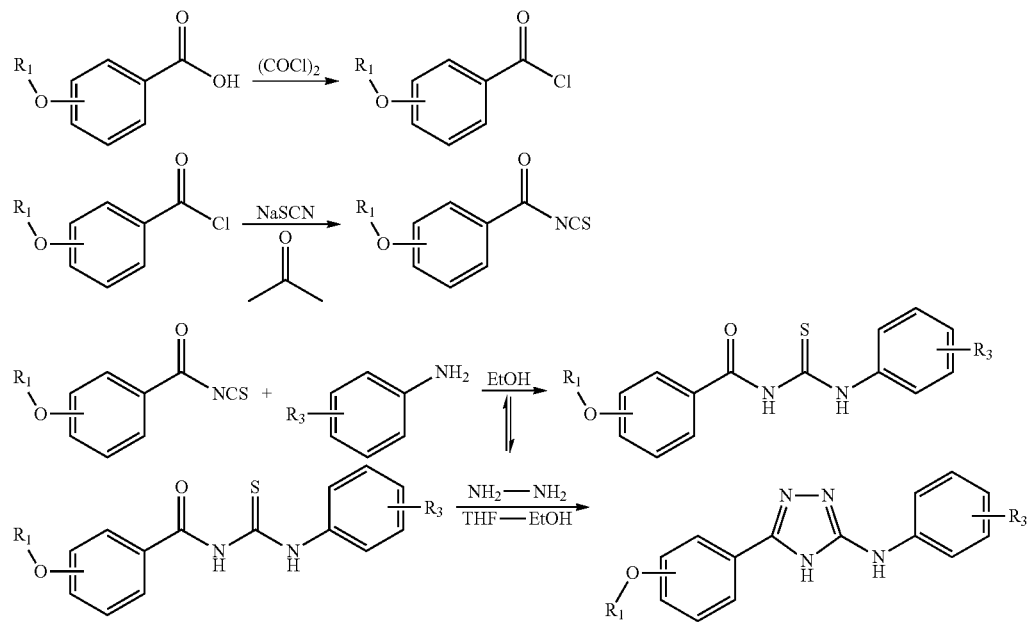
1,2,4-triazoles of the type (VI) described above, can be made as shown in Scheme VIII or by an alternative route as outlined in Scheme IX.
Scheme VIII
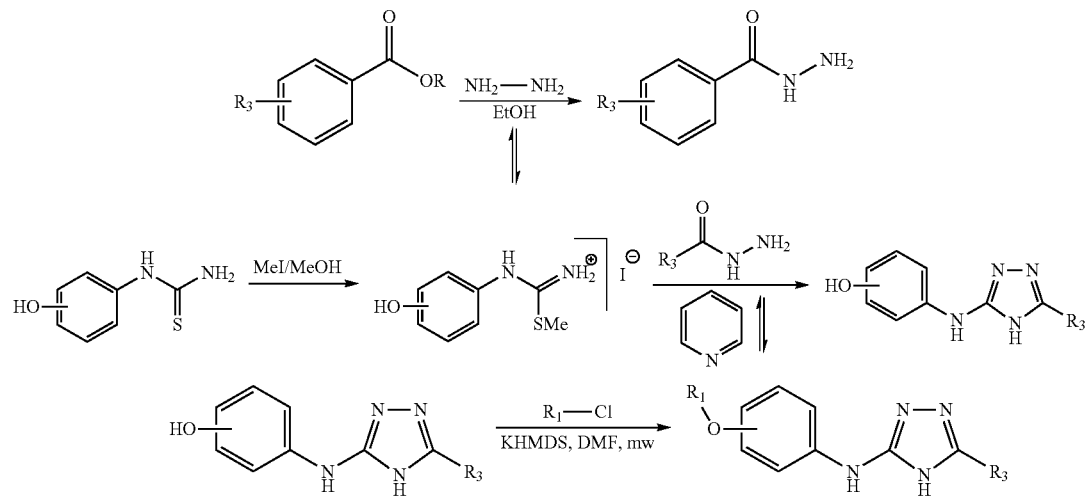
Scheme IX
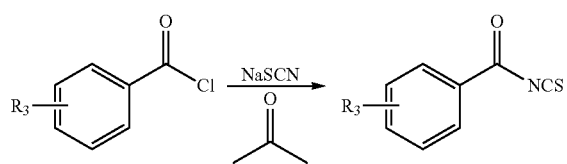

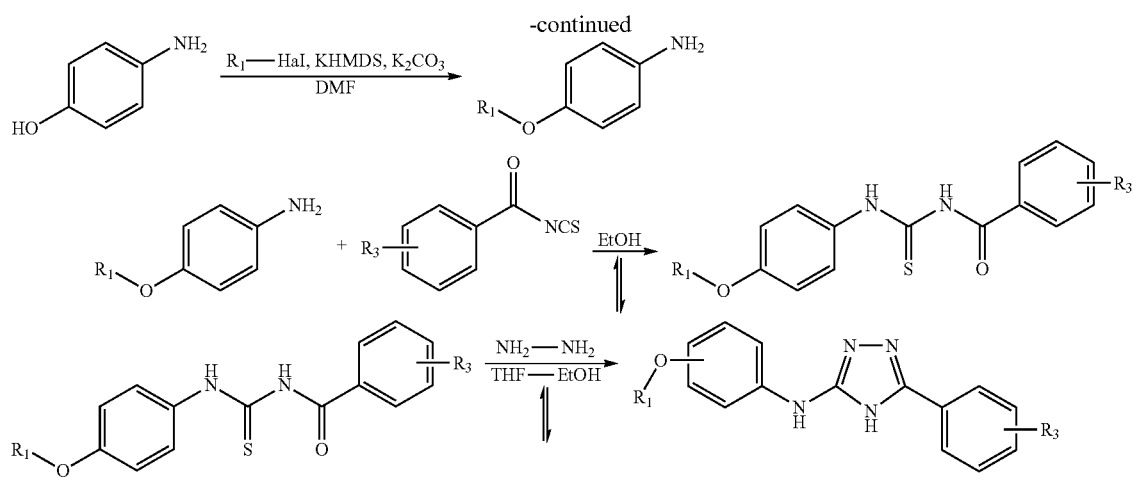
Appropriately substituted 2-amino-1,3,4-oxadoazoles of type (VIII), can be synthesized using one of several reaction schemes, for example, as shown by Schemes X, XI and XII.
Scheme X
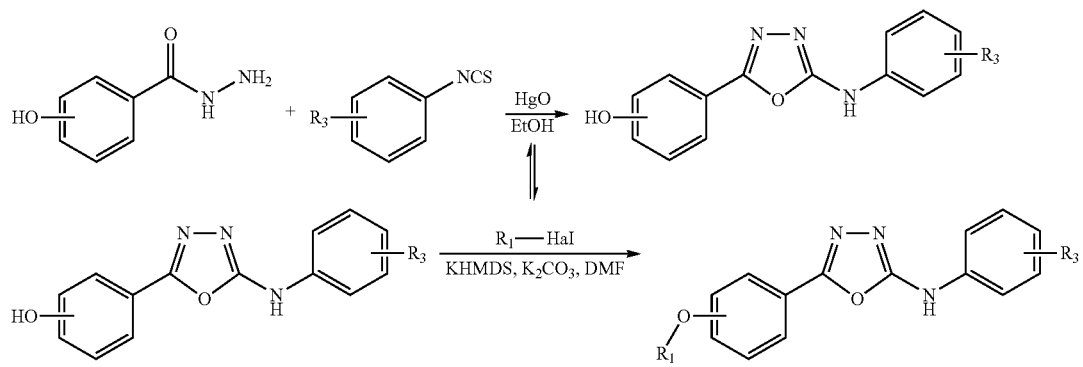
Scheme XI
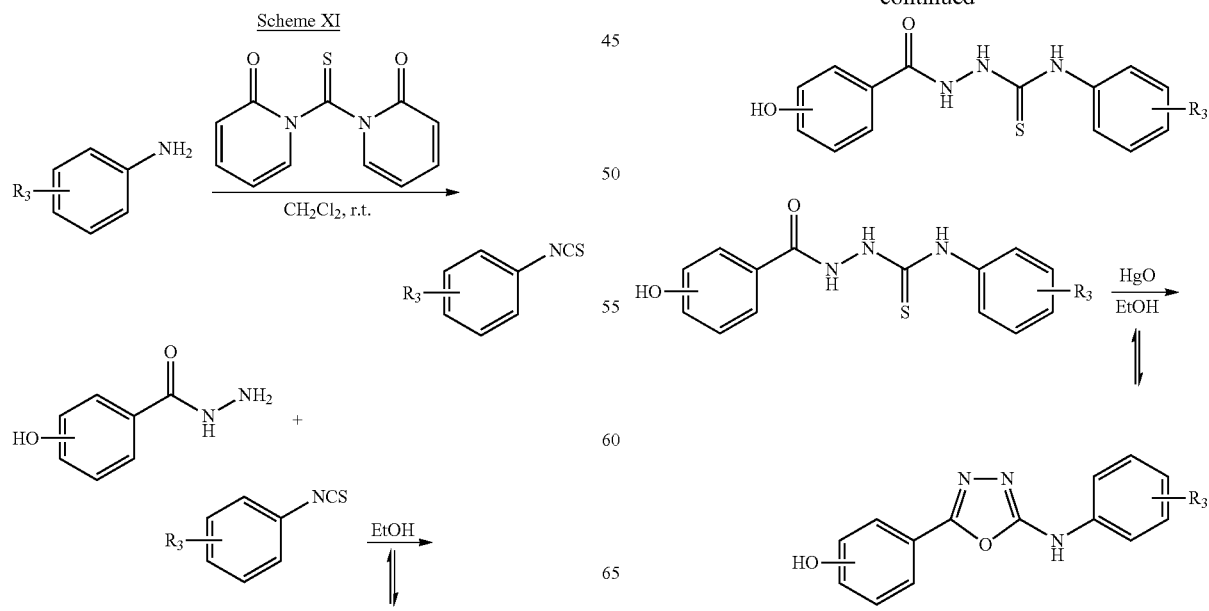

85
-continued
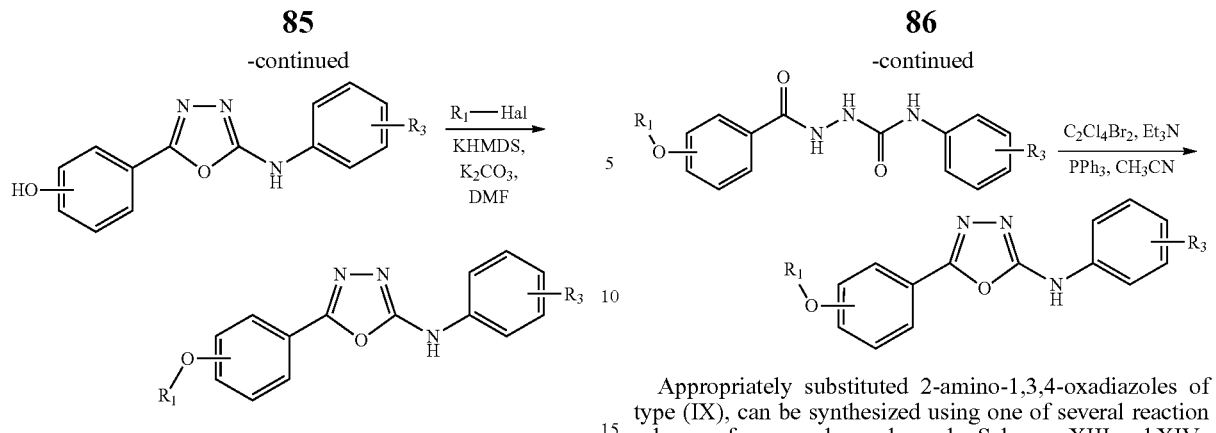
86
-continued
Appropriately substituted 2-amino-1,3,4-oxadiazoles of type (IX), can be synthesized using one of several reaction schemes, for example, as shown by Schemes XIII and XIV.
Scheme XII
Scheme XIII
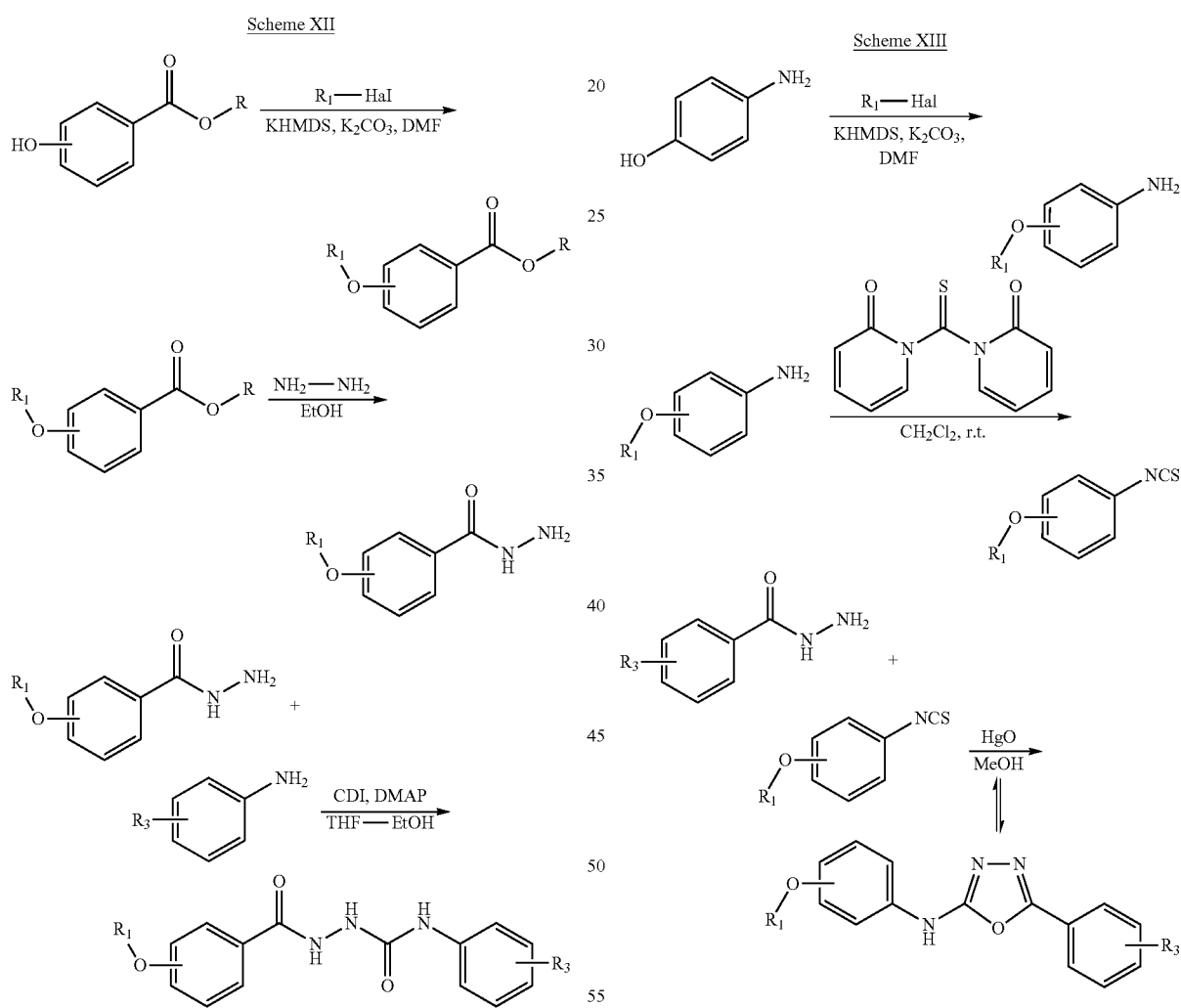
Scheme XIV
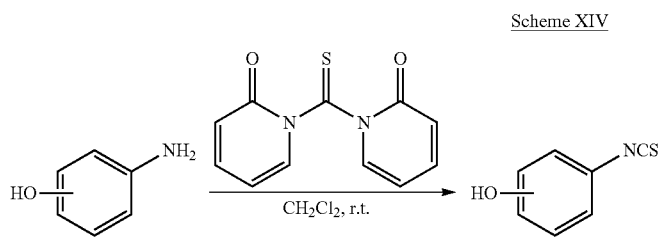

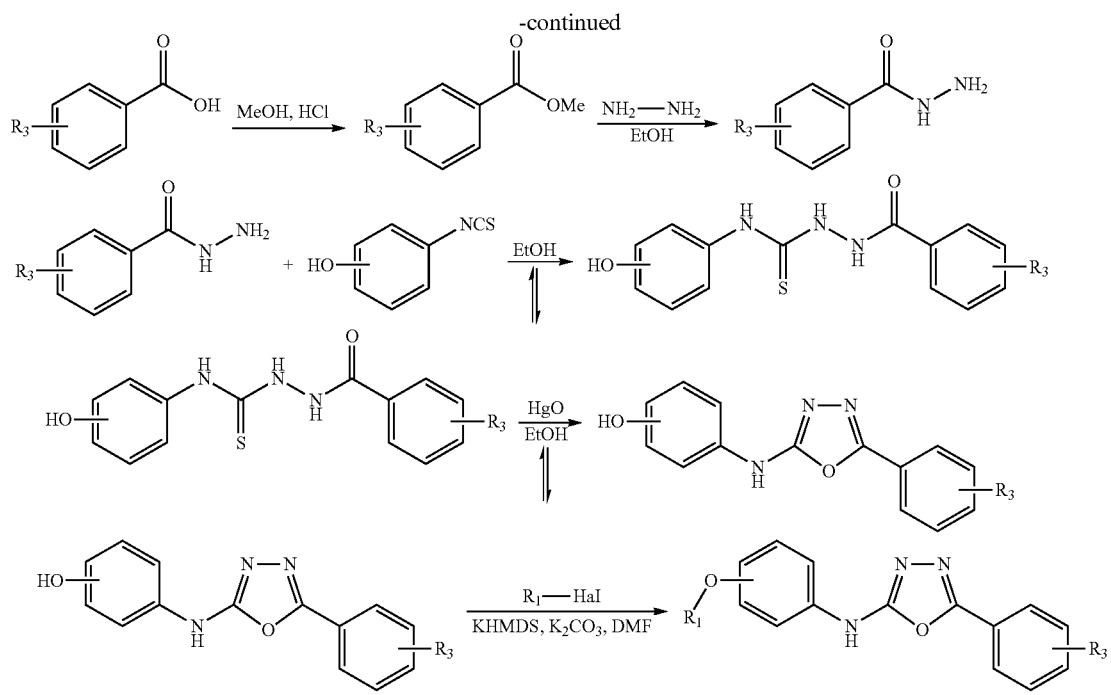
Appropriately substituted 2-amino-1,3,4-thiadiazoles of type (XI), can be prepared by a method which is outlined in Scheme XV.
Scheme XV
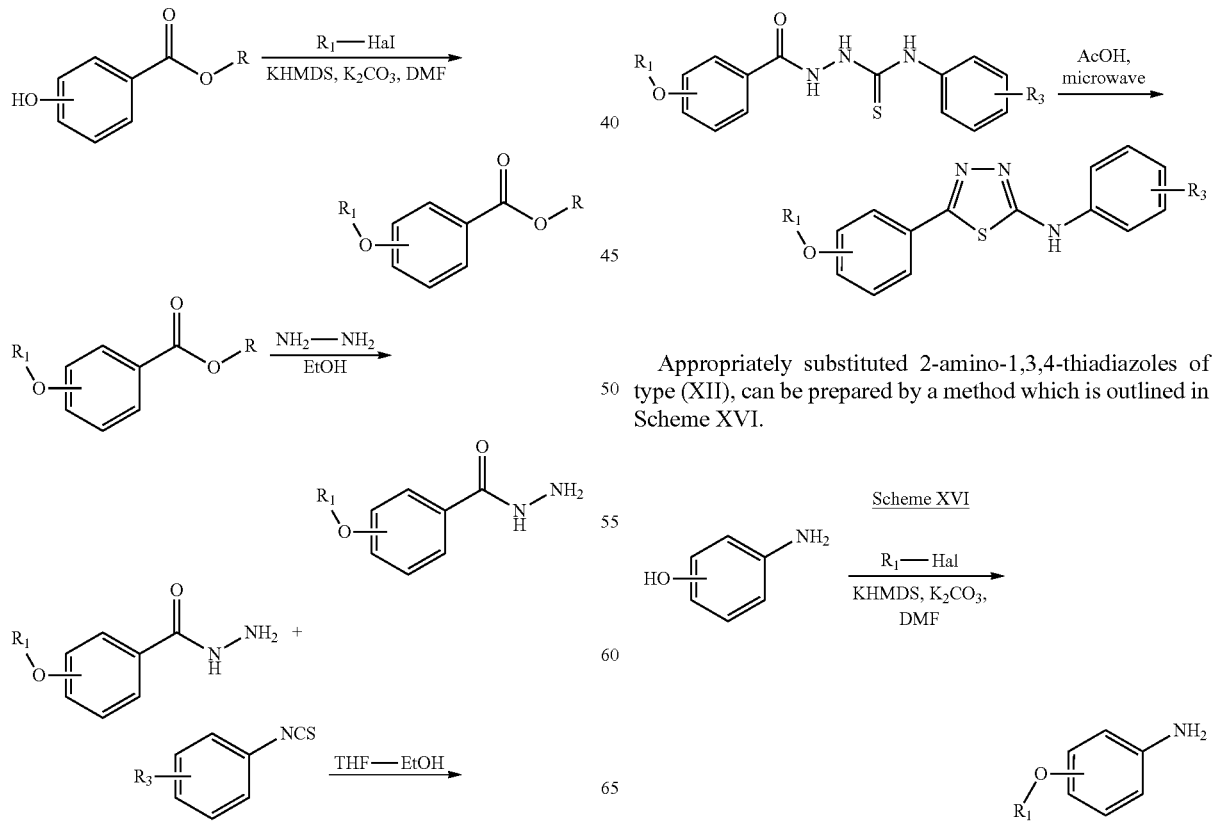
Appropriately substituted 2-amino-1,3,4-thiadiazoles of type (XII), can be prepared by a method which is outlined in Scheme XVI.
Scheme XVI

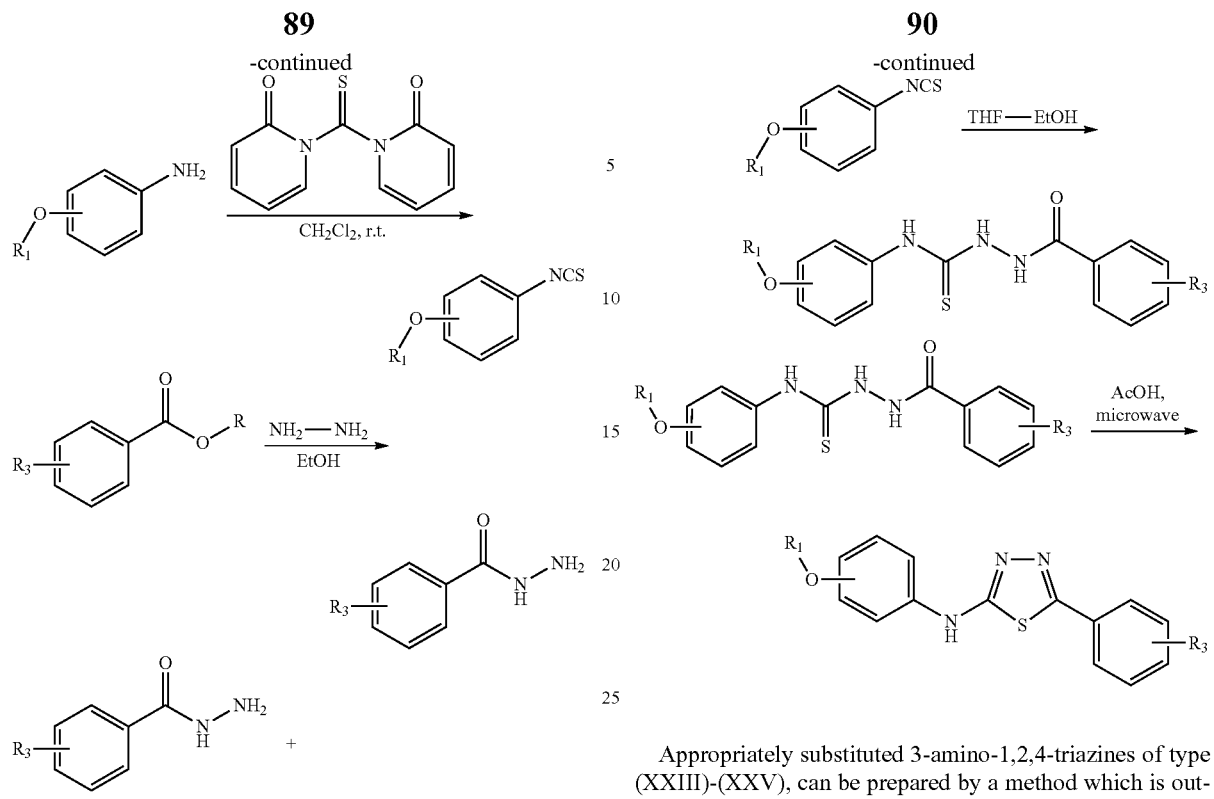
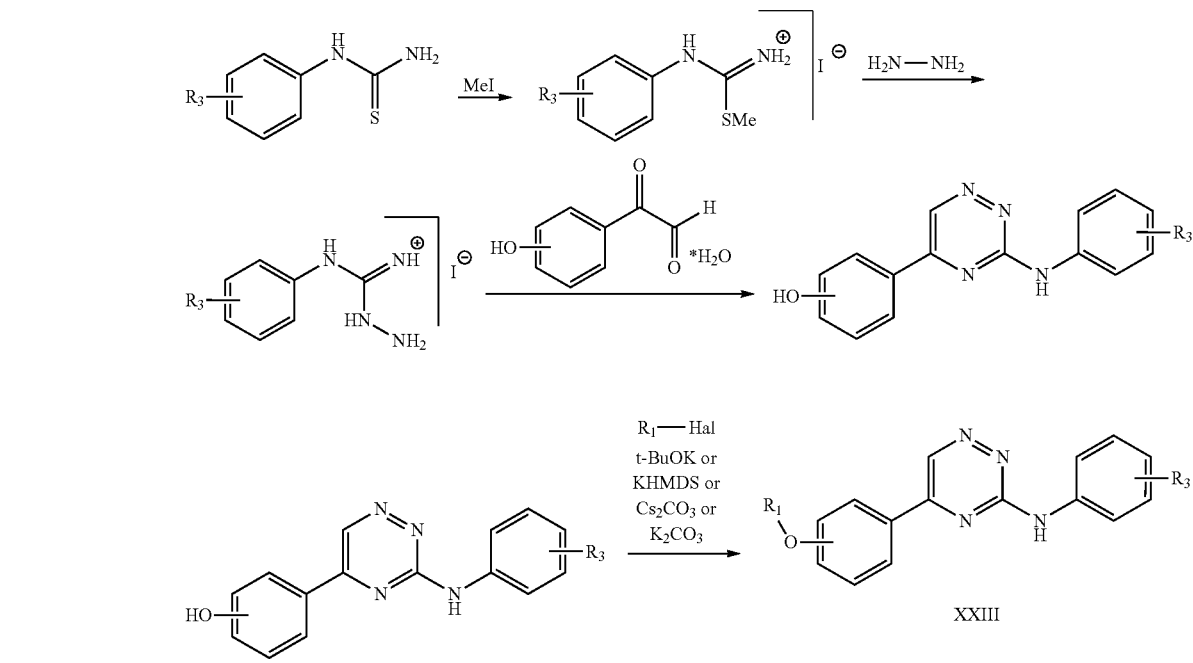
Appropriately substituted 3-amino-1,2,4-triazines of type (XXIII)-(XXV), can be prepared by a method which is outlined in Scheme XVII.
Scheme XVII
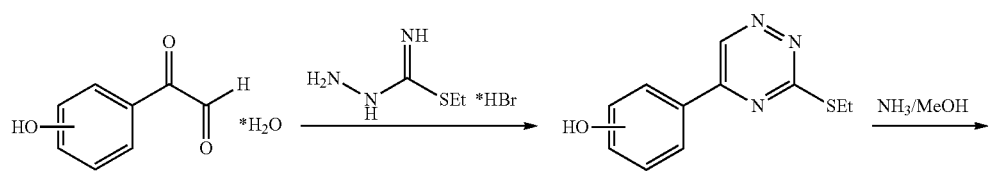

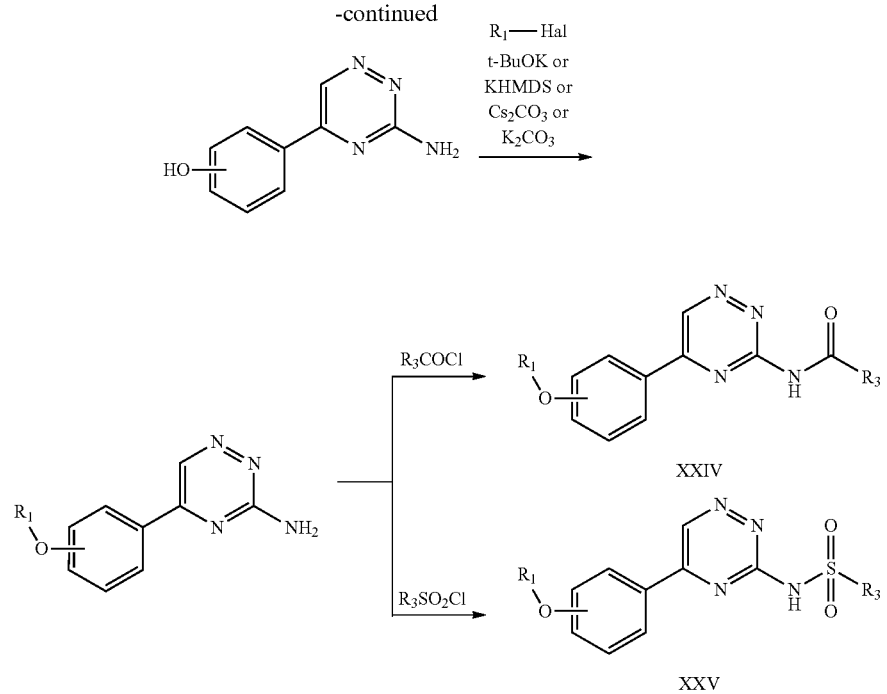
Appropriately substituted 3-amino-1,2,4-triazines of type (XXVI)-XXVIII), be prepared by a method which is outlined in Scheme XVIII.
Scheme XVIII
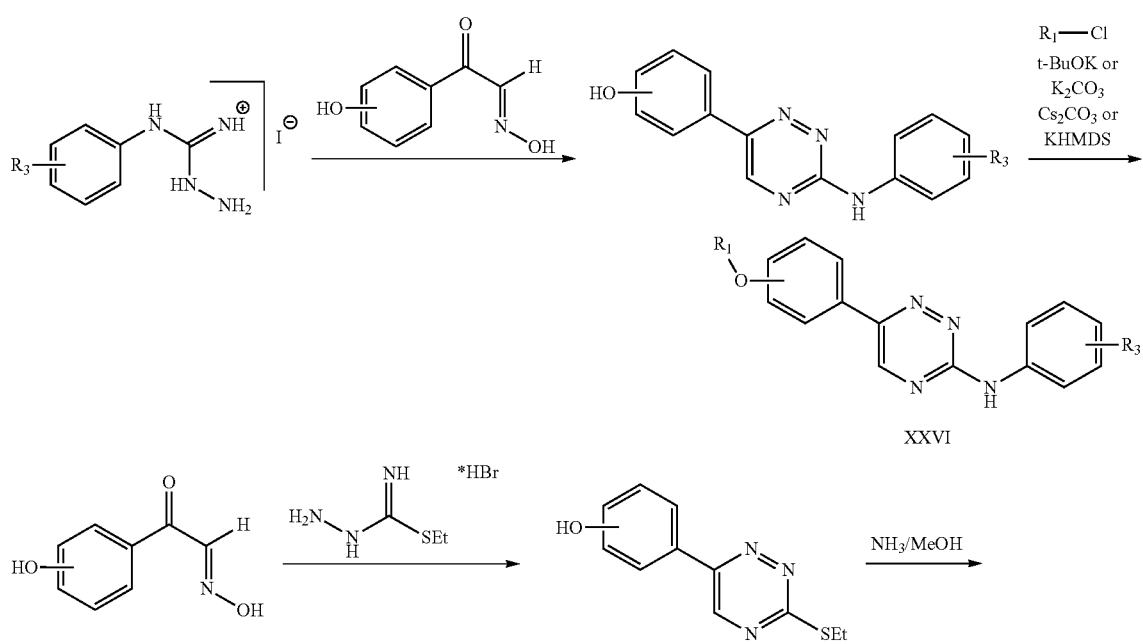

-continued

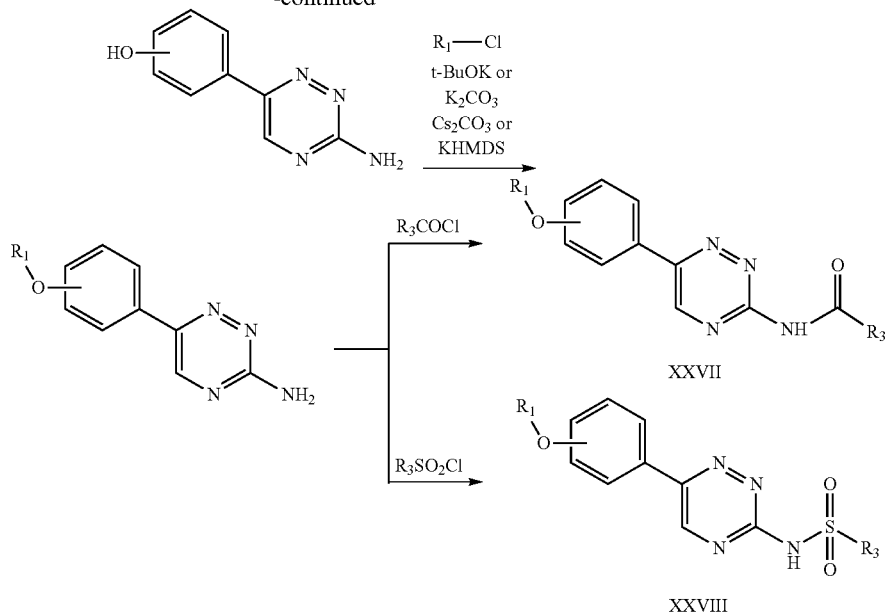

The compounds and methods of the present invention, either when administered alone or in combination with other agents (e.g., chemotherapeutic agents or protein therapeutic agents described below) are useful in treating a variety of disorders, including, but not limited to, for example, cancer, eye disease, inflammation, psoriasis, and a viral infection. The kinds of cancer that can be treated include, but are not limited to, an alimentary/gastrointestinal tract cancer, colon cancer, liver cancer, skin cancer, breast cancer, ovarian cancer, prostate cancer, lymphoma, leukemia, kidney cancer, lung cancer, muscle cancer, bone cancer, bladder cancer or brain cancer.

Embodiments of the present invention also provide articles of manufacture that can include a packaging material and a pharmaceutical composition contained within the packaging material. The packaging material can comprise a label which indicates that the pharmaceutical composition can be used for treatment of one or more disorders identified above.

The pharmaceutical composition can include a compound according to the present invention. In addition to a compound of the present invention, the pharmaceutical may also contain other therapeutic agents, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques known in the art of pharmaceutical formulation.

Thus, in one embodiment, the invention provides a pharmaceutical composition including a therapeutic agent and a compound of the invention. The compound is present in a concentration effective to treat cancer.

The compounds of the invention may be formulated into therapeutic compositions as natural or salt forms. Pharmaceutically acceptable, non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like.

Salts of the invention can include amine salts formed by the protonation of an amino group with inorganic acids such as hydrochloric acid, hydrobromic acid, hydroiodic acid, sulfuric acid, phosphoric acid, and the like. Salts of the invention can also include amine salts formed by the protonation of an amino group with suitable organic acids, such as p-toluenesulfonic acid, acetic acid, methanesulfonic acid and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs of the invention compounds are included in the present invention.

Pharmaceutical compositions of the invention may be administered by any suitable means, for example, orally, such as in the form of tablets, capsules, granules or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The pharmaceutical compositions for the administration of the compounds of this embodiment, either alone or in combination with other therapeutic agents, may conveniently be presented in dosage unit form and may be prepared by any of the methods well known in the art of pharmacy. All methods include bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butanediol, polyethylene glycols, polypropylene glycols, ethanol or other alcohols, povidones, various brands of TWEEN surfactant, sodium dodecyl sulfate, sodium deoxycholate, dimethylacetamide, polysorbates, poloxamers, cyclodextrins, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton, Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles).

In one embodiment, the invention compounds are administered in combination with an anti-inflammatory agent, antihistamines, chemotherapeutic agent, immunomodulator, therapeutic antibody or a protein kinase inhibitor, e.g., a tyrosine kinase inhibitor, to a subject in need of such treatment. While not wanting to be limiting, chemotherapeutic agents include antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), and the like. Other chemotherapeutic agents include, for example, a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine. While not wanting to be limiting, therapeutic antibodies include antibodies directed against the HER2 protein, such as trastuzumab; antibodies directed against growth factors or growth factor receptors, such as bevacizumab, which targets vascular endothelial growth factor, and OSI-774 which targets epidermal growth factor; antibodies targeting integrin receptors, such as Vitaxin (also known as MEDI-522), and the like. Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-16], and Teniposide [VM-26], etc.), and agents that target topoisomerase I (e.g., Camptothecin and Isirinotecan [CPT-11], etc.); 2) covalent DNA-binding agents [alkylating agents], including, nitrogen mustards (e.g., Mechlorethamine, Chlorambucil, Cyclophosphamide, Ifosphamide, and Busulfan [Myleran], etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents [antitumor antibiotics], including, nucleic acid inhibitors (e.g., Dactinomycin [Actinomycin D], etc.), anthracyclines (e.g., Daunorubicin [Daunomycin, and Cerubidine], Doxorubicin [Adriamycin], and Idarubicin [Idamycin], etc.), anthracenediones (e.g., anthracycline analogues, such as, [Mitoxantrone], etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine [6-MP, Purinethol], 6-Thioguanine [6-TG], Azathioprine, Acyclovir, Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)] etc.), and cytosine arabinosides (e.g., Cytosar [ara-C] and Fludarabine, etc.); 5) enzymes, including, L-asparaginase; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole [Arimidex], etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons [e.g., IFN-.alpha., etc.] and interleukins [e.g., IL-2, etc.], etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) inhibitors of angiogenesis.

The pharmaceutical composition and method of the present invention may further comprise other therapeutically active compounds as noted herein which are usually applied in the treatment of the above mentioned pathological conditions. Examples of other therapeutic agents include the following: cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD 80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

Other agents that may be administered in combination with invention compounds include protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay.

The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

When other therapeutic agents are employed in combination with the compounds of the present invention they may be used for example in amounts as noted in the Physician Desk Reference (PDR) or as otherwise determined by one having ordinary skill in the art.

In the treatment or prevention of conditions which involve cellular proliferation, an appropriate dosage level can generally be between about 0.01 and about 1000 mg per 1 kg of patient body weight per day which can be administered in single or multiple doses. For example, the dosage level can be between about 0.01 and about 250 mg/kg per day; more narrowly, between about 0.5 and about 100 mg/kg per day. A suitable dosage level can be between about 0.01 and about 250 mg/kg per day, between about 0.05 and about 100 mg/kg per day, or between about 0.1 and about 50 mg/kg per day, or about 1.0 mg/kg per day. For example, within this range the dosage can be between about 0.05 and about 0.5 mg/kg per day, or between about 0.5 and about 5 mg/kg per day, or between about 5 and about 50 mg/kg per day. For oral administration, the compositions can be provided in the form of tablets containing between about 1.0 and about 1,000 mg of the active ingredient, for example, about 1.0, about 5.0, about 10.0, about 15.0, about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, and about 1,000.0 mg of the active ingredient for the symptomatic adjustment of the dosage to the patient to be treated. The compounds can be administered on a regimen of 1 to 4 times per day, such as once or twice per day. There may be a period of no administration followed by another regimen of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of the present invention can be used, alone or in combination with an effective amount of a therapeutic antibody or chemically attached to a tumor tissue targeting antibody (or therapeutic fragment thereof), a chemotherapeutic or an immunotoxic agent, for treatment of tumors. Illustrative examples of chemotherapeutic agents that can be used for this purpose include doxorubicin, docetaxel, or taxol. It should be further understood that the invention includes combination therapy including a compound of the invention, including but not limited to vasculostatic agents, such as tyrosine, serine or threonine kinase inhibitors, for example, Src-family inhibitors, and any chemotherapeutic agent or therapeutic antibody.

The present invention also provides screening assays using appropriate cells which express any kinases within the MAPK pathway. Such cells include cells from mammals, yeast, Drosophila or E. coli. For example, cells which express the Raf polypeptide or any kinase downstream of Raf such as MEK or ERK1/2 or respond to Raf polypeptide or MAPK pathway polypeptides are contacted with a test compound to observe binding, or stimulation or inhibition of a functional response. The cells which are contacted with the candidate compound are compared with the same cells which are not contacted for Raf polypeptide or MAPK pathway polypeptide activity This invention contemplates the treatment and/or amelioration of such diseases by administering a MAPK pathway polypeptides inhibiting amount of a compound. Without wishing to be bound by any particular theory of the functioning of the MAPK pathway polypeptides, it is believed that among the useful inhibitors of MAPK pathway polypeptides function are those compounds which inhibit the kinase activity of the MAPK pathway polypeptides. Other sites of inhibition are, of course, possible owing to its position in a signal transduction cascade. Inhibitors of protein-protein interactions between, for example Raf polypeptide or MAPK pathway polypeptides and other factors could lead to the development of pharmaceutical agents for the modulation of Raf polypeptide or MAPK pathway polypeptides activity.

Targeting an allosteric site of the protein is a very promising approach for pharmaceutical intervention. Further, the traditional approach of inhibiting various protein kinases includes targeting the ATP binding site. The invention is not meant to be limited by any particular mechanism of inhibition. The assays of the invention may test binding of a candidate compound wherein adherence to the cells bearing the Raf polypeptide or MAPK pathway polypeptides is detected by means of a label directly or indirectly associated with the candidate compound or in an assay involving competition with a labeled competitor. Further, these assays may test whether the candidate compound results in a signal generated by activation of MAPK pathway polypeptides, using detection systems appropriate to the cells bearing the Raf polypeptide or MAPK pathway polypeptides. Inhibitors of activation are generally assayed in the presence of a known agonist and the effect on activation by the agonist by the presence of the candidate compound is observed. Standard methods for conducting such screening assays are well understood in the art and are also illustrated in the examples below (e.g., direct and raf1-MEK1 assays or MAPK pathway cellular assays).

The following examples are provided to further illustrate the advantages and features of the present invention, but are not intended to limit the scope of the invention.

Example 1

General Methods

Example 1 describes general synthetic procedures that were used to make the compounds described in the subsequent examples. All solvents were used without further purification. Reactions can be usually conducted without an inert gas atmosphere unless specified otherwise. The reported yields are based on unoptimized conditions and single test runs. The yields can be optimized by changing the reaction conditions, such as solvent, use of base or acid, temperature, use of catalyst and the time of the reaction. Microwave reactions were run in Emrys™ Process vials (2-5 mL) using Initiator module (Biotage/Personal chemistry). All $^1$H NMR were run on a 500 MHz Bruker NMR or Bruker Avance 400 MHz NMR. Chemical shifts are reported in delta ($\delta$) units, parts per million (ppm) downfield from tetramethylsilane. Coupling constants are reported in hertz (Hz). A Waters LC/MS system is used in identity and purity analysis. This system includes a 2795 separation module, a 996 photodiode array detector and a ZQ2000 mass spectrometer, A Zorbax SB column (150×4.6 mm 3.5μ, Agilent Technologies) was used for the LC. Column temperature was 40° C. Compounds were separated using gradient elution with mobile phases of water (0.05% TFA (A)) and acetonitrile (0.05% TFA (B)). Flow rate was 1 mL/min. The gradient program used in separation was 0-15 min: 5-60% B; 15-15.5 min: 60-100% B; 15.5-17 min: 100% B.

Example 2

Synthesis of 3-amino-benzo[1,2,4]triazine-7-ol-1-oxide

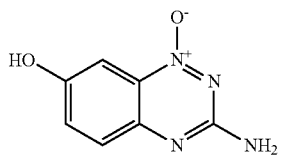 [SMILES: Nc1nc2ccc(O)cc2[n+]([O-])n1]

7.7 g (0.05 mol) of 4-amino-3-nitrophenol was dissolved in 20 mL of glacial acetic acid and the resulting bright-red solution was heated to approximately 100° C. in 500 mL round-bottom flask equipped with a long condenser. To this solution was added a solution of 16.81 g (8.0 equivalent, 0.4 mol) of cyanamide in 20 mL of concentrated hydrochloric acid. In approximately 5-10 min the reaction mixture started to boil vigorously, so the heating was removed and it was stirred without heating until boiling subsided. Then the heating was reapplied and the reaction mixture was refluxed for 48 hrs. Then 150 mL of 30% NaOH was added and the resulting dark-reddish solution was refluxed for additional 3 hrs. Then it was cooled down to room temperature and dark-red slurry was formed. The red precipitate was filtered, re-dissolved in 200 mL of water and 1N HCl was added in portions with stirring until pH reached 5-4. The solution changed color from dark-red into light-yellow and a light-yellow fine precipitate was formed. The precipitate was filtered, washed twice with 50 mL of water, twice with 50 mL of acetonitrile and finally twice with 50 mL of diethyl ether and dried in vacuum to give 4.6 g of a bright-yellow solid. Yield: 51.7%.

$^1$H NMR (DMSO-$d_6$): δ 6.96 (s, 2H), 7.35-7.38 (m, 2H), 7.45-7.47 (m, 1H), 10.36 (s, 1H).

Example 3

Synthesis of 3-amino-benzo[1,2,4]triazine-7-ol

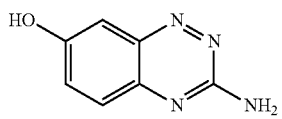 [SMILES: Nc1nnc2cc(O)ccc2n1]

4.6 g (25.82 mmol) of 3-amino-benzo[1,2,4]triazine-7-ol-1-oxide was dissolved in 200 mL of 1:1 mixture of dimethylformamide and methanol. 0.5 g of 10% Pd/C was added to this solution and H$_2$ gas was bubbled through the solution for 3 hours. The progress of the reaction was monitored by TLC, using a 9:1 mixture of dichloromethane/methanol as an eluent and a UV lamp. The starting material is highly fluorescent under UV, while the product is not. When the reaction was complete, the resulting dark solution was filtered through a short pad of silica gel and solvent was removed in vacuum to produce a dirty-brown solid. 40 mL of ethyl acetate and 40 mL of methanol were added to the solid and the resulting suspension was heated to reflux for about 10 min. Then the suspension was allowed to cool down to ambient temperature. The solid was collected by filtration, washed with 40 mL of ethyl acetate, 40 mL of diethyl ether and dried in vacuum to yield 3.2 g of the product in a form of a greenish solid. Yield: 76%.

$^1$H NMR (DMSO-$d_6$): δ 7.18 (s, 1H), 7.36 (d, J=2.6 Hz, 1H), 7.40-7.42 (dd, $J_1$=9.1 Hz, $J_2$=2.6 Hz, 1H), 7.45-7.46 (d, J=9.1 Hz, 1H).

Example 4

Synthesis of 4-chloro-pyridine-2-carboxylic acid methyl ester hydrochloride salt

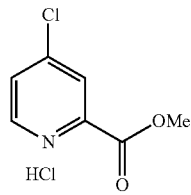 [SMILES: COC(=O)c1cc(Cl)ccn1 ; Cl]

2.4 mL (0.031 mol, 0.16 equivalent) of anhydrous N,N-dimethylformamide was added dropwise to 72 mL (1.23 mol, 5.0 equivalent) of thionyl chloride in a temperature range of 40-50° C. under argon blanket. The solution was stirred at this temperature for 10 min, then 24.0 g (0.195 mol, 1.0 equivalent) of picolinic acid was added slowly in portions. The reaction mixture was heated at 70-75° C. with a reflux condenser under argon for 30 hours. Evolution of SO$_2$ gas was observed. The reaction mixture changed colors from green to orange, then to purple over 2 hours, then resulted in an orange solution with a yellow precipitate. It was cooled down to ambient temperature and 150 mL of anhydrous toluene was added. The suspension was concentrated to about 50 mL total on rotovap. This process was repeated three times.

The resulting orange suspension was cooled down to −20° C. and 200 mL of methanol was added. The reaction mixture was left to stir at ambient temperature for 18 hours. Then the clear-yellow solution was transferred into a round-bottom flask and solvent was removed in vacuum. The resulting yellow solid was dissolved with heating to 50° C. in 50 mL of methanol, upon cooling 300 mL of diethyl ether were added. The solution was left to stand at 0° C. for 18 hours. The white precipitate that formed was collected by filtration, washed extensively with diethyl ether and dried in vacuum to yield 29.05 g of the product as a white fluffy solid. Yield: 71.5%.

$^1$H NMR (DMSO-$d_6$): δ 3.88 (s, 3H), 7.81-7.83 (dd, $J_1$=1.9 Hz, $J_2$=5.4 Hz, 1H), 8.06-8.07 (d, J=1.9 Hz, 1H), 8.68-8.69 (d, J=5.4 Hz, 1H).

Example 5

Synthesis of 4-chloro-pyridine-2-carboxylic acid methyl amide

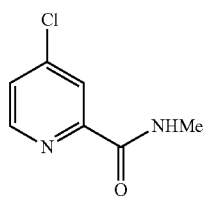 [SMILES: CNC(=O)c1cc(Cl)ccn1]

A suspension of 17.8 g (0.103 mol, 1 eq) of 4-chloro-pyridine-2-carboxylic acid methyl ester hydrochloride in 15 mL, of methanol was cooled to 0° C. and slowly treated with a 2.0 M solution of methylamine in tetrahydrofuran at a rate that kept internal temperature below 5° C. The reaction mixture was stirred at 0° C. for 2 hours, then slowly allowed to warm up to ambient temperature and stirred for 18 hours. Solvent was removed in vacuum, approx. 200 mL of ethyl acetate was added and the resulting suspension was filtered. The precipitate was washed with 100 mL of ethyl acetate. The combined ethyl acetate solutions were washed three times with 100 mL of brine and dried over sodium sulfate. Solvent was removed in vacuum to yield 14.16 g of the product as orange oil. Yield: 80.5%.

$^1$H NMR (DMSO-$d_6$): δ 2.81-2.82 (d, J=4.8 Hz, 3H), 7.73-7.75 (dd, $J_1$=2.1 Hz, $J_2$=5.4 Hz, 1H), 8.00-8.01 (d, J=2.1 Hz, 1H), 8.60-8.61 (d, J=5.4 Hz, 1H), 8.84 (q, J=4.8 Hz, 1H).

Example 6

Synthesis of 4-(3-amino-benzo[1,2,4]triazin-7-yloxy)-pyridine-2-carboxylic acid methylamide

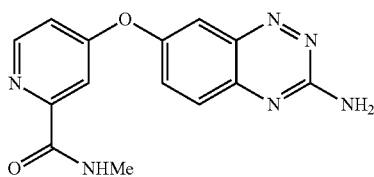 [SMILES: CNC(=O)c1cc(Oc2ccc3nc(N)nnc3c2)ccn1]

3.2 g (19.73 mmol) of 3-amino-benzo[1,2,4]triazine-7-ol was dissolved in 80 mL of anhydrous dimethylformamide under argon atmosphere. 2.44 g (21.71 mmol, 1.1 equivalent) of solid potassium tert-butoxide was added to the solution. The resulting dark-red mixture was heated to about 100° C. and stirred at that temperature for 15 min. A solution of 3.7 g (21.71 mmol, 1.1 equivalent) of 4-chloro-pyridine-2-carboxylic acid methylamide in 10 mL of anhydrous dimethylformamide was added, followed by 3.28 g (23.68 mmol, 1.2 equivalent) of anhydrous $K_2CO_3$. The reaction mixture was heated at 140° C. for 30 hrs. The progress of the reaction was monitored by LC/MS. Then it was allowed to cool down to ambient temperature. The resulting dark-brown slurry was poured into 500 mL of water and 100 mL of ethyl acetate. The formed precipitate was collected by filtration, washed with 50 mL of water, 50 mL of methanol, 50 mL of diethyl ether and dried in vacuum to produce 3.22 g of the product as a dirty-yellow solid. The filtrate was extracted four times with 100 mL of ethyl acetate. The combined extracts were washed 3 times with 100 mL of water, then with brine and dried over anhydrous sodium sulfate. Solvent was removed in vacuum to yield additional 1.2 g of the product in a form of a yellow solid. Yield: 75% combined.

$^1$H NMR (DMSO-$d_6$): δ 2.78-2.79 (d, J=4.8 Hz, 3H), 7.25-7.27 (dd, $J_1$=2.6 Hz, $J_2$=5.6 Hz, 1H), 7.50-7.51 (d, J=2.6 Hz, 1H), 7.66-7.68 (d, J=9.2 Hz, 1H), 7.71-7.73 (dd, $J_1$=2.7 Hz, $J_2$=9.2 Hz, 1H), 7.71 (s, 2H), 8.03-8.05 (d, J=2.7 Hz, 1H), 8.54-8.55 (d, J=5.6 Hz, 1H), 8.78-8.80 (q, J=4.8 Hz, 1H).

Example 7

Synthesis of 4-[3-(4-chloro-3-trifluoromethyl-phenylamino)-benzo[1,2,4]triazin-7-yloxy]-pyridine-2-carboxylic acid methylamide trifluoroacetate salt

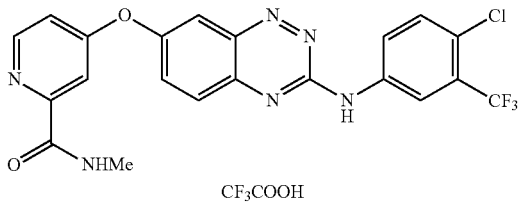 [SMILES: CNC(=O)c1cc(Oc2ccc3nc(Nc4ccc(Cl)c(C(F)(F)F)c4)nnc3c2)ccn1 ; "CF3COOH"]

CF$_3$COOH

To a vial with 2 mL of anhydrous dimethylformamide under argon atmosphere were added 15.4 mg (0.0168 mmol, 0.05 equivalent) of tris(dibenzyllideneatone) dipalladium(0), 21.0 mg (0.033 mmol, 0.1 equivalent) of BINAP, 220.0 mg (0.675 mmol, 2.0 equivalent) of anhydrous cesium carbonate, 175.1 mg (0.675 mmol, 2.0 equivalent) of 5-bromo-2-chlorobenzotrifluoride, and 100 mg (0.337 mmol, 1.0 equivalent) of 4-(3-amino-benzo[1,2,4]triazin-7-yloxy)-pyridine-carboxylic acid methylamide, in that particular order. Argon gas was bubbled through the mixture for 5 min. Then the vial was capped and the reaction mixture was heated to 120° C. with stirring under argon atmosphere for 18 hours. At this point LC/MS indicated about 40% conversion to the product. As pointed out in the previous examples, the longer reaction times result in the formation of the by-product and partial decomposition. So, the reaction mixture was allowed to cool down to ambient temperature, filtered through 0.3 μm syringe filter and purified by reverse-phase prep-HPLC using acetonitrile/water mixture with 0.1% of TFA.

ESI-MS: [M+H]$^+$, 475, 477. $^1$H NMR (DMSO-$d_6$): δ 2.79-2.90 (d, J=4.8 Hz, 3H), 7.31-7.33 (dd, $J_1$=2.4 Hz, $J_2$=5.4 Hz, 1H), 7.55-7.55 (d, J=2.4 Hz, 1H), 7.73-7.75 (d, J=8.9 Hz, 1H), 7.89-7.91 (dd, $J_1$=2.5 Hz, $J_2$+9.2 Hz, 1H), 7.94-7.95 (d, J=9.2 Hz, 1H), 8.24 (d, J=2.5 Hz, 2H), 8.25-8.27 (dd, $J_1$=2.6 Hz, $J_2$=8.9 Hz, 1H), 8.55 (d, J=2.6 Hz, 1H), 8.60 (d, J=5.4 Hz, 1H), 8.81-8.82 (q, J=4.8 Hz, 1H), 11.36 (s, 1H).

Example 8

Synthesis of 4-[3-(4-chloro-phenylamino)-benzo[1,2,4]triazin-7-yloxy]-pyridine-2-carboxylic acid methylamide trifluoroacetate salt

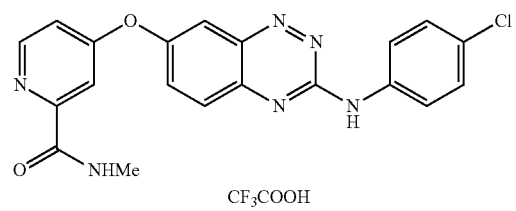 [SMILES: CNC(=O)c1cc(Oc2ccc3nc(Nc4ccc(Cl)cc4)nnc3c2)ccn1 ; "CF3COOH"]

CF$_3$COOH

To a vial with 2 mL of anhydrous dimethylformamide under argon atmosphere were added 15.4 mg (0.0168 mmol, 0.05 equivalent) of tris(dibenzyllideneatone) dipalladium(0), 21.0 mg (0.033 mmol, 0.1 equivalent) of BINAP, 220.0 mg (0.675 mmol, 2.0 equivalent) of anhydrous cesium carbonate, 161.0 mg (0.675 mmol, 2.0 equivalent) of 1-chloro-4-iodobenzene, and 100 mg (0.337 mmol, 1.0 equivalent) of 4-(3-amino-benzo[1,2,4]triazin-7-yloxy)-pyridine-carboxylic acid methylamide, in that particular order. Argon gas was bubbled through the mixture for 5 min. Then the vial was capped and the reaction mixture was heated to 120° C. with stirring under argon atmosphere for 18 hours. At this point LC/MS indicated about 30% conversion to the product. As it was observed from previous examples, the longer reaction times result in the formation of the by-product and partial decomposition. The reaction mixture was allowed to cool down to ambient temperature, filtered, through 0.22μ syringe filter and purified by reverse-phase preperative HPLC using acetonitrile/water mixture with 0.1% of TFA.

ESI-MS: [M+H]$^+$, 407, 409. $^1$H NMR (DMSO-d$_6$): δ 2.79-2.80 (d, J=4.88 Hz, 3H), 7.30-7.32 (dd, J$_1$=2.6 Hz, J$_2$=5.6 Hz, 1H), 7.44-7.46 (d, J=6.8 Hz, 2H), 7.54-7.55 (d, J=2.6 Hz, 1H), 7.84-7.87 (dd, J$_1$=2.6 Hz, J$_2$=9.05 Hz, 1H), 7.92-7.94 (d, J=9.05 Hz, 1H), 8.00-8.01 (d, J=6.8 Hz, 2H), 8.19-8.20 (d, J=2.6 Hz, 1H), 8.58-8.59 (d, J=5.6 Hz, 1H), 8.81-8.82 (q, J=4.88 Hz, 1H), 11.08 (s, 1H).

Example 9

Synthesis of 4-[3-(3-trifluoromethyl-benzenesulfonylamino)-benzo[1,2,4]triazin-7-yloxy]-pyridine-2-carboxylic acid methyl amide trifluoroacetate salt

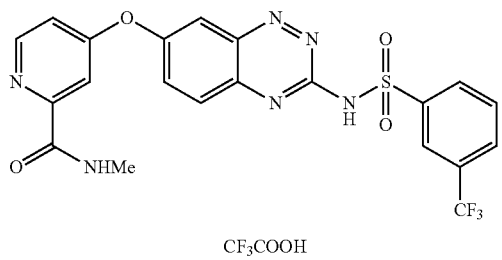 [SMILES: CNC(=O)c1cc(Oc2ccc3nc(NS(=O)(=O)c4cccc(C(F)(F)F)c4)nnc3c2)ccn1 ; "CF3COOH"]

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous dimethylformamide with heating to about 100° C. 45.4 mg (0.405 mmol, 1.2 equivalent) of solid tert-BuOK was added to the solution. The resulting dark-red solution was stirred at 100° C. for 30 min, then it was allowed to cool down to ambient temperature. 100 mg (0.405 mmol, 1.2 equivalent) of 3-trifluoromethyl-benzenesulfonyl chloride was added to the mixture via a syringe. It was allowed to stir at ambient temperature for 2 hours. The reaction mixture was filtered through 0.22μ syringe filter and purified by reverse-phase preperative HPLC using acetonitrile/water mixture with 0.1% of TFA.

ESI-MS: [M+H]$^+$, 505, 506, 507. $^1$H NMR (DMSO-d$_6$): δ 2.78-2.79 (d, J=4.8 Hz, 3H), 7.29-7.31 (dd, J$_1$=2.6 Hz, J$_2$=5.7 Hz, 1H), 7.56 (d, J=2.6 Hz, 1H), 7.87-7.90 (t, J=7.8 Hz, 1H), 7.93-7.94 (d, J=9.2 Hz, 1H), 7.97-7.99 (dd, J$_1$=2.6 Hz, J$_2$=9.2 Hz, 1H), 8.06-8.08 (d, J=7.8 Hz, 1H), 8.21 (d, J=2.5 Hz, 1H), 8.43-8.46 (m, 2H), 8.57-8.58 (d, J=5.7 Hz, 1H), 8.80-8.81 (q, J=4.8 Hz, 1H).

Example 10

Synthesis of 4-[3-(3-trifluoromethyl-benzoylamino)-benzo[1,2,4]triazin-7-yloxy]-pyridine-2-carboxylic acid methyl amide trifluoroacetate salt

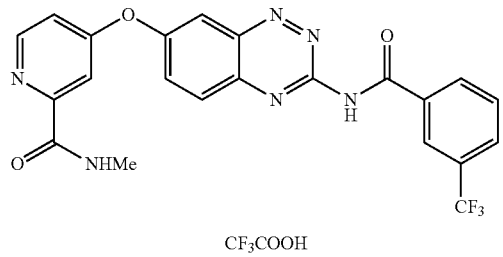 [SMILES: CNC(=O)c1cc(Oc2ccc3nc(NC(=O)c4cccc(C(F)(F)F)c4)nnc3c2)ccn1 ; "CF3COOH"]

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous dimethylformamide with heating to about 100° C. 45.4 mg (0.405 mmol, 1.2 equivalent) of solid tert-BuOK was added to the solution. The resulting dark-red solution was stirred at 100° C. for 30 min, then it was allowed to cool down to ambient temperature. 84.5 mg (0.405 mmol, 1.2 equivalent) of 3-trifluoromethyl-benzoyl chloride was added to the mixture via a syringe. It was allowed to stir at ambient temperature for 2 hours. The reaction mixture was filtered through 0.22μ syringe filter and purified by reverse-phase prep-HPLC using acetonitrile/water mixture with 0.1% of TFA.

ESI-MS: [M+H]$^+$, 469, 470. $^1$H NMR (DMSO-d$_6$): δ 2.80-2.81 (d, J=4.88 Hz, 3H), 7.37-7.39 (dd, J$_1$=2.6 Hz, J$_2$=5.7 Hz, 1H), 7.64 (d, J=2.6 Hz, 1H), 7.81-7.84 (t, J=7.8 Hz, 1H), 8.03-8.06 (m, 2H), 8.15-8.17 (d, J=9.2 Hz, 1H), 8.33-8.34 (d, J=2.6 Hz, 1H), 8.36-8.38 (d, J=8.0 Hz, 1H), 8.45 (s, 1H), 8.62-8.63 (d, J=5.7 Hz, 1H), 8.84-8.85 (q, J=4.88 Hz, 1H), 12.29 (s, 1H).

Example 11

Synthesis of 4-[4-(trifluoromethoxy-benzoylamino)-benzo[1,2,4]triazin-7-yloxy]-pyridine-2-carboxylic acid methyl amide trifluoroacetate salt

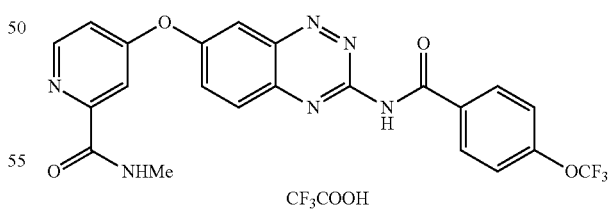

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous DMF with heating to about 100° C. 45.4 mg (0.405 mmol, 1.2 equivalent) of solid t-BuOK was added to the solution. The resulting dark-red solution was stirred at 100° C. for 30 min, then allowed to cool down to ambient temperature. 64 μL (91.0 mg, 0.405 mmol, 1.2 equivalent) of 4-trifluoromethoxy-benzoyl chloride was added to the mixture via a syringe. It was allowed to stir at ambient temperature for 2 hours. The reaction mixture was filtered through 0.22μ syringe filter and purified by reverse-phase prep-HPLC using acetonitrile/water mixture with 0.1% of TFA as a solvent system.

ESI-MS: [M+H]$^+$, 485, 486. $^1$H NMR (DMSO-d$_6$): δ 2.80-2.81 (d, J=4.8 Hz, 3H), 7.37-7.38 (dd, J$_1$=2.6 Hz, J$_2$=5.6 Hz, 1H), 7.55-7.57 (d, J=8.8 Hz, 2H), 7.63-7.64 (d, J=2.6 Hz, 1H), 8.03-8.05 (dd, J$_1$=2.7 Hz, J$_2$=9.1 Hz, 1H), 8.14-8.15 (d, J=9.1 Hz, 1H), 8.20-8.22 (d, J=8.8 Hz, 2H), 8.32-8.33 (d, J=2.7 Hz, 1H), 8.83-8.84 (q, J=4.8 Hz, 1H), 12.12 (s, 1H).

Example 12

Synthesis of 4-[3-(trifluoromethoxy-benzoylamino)-benzo[1,2,4]triazin-7-yloxy]-pyridine-2-carboxylic acid methyl amide trifluoroacetate salt

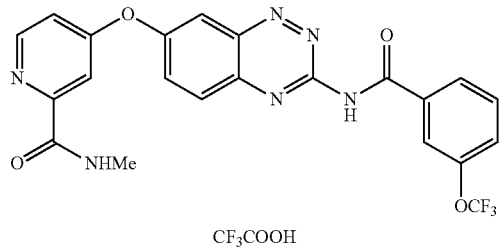 [SMILES: CNC(=O)c1cc(Oc2ccc3nc(NC(=O)c4cccc(OC(F)(F)F)c4)nnc3c2)ccn1 ; "CF3COOH"]

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous DMF with heating to about 100° C. 45.4 mg (0.405 mmol, 1.2 equivalent) of solid t-BuOK was added to the solution. The resulting dark-red solution was stirred at 100° C. for 30 min, then it was allowed to cool down to ambient temperature. 64 μL (91.0 mg, 0.405 mmol, 1.2 equivalent) of 3-trifluoromethoxy-benzoyl chloride was added to the mixture via a syringe. It was allowed to stir at ambient temperature for 2 hours. The reaction mixture was filtered through 0.22μ syringe filter and purified by reverse-phase prep-HPLC using acetonitrile/water mixture with 0.1% of TFA as a solvent system.

ESI-MS: [M+H]$^+$, 485, 486. $^1$H NMR (DMSO-d$_6$): δ 2.80-2.81 (d, J=4.8 Hz, 3H), 7.37-7.39 (dd, J$_1$=2.5 Hz, J$_2$=5.6 Hz, 1H), 7.63-7.64 (d, J=2.6 Hz, 1H), 7.67-7.74 (m, 2H), 8.03-8.05 (dd, J$_1$=2.8 Hz, J$_2$=9.36 Hz, 1H), 8.05 (m, 1H), 8.12-8.14 (m, 1H), 8.14-8.16 (d, J=9.36 Hz, 1H), 8.33 (d, J=2.8 Hz, 1H), 8.62-8.63 (d, J=5.7 Hz, 1H), 8.83-8.84 (q, J=4.8 Hz, 1H), 12.21 (s, 1H).

Example 13

Synthesis of 4-[3-(chloro-benzenesulfonylamino)-benzo[1,2,4]triazin-7-yloxy]-pyridine-2-carboxylic acid methyl amide trifluoroacetate salt

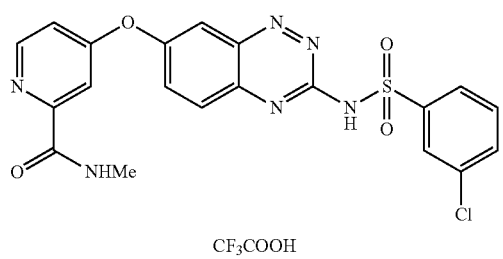 [SMILES: CNC(=O)c1cc(Oc2ccc3nc(NS(=O)(=O)c4cccc(Cl)c4)nnc3c2)ccn1 ; "CF3COOH"]

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous DMF with heating to about 100° C. 45.4 mg (0.405 mmol, 1.2 equivalent) of solid t-BuOK was added to the solution. The resulting dark-red solution was stirred at 100° C. for 30 min, then it was allowed to cool down to ambient temperature. 85.8 mg (0.405 mmol, 1.2 equivalent) of 3-chloro-benzene sulfonyl chloride was added to the mixture via a syringe. It was allowed to stir at ambient temperature for 2 hours. The reaction mixture was filtered through 0.22μ syringe filter and purified by reverse-phase prep-HPLC using acetonitrile/water mixture with 0.1% of TFA.

ESI-MS: [M+H]$^+$, 471, 473, 474. $^1$H NMR (DMSO-d$_6$): δ 2.78-2.79 (d, J=4.9 Hz, 3H), 7.30-7.32 (dd, J$_1$=2.6 Hz, J$_2$=5.6 Hz, 1H), 7.57 (d, J=2.6 Hz, 1H), 7.65-7.68 (t, J=9.0 Hz, 1H), 7.75-7.77 (m, 1H), 7.98-7.99 (m, 2H), 8.10-8.12 (d, J=7.8 Hz, 1H), 8.15 (t, J=1.8 Hz, 1H), 8.22 (d, J=2.5 Hz, 1H), 8.57-8.58 (d, J=5.4 Hz, 1H), 8.80-8.83 (q, J=4.9 Hz, 1H).

Example 14

Synthesis of 4-[2-(trifluoromethyl-benzenesulfonylamino)-benzo[1,2,4]triazin-7-yloxy]-pyridine-2-carboxylic acid methyl amide trifluoroacetate salt

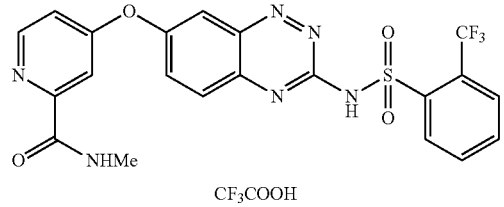 [SMILES: CNC(=O)c1cc(Oc2ccc3nc(NS(=O)(=O)c4ccccc4C(F)(F)F)nnc3c2)ccn1 ; "CF3COOH"]

CF$_3$COOH 100 mg (0.337 mmol, 1.0 equivalent) of 4-(3-amino-benzo[1,2,4]triazin-7-yloxy)-pyridine-carboxylic acid methylamide were dissolved in 2 mL of anhydrous DMF with heating to about 100° C. 45.4 mg (0.405 mmol, 1.2 equivalent) of solid t-BuOK was added to the solution. The resulting dark-red solution was stirred at 100° C. for 30 min, then it was allowed to cool down to ambient temperature. 100 mg (0.405 mmol, 1.2 equivalent) of 2-trifluoromethyl-benzenesulfonyl chloride was added to the mixture via a syringe. It was allowed to stir at ambient temperature for 2 hours. The reaction mixture was filtered through 0.22μ syringe filter and purified by reverse-phase prep-HPLC using acetonitrile/water mixture with 0.1% of TFA.

ESI-MS: [M+H]$^+$, 505, 506, 507. $^1$H NMR (DMSO-d$_6$): δ 2.78-2.79 (d, J=4.8 Hz, 3H), 7.29-7.31 (dd, J$_1$=2.6 Hz, J$_2$=5.7 Hz, 1H), 7.56 (d, J=2.6 Hz, 1H), 7.87-7.99 (m, 5H), 8.21 (d, J=2.6 Hz, 1H), 8.56-8.58 (d, 1H), 8.59-8.60 (d, J=8.0 Hz, 1H), 8.80-8.81 (q, J=4.8 Hz, 1H).

Example 15

Synthesis of 4-[2-chloro-5-(trifluoromethyl-benzenesulfonylamino)-benzo[1,2,4]triazin-7-yloxy]-pyridine-2-carboxylic acid methyl amide trifluoroacetate salt

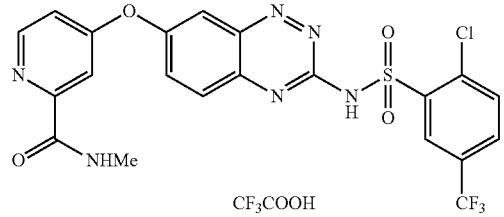 [SMILES: CNC(=O)c1cc(Oc2ccc3nc(NS(=O)(=O)c4cc(C(F)(F)F)ccc4Cl)nnc3c2)ccn1 ; "CF3COOH"]

CF$_3$COOH

The experimental procedure that was used was the same as described in Example 9.

ESI-MS: [M+H]$^+$, 539, 541, 542. $^1$H NMR (DMSO-d$_6$): δ (ppm) 2.78-2.79 (d, J=4.9 Hz, 3H), 7.27-7.29 (dd, J$_1$=2.6 Hz, J$_2$=5.7 Hz, 1H), 7.55 (d, J=2.6 Hz, 1H), 7.63-7.65 (d, J=9.1 Hz, 1H), 7.86-7.88 (d, J=8.4 Hz, 1H), 7.91-7.94 (dd, J$_1$=2.6 Hz, J$_2$=9.1 Hz, 1H), 8.04-8.06 (dd, J$_1$=2.0 Hz, J$_2$=8.4 Hz, 1H), 8.17-8.18 (d, J=2.6 Hz, 1H), 8.56-8.57 (d, J=5.7 Hz, 1H), 8.60-8.61 (d, J=2.0 Hz, 1H), 8.80-8.81 (q, J=4.9 Hz, 1H).

Example 16

Synthesis of 4-[3-chloro-6-methoxy-benzenesulfonylamino)-benzo[1,2,4]triazin-7-yloxy]-pyridine-2-carboxylic acid methyl amide trifluoroacetate salt

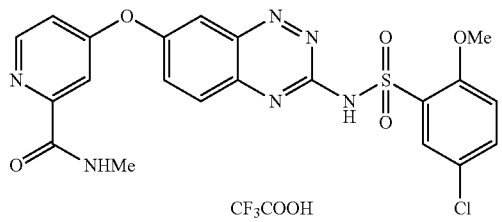 [SMILES: CNC(=O)c1cc(Oc2ccc3nc(NS(=O)(=O)c4cc(Cl)ccc4OC)nnc3c2)ccn1 ; "CF3COOH"]

The experimental procedure that was used was the same as described in Example 9.

ESI-MS: [M+H]$^+$, 501, 503, 504. $^1$H NMR (DMSO-d$_6$): δ (ppm) 2.78-2.79 (d, J=4.9 Hz, 3H), 3.85 (s, 3H), 7.20-7.22 (d, J=8.9 Hz, 1H), 7.29-7.31 (dd, J=2.6 Hz, J$_2$=5.7 Hz, 1H), 7.55 (d, J=2.6 Hz, 1H), 7.67-7.70 (dd, J$_1$=2.8 Hz, J$_2$=8.9 Hz, 1H), 7.80-7.81 (d, J=9.2 Hz, 1H), 7.92-7.95 (dd, J$_1$=2.8 Hz, J$_2$=9.2 Hz, 1H), 8.05-8.06 (d, J=2.8 Hz, 1H), 8.19-8.20 (d, J=2.6 Hz, 1H), 8.57-8.58 (d, J=5.6 Hz, 1H), 8.80-8.81 (q, J=4.9 Hz, 1H), 13.00 (br.s. 1H).

Example 17

Synthesis of 4-[3-(5-chloro-thiophene-2-sulfonylamino)-benzo[1,2,4]triazin-7-yloxy]-pyridine-2-carboxylic acid methyl amide trifluoroacetate salt

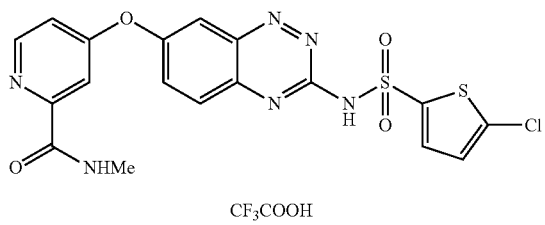 [SMILES: CNC(=O)c1cc(Oc2ccc3nc(NS(=O)(=O)c4ccc(Cl)s4)nnc3c2)ccn1 ; "CF3COOH"]

The experimental procedure that was used was the same as described in Example 9.

ESI-MS: [M+H]$^+$, 477, 479. $^1$H NMR (DMSO-d$_6$): δ (ppm) 2.79-2.80 (d, J=4.8 Hz, 3H), 7.26-7.27 (d, J=4.1 Hz, 1H), 7.32-7.34 (dd, J$_1$=2.6 Hz, J$_2$=5.6 Hz, 1H), 7.59 (d, J=2.6 Hz, 1H), 7.88-7.89 (d, J=4.1 Hz, 1H), 7.99-8.02 (dd, J$_1$=2.7 Hz, J$_2$=9.1 Hz, 1H), 8.12-8.14 (d, J=9.1 Hz, 1H), 8.26 (d, J=2.7 Hz, 1H), 8.59 (d, J=5.6 Hz, 1H), 8.82-8.83 (q, J=4.8 Hz, 1H), 13.00 (br.s. 1H).

Example 18

Synthesis of 4-[2-chloro-3-trifluoromethyl-benzoylamino)-benzo[1,2,4]triazin-7-yloxy]-pyridine-2-carboxylic acid methyl amide trifluoroacetate salt

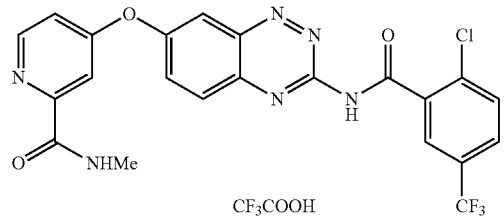 [SMILES: CNC(=O)c1cc(Oc2ccc3nc(NC(=O)c4cc(C(F)(F)F)ccc4Cl)nnc3c2)ccn1 ; "CF3COOH"]

The experimental procedure that was used was the same as described in Example 10.

ESI-MS: [M+H]$^+$, 503, 505, 506. $^1$H NMR (DMSO-d$_6$): δ (ppm) 2.80-2.81 (d, J=4.8 Hz, 3H), 7.36-7.37 (dd, J$_1$=2.6 Hz, J$_2$=5.6 Hz, 1H), 7.61 (d, J=2.6 Hz, 1H), 7.82-7.83 (d, J=8.4 Hz, 1H), 7.90-7.92 (dd, J$_1$=2.1 Hz, J$_2$=8.4 Hz, 1H), 8.00-8.03 (m, 2H), 8.09 (m, 1H), 8.29 (m, 1H), 8.61-8.62 (d, J=5.6 Hz, 1H), 8.83-8.84 (q, J=4.8 Hz, 1H), 12.41 (s, 1H).

Example 19

Synthesis of 4-[2-chloro-3-trifluoromethyl-benzoylamino)-benzo[1,2,4]triazin-7-yloxy]-pyridine-2-carboxylic acid methyl amide trifluoroacetate salt

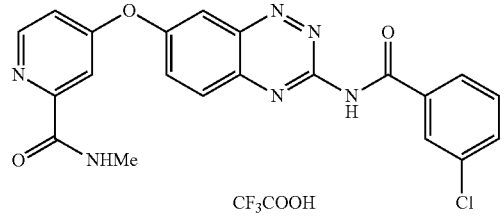 [SMILES: CNC(=O)c1cc(Oc2ccc3nc(NC(=O)c4cccc(Cl)c4)nnc3c2)ccn1 ; "CF3COOH"]

The experimental procedure that was used was the same as described in Example 10.

ESI-MS: [M+H]$^+$, 435, 437. $^1$H NMR (DMSO-d$_6$): δ (ppm) 2.80-2.81 (d, J=4.8 Hz, 3H), 7.37-7.39 (dd, J$_1$=2.6 Hz, J$_2$=5.6 Hz, 1H), 7.59-7.62 (t, J=7.8 Hz, 1H), 7.63-7.64 (d, J=2.6 Hz, 1H), 7.72-7.74 (m, 1H), 8.03-8.05 (m, 2H), 8.13 (m, 1H), 8.15 (d, J=9.1 Hz, 1H), 8.33 (d, J=2.6 Hz, 1H), 8.62-8.63 (d, J=5.6 Hz, 1H), 8.83-8.84 (q, J=4.8 Hz, 1H), 12.12 (s, 1H).

Example 20

Synthesis of 4-[2,4-dichloro-benzoylamino)-benzo[1,2,4]triazin-7-yloxy]-pyridine-2-carboxylic acid methyl amide trifluoroacetate salt

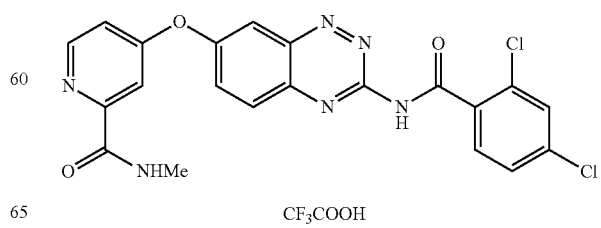

The experimental procedure that was used was the same as described in Example 10.

ESI-MS: [M+H]$^+$, 469, 471, 472. $^1$H NMR (DMSO-d$_6$): δ (ppm) 2.80-2.81 (d, J=4.8 Hz, 3H), 7.35-7.37 (dd, J$_1$=2.6 Hz, J$_2$=5.6 Hz, 1H), 7.55-7.57 (dd, J$_1$=1.9 Hz, J$_2$=8.3 Hz, 1H), 7.61 (d, J=2.6 Hz, 1H), 7.68-7.69 (d, J=8.3 Hz, 1H), 7.76-7.77 (d, J=1.9 Hz, 1H), 8.01 (m, 2H), 8.28-8.29 (m, 1H), 8.61 (d, J=5.6 Hz, 1H), 8.83-8.84 (q, J=4.8 Hz, 1H), 12.28 (s, 1H).

Example 21

Synthesis of 4-[2-fluoro-3-chloro-5-trifluoromethyl-benzoylamino)-benzo[1,2,4]triazin-7-yloxy]-pyridine-2-carboxylic acid methyl amide trifluoroacetate salt

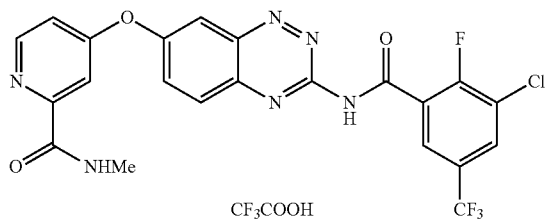 [SMILES: CNC(=O)c1cc(Oc2ccc3nc(NC(=O)c4cc(C(F)(F)F)cc(Cl)c4F)nnc3c2)ccn1 ; "CF3COOH"]

The experimental procedure that was used was the same as described in Example 10.

ESI-MS: [M+H]$^+$, 521, 523, 524, $^1$H NMR (DMSO-d$_6$): δ (ppm) 2.80-2.81 (d, J=4.8 Hz, 3H), 7.36-7.38 (dd, J$_1$=2.6 Hz, J$_2$=5.6 Hz, 1H), 7.62 (d, J=2.6 Hz, 1H), 8.02-8.05 (dd, J$_1$=2.6 Hz, J$_2$=9.2 Hz, 1H), 8.07-8.09 (d, J=9.2 Hz, 1H), 8.14-8.15 (dd, 1H), 8.31-8.32 (d, 2.6 Hz, 1H), 8.33-8.34 (dd, J$_1$=2.1 Hz, J$_2$=6.4 Hz, 1H), 8.62 (d, J=5.6 Hz, 1H), 8.83-8.84 (q, J=4.8 Hz, 1H), 12.45 (s, 1H).

Example 22

Synthesis of 4-[3-(4-chloro-3-trifluoromethyl-benzoylamino)-benzo[1,2,4]triazin-7-yloxy]pyridine-2-carboxylic acid meth amide trifluoroacetate salt

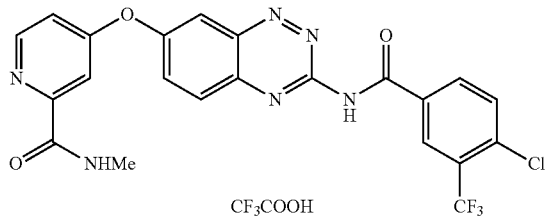 [SMILES: CNC(=O)c1cc(Oc2ccc3nc(NC(=O)c4ccc(Cl)c(C(F)(F)F)c4)nnc3c2)ccn1 ; "CF3COOH"]

The experimental procedure that was used was the same as described in Example 10, ESI-MS: [M+H]$^+$, 503, 505, 506. $^1$H NMR (DMSO-d$_6$): δ (ppm) 2.80-2.81 (d, J=4.8 Hz, 3H), 7.37-7.39 (dd, J$_1$=2.6 Hz, J$_2$=5.6 Hz, 1H), 7.63-7.64 (d, J=2.6 Hz, 1H), 7.95-7.97 (d, J=8.4 Hz, 1H), 8.04-8.06 (dd, J$_1$=2.7 Hz, J$_2$=9.3 Hz, 1H), 8.15-8.17 (d, J=9.3 Hz, 1H), 8.33-8.34 (d, J=2.7 Hz, 1H), 8.34-8.36 (dd, J$_1$=2.1 Hz, J$_2$=8.4 Hz, 1H), 8.54-8.56 (d, J=2.1 Hz, 1H), 8.62-8.63 (d, J=5.6 Hz, 1H), 8.83-8.84 (q, J=4.8 Hz, 1H), 12.35 (s, 1H).

Example 23

Synthesis of 4-[3-(2-chloro-3-trifluoromethyl-benzoylamino)-benzo[1,2,4]triazin-7-yloxy]-pyridine-2-carboxylic acid methyl amide trifluoroacetate salt

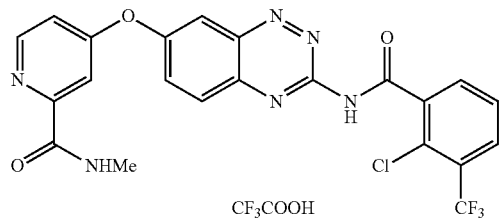 [SMILES: CNC(=O)c1cc(Oc2ccc3nc(NC(=O)c4cccc(C(F)(F)F)c4Cl)nnc3c2)ccn1 ; "CF3COOH"]

The experimental procedure that was used was the same as described in Example 10.

ESI-MS: [M+H]$^+$, 503, 505, 506. $^1$H NMR (DMSO-d$_6$): δ (ppm) 2.80-2.81 (d, J=4.8 Hz, 3H), 7.35-7.36 (dd, J$_1$=2.6 Hz, J$_2$=5.5 Hz, 1H), 7.60-7.61 (d, J=2.6 Hz, 1H), 7.66-7.69 (t, J=7.8 Hz, 1H), 7.92-7.94 (m, 2H), 7.99-8.02 (m, 2H), 8.29 (d, J=2.8 Hz, 1H), 8.61-8.62 (d, J=5.6 Hz, 1H), 8.83-8.84 (q, J=4.8 Hz, 1H), 12.43 (s, 1H).

Example 24

Synthesis of 4-[3-(3-trifluoromethoxy-benzoylamino)-benzo[1,2,4]triazin-7-yloxy]-pyridine-2-carboxylic acid methyl amide trifluoroacetate salt

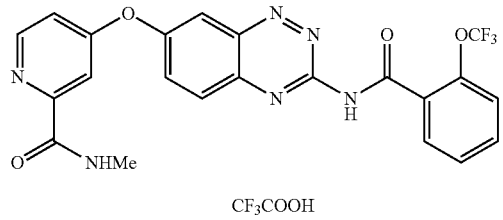 [SMILES: CNC(=O)c1cc(Oc2ccc3nc(NC(=O)c4ccccc4OC(F)(F)F)nnc3c2)ccn1 ; "CF3COOH"]

The experimental procedure that was used was the same as described in Example 10, ESI-MS: [M+H]$^+$, 485, 486, 487. $^1$H NMR (DMSO-d$_6$): δ (ppm) 2.80-2.81 (d, J=4.8 Hz, 3H), 7.35-7.37 (dd, J$_1$=2.6 Hz, J$_2$=5.6 Hz, 1H), 7.48-7.50 (d, J=8.3 Hz, 1H), 7.53-7.56 (dt, J$_1$=0.9 Hz, J$_2$=7.6 Hz, 1H), 7.62 (d, J=2.6 Hz, 1H), 7.66-7.68 (dt, J$_1$=1.7 Hz, J$_2$=8.0 Hz, 1H), 7.78-7.79 (dt, J$_1$=1.7 Hz, J$_2$=7.6 Hz, 1H), 7.99-8.02 (m, 2H), 8.29 (d, J=2.6 Hz, 1H), 8.61 (d, J=5.6 Hz, 1H), 8.83-8.84 (q, J=4.8 Hz, 1H), 12.22 (s, 1H).

Example 25

Synthesis of 4-{3-[(5-Methyl-isoxazole-3-carbonyl)-amino]-benzo[1,2,4]triazin-7-yloxy]-pyridine-2-carboxylic acid methyl amide trifluoroacetate salt

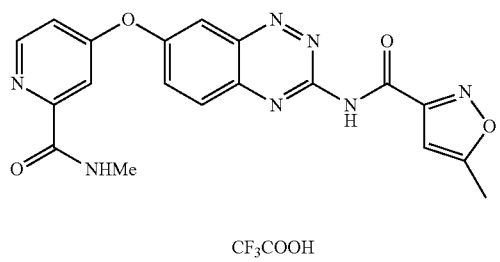 [SMILES: CNC(=O)c1cc(Oc2ccc3nc(NC(=O)c4cc(C)on4)nnc3c2)ccn1 ; "CF3COOH"]

CF$_3$COOH

The experimental procedure that was used was the same as described in Example 10. $^1$H NMR (DMSO-d$_6$): δ (ppm) 2.53 (s, 3H), 2.80-2.81 (d, J=4.8 Hz, 3H), 6.79 (s, 1H), 7.37-7.38 (dd, J$_1$=2.5 Hz, J$_2$=5.5 Hz, 1H), 7.63-7.64 (d, J=2.4 Hz, 1H), 8.04-8.06 (dd, J$_1$=2.5 Hz, J$_2$=9.2 Hz, 1H), 8.15-8.17 (d, J=9.2 Hz, 1H), 8.32-8.33 (d, J=2.5 Hz, 1H), 8.61-8.62 (d, J=5.5 Hz, 1H), 8.83-8.84 (q, J=4.8 Hz, 1H), 12.04 (s, 1H).

Example 26

Testing of Inhibition of Raf Kinase In Vitro

The ability of compounds of general structure (A) of the present invention to inhibit the kinase activity of Raf1 was evaluated using two methods: a direct and a Raf1-MEK1 assay. In the direct assay, kinase reactions were conducted in 96-well plates by combining recombinant human raf1 (29.4 U/well, Upstate, Lake Placid, N.Y.), ATP (3 μM), myelin basic protein substrate (MBP, 1 mg/ml, Upstate, Lake Placid, N.Y.), and test agents (at concentrations ranging from about 1 nM/l to about 10 μM), in the presence of kinase reaction buffer. The Raf1-MEK1 assay utilized 2.9 U/well raf1 and 0.25 ug/well inactive MEK1 (MEK1 inactive, Upstate, Lake Placid, N.Y.) and 3 uM ATP. After reacting for 60 minutes at 30° C., residual ATP was measured using a luciferase-based assay (KinaseGlo, Promega Corp.) as a measure of kinase activity. Data from four wells were then averaged and used to determine IC$_{50}$ values for the test compounds (Prism software package, GraphPad Software, San Diego Calif.).

The test results were as follows: a known Raf inhibitor, compound A, displayed an IC$_{50}$ of 16 nM; a known Raf inhibitor, compound B, displayed an IC$_{50}$ of 43 nM; and an invention compound C, showed an IC$_{50}$ of 76 nM. Other invention compounds exemplified in FIG. 1, displayed an IC$_{50}$ below 100 μM.

Example 27

Testing of Inhibition of MAPK Pathway in Cellular Assay

Western Blot: Early passage primary human umbilical vein endothelial cells (HUVECs) were maintained in EGM-2 containing SingleQuots (Cambrex, East Rutherford, N.J.), 10% FBS, 10 mM HEPES, and 50 μg/ml gentamicin. Prior to treatment of the cells with inhibitor, the HUVECs were starved for 18 h by replacing serum-containing complete media with serum-free and SingleQuot-free media. The starved cells were pre-treated with inhibitors for 60 min at various concentrations (0-20 μM). Next the HUVECs were treated with 50 ng/ml VEGF or FGF (Peprotech, Rocky Hill, N.J.) for 6 min and the cells were immediately washed with ice-cold PBS. Cells were lysed with ice-cold RIPA buffer containing 100 mM Tris pH 7.5, 150 mM NaCl, 1 mM EDTA, 1% deoxycholate, 1% Triton X-100, 0.1% SDS, 2 mM PMSF, one Complete-Mini protease inhibitor tablet (Roche, Indianapolis, Ind.; 1 tablet/7 ml of lysis buffer) and the phophatase inhibitors NaF (500 mM) and orthovanadate (1 mM). The cells were scraped and lysates transferred and centrifuged at 15,000 g for 10 min. Supernatants were transferred to new tubes and protein concentration was quantitated using the BCA protein reagent (Pierce, Rockford, Ill.). Cell lysates containing 20 μg of total protein were separated by 10% SDS-PAGE, transferred to nitrocellulose, and blocked in 5% milk in TBST. Anti phospho-ERK Thr 202/Tyr 204 (Cell Signaling, Beverly, Mass.), anti-phospho-MEK Ser217/221 (Cell Signaling), and c-Raf (BD Biosciences Pharmingen, San Diego, Calif.) used as primary antibodies were detected with horseradish peroxidase-conjugated goat anti-mouse or rabbit secondary antibodies and bands were visualized using the SuperSignal West Pico chemiluminescence reagent system (Pierce) and Kodak X-ray film (Rochester, N.Y.).

Bay 43-9006 (Raf/FGF inhibitor) showed reduction of expression of p-MEK and p-ERK with IC50 between 200 and 300 mM when tested in this assay. U0126 (MEK inhibitor) showed reduction in p-Erk levels with IC$_{50}$ between 200 and 300 nM, while p-MEK levels were unaffected. The results are shown in Table 1. As can be seen, compounds of the invention showed reduction in p-MEK and p-ERK levels with IC$_{50}$ between 400 nM and 20 μM.

Example 28

Cell Viability Assay

XTT assay: HUVECs were seeded at 10,000 cells/well of a tissue culture treated 96-well plate treated with collagen type I and grown overnight in the complete EGM-2 media as described above. The following morning, the inhibitors were serial diluted with DMSO and added to the cells with a final DMSO concentration of 1%. After 24-48 hours cell viability was measured with an XTT assay (Sigma, St. Louis, Mo.). The cells were also photographed to compare morphological differences to the XTT trends observed. Determination of the IC$_{50}$ values was performed with quantitative software (Prism software package, GraphPad Software, San Diego Calif.). Several inhibitors blocked cell proliferation and induced apoptosis at concentrations below 1 μM and experiments were repeated three times to confirm the observations. The compounds of the invention displayed IC$_{50}$ between 100 nM and 40 uM in this assay (Table 1).

TABLE 1

Test Results for Examples 26, 27 and 28.

| Structure | Examples | RAF-MEK assay (biochemical assay) | Western Blot | Inhibition of HUVEC cell prolifration (IC50) |
|---|---|---|---|---|
| 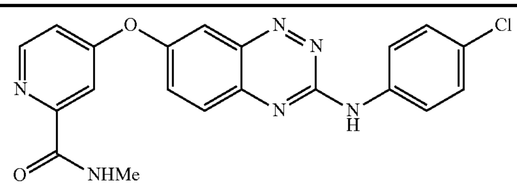 | 4-[3-(4-Chloro-phenylamino)-benzo[1,2,4]triazin-7-yloxy]-pyridine-2-carboxylic acid methyl amide | 10-50 uM in Raf-Mek; 77 nM in direct assay; 100% window | not active at 5 uM | |
| 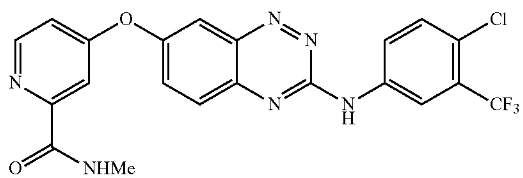 [SMILES: CNC(=O)c1cc(Oc2ccc3nc(Nc4ccc(Cl)c(C(F)(F)F)c4)nnc3c2)ccn1] | 4-[3-(4-Chloro-3-trifluoromethyl-phenylamino)-benzo[1,2,4]triazin-7-yloxy]-pyridine-2-carboxylic acid methyl amide | 11.6 nM; ~20% window | not active at 5 uM | |
| 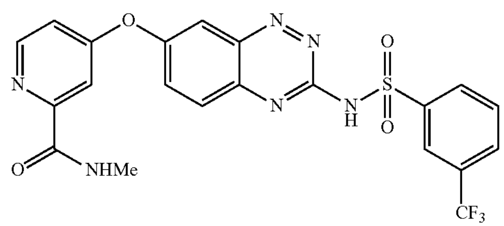 [SMILES: CNC(=O)c1cc(Oc2ccc3nc(NS(=O)(=O)c4cccc(C(F)(F)F)c4)nnc3c2)ccn1] | 4-[3-(3-Trifluromethyl-benezenesulfonylamino)-benzo[1,2,4]triazin-7-yloxy] pyridine-2-carboxylic acid methyl amide | flat | not active at 5 uM | |
| | 4-[3-(4-Chloro-benzenesulfonylamino)-benzo[1,2,4]triazin-7-yloxy]-pyridine-2-carboxylic acid methyl amide | flat | not active at 5 uM | |

TABLE 1-continued

Test Results for Examples 26, 27 and 28.

| Structure | Examples | RAF-MEK assay (biochemical assay) | Western Blot | Inhibition of HUVEC cell proliferation (IC50) |
|---|---|---|---|---|
| | 4-[3-(2-trifluromethyl-benzenesulfonylamino)-benzo[1,2,4]triazin-7-yloxy] pyridine-2-carboxylic acid methyl amide | flat | not active at 5 uM | |
| 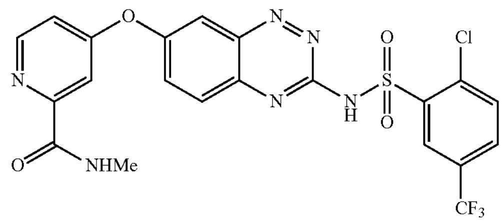 [SMILES: CNC(=O)c1cc(Oc2ccc3nc(NS(=O)(=O)c4cc(C(F)(F)F)ccc4Cl)nnc3c2)ccn1] | 4-[3-(2-chloro-5-trifluoromethyl-benzenesulfonylamino)-benzo[1,2,4]triazin-7-yloxy] pyridine-2-carboxylic acid methyl amide | 50 uM | not active at 5 uM | |
| 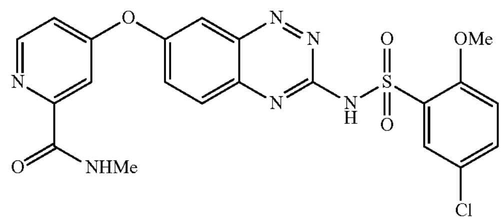 [SMILES: CNC(=O)c1cc(Oc2ccc3nc(NS(=O)(=O)c4cc(Cl)ccc4OC)nnc3c2)ccn1] | 4-[3-(5-chloro-2-methoxy-benzenesulfonylamino)-benzo[1,2,4]triazin-7-yloxy] pyridine-2-carboxylic acid methyl amide | >50 uM | not active at 5 uM | |
| 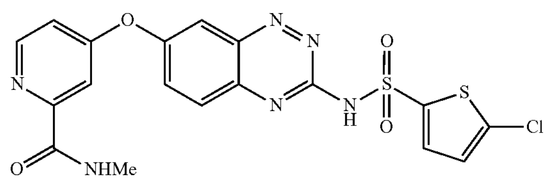 [SMILES: CNC(=O)c1cc(Oc2ccc3nc(NS(=O)(=O)c4ccc(Cl)s4)nnc3c2)ccn1] | 4-[3-(5-chloro-thiophene-2-sulfonylamino)-benzo[1,2,4]triazin-7-yloxy] pyridine-2-carboxylic acid methyl amide | >50 uM | not active at 5 uM | |

TABLE 1-continued

Test Results for Examples 26, 27 and 28.

| Structure | Examples | RAF-MEK assay (biochemical assay) | Western Blot | Inhibition of HUVEC cell proliferation (IC50) |
|---|---|---|---|---|
| 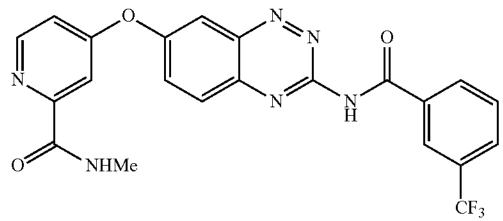 | 4-[3-(3-Trifluromethyl-benzoylamino)-benzo[1,2,4]triazin-7-yloxy]-pyridine-2-carboxylic acid methyl amide | 655 nM; ~70% window | not active at 5 uM |  |
| 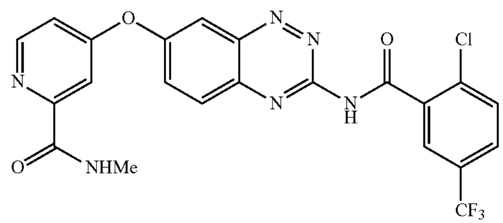 [SMILES: CNC(=O)c1cc(Oc2ccc3nc(NC(=O)c4cc(C(F)(F)F)ccc4Cl)nnc3c2)ccn1] | 4-[3-(2-Chloro-5-trifluromethyl-benzoylamino)-benzo[1,2,4]triazin-7-yloxy]-pyridine-2-carboxylic acid methyl amide |  | not active at 5 uM |  |
| 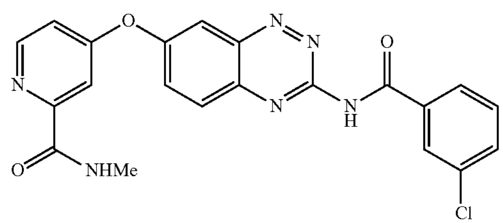 [SMILES: CNC(=O)c1cc(Oc2ccc3nc(NC(=O)c4cccc(Cl)c4)nnc3c2)ccn1] | 4-[3-(3-Chloro-benzoylamino)-benzo[1,2,4]triazin-7-yloxy]-pyridine-2-carboxylic acid methyl amide | flat | not active at 5 uM |  |
| 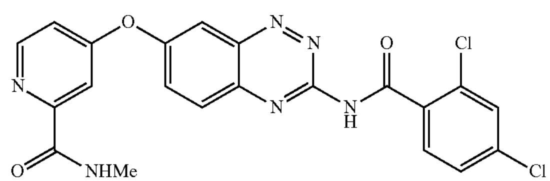 [SMILES: CNC(=O)c1cc(Oc2ccc3nc(NC(=O)c4ccc(Cl)cc4Cl)nnc3c2)ccn1] | 4-[3-(2,4-Dichloro-benzoylamino)-benzo[1,2,4]triazin-7-yloxy]-pyridine-2-carboxylic acid methyl amide | flat | not active at 5 uM |  |

TABLE 1-continued

Test Results for Examples 26, 27 and 28.

| Structure | Examples | RAF-MEK assay (biochemical assay) | Western Blot | Inhibition of HUVEC cell proliferation (IC50) |
|---|---|---|---|---|
| | 4-[3-(3-Chloro-2-fluoro-5-trifluoromethyl-benzoyl)amino]-benzo[1,2,4]triazin-7-yloxy]-pyridine-2-carboxylic acid methyl amide | 723 nM; ~30% window | not active at 5 uM | |
| | 4-[3-(4-Chloro-5-trifluromethyl-benzoyl)amino)-benzo[1,2,4]triazin-7-yloxy]-pyridine-2-carboxylic acid methyl amide | 10-50 uM | not active at 5 uM | |
| | 4-[3-(2-Chloro-3-trifluromethyl-benzoyl)amino)-benzo[1,2,4]triazin-7-yloxy]-pyridine-2-carboxylic acid methyl amide | flat | not active at 5 uM | |
| | 4-{3-[Methyl-(4-trifluoromethoxy-benzoyl)-amino]-benzo[1,2,4]triazin-7-yloxy}-pyridine-2-carboxylic acid dimethyl amide | | partially active at 5 uM | |

TABLE 1-continued

Test Results for Examples 26, 27 and 28.

| Structure | Examples | RAF-MEK assay (biochemical assay) | Western Blot | Inhibition of HUVEC cell proliferation (IC50) |
|---|---|---|---|---|
| 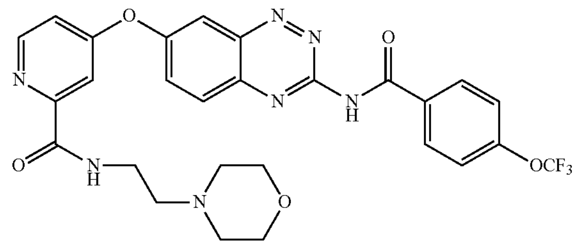 [SMILES: O=C(Nc1nnc2cc(Oc3ccnc(C(=O)NCCN4CCOCC4)c3)ccc2n1)c1ccc(OC(F)(F)F)cc1] | 4-[3-(4-Trifluoromethoxy-benzoylamino)-benzo[1,2,4]triazin-7-yloxy]-pyridine-2-carboxylic acid (2-morpholin-4-yl-ethyl)-amide | | active at 5 uM | 1.48 uM |
| | 4-{3-Methyl-(4-trifluoromethoxy-benzoyl)-amino]-benzo[1,2,4]triazin-7-yloxy}-pyridine-2-carboxylic acid (2-morpholin-4-yl-ethyl)-amide | | partially active at 5 uM | 3.084 uM |
| | 4-{3-Methyl-(4-trifluoromethoxy-benzoyl)-amino]-benzo[1,2,4]triazin-7-yloxy}-pyridine-2-carboxylic acid (2-morpholin-4-yl-ethyl)-amide | | partially active at 5 uM | |

TABLE 1-continued

Test Results for Examples 26, 27 and 28.

| Structure | Examples | RAF-MEK assay (biochemical assay) | Western Blot | Inhibition of HUVEC cell prolifration (IC50) |
|---|---|---|---|---|
| 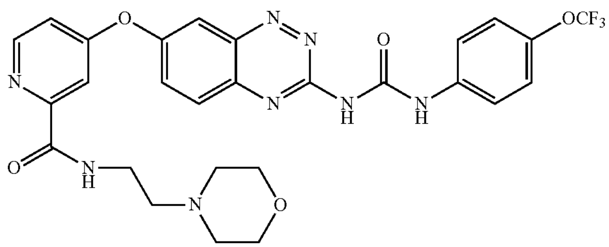 [SMILES: O=C(Nc1ccc(OC(F)(F)F)cc1)Nc1nnc2cc(Oc3ccnc(C(=O)NCCN4CCOCC4)c3)ccc2n1] | 4-{3-[3-(4-Trifluoromethoxy-phenyl)-ureido]-benzo[1,2,4]triazin-7-yloxy}-pyridine-2-carboxylic acid (2-morpholin-4-yl-ethyl)-amide | | not active at 5 uM | |
| 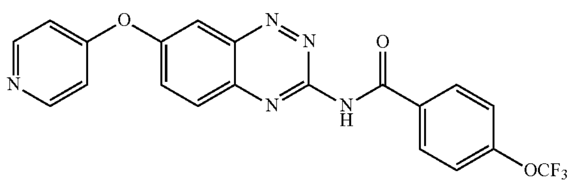 [SMILES: O=C(Nc1nnc2cc(Oc3ccncc3)ccc2n1)c1ccc(OC(F)(F)F)cc1] | N-[7-(Pyridin-4-yloxy)-benzo[1,2,4]triazin-3-yl]-4-trifluoromethoxy-benzamide | | not active at 5 uM | 7.38 uM |

Example 29

Synthesis of S-methyl N-[4-chloro-3 (trifluoromethyl)phenyl]isothiourea hydroiodide

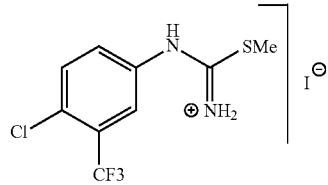 [SMILES: CSC(=[NH2+])Nc1ccc(Cl)c(C(F)(F)F)c1 ; [I-]]

4-Chloro-3-trifluoromethyl-phenylthiourea (5.0 g, 19.63 mmol) was dissolved in ca. 80 mL of anhydrous MeOH and methyl iodide (2.93 g, 20.61 mmol) was added via a syringe. The reaction mixture was refluxed for 12 hours. Then it was cooled down to ambient temperature and solvent was removed in vacuo to give colorless oil (7.85 g), which was taken to the next step without further purifications.

S-methyl N-[4-trifluoromethoxyphenyl]isothiourea hydroiodide, S-methyl N-[4-hydroxy-phenyl]isothiourea hydroiodide, S-methyl N-[3-hydroxy-phenyl]isothiourea hydroiodide and S-methyl N-[3-(trifluoromethyl)phenyl] isothiourea hydroiodide were prepared according to the method of this example.

In the case of 1,2,4-triazoles three tautomeric structures can be present, as shown below:

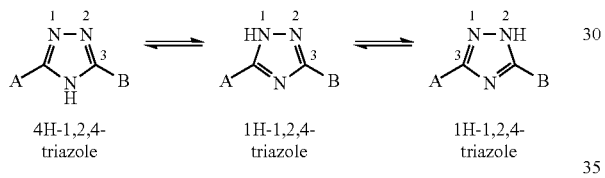

Even though all three tautomeric structures can exist, all the generic structures and all the examples having 1,2,4-triazole moiety are shown only in one tautomeric form, such as 4H-1,2,4-triazole for simplicity and for the comparison with its direct analogues, such as examples containing 1,3,4-oxadiazole moiety. The prevailing tautomeric structure depends on the substituents on the triazole moiety and on the reaction conditions. As has been shown in the literature, 1H-1,2,4-triazole is usually the most common tautomeric form, especially if an amino substituent is attached to the ring. Using only 4H-tautomeric form to draw the structures for the sake of simplicity, does not imply that the compounds of the examples that follow necessarily exist in that particular tautomeric form. Using this approach, the IUPAC names for the examples below are provided for 4H-tautomeric form only, however it is understood, that upon the elucidation of the exact tautomeric structure the numbering of the substituents may differ from the one that is provided.

Example 30

Synthesis of 4-[5-(4-chloro-3-trifluoromethyl-phenylamino)-4H[1,2,4]triazol-3-yl]-phenol

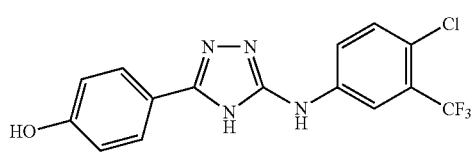 [SMILES: Oc1ccc(-c2nnc(Nc3ccc(Cl)c(C(F)(F)F)c3)[nH]2)cc1]

4-hydroxybenzoic acid hydrazide (3.0 g, 19.66 mmol) and S-methyl N-[4-chloro-3-(trifluoromethyl)phenyl]isothiourea hydroiodide (7.8 g, 19.66 mmol) were suspended in 100 mL of anhydrous pyridine. The reaction mixture was refluxed for 18 hours under Ar atmosphere. Then it was cooled down to ambient temperature and pyridine was removed in vacuo. The resulting yellow oil was re-dissolved in a small amount of ethyl acetate, loaded on a short pad of silica gel and eluted with 5:1 hexane/ethyl acetate, then with 100% ethyl acetate to collect the product. The product was re-purified by a second silica gel column chromatography, using ISCO system (80 g pre-packed column, 25 min run, 20% to 50% EtOAc gradient in hexane). Solvent was removed in vacuo to give the title product as a white solid (2.83 g). Yield 40.4%.

ESI-MS: [M+H]$^+$ 355.1, 356.8. $^1$H NMR (DMSO-d$_6$): δ 6.89-6.91 (d, J=8.7 Hz, 2H), 7.53-7.55 (d, J=8.8 Hz, 1H), 7.70-7.72 (dd, J$_1$=8.8 Hz, J$_2$=2.6 Hz, 1H), 7.77-7.79 (d, J=8.7 Hz, 2H), 8.24-8.25 (d, J=2.6 Hz, 1H), 9.81 (s, 1H), 9.98 (s, 1H), 13.62 (s, 1H).

Example 31

Synthesis of 4-{4-[5-(4-chloro-3-trifluoromethyl-phenylamino)-4H-[1,2,4]triazol-3-yl]-phenoxy}-pyridine-2-carboxylic acid methylamide trifluoro-acetic acid salt

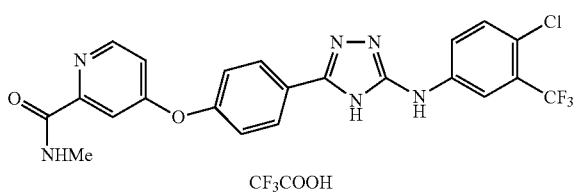 [SMILES: CNC(=O)c1cc(Oc2ccc(-c3nnc(Nc4ccc(Cl)c(C(F)(F)F)c4)[nH]3)cc2)ccn1 ; "CF3COOH"]

ESI-MS: [M+H]$^+$, 490, 491. $^1$H NMR (DMSO-d$_6$): δ 2.78-2.79 (d, J=4.8 Hz, 3H), 7.24-7.25 (m, 1H), 7.40-7.42 (d, J=8.7 Hz, 2H), 7.48 (s, 1H), 7.56-7.58 (d, J=8.8 Hz, 1H), 7.79-7.82 (dd, J$_1$=2.6 Hz, J$_2$=8.8 Hz, 1H), 8.07-8.09 (d, J=8.7 Hz, 2H), 8.24-8.25 (d, J=2.6 Hz, 1H), 8.55-8.56 (m, 1H), 8.80-8.81 (m, 1H), 9.95 (s, 1H).

Example 32

Synthesis of (4-chloro-3-trifluoromethyl-phenyl)-{5-[4-(pyridin-3-yloxy)-phenyl]-4H-[1,2,4]triazol-3-yl}-amine trifluoroacetic acid salt

4-[5-(4-chloro-3-trifluoromethyl-phenylamino)-4H[1,2,4]triazol-3-yl]-phenol (127.8 mg, 0.36 mmol) was dissolved in 3 mL of anhydrous DMF in a 5 mL microwave vial (Personal Chemistry). Solid potassium bis(trimethylsilyl)amide (144.0 mg, 0.72 mmol) was added and the reaction mixture was stirred with heating at 80° C. for 15 min, then 3-bromopyridine (68.3 mg, 0.432 mmol) was added, followed by anhydrous $K_2CO_3$ (50.0 mg, 0.36 mmol). Then the vial was capped and microwaved at 250° C. for 30 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (15.1 mg).

ESI-MS: $[M+H]^+$, 432, 433. $^1$H NMR (DMSO-$d_6$): δ 7.19-7.21 (d, J=8.8 Hz, 2H), 7.49-7.51 (dd, $J_1$=4.5 Hz, $J_2$=8.6 Hz, 1H), 7.53-7.55 (d, J=8.8 Hz, 1H), 7.58-7.60 (m, 1H), 7.74-7.76 (m, 1H), 7.95-7.98 (d, J=8.8 Hz, 2H), 8.21-8.21 (d, J=2.6 Hz, 1H), 8.44 (m, 1H), 8.48 (m, 1H), 9.88 (s, 1H).

Example 33

Synthesis of methyl 4-(pyridine-3-yloxy)benzoate

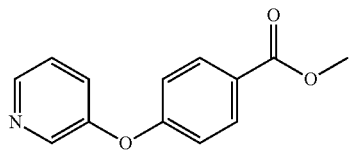 [SMILES: COC(=O)c1ccc(Oc2cccnc2)cc1]

3-hydroxypyridine (6.17 g, 64.87 mmol) was dissolved in 100 mL of anhydrous DMF under argon atmosphere. Solid $K_2CO_3$ (8.96 g, 64.87 mmol) was added, followed by neat methyl 4-fluorobenzoate (10.0 g, 64.87 mmol). The reaction mixture was heated at 135° C. for 10 hrs. The absence of the starting material was confirmed by LC/MS. The reaction mixture was cooled down to ambient temperature and poured into ca. 500 mL of $H_2O$. The resulting solution was extracted 3 times with ca. 150 mL of EtOAc (during the extraction small volumes of MeOH, $Et_2O$ and brine were added to facilitate the separation). Combined EtOAc layers were washed twice with sat. $NaHCO_3$, twice with brine and dried over anhydrous $Na_2SO_4$. Solvent was removed in vacuo to give dark-red oil, which was purified by silica gel chromatography using 1:1 mixture of EtOAc/Hexane as eluent to give the title product (4.8 g, 32.3% yield) as yellow solid.

ESI-MS: $[M+H]^+$, 230, 231. $^1$H NMR (DMSO-$d_6$): δ 3.83 (s, 3H), 7.09-7.12 (d, J=8.8 Hz, 2H), 7.48-7.51 (dd, $J_1$=8.4 Hz, $J_2$=4.9 Hz, 1H), 7.58-7.61 (dq, $J_1$=8.4 Hz, $J_2$=1.4 Hz, 1H), 7.96-7.99 (d, J=8.8 Hz, 2H), 8.46-8.47 (m, 2H).

Example 34

Synthesis of 4-(pyridine-3-yloxy)benzohydrazide

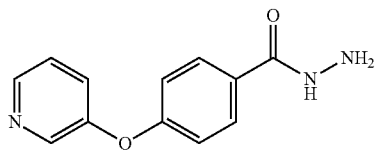 [SMILES: NNC(=O)c1ccc(Oc2cccnc2)cc1]

Methyl 4-(pyridine-3-yloxy)benzoate (4.8 g, 20.94 mmol) was dissolved in ca. 150 mL of EtOH and anhydrous hydrazine (4.08 g, 4.0 mL) was added via a syringe. The resulting yellow solution was refluxed for 24 hrs. Then solvent was removed in vacuo to give the title product (4.8 g, 100% yield) as yellow viscous oil, which upon standing slowly solidified.

ESI-MS: $[M+H]^+$, 230, 231. $^1$H NMR (DMSO-$d_6$): δ 4.13 (br s., 2H), 7.06-7.09 (d, J=8.7 Hz, 2H), 7.45-7.47 (dd, $J_1$=8.4 Hz, $J_2$=4.9 Hz, 1H), 7.51-7.54 (dq, $J_1$=8.4 Hz, $J_2$=1.4 Hz, 1H), 7.85-7.88 (d, J=8.8 Hz, 2H), 8.42-8.43 (m, 2H), 9.74 (s, 1H).

Example 35

Synthesis of (4-chloro-3-trifluoromethyl-phenyl)-{5-[4-(pyridin-3-yloxy)-phenyl]-4H-[1,2,4]triazol-3-yl}-amine

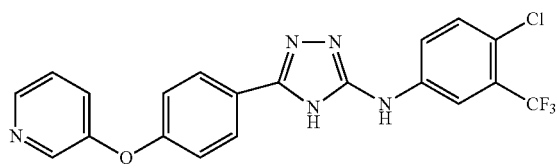 [SMILES: FC(F)(F)c1cc(Nc2nnc(-c3ccc(Oc4cccnc4)cc3)[nH]2)ccc1Cl]

4-(pyridine-3-yloxy)benzohydrazide (2.33 g, 10.2 mmol) was dissolved in ca. 70 mL of anhydrous pyridine and S-methyl N-[4-chloro-3-(trifluoromethyl)phenyl]isothiourea hydroiodide (4.04 g, 10.2 mmol) was added. The reaction mixture was refluxed for 18 hrs under Ar. The pyridine was removed in vacuo and the resulting residue was purified by silica gel chromatography using EtOAc as eluent to give the title product (0.56 g) as a white solid.

ESI-MS: $[M+H]^+$, 432, 433. $^1$H NMR (DMSO-$d_6$): δ 7.20-7.23 (d, J=8.8 Hz, 2H), 7.46-7.49 (dd, $J_1$=8.4 Hz, $J_2$=4.5 Hz, 1H), 7.54-7.57 (m, 2H), 7.75-7.77 (dd, $J_1$=8.8 Hz, $J_2$=2.6 Hz, 1H), 7.97-7.99 (d, J=8.8 Hz, 2H), 8.23-8.24 (d 2.6 Hz, 1H), 8.43 (m, 1H), 8.46 (d, J=2.6 Hz, 1H), 9.88 (s, 1H), 13.91 (s, 1H).

Example 36

Synthesis of 6-{4-[5-(4-chloro-3-trifluoromethyl-phenylamino)-4H-[1,2,4]-triazol-3-yl]-phenoxy}-pyrimidine-2,4-diamine

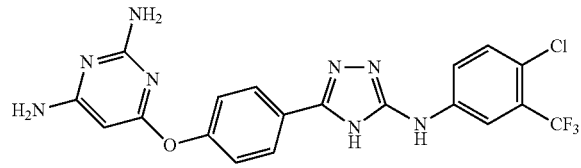 [SMILES: Nc1cc(Oc2ccc(-c3nnc(Nc4ccc(Cl)c(C(F)(F)F)c4)[nH]3)cc2)nc(N)n1]

4-[5-(4-chloro-3-trifluoromethyl-phenylamino)-4H[1,2,4]triazol-3-yl]-phenol (1.3 g, 3.66 mmol) was dissolved in 18 mL of anhydrous dioxane in a 10-20 md microwave vial (Personal Chemistry). Solid $Cs_2CO_3$ (1.19 g, 3.66 mmol, 1.0 eq) was added and the reaction mixture was stirred with heating at 80° C. for 10 min, then 4-chloro-2,4-diaminopyrimidine (0.530 g, 3.66 mmol) was added. The vial was capped and microwaved at 200° C. for 25 min. Then the reaction mixture was diluted with ca. 10 mL of MeOH, transferred into a round-bottom flask and concentrated in vacuo to ca. 20 mL. The resulting reddish solution was loaded on a short pad of silica gel and eluted first with 100% ethyl acetate to remove the unreacted starting material and then with 20% MeOH in EtOAc to elute the product. The product was further purified by ISCO system (80 g pre-packed column, 40 min method, 0% to 10% MeOH gradient in ethyl acetate). Solvent was removed in vacuo to give the title product as an off-white solid (0.785 g). Yield 46.3%.

ESI-MS: [M+H]$^+$, 463, 464, 465. $^1$H NMR (DMSO-d$_6$): δ 5.15 (s, 1H), 6.03 (s, 2H), 6.31 (s, 2H), 7.25-7.27 (d, J=8.6 Hz, 2H), 7.55-7.57 (d, J=8.8 Hz, 1H), 7.77-7.78 (m, 1H), 7.96-7.97 (d, J=8.8 Hz, 2H), 8.25-8.26 (d, J=2.6 Hz, 1H), 9.91 (s, 1H), 13.91 (s, 1H). Anal. Calcd for (C$_{19}$H$_{14}$ClF$_3$N$_8$O×0.4 EtOAc): C, 49.68; H, 3.48; N, 22.50. Found: C, 49.61; H, 3.55; N, 22.90.

Example 37

Synthesis of 6-{4-[5-(4-chloro-3-trifluoromethyl-phenylamino)-4H-[1,2,4]triazol-3-yl]-phenoxy}-pyrimidine-2,4-diamine methanesulfonic acid salt

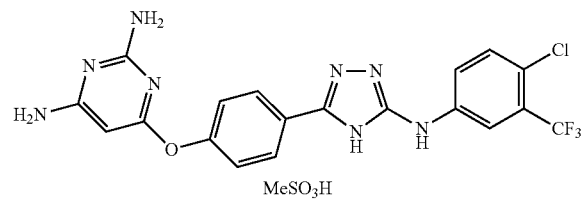 [SMILES: "MeSO3H" ; Nc1cc(Oc2ccc(-c3nnc(Nc4ccc(Cl)c(C(F)(F)F)c4)[nH]3)cc2)nc(N)n1]

MeSO$_3$H

6-{4-[5-(4-Chloro-3-trifluoromethyl-phenylamino)-4H-[1,2,4]triazol-3-yl]-phenoxy}-pyrimidine-2,4-diamine×0.4 EtOAc complex (470.0 mg, 0.943 mmol) was dissolved in ca. 50 mL of anhydrous methanol and methasulfonic acid (0.0612 mL, 0.943 mmol, 1.0 eq.) was added. The resulting solution was stirred for 30 min. Solvent was removed in vacuo and the resulting light-yellow foam was dried at 70° C. in high vacuum for 3 hrs to give the title compound as an off-white solid (527.3 mg). Yield 100%.

ESI-MS: [M+H]$^+$, 463, 464. $^1$H NMR (DMSO-d$_6$): δ 2.36 (s, 3H), 5.40 (s, 1H), 7.39-7.40 (d, J=8.6 Hz, 2H), 7.57-7.58 (d, J=8.8 Hz, 1H), 7.78 (m, 1H), 7.80 (br.s., 4H), 8.02-8.03 (d, J=8.8 Hz, 2H), 8.25-8.26 (d, J=2.6 Hz, 1H), 9.94 (s, 1H), 13.98 (br, s, 1H). Anal. Calcd for (C$_{19}$H$_{14}$ClF$_3$N$_8$O×1 CH$_3$SO$_3$H): C, 42.98; H, 3.25; N, 20.05. Found: C, 42.93; H, 3.62; N, 20.12.

Example 38

Synthesis of methyl 4-[(2,6-diaminopyrimidin-4-yl)oxy]benzoate

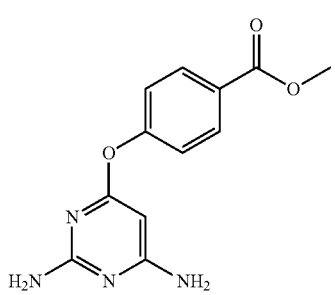 [SMILES: COC(=O)c1ccc(Oc2cc(N)nc(N)n2)cc1]

Methyl 4-hydroxybenzoate (1.52 g, 10.0 mmol) was dissolved in 18 mL of anhydrous dioxane in 10-20 mL microwave vial (Personal Chemistry) and solid Cs$_2$CO$_3$ was added to this solution. The suspension was stirred at ambient temperature for 10 min, then 4-chloro-2,6-diaminopyrimidine (1.45 g, 10.0 mmol) was added. The vial was capped and microwaved at 200° C. for 40 min. Then MeOH was added to dissolve the formed suspension to produce a clear amber solution. The solution was transferred into a round-bottom flask and concentrated down to ca. 20 mL. This solution was purified by silica gel chromatography using 100% ethyl acetate as eluent. The product was additionally re-crystallized from ca. 50 mL of 4:1 mixture of EtOAc/MeOH. The product was filtered, washed with 40 mL of EtOAc, 40 mL of anhydrous Et$_2$O and dried in vacuo to give the title product as a white solid (0.812 g). Yield 31.2%.

ESI-MS: [M+H]$^+$, 261.01. $^1$H NMR (DMSO-d$_6$): δ 3.84 (s, 3H), 5.19 (s, 1H), 6.06 (br. s, 2H), 6.37 (br.s, 2H), 7.19-7.21 (d, J=8.7 Hz, 2H), 7.95-7.97 (d, J=8.7 Hz, 2H). $^{13}$C NMR (DMSO-d6) 52.1, 78.3, 121.0, 125.3, 130.9, 157.8, 163.2, 165.7, 166.6, 169.2.

Example 39

Synthesis of 4-[(2,6-diaminopyrimidin-4-yl)oxy]benzohydrazide

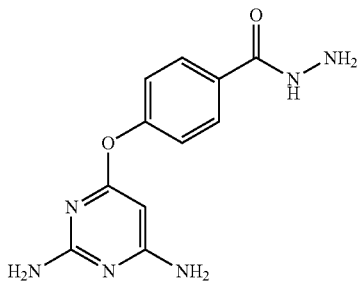 [SMILES: NNC(=O)c1ccc(Oc2cc(N)nc(N)n2)cc1]

Methyl 4-[(2,6-diaminopyrimidin-4-yl)oxy]benzoate (2.74 g, 10.52 mmol) was suspended in ca. 180 mL of anhydrous methanol and anhydrous hydrazine (1.021 g, 1.0 mL, 31.85 mmol, 3.03 eq) was added to this suspension. The reaction mixture was refluxed for 3 hours, then MeOH was very slowly distilled off till the total volume reached ca. 30 mL. This solution was allowed to stand at ambient temperature for 48 hrs. A white precipitate slowly crystallized out. It was collected, washed with 40 mL of EtOAc, 40 mL of anhydrous Et$_2$O and dried in vacuo to give the title product as a fine white powder (2.02 g). Yield 73.7%.

ESI-MS: [M+H]$^+$, 261.12. NMR (DMSO-d$_6$): δ 4.54 (br.s., 2171), 5.13 (s, 1H), 6.01 (br. s, 2H), 6.30 (br.s, 2H), 7.13-7.14 (d, J=8.7 Hz, 2H), 7.83-7.84 (d, J=8.7 Hz, 2H), 9.75 (s, 1H). $^{13}$C NMR (DMSO-d6) 77.9, 120.9, 128.5, 129.3, 155.8, 163.3, 165.4, 166.6, 169.7.

Example 40

Synthesis of 6-{4-[5-(4-chloro-3-trifluoromethyl-phenylamino)-4H-[1,2,4]triazol-3-yl]phenoxy}-pyrimidine-2,4-diamine

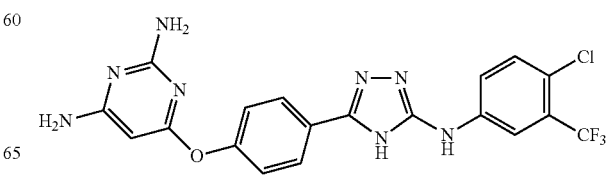

4-[(2,6-diaminopyrimidin-4-yl)oxy]benzohydrazide (1.48 g, 5.68 mmol) and S-methyl N-[4-chloro-3-(trifluoromethyl)phenyl]isothiourea hydroiodide (2.33 g, 5.89 mmol) were suspended in 30 mL of anhydrous pyridine. The reaction mixture was refluxed for 18 hours under Ar atmosphere. The formed yellow solution was cooled down to ambient temperature and pyridine was removed in vacuo. The resulting yellow foamy solid was re-dissolved in 50 mL of 5:1 EtOAc/MeOH; ca. 15 g of silica gel was added and solvent was removed in vacuo. The impregnated silica gel was packed into ISCO column and the product was purified using ISCO system (80 g pre-packed column, 50 min run, 0% to 10% gradient of solvent B in solvent A [Solvent A—4 mL of MeOH, 4 ml, of Et$_3$N in 4 L of CH$_2$Cl$_2$; Solvent B—4 mL of Et$_3$N in 4 L of MeOH]). Solvent was removed in vacuo to give the title product as a white solid (1.33 g). Yield 50.5%.

ESI-MS: [M+H]$^+$, 463, 464. $^1$H NMR (DMSO-d$_6$): δ 5.15 (s, 1H), 6.03 (s, 2H), 6.31 (s, 2H), 7.25-7.27 (d, J=8.6 Hz, 2H), 7.55-7.57 (d, J=8.8 Hz, 1H), 7.77-7.78 (m, 1H), 7.96-7.97 (d 8.8 Hz, 2H), 8.25-8.26 (d, J=2.6 Hz, 1H), 9.91 (s, 1H), 13.91 (s, 1H). Anal. Calcd for (C$_{19}$H$_{14}$ClF$_3$N$_8$O×0.4 EtOAc): C, 49.68; H, 3.48; N, 22.50. Found: C, 49.61; H, 3.55; N, 22.90.

Example 41

Synthesis of 6-{4-[5-(4-chloro-3-trifluoromethyl-phenylamino)-4H-[1,2,4]triazol-3-yl]-phenoxy}-pyridazin-3-ylamine trifluoroacetic acid salt

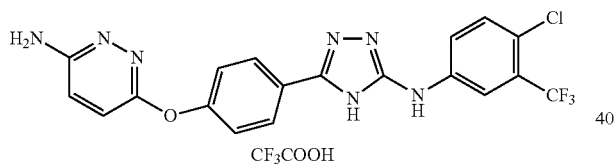

CF$_3$COOH

4-[5-(4-chloro-3-trifluoromethyl-phenylamino)-4H[1,2,4]triazol-3-yl]-phenol (120.0 mg, 0.338 mmol) was dissolved in 3 mL of anhydrous DMF in a 5 mL microwave vial (Personal Chemistry). Solid potassium bis(trimethylsilyl)amide (81.0 mg, 0.406 mmol) was added and the reaction mixture was stirred with heating at 80° C. for 15 min, then 3-amino-6-chloro-pyridazine (48.2 mg, 0.372 mmol) was added, followed by anhydrous K$_2$CO$_3$ (46.7 mg, 0.338 mmol). Then the vial was capped and microwaved at 200° C. for 30 min. After reaction was complete, the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (18.2 mg).

ESI-MS: [M+H]$^+$, 448, 449. $^1$H NMR (DMSO-d$_6$): δ 7.42-7.43 (d, J=8.7 Hz, 2H), 7.54-7.56 (d, J=9.7 Hz, 1H), 7.56-7.58 (d, J=8.8 Hz, 1H), 7.76-7.79 (m, 1H), 7.78-7.80 (d, J=9.7 Hz, 1H), 8.01-8.04 (d J=8.8 Hz, 2H), 8.25-8.26 (d, J=2.6 Hz, 1H), 8.49 (br.s., 2H), 9.94 (s, 1H).

Example 42

Synthesis of 4-[5-(4-trifluoromethoxy-phenylamino)-4H[1,2,4]triazol-3-yl]-phenol

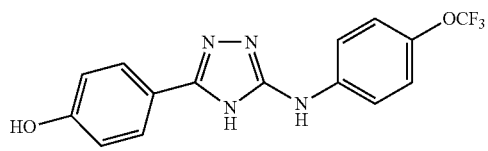 [SMILES: Oc1ccc(-c2nnc(Nc3ccc(OC(F)(F)F)cc3)[nH]2)cc1]

4-hydroxybenzoic acid hydrazide (0.643 g, 4.23 mmol) and S-methyl N-[4-(trifluoromethoxy)phenyl]isothiourea hydroiodide (1.6 g, 4.23 mmol) were suspended in 10 mL of anhydrous pyridine. The reaction mixture was refluxed for 24 hours, during which time it changed color from yellow into orange-red. Then it was cooled down to ambient temperature and poured with stirring into 150 mL of ice-water. The formed white solid was collected, washed thoroughly with water and dried in air. The resulting residue was purified by silica gel chromatography using Isco column with 10% to 100% gradient of ethyl acetate in hexane. Solvent was removed in vacuo to give the title product as a pinkish solid (575.2 mg). Yield 40.4%.

ESI-MS: [M+H]$^+$ 337, 338. $^1$H NMR (DMSO-d$_6$): δ 6.85-6.87 (d, J=8.0 Hz, 2H), 7.19-7.20 (d, J=8.0 Hz, 2H), 7.61-7.63 (d, J=8.7 Hz, 2H), 7.75-7.77 (d, J=8.7 Hz, 2H), 9.39 (s, 1H), 9.92 (s, 1H), 13.42 (s, 1H).

Example 43

Synthesis of 4-{4-[5-(4-trifluoromethoxy-phenylamino)-4H-[1,2,4]triazol-3-yl]-phenoxy}-pyridine-2-carboxylic acid methylamide trifluoroacetic acid salt

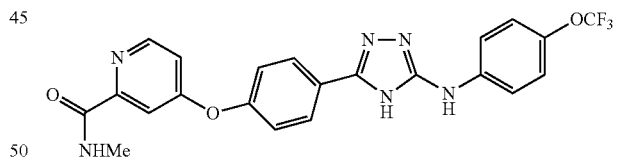

4-[5-(4-trifluoromethoxy-phenylamino)-4H[1,2,4]triazol-3-yl]-phenol (66.4 mg, 0,197 mmol) was dissolved in 2 mL of anhydrous DMF in a 5 mL microwave vial (Personal Chemistry). Solid potassium bis(trimethylsilyl)amide (39.4 mg, 0.197 mmol) was added and the reaction mixture was stirred with heating at 80° C. for 15 min, then 4-chloro-2-pyridinecarboxamide (33.7 mg, 0.197 mmol) was added, followed by anhydrous K$_2$CO$_3$ (27.3 mg, 0.197 mmol). Then the vial was capped and microwaved at 200° C. for 15 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (46.6 mg).

ESI-MS: [M+H]$^+$ 471, 472. $^1$H NMR (DMSO-d$_6$): δ 2.78-2.79 (d, J=4.8 Hz, 3H), 7.23-7.25 (dd, J$_1$=5.6 Hz, J$_2$=2.6 Hz,

1H), 7.25-7.27 (d, J=8.6 Hz, 2H), 7.38-7.40 (d, J=8.6 Hz, 2H), 7.47-7.47 (d, J=2.6 Hz, 1H), 7.66-7.70 (d, J=8.7 Hz, 2H), 8.08-8.11 (d, J=8.7 Hz, 2H), 8.55-8.56 (d, J=5.6 Hz, 1H), 8.79-8.82 (t, J=4.8 Hz, 1H), 9.58 (s, 1H).

Example 44

Synthesis of {5-[4-(pyridin-4-yloxy)-phenyl]-4H-[1,2,4]triazol-3-yl]-(4-trifluoromethoxy-phenyl)-amine trifluoroacetic acid salt

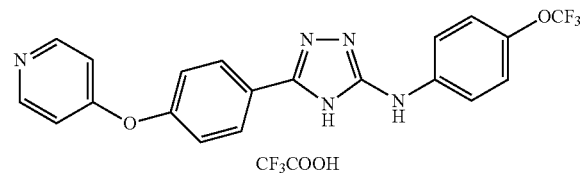

CF₃COOH

4-[5-(4-trifluoromethoxy-phenylamino)-4H[1,2,4]triazol-3-yl]-phenol (106.0 mg, 0.315 mmol) was dissolved in 2 mL of anhydrous DMF in a 5 mL microwave vial (Personal Chemistry). Solid potassium bis(trimethylsilyl)amide (157.2 mg, 0.788 mmol) was added and the reaction mixture was stirred with heating at 80° C. for 15 min, then 4-chloropyridine hydrochloride (56.7 mg, 0.378 mmol) was added, followed by anhydrous K₂CO₃ (44.0 mg, 0.315 mmol). Then the vial was capped and microwaved at 250° C. for 20 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (66.5 mg of off-white solid).

ESI-MS: [M+H]⁺, 415, 416. ¹H NMR (DMSO-d₆): δ 7.26-7.27 (d, J=8.7 Hz, 2H), 7.46-7.48 (m, 2H), 7.46-7.48 (d, J=7.1 Hz, 2H), 7.67-7.70 (d, J=8.7 Hz, 2H), 8.13-8.16 (d, 8.7 Hz, 2H), 8.77-8.78 (d, J=7.1 Hz, 2H), 9.64 (s, 1H).

Example 45

Synthesis of 6-{4-[5-(4-trifluoromethoxy-phenylamino)-4H-[1,2,4]triazol-3-yl]-phenoxy}-pyridazin-3-ylamine trifluoroacetic acid salt

CF₃COOH

4-[5-(4-trifluoromethoxy-phenylamino)-4H[1,2,4]triazol-3-yl]-phenol (112.0 mg, 0.33 mmol) was dissolved in 2 mL of anhydrous DMF in a 5 mL microwave vial (Personal Chemistry). Solid potassium bis(trimethylsilyl)amide (132.8 mg, 0.66 mmol) was added and the reaction mixture was stirred with heating at 80° C. for 15 min, then 3-amino-6-chloropyridazine (47.4 mg, 0.366 mmol) was added, followed by anhydrous K₂CO₃ (46.0 mg, 0.33 mmol). Then the vial was capped and microwaved at 250° C. for 15 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (52.1 mg of brown crystalline solid).

ESI-MS: [M+H]⁺, 431. ¹H NMR (DMSO-d₆): δ 7.25-7.26 (d, J=8.7 Hz, 2H), 7.39-7.41 (d, J=8.7 Hz, 2H), 7.52-7.54 (d, J=9.7 Hz, 1H), 7.67-7.68 (d, J=8.7 Hz, 2H), 7.76-7.78 (d, J=9.7 Hz, 1H), 8.03-8.06 (d, J=8.7 Hz, 2H), 9.58 (s, 1H).

Example 46

Synthesis of 6-{4-[5-(4-trifluoromethoxy-phenylamino)-4H-[1,2,4]triazol-3-yl]-phenoxy}-pyrimidine-2,4-diamine trifluoroacetic acid salt

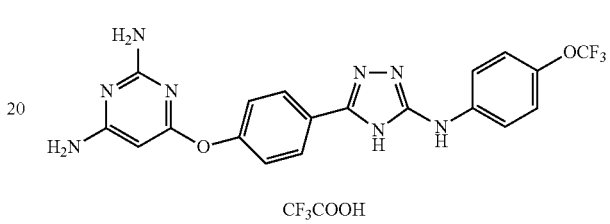

CF₃COOH

4-[5-(4-tTrifluoromethoxy-phenylamino)-4H[1,2,4]triazol-3-yl]-phenol (112.0 mg, 0.33 mmol) was dissolved in 2 mL of anhydrous DMF in a 5 mL microwave vial (Personal Chemistry). Solid potassium bis(trimethylsilyl)amide (132.8 mg, 0.66 mmol) was added and the reaction mixture was stirred with heating at 80° C., for 15 min, then 4-chloro-2,6-diamino-pyrimidine (53.0 mg, 0.366 mmol) was added, followed by anhydrous K₂CO₃ (46.0 mg, 0.33 mmol). Then the vial was capped and microwaved at 250° C. for 15 min. Then the reaction mixture was diluted with ca. 1 mL of MeOH, filtered through 0.22 um syringe filter and purified by reverse-phase preparative HPLC in acetonitrile/water system with 0.01% TEA. The product was isolated as a TFA salt (51.1 mg of beige solid).

ESI-MS: [M+H]⁺, 445, 446. ¹H NMR (DMSO-d₆): δ 5.36 (s, 1H), 7.25-7.27 (br. d, J=8.0 Hz, 2H), 7.35-7.36 d, J=8.0 Hz, 2H), 7.67-7.68 (d, J=8.7 Hz, 2H), 7.67 (br.s., 4H), 8.02-8.04 (d, J=8.7 Hz, 2H), 9.57 (br. s, 1H).

Example 47

Synthesis of 4-(5-{[3-(trifluoromethyl)phenyl]amino}-4H-1,2,4-triazol-3-yl)-phenol

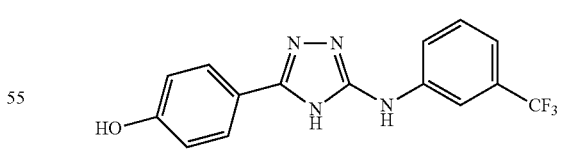

S-methyl N-[3-(trifluoromethyl)phenyl]isothiourea hydroiodide (9.09 g, 25.11 mmol) and 4-hydroxybenzoic acid hydrazide (3.82 g, 25.11 mmol) were suspended in ca. 50 mL of anhydrous pyridine under Ar. The mixture was brought to reflux and refluxed under Ar for 12 hrs. Then the dark-yellow solution was cooled down to ambient temperature and pyridine was removed in vacuo. The resulting reddish-yellow solid was re-dissolved in ca. 50 mL of 4:1 mixture of EtOAc/MeOH, ca. 20 g of silica gel was added and solvent was removed in vacuo. The impregnated silica gel was loaded into 25 g ISCO sample cartridge and the product was purified using ISCO system (solid method, 80 g column, 45 min, 0% to 50% EtOAc gradient in hexane). Solvent was removed in vacuo to give the title product as a white solid (3.83 g). Yield 47.6%.

ESI-MS: [M+H]$^+$, 321.09. $^1$H NMR (DMSO-d$_6$): δ 6.89-6.90 (d, J=8.6 Hz, 2H), 7.09-7.11 (d, J=7.3 Hz, 1H), 7.42-7.46 (t, J=7.9 Hz, 1H), 7.73-7.74 (d. J=7.0 Hz, 1H), 7.77-7.79 (d, J=8.6 Hz, 2H), 8.09 (s, 1H), 9.65 (s, 1H), 9.97 (br. s., 1H).

Example 48

Synthesis of 6-[4-(5-{[3-(trifluoromethyl)phenyl]amino}-4H-[1,2,4]triazol-3-yl)-phenoxy]-pyrimidine-2,4-diamine

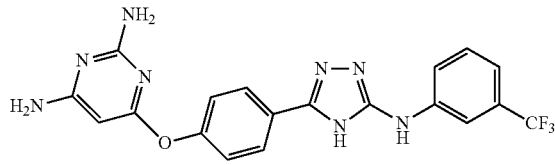 [SMILES: Nc1cc(Oc2ccc(-c3nnc(Nc4cccc(C(F)(F)F)c4)[nH]3)cc2)nc(N)n1]

4-(5-{[3-(trifluoromethyl)phenyl]amino}-4H-1,2,4-triazol-3-yl)phenol (160 mg, 0.5 mmol) was dissolved in 3 mL of anhydrous dioxane in 2-5 mL microwave vial (Personal Chemistry). Solid Cs$_2$CO$_3$ (163.0 mg, 0.5 mmol) was added, followed by 4-chloro-2,6,-diaminopyrimidine (79.5 mg, 0.55 mmol). The vial was capped and microwaved at 200° C. for 20 min. Then ca. 3 mL of MeOH was added to dissolve the formed suspension, the solution was transferred into a round-bottom flask and solvent was removed in vacuo. The residue was re-dissolved in 3 mL of DMF, filtered through 0.22 u syringe filter and purified by reverse phase preparative HPLC using acetonitrile/water system with 0.01% of TFA.

The fractions containing the product were collected and partitioned between EtOAc and saturated aqueous NaHCO$_3$. Ethyl acetate layer was washed with brine, dried over anhydrous sodium sulfate and filtered. Solvent was removed in vacuo to give the title compound as an off-white solid (92.2 mg).

ESI-MS: [M+H]$^+$, 429.08. $^1$H NMR (DMSO-d$_6$): δ 5.15 (s, 1H), 6.02 (s, 2H), 6.30 (s, 2H), 7.12 (m, 1H), 7.25-7.27 (d, J=7.4 Hz, 2H), 7.45-7.47 (m, 1H), 7.75-7.76 (m, 1H), 7.95-7.97 (d, J=8.6 Hz, 2H), 8.10 (s, 1H), 9.73 (s, 1H), 13.84 (s, 1H).

Example 49

Synthesis of 5-[4-(pyrimidin-5-yloxy)phenyl]-N-[3-(trifluoromethyl)phenyl]-4H-1,2,4-triazol-3-amine

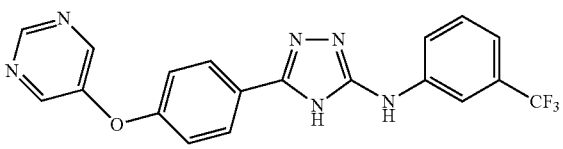 [SMILES: FC(F)(F)c1cccc(Nc2nnc(-c3ccc(Oc4cncnc4)cc3)[nH]2)c1]

4-(5-{[3-(trifluoromethyl)phenyl]amino}-4H-1,2,4-triazol-3-yl-phenol (100 mg, 0.31 mmol) was dissolved in 3 mL of anhydrous dioxane in 2-5 mL microwave vial (Personal Chemistry). Solid Cs$_2$CO$_3$ (203.4 mg, 0.62 mmol) was added, followed by 5-bromo-pyrimidine (100 mg, 0.62 mmol). Then 1 mL of anhydrous DMF was added, the vial was capped and microwaved at 250° C. for 30 min. Then ca. 3 mL of MeOH was added to dissolve the formed suspension, the solution was transferred into a round-bottom flask and solvent was removed in vacuo. The residue was re-dissolved in 3 mL of DMF, filtered through 0.22 u syringe filter and purified by reverse phase preparative HPLC using acetonitrile/water system with 0.01% of TFA. The fractions containing the product were collected and partitioned between EtOAc and saturated aqueous NaHCO$_3$. Ethyl acetate layer was washed with brine, dried over anhydrous sodium sulfate and filtered. Solvent was removed in vacuo to give the title compound as a light-brown foamy solid (34.7 mg).

ESI-MS: [M+H]$^+$, 399.06. $^1$H NMR (DMSO-d$_6$): δ 7.12 (m, 1H), 7.30-7.32 (d, J=7.4 Hz, 2H), 7.46 (m, 1H), 7.76 (m, 1H), 8.00-8.02 (d, J=8.6 Hz, 2H), 8.09 (s, 1H), 8.73 (s, 2H), 9.06 (s, 1H), 9.73 (s, 1H), 13.95 (s, 1H).

Example 50

Synthesis of 5-[4-(pyridin-3-yloxy)phenyl]-N-[3-trifluoromethyl)phenyl]-4H-[1,2,4]triazol-3-amine

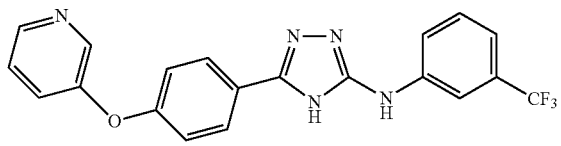 [SMILES: FC(F)(F)c1cccc(Nc2nnc(-c3ccc(Oc4cccnc4)cc3)[nH]2)c1]

4-(5-{[3-(trifluoromethyl)phenyl]amino}-4H-1,2,4-triazol-3-yl)phenol (100 mg, 0.31 mmol) was dissolved in 2 mL of anhydrous DMF in 2-5 mL microwave vial (Personal Chemistry). Solid Cs$_2$CO$_3$ (203.4 mg, 0.62 mmol) was added, followed by 3-bromopyridine (74.0 mg, 0.468 mmol). The vial was capped and microwaved at 250° C. for 30 min. Then ea, 1 mL of MeOH was added to dissolve the formed suspension. The resulting reddish-brown solution was filtered through 0.22 u syringe filter and purified by reverse phase preparative HPLC using acetonitrile/water system with 0.01% of TFA. The fractions, containing the product, were collected and partitioned between EtOAc and saturated aqueous NaHCO$_3$. Ethyl acetate layer was washed with brine, dried over anhydrous sodium sulfate and filtered. Solvent was removed in vacuo to give the title compound as a yellow solid (22.4 mg).

ESI-MS: [M+H]$^+$, 398.11. $^1$H NMR (DMSO-d$_6$): δ 7.09 (d, J=7.6 Hz, 1H), 7.20-7.22 (d, J=8.6 Hz, 2H), 7.46-7.48 (m, 2H), 7.52-7.54 (m, 1H), 7.75-7.76 (d, J=8.2 Hz, 1H), 7.99-8.02 (d, J=8.6 Hz, 2H), 8.09 (s, 1H), 8.42-8.43 (d, J=4.5 Hz, 1H), 8.45-8.46 (d, J=2.6 Hz, 1H), 9.73 (s, 1H), 13.85 (s, 1H).

Example 51

Synthesis of 4-Methoxy-6-[4-(5-{[3-(trifluoromethyl)phenyl]amino}-4H-1,2,4-triazol-3-yl)phenoxy]pyrimidin-2-amine

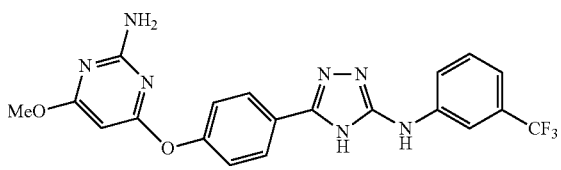 [SMILES: COc1cc(Oc2ccc(-c3nnc(Nc4cccc(C(F)(F)F)c4)[nH]3)cc2)nc(N)n1]

4-(5-{[3-(trifluoromethyl)phenyl]amino}-4H-1,2,4-triazol-3-yl)phenol (100 mg, 0.31 mmol) was dissolved in 3 mL of anhydrous dioxane in 2-5 mL microwave vial (Personal Chemistry). Solid Cs$_2$CO$_3$ (101.7 mg, 0.31 mmol) was added, followed by 2-amino-4-chloro-6-methoxypyrimidine (55.0 mg, 0.34 mmol). The vial was capped and microwaved at 200° C. for 15 min. Then ca. 3 mL of MeOH was added to dissolve the formed suspension. The resulting reddish-brown solution was transferred into a round-bottom flask and solvent was removed in vacuo. The residue was re-dissolved in 3 mL of DMF, filtered through 0.22 u syringe filter and purified by reverse phase preparative HPLC using acetonitrile/water system with 0.01% of TEA. The fractions, containing the product, were collected and partitioned between EtOAc and saturated aqueous NaHCO$_3$. Ethyl acetate layer was washed with brine, dried over anhydrous sodium sulfate and filtered. Solvent was removed in vacuo to give the title compound as an off-white solid (55.6 mg).

ESI-MS: [M+H]$^+$, 443.87. $^1$H NMR (DMSO-d$_6$): δ 3.80 (s, 3H), 5.53 (s, 1H), 6.70 (s, 2H), 7.11-7.12 (d, J=7.4 Hz, 1H), 7.30-7.32 (d, J=8.4 Hz, 2H), 7.44-7.47 (t, J=7.6 Hz, 1H), 7.74-7.76 (d, J=8.4 Hz, 1H), 7.97-7.98 (d, J=8.4 Hz, 2H), 8.10 (s, 1H), 9.73 (s, 1H), 13.88 (s, 1H).

Example 52

Synthesis of 6-[4-(5-{[3-(trifluoromethyl)phenyl]amino}-4H-[1,2,4]triazol-3-yl)-phenoxy]-pyrimidin-4-amine

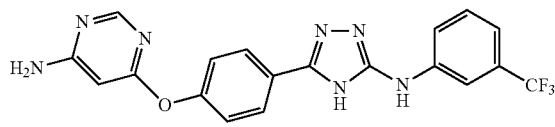 [SMILES: Nc1cc(Oc2ccc(-c3nnc(Nc4cccc(C(F)(F)F)c4)[nH]3)cc2)ncn1]

4-(5-{[3-(trifluoromethyl)phenyl]amino}-4H-1,2,4-triazol-3-yl)phenol (100 mg, 0.31 mmol) was dissolved in 3 mL of anhydrous dioxane in 2-5 mL microwave vial (Personal Chemistry). Solid Cs$_2$CO$_3$ (101.7 mg, 0.31 mmol) was added, followed by 4-amino-6-chloro-pyrimidine (48.5 mg, 0.37 mmol). The vial was capped and microwaved at 200° C., for 5 min. Then ca. 3 mL of MeOH was added to dissolve the formed suspension. The resulting reddish-brown solution was transferred into a round-bottom flask and solvent was removed in vacuo. The residue was re-dissolved in 3 mL of DMF, filtered through 0.22 u syringe filter and purified by reverse phase preparative HPLC using acetonitrile/water system with 0.01% of TFA. The fractions, containing the product, were collected and partitioned between EtOAc and saturated aqueous NaHCO$_3$. Ethyl acetate layer was washed with brine, dried over anhydrous sodium sulfate and filtered. Solvent was removed in vacuo to give the title compound as a white solid (76.6 mg).

ESI-MS: [M+H]$^+$, 461.0. $^1$H NMR (DMSO-d$_6$): δ 2.31 (s, 3H), 5.49 (s, 1H), 6.93 (s, 2H), 7.14 (m, 1H), 7.33-7.35 (d, J=7.5 Hz, 2H), 7.45-7.48 (t, J=7.6 Hz, 1H), 7.75 (m, 1H), 8.00-8.02 (d, J=8.6 Hz, 2H), 8.10 (s, 1H), 9.75 (s, 1H), 13.88 (s, 1H).

Example 53

Synthesis of 2-(Methylthio)-6-[4-(5-{[3-(trifluoromethyl)phenyl]amino}-4H-1,2,4-triazol-3-yl)-phenoxy]-pyrimidin-4-amine

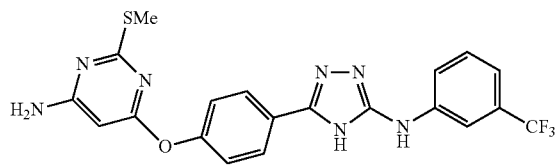 [SMILES: CSc1nc(N)cc(Oc2ccc(-c3nnc(Nc4cccc(C(F)(F)F)c4)[nH]3)cc2)n1]

4-(5-{[3-(trifluoromethyl)phenyl]amino}-4H-1,2,4-triazol-3-yl)phenol (100 mg, 0.31 mmol) was dissolved in 3 mL of anhydrous dioxane in 2-5 mL microwave vial (Personal Chemistry). Solid Cs$_2$CO$_3$ (101.7 mg, 0.31 mmol) was added, followed by 4-amino-6-chloro-2-(methylthio)-pyrimidine (60.3 mg, 0.34 mmol). The vial was capped and microwaved at 200° C. for 10 min. Then ca. 3 mL of MeOH was added to dissolve the formed suspension. The resulting reddish-brown solution was transferred into a round-bottom flask and solvent was removed in vacuo. The residue was re-dissolved in 3 mL of DMF, filtered through 0.22 u syringe filter and purified by reverse phase preparative HPLC using acetonitrile/water system with 0.01% of TFA. The fractions, containing the product, were collected and partitioned between EtOAc and saturated aqueous NaHCO$_3$. Ethyl acetate layer was washed with brine, dried over anhydrous sodium sulfate and filtered. Solvent was removed in vacuo to give the title compound as a white solid (39.5 mg).

ESI-MS: [M+H]$^+$, 461.0. $^1$H NMR (DMSO-d$_6$): δ 3.80 (s, 3H), 5.53 (s, 1H), 6.70 (s, 2H), 6.30 (s, 2H), (d, J=8.6 Hz, 2H).

Example 54

Synthesis of 4-[5-(4-trifluoromethoxy-phenyl)-4H-[1,2,4]triazol-3-ylamino]-phenol

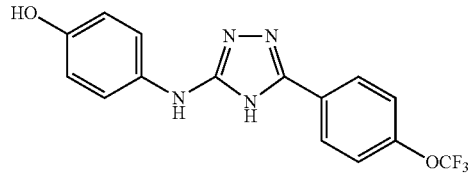 [SMILES: Oc1ccc(Nc2nnc(-c3ccc(OC(F)(F)F)cc3)[nH]2)cc1]

4-trifluoromethoxybenzoic acid hydrazide (1.1 g, 5.0 mmol) and S-methyl N-[4-hydroxy-phenyl]isothiourea hydroiodide (1.55 g, 5.0 mmol) were suspended in 10 mL of anhydrous pyridine. The reaction mixture was refluxed for 24 hours, during which time it changed color from yellow into orange-red. Then it was cooled down to ambient temperature and poured with stirring into 150 mL of ice-water. The aqueous layer was decanted and the resulting residue was purified by silica gel chromatography using 1:1 mixture of ethyl acetate/hexane. Solvent was removed in vacuo to give the title product as a pinkish-grey solid (684.0 mg). 40.6% yield.

ESI-MS: [M+H]⁺, 337, 338. ¹H NMR (DMSO-d₆): δ 7.68-6.71 (d, J=8.8 Hz, 2H), 7.32-7.35 (d, J=8.8 Hz, 2H), 7.47-7.49 (d, J=8.8 Hz, 2H), 8.04-8.07 (d, 8.8 Hz, 2H), 9.05 (br. s, 1H).

Example 55

Synthesis of 4-{4-[5-(4-trifluoromethoxy-phenyl)-4H-[1,2,4]triazol-3-ylamino]-phenoxy}-pyridine-2-carboxylic acid methylamide trifluoroacetic acid salt

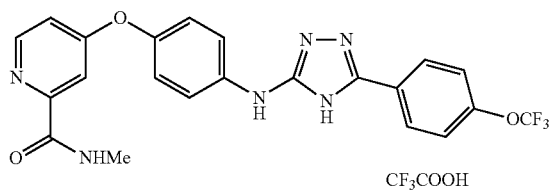 [SMILES: CNC(=O)c1cc(Oc2ccc(Nc3nnc(-c4ccc(OC(F)(F)F)cc4)[nH]3)cc2)ccn1 ; "CF3COOH"]

4-[5-(4-trifluoromethoxy-phenyl)-4H[1,2,4]triazol-3-ylamino]-phenol (134.5 mg, 0.4 mmol) was dissolved in 2 mL of anhydrous DMF in a 5 mL microwave vial (Personal Chemistry). Solid potassium bis(trimethylsilyl)amide (120.0 mg, 0.6 mmol) was added and the reaction mixture was stirred with heating at 80° C. for 15 min, then 4-chloro-2-pyridine-carboxamide (68.2 mg, 0.4 mmol) was added, followed by anhydrous K₂CO₃ (62.0 mg, 0.44 mmol). Then the vial was capped and microwaved at 150° C. for 30 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (31.7 mg of white solid).
ESI-MS [M+H]⁺ 471, 472. ¹H NMR DMSO-d₆): δ 2.77-2.78 (d, J=4.8 Hz, 3H), 7.13-7.15 (d, J=8.3 Hz, 2H), 7.13 (m, 1H), 7.40 (br, s, 1H), 7.51-7.53 (d, J=8.3 Hz, 2H), 7.70-7.73 (d, J=8.8 Hz, 2H), 8.09-8.11 (d, J=8.8 Hz, 2H), 8.48-8.49 (d, J=5.3 Hz, 1H), 8.77-8.78 (q, J=4.8 Hz, 1H), 9.56 (s, 1H).

Example 56

Synthesis of 3-[5-(4-chloro-3-trifluoromethyl-phenylamino)-4H[1,2,4]triazol-3-yl]-phenol

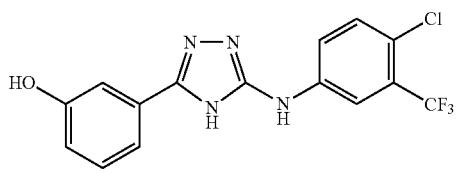 [SMILES: Oc1cccc(-c2nnc(Nc3ccc(Cl)c(C(F)(F)F)c3)[nH]2)c1]

3-hydroxybenzoic acid hydrazide (2.98 g, 19.58 mmol) and S-methyl N-[4-chloro-3-(trifluoromethyl)phenyl] isothiourea hydroiodide (7.78 g, 19.63 mmol) were suspended in 40 mL of anhydrous pyridine. The reaction mixture was refluxed for 18 hours, during which time it changed color from yellow into dark-red. Then it was cooled down to ambient temperature and poured with stirring into 250 mL of ice-water. The aqueous solution was decanted and the oily residue was purified by silica gel chromatography on Isco column using 0=>50% gradient of ethyl acetate in hexane. Solvent was removed in vacuo to give the title product as a white solid (2.176 g). 31.3% yield.

ESI-MS: [M+H]⁺ 355.1, 356.8. ¹H NMR (DMSO-d₆): δ 6.88-6.90 (dq, J₁=7.9 Hz, J₂=0.9 Hz, 1H), 7.31-7.34 (t, J=7.9 Hz, 1H), 7.35-7.39 (m, 2H), 7.54-7.56 (d, J=8.8 Hz, 1H), 7.74-7.76 (dd, J₁=8.8 Hz, J₂=2.7 Hz, 1H), 8.23-8.24 (d, J=2.7 Hz, 1H), 9.79 (s, 1H), 9.87 (s, 1H), 13.86 (s, 1H).

Example 57

Synthesis of 4-{3-[5-(4-chloro-3-trifluoromethyl-phenylamino)-4H-[1,2,4]triazol-3-yl]-phenoxy}-pyridine-2-carboxylic acid methylamide trifluoroacetic acid salt

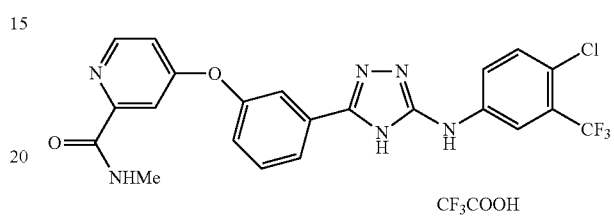

3-[5-(4-chloro-3-trifluoromethyl-phenylamino)-4H[1,2,4]triazol-3-yl]-phenol (100 mg, 0.282 mmol) was dissolved in 2 mL of anhydrous DMF in a 5 mL microwave vial (Personal Chemistry). Solid potassium bis(trimethylsilyl)amide (140.6 mg, 0.705 mmol) was added and the reaction mixture was stirred with heating at 80° C. for 15 min, then 4-chloro-2-pyridine-carboxamide (52.9 mg, 0.31 mmol) was added, followed by anhydrous K₂CO₃ (19.5 mg, 0.141 mmol). Then the vial was capped and microwaved at 250° C. for 20 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (25.0 rug of white solid).
ESI-MS: [M+H]⁺ 489, 490, 491. ¹H NMR (DMSO-d₆): δ 2.78-2.79 (d, J=4.8 Hz, 3H), 7.25-7.26 (dd, J₁=2.5 Hz, J₂=5.5 Hz, 1H), 7.38 (m, 1H), 7.48-7.49 (d, J=2.5 Hz, 1H), 7.55-7.57 (d, J=8.8 Hz, 1H), 7.67-7.70 (t, J=7.8 Hz, 1H), 7.73 (br. s., 1H), 7.78 (br. s., 1H), 7.91-7.93 (d, J=7.8 Hz, 1H), 8.20-8.21 (d, J=2.6 Hz, 1H), 8.56-8.57 (d, j=5.5 Hz, 1H), 8.80-8.81 (q, J=4.8 Hz, 1H), 9.93 (s, 1H).

Example 58

Synthesis of 6-{3-[5-(4-chloro-3-trifluoromethyl-phenylamino)-4H-[1,2,4]triazol-3-yl]-phenoxy}-pyrimidine-2,4-diamine trifluoroacetic acid salt

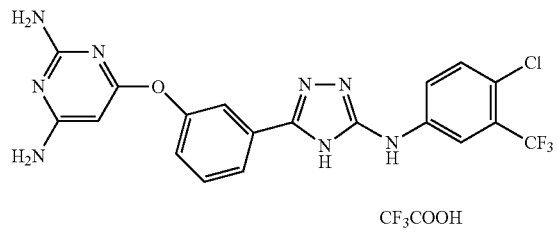 [SMILES: Nc1cc(Oc2cccc(-c3nnc(Nc4ccc(Cl)c(C(F)(F)F)c4)[nH]3)c2)nc(N)n1 ; "CF3COOH"]

3-[5-(4-chloro-3-trifluoromethyl-phenylamino)-4H[1,2,4]triazol-3-yl]-phenol (100 mg, 0.282 mmol) was dissolved in 2 mL of anhydrous DMF in a 5 mL microwave vial. Solid potassium bis(trimethylsilyl)amide (140.6 mg, 0.705 mmol) was added and the reaction mixture was stirred with heating at 80° C. for 15 min, then 4-chloro-2,6-diamino-pyrimidine (44.8 mg, 0.31 mmol) was added, followed by anhydrous K₂CO₃ (19.5 mg, 0.141 mmol). Then the vial was capped and microwaved at 250° C. for 20 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (37.8 mg of beige solid).

ESI-MS: [M+H]⁺ 464, 465. ¹H NMR (DMSO-$d_6$): δ 5.40 (s, 1H), 7.33-7.35 (d, J=7.6 Hz, 1H), 7.57-7.59 (d, J=8.8 Hz, 1H), 7.62-7.65 (t, J=7.8 Hz, 1H), 7.73 (br. s., 1H), 7.80 (br. m., 1H), 7.88-7.89 (d, J=7.8 Hz, 1H), 8.21-8.22 (d, J=2.6 Hz, 1H), 9.96 (s, 1H).

Example 59

Synthesis of (4-chloro-3-trifluoromethyl-phenyl)-{5-[3-(pyridin-4-yloxy)-phenyl]-4H-[1,2,4]triazol-3-yl}-amine trifluoroacetic acid salt

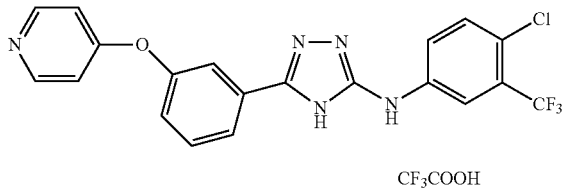 [SMILES: FC(F)(F)c1cc(Nc2nnc(-c3cccc(Oc4ccncc4)c3)[nH]2)ccc1Cl ; "CF3COOH"]

CF₃COOH

3-[5-(4-chloro-3-trifluoromethyl-phenylamino)-4H[1,2,4]triazol-3-yl]-phenol (100 mg, 0.282 mmol) was dissolved in 2 mL of anhydrous DMF in a 5 mL microwave vial. Solid potassium bis(trimethylsilyl)amide (140.6 rug, 0.705 mmol) was added and the reaction mixture was stirred with heating at 80° C. for 15 min, then 4-chloro-pyridine hydrochloride (46.5 mg, 0.31 mmol) was added, followed by anhydrous K₂CO₃ (19.5 rug, 0.141 mmol). Then the vial was capped and microwaved at 250° C. for 20 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (34.6 mg of beige solid).

ESI-MS: [M+H]⁺ 432, 433. ¹H NMR (DMSO-$d_6$): δ 7.43-7.45 (br. s, 1H), 7.46-7.47 (d, J=7.0 Hz, 2H), 7.56-7.58 (d, J=8.8 Hz, 1H), 7.72-7.75 (t, 0.1=7.8 Hz, 1H), 7.80 (br. s., 1H), 7.81 (br. s, 1H), 7.98-8.00 (d, f=7.8 Hz, 1H), 8.21-8.22 (d, J=2.6 Hz, 1H, 8.76-8.78 (d, J=7.0 Hz, 1H), 9.98 (s, 1H).

Example 60

Synthesis of 6-{3-[5-(4-chloro-3-trifluoromethyl-phenylamino)-4H-[1,2,4]triazol-3-yl]-phenoxy}-pyridazin-3-ylamine trifluoroacetic acid salt

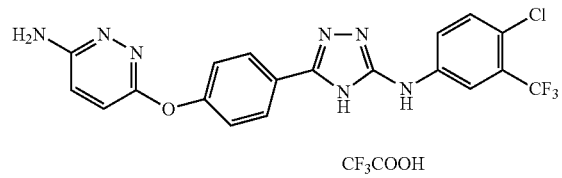 [SMILES: Nc1ccc(Oc2ccc(-c3nnc(Nc4ccc(Cl)c(C(F)(F)F)c4)[nH]3)cc2)nn1 ; "CF3COOH"]

CF₃COOH

3-[5-(4-chloro-3-trifluoromethyl-phenylamino)-4H[1,2,4]triazol-3-yl]-phenol (100 mg, 0.282 mmol) was dissolved in 2 mL of anhydrous DMF in a 5 mL microwave vial. Solid potassium bis(trimethylsilyl)amide (140.6 mg, 0.705 mmol) was added and the reaction mixture was stirred with heating at 80° C. for 15 min, then 3-amino-6-chloro-pyridazine (40.2 mg, 0.31 mmol) was added, followed by anhydrous K₂CO₃ (19.5 rug, 0.141 mmol). Then the vial was capped and microwaved at 250° C. for 20 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (35.5 mg of light-brown solid).

ESI-MS: [M+H]⁺ 448, 449. ¹H NMR (DMSO-$d_6$): δ 7.38-7.39 (br. s. 1H), 7.55-7.57 (d, J=9.6 Hz, 1H), 7.57-7.58 (d, J=8.6 Hz, 1H), 7.62-7.65 (t, J=7.8 Hz, 1H), 7.78 (br. s., 1H), 7.80 (br. s, 1H), 7.82-7.84 (d, J=9.6 Hz, 1H), 7.86-7.88 (d, J=7.8 Hz, 1H), 8.22-8.23 (d, J=2.6 Hz, 1H), 8.52 (br.s., 2H), 9.94 (s, 1H).

Example 61

Synthesis of 4-(5-{[4-chloro-3-(trifluoromethyl)-phenyl]amino}-1,3,4-oxadiazol-2-yl)phenol

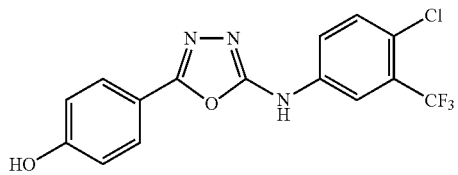

Mercury (II) oxide (yellow) (4.55 g, 21.0 mmol) was suspended in 60 mL of anhydrous MeOH under Ar. A bright-orange suspension was formed. To this suspension was added 4-hydroxybenzoic acid hydrazide (3.20 g, 21.0 mmol) and 4-chloro-3-trifluoromethyl-phenylisothiocyanate (5.0 g, 21.0 mmol). The reaction mixture was refluxed for 2 hours. The solvent was removed in vacuo. The black residue was redissolved in 100 mL of EtOAc and the resulting black suspension was filtered through a short pad of silica gel. The filtrate was mixed with 10 g of dry silica gel and solvent was removed in vacuo. The impregnated silica gel was loaded on silica gel column and the product was separated using a gradient of hexane:ethyl acetate mixture starting from 50:50 ratio and finishing at 0:100. All fractions containing the product were combined; solvent was removed in vacuo to give a grey solid. The solid was heated in 50 mL of 4:1 mixture of EtOAc/MeOH. The formed suspension was cooled down to ambient temperature and filtered to give the title product as a white crystalline solid (4.54 g, 60.7% yield).

ESI-MS: [M+H]⁺ 356.0. ¹H NMR (DMSO-$d_6$): δ 6.92-6.95 (d, J=8.8 Hz, 2H), 7.69-7.70 (d, J=8.8 Hz, 1H), 7.71-7.73 (d, J=8.8 Hz, 2H), 7.82-7.84 (dd, J₁=8.8 Hz, J₂=2.6 Hz, 1H), 8.16-8.17 (d, J=2.6 Hz, 1H), 10.21 (br s., 1H), 11.11 (br s., 1H).

Example 62

Synthesis of 6-[4-(5-{[4-Chloro-3-trifluoromethyl-phenyl]amino}-1,3,4-oxadiazol-2-yl)-phenoxy]-pyrimidine-2,4-diamine

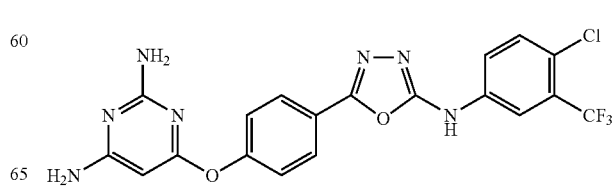

4-(5-{[4-chloro-3-(trifluoromethyl-phenyl]amino}-1,3,4-oxadiazol-2-yl)phenol (1.067 g, 3.0 mmol) was dissolved in ca. 70 mL of anhydrous DMF under argon. Solid potassium bis(trimethylsilyl)amide (0.718 g, 3.6 mmol) was added and the resulting yellow solution was heated at 70° C. for 1.5 hours. Then solid $K_2CO_3$ (0.414 g, 3.0 mmol) was added, followed by 2,6-diamino-4-chloropyrimidine (0.520 g, 3.6 mmol). The reaction mixture was lets to reflux under argon for 30 hours. Then it was allowed to cool down to ambient temperature and poured into ca. 500 mL of water. The aqueous mixture was extracted 5 times with 100 mL of EtOAc. Combined EtOAc extracts were washed three times with 100 mL of brine, and dried over anhydrous $Na_2SO_4$. Solvent was removed in vacuo to a give a reddish-yellow residue, which was purified by silica gel chromatography using EtOAc as an eluent. Fractions, containing the product, were collected; solvent was removed in vacuo to give the product as a reddish-yellow solid. The solid was re-crystallized from 10 mL of EtOAc, collected, washed thoroughly with diethyl ether and dried in vacuo to give the title compound (0.527 g, 38% yield) as beige solid.

ESI-MS: [M+H]$^+$ 464, 465. $^1$H NMR (DMSO-d$_6$): δ 5.20 (s, 1H), 6.05 (br s., 2H), 6.34 (br.s., 2H), 7.27-7.30 (d, J=8.7 Hz, 2H), 7.71-7.72 (d, J=8.8 Hz, 1H), 7.84-7.88 (dd, 8.8 Hz, $J_2$=2.6 Hz, 1H), 7.89-7.91 (d, J=8.7 Hz, 2H), 8.18-8.19 (d, J=2.6 Hz, 1H), 11.26 (s, 1H). Anal. Calcd for $C_{19}H_{13}ClF_3N_7O_2$: C, 49.20; H, 2.83; N, 21.14. Found: C, 49.08; H, 3.21; N, 20.95.

Example 63

Synthesis of 6-[4-(5-{[4-chloro-3-trifluoromethyl-phenyl]amino}-1,3,4-oxadiazol-2-yl)-phenoxy]-pyrimidine-2,4-diamine trifluoroacetic acid salt

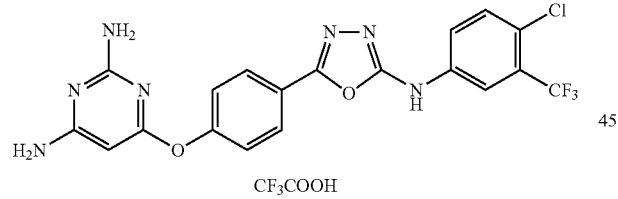

CF$_3$COOH 4-(5-{[4-chloro-3-(trifluoromethyl)-phenyl]amino}-1,3,4-oxadiazol-2-yl)phenol (100 mg, 0.281 mmol) was dissolved in 2.5 mL of anhydrous DMF in a 5 mL microwave vial. Solid potassium bis(trimethylsilyl)amide (140.6 mg, 0.703 mmol) was added and the reaction mixture was stirred with heating at 80° C. for 15 min, then 6-chloro-2,4-diamino-pyrimidine (81.3 mg, 0.562 mmol) was added, followed by anhydrous $K_2CO_3$ (19.5 mg, 0.141 mmol). Then the vial was capped and microwaved at 200° C. for 15 min. Then the reaction mixture was diluted with ca. 1 mL of MeOH, filtered through 0.22 um syringe filter and purified by reverse-phase preparative HPLC in acetonitrile/water system with 0.01% TFA. The product was isolated as a TFA salt (75.8 mg of beige solid).

ESI-MS: [M+H]$^+$ 464, 465. $^1$H NMR (DMSO-d$_6$): δ 5.41 (s, 1H), 7.39-7.42 (d, J=8.7 Hz, 2H), 7.63 (br s., 4H), 7.72-7.74 (d, J=8.8 Hz, 1H), 7.85-7.87 (dd, $J_1$=8.8 Hz, $J_2$=2.7 Hz, 1H), 7.95-7.97 (d, J=8.7 Hz, 2H), 8.20 (d, J=2.7 Hz, 1H), 11.29 (s, 1H).

Example 64

Synthesis of N-[4-chloro-3-(trifluoromethyl)phenyl]-5-[4-(pyridin-3-yloxy)phenyl]-1,3,4-oxadiazol-2-amine trifluoroacetate salt

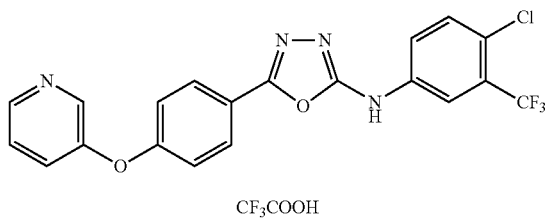

CF$_3$COOH 4-(5-{[4-chloro-3-(trifluoromethyl)-phenyl]amino}-1,3,4-oxadiazol-2-yl)phenol (100 mg, 0.281 mmol) was dissolved in ca. 2 mL of anhydrous DMF under argon. Solid potassium bis(trimethylsilyl)amide (140.2 mg, 0.702 mmol) was added and the resulting yellow solution was heated at 80° C. for 15 min. Then solid $K_2CO_3$ (19.4 mg, 0.140 mmol) was added, followed by 3-bromopyridine (89.0 mg, 0.562 mmol). The reaction mixture was microwaved at 250° C. for 10 min. Then it was diluted with 1 mL of MeOH, filtered and purified by preparative reverse-phase chromatography using acetonitrile/water with 0.1% TFA gradient. The major peak having the mass of the product was collected; solvent was removed in vacuo to give the title product as a brown oil (20.6 mg).

ESI-MS: [M+H]$^+$ 433.5, 434.3. $^1$H NMR (DMSO-d$_6$): δ 7.24-7.26 (d, J=8.8 Hz, 2H), 7.57-7.59 (dd, $J_1$=8.4 Hz, $J_2$=4.7 Hz, 1H), 7.68-7.71 (dq, $J_1$=8.4 Hz, $J_2$=1.4 Hz, 1H), 7.71-7.73 (d, J=8.8 Hz, $^{1H}$), 7.84-7.86 (dd, $J_1$=8.8 Hz, $J_2$=2.7 Hz, 1H), 7.92-7.94 (d, J=8.8 Hz, 2H), 8.17-8.18 (d, J=2.7 Hz, 1H), 8.50 (br d, J=4.0 Hz, 1H), 8.54 (br s, 1H), 1.24 (s, 1H).

Example 65

Synthesis of N-[4-chloro-3-(trifluoromethyl)phenyl]-5-[4-(pyridin-4-yloxy)phenyl]-1,3,4-oxadiazol-2-amine trifluoroacetate salt

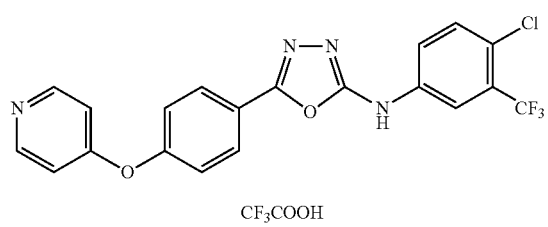 [SMILES: FC(F)(F)c1cc(Nc2nnc(-c3ccc(Oc4ccncc4)cc3)o2)ccc1Cl ; "CF3COOH"]

CF$_3$COOH 4-(5-{[4-chloro-3-(trifluoromethyl)-phenyl]amino}-1,3,4-oxadiazol-2-yl)phenol (100 mg, 0.281 mmol) was dissolved in ca. 2 mL of anhydrous DMF under argon. Solid potassium bis(trimethylsilyl)amide (225 mg, 1.12 mmol) was added and the resulting yellow solution was heated at 80° C. for 15 min. Then solid $K_2CO_3$ (38.8 mg, 0.281 mmol) was added, followed by 4-chloropyridine hydrochloride (84.3 mg, 0.562 mmol). The reaction mixture was microwaved at 200°

C. for 25 min (Initiator, Biotage). Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give the title product as a white fluffy solid (85.6 mg).

ESI-MS: [M+H]+ 435.3. 1H NMR (DMSO-d6): δ 7.37-7.38 (d, J=4.8 Hz, 2H), 7.48-7.50 (d, J=8.8 Hz, 2H), 7.72-7.74 (d, J=8.8 Hz, 1H), 7.85-7.88 (dd, J=8.8 Hz, J2=2.7 Hz, 1H), 8.03-8.06 (d, J=8.8 Hz, 1H), 8.19-8.20 (d, J=2.7 Hz, 1H), 8.74 (br s., 2H), 11.31 (s, 1H).

Example 66

Synthesis of N-[4-chloro-3-(trifluoromethyl)phenyl]-5-[4-(pyrimidin-5-yloxy)phenyl]-1,3,4-oxadiazol-2-amine trifluoroacetate salt

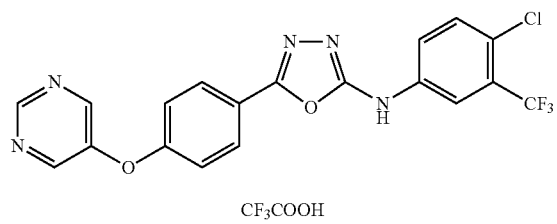

CF3COOH 4-(5-{[4-chloro-3-(trifluoromethyl)-phenyl]amino}-1,3,4-oxadiazol-2-yl)phenol (100 mg, 0.281 mmol) was dissolved in ca. 2 mL of anhydrous DMF under argon. Solid potassium bis(trimethylsilyl)amide (140.2 mg, 0.702 mmol) was added and the resulting yellow solution was heated at 80° C. for 15 min. Then solid K2CO3 (19.4 mg, 0.140 mmol) was added, followed by 3-bromopyrimidine (89.4 mg, 0.562 mmol). The reaction mixture was microwaved at 200° C. for 15 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give the title product as a white fluffy solid (73.0 mg of white crystalline solid).

ESI-MS: [M+H]+ 434.3, 435.3. 1H NMR (DMSO-d6): δ 7.31-7.33 (d, J=8.8 Hz, 2H), 7.71-7.73 (d, J=8.8 Hz, 1H), 7.84-7.86 (dd, J1=8.8 Hz, J2=2.7 Hz, 1H), 7.93-7.95 (d, J=8.8 Hz, 2H), 8.17-8.18 (d, J=2.7 Hz, 1H), 8.77 (s, 2H), 9.09 (s, 1H), 11.25 (s, 1H).

Example 67

Synthesis of 4-[4-(5-{[4-chloro-3-(trifluoromethyl)phenyl]amino}-1,3,4-oxadiazol-2-yl)phenoxy]-N-methylpyridine-2-carboxamide trifluoroacetate salt

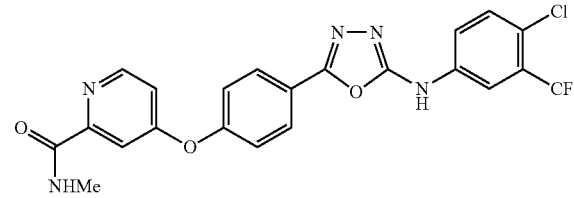

CF3COOH 4-(5-{[4-chloro-3-(trifluoromethyl)-phenyl]amino}-1,3,4-oxadiazol-2-yl)phenol (100 mg, 0.281 mmol) was dissolved in ca. 2 mL of anhydrous DMF under argon. Solid potassium bis(trimethylsilyl)amide (140.2 mg, 0.702 mmol) was added and the resulting yellow solution was heated at 80° C. for 15 min. Then solid K2CO3 (19.4 mg, 0.140 mmol) was added, followed by 4-chloro-2-pyridine-carboxamide (52.7 mg, 0.309 mmol). The reaction mixture was microwaved at 200 C for 15 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give the title product as a white solid (67.5 mg).

ESI-MS: [M+H]+ 490.4, 491.3. 1H NMR (DMSO-d6): δ 2.79-2.80 (d, J=4.9 Hz, 3H), 7.26-7.28 (dd, J1=5.6 Hz, J2=2.6 Hz, 1H), 7.43-7.44 (d, J=6.8 Hz, 2H), 7.49 (d, J=2.6 Hz, 1H), 7.72-7.74 (d, J=8.8 Hz, 1H), 7.85-7.86 (dd, J=8.8 Hz, J2=2.6 Hz, 1H), 8.01-8.03 (d, J=6.8 Hz, 2H), 8.19 (d, J=2.6 Hz, 1H), 8.57-8.58 (d, J=5.7 Hz, 1H), 8.79-8.81 (q, J=4.9 Hz, 1H), 11.28 (s, 1H).

Example 68

Synthesis of 4-[5-(4-chloro-3-(trifluromethyl)-phenyl)-4H-1,2,4-triazol-3-ylamino]phenol

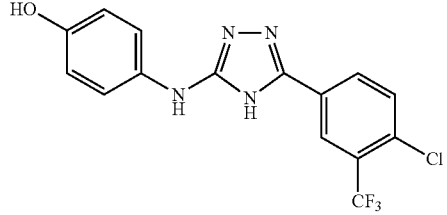

4-chloro-3-trifluoromethylbenzoic acid hydrazide (2.89 g, 12.1 mmol) and S-methyl N-(4-hydroxyphenyl)isothiourea hydroiodide (3.75 g, 12.1 mmol) were suspended in 40 mL of anhydrous pyridine. The reaction mixture was refluxed for 18 hours, during which time it changed color from yellow into dark-red. Then it was cooled down to ambient temperature and poured with stirring into 250 mL of ice-water. The aqueous solution was decanted and the oily residue was purified by silica gel chromatography using 1:1 mixture of ethyl acetate/hexane. Solvent was removed in vacuo to give the title product as a white solid (1.95 g). Yield 45.5%.

Example 69

Synthesis of 6-[4-({5-[4-chloro-3-(trifluoromethyl)phenyl-4H-1,2,4-triazol-3-yl}amino)phenoxy]pyrimidine-2,4-diamine trifluoroacetate salt

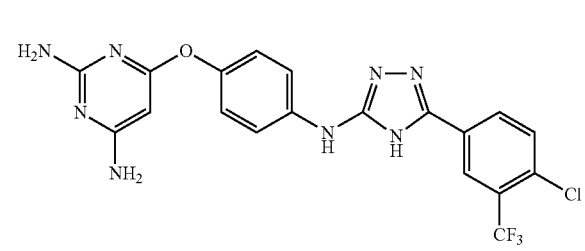

CF3COOH

4-[5-(4-chloro-3-(trifluoromethyl)-phenyl)-4H-1,2,4-triazol-3-ylamino]phenol (100 mg, 0.282 mmol) was dissolved in 2 mL of anhydrous DMF. Solid potassium bis(trimethylsilyl)amide (140.6 mg, 0.705 mmol) was added and the resulting solution was heated at 80° C. for 15 min. Then solid K$_2$CO$_3$ (20 mg, 0.141 mmol) was added, followed by 4-chloro-2,6-diamino-pyrimidine (61.1 mg, 0.422 mmol). The reaction mixture was microwaved at 200° C. for 20 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected, solvent was removed in vacuo to give trifluoroacetate salt of the product as a white solid (28.6 mg).

ESI-MS: [M+H]$^+$ 463.4, 464.4. $^1$H NMR (DMSO-d$_6$): δ5.24 (s, 1H), 7.14-7.16 (d, J=8.8 Hz, 2H), 7.65-7.66 (d, J=8.8 Hz, 2H), 7.81 (br s., 4H), 7.88-7.90 (d, J=8.4 Hz, 1H), 8.23-8.25 (dd, J$_1$=8.4 Hz, J$_2$=1.7 Hz, 1H), 8.37 (s, 1H), 9.66 (br s., 1H).

Example 70

Synthesis of 5-[4-chloro-3-(trifluoromethyl)phenyl]-N-[4-(pyridine-4-yloxy)phenyl]-4H-1,2,4-triazol-3-amine trifluoroacetate salt

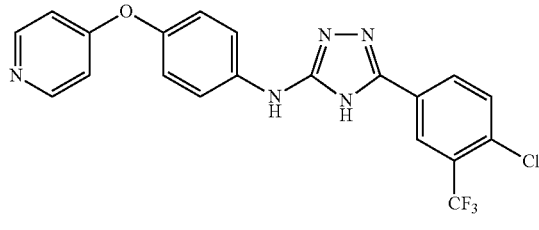

CF$_3$COOH

4-[5-(4-chloro-3-(trifluoromethyl)-phenyl)-4H-1,2,4-triazol-3-ylamino]phenol (100 mg, 0.282 mmol) was dissolved in 2 mL of anhydrous DMF. Solid potassium bis(trimethylsilyl)amide (196.2 mg, 0.983 mmol) was added and the resulting solution was heated at 80° C. for 15 min. Then solid K$_2$CO$_3$ (20 mg, 0.141 mmol) was added, followed by 4-chloropyridine hydrochloride (63.2 mg, 0.421 mmol). The reaction mixture was microwaved at 220° C. for 30 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected, solvent was removed in vacuo to give trifluoroacetate salt of the product as a light-brown solid (23.5 mg).

ESI-MS: [M+H]$^+$ 432, 433. $^1$H NMR (DMSO-d$_6$): δ 7.23-7.25 (d, J=8.8 Hz, 2H), 7.39-7.40 (d, J=7.2 Hz, 2H), 7.74-7.77 (d, J=8.8 Hz, 2H), 7.89-7.90 (m, 1H), 8.24-8.26 (dd, J$_1$=8.4 Hz, J$_2$=2.0 Hz, 1H), 8.38 (s, 1H), 8.73-8.74 (d, J=7.2 Hz, 2H), 9.75 (br s., 1H).

Example 71

Synthesis of 5-[4-chloro-3-(trifluoromethyl)phenyl]-N-[4-(pyrimidin-5-yloxy)phenyl]-4H-1,2,4-triazol-3-anine trifluoroacetate salt

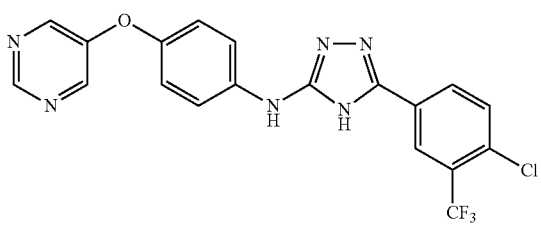

CF$_3$COOH

4-[5-(4-chloro-3-(trifluoromethyl)-phenyl)-4H-1,2,4-triazol-3-ylamino]phenol (100 mg, 0.282 mmol) was dissolved in 2 mL of anhydrous DMF. Solid potassium bis(trimethylsilyl)amide (84.1 mg, 0.421 mmol) was added and the resulting solution was heated at 80° C. for 15 min. Then solid K$_2$CO$_3$ (20 mg, 0.141 mmol) was added, followed by 5-bromopyrimidine (67.0 mg, 0.421 mmol). The reaction mixture was microwaved at 220° C. for min. Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give trifluoroacetate salt of the product as a light-brown solid (25.0 mg).

ESI-MS: [M+H]$^+$ 432.9, 435. $^1$H NMR (DMSO-d$_6$): δ 7.14-7.16 (d, J=8.9 Hz, 2H), 7.63-7.67 (d, J=8.9 Hz, 2H), 7.87-7.89 (d, J=8.4 Hz, 1H), 8.22-8.24 (dd, J$_1$=8.4 Hz, J$_2$=2.0 Hz, 1H), 8.36 (s, 1H), 8.54 (s, 2H), 8.93 (s, 1H), 9.57 (br s., 1H).

Example 72

Synthesis of 6-[4-({5-[4-chloro-3-(trifluoromethyl)phenyl]-4H-1,2,4-triazol-3-yl}amino)phenoxy]pyridazin-3-amine trifluoroacetate salt

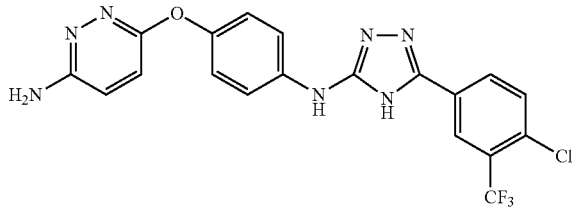

CF$_3$COOH

4-[5-(4-chloro-3-(trifluoromethyl)-phenyl)-4H-1,2,4-triazol-3-ylamino]phenol (100 mg, 0.282 mmol) was dissolved in 2 mL of anhydrous DMF. Solid potassium bis(trimethylsilyl)amide (140.6 mg, 0.705 mmol) was added and the resulting solution was heated at 80° C. for 15 min. Then solid K$_2$CO$_3$ (20 mg, 0.141 mmol) was added, followed by 3-amino-6-chloropyridazine (54.6 mg, 0.421 mmol). The reaction mixture was microwaved at 220° C. for 40 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give trifluoroacetate salt of the product as a light-brown solid (23.1 mg).

ESI-MS: [M+H]$^+$ 448, 449. $^1$H NMR (DMSO-d$_6$): δ 7.16-7.18 (d, J=8.9 Hz, 2H), 7.51-7.53 (d, J=9.7 Hz, 1H), 7.62-7.66 (d, J=8.9 Hz, 2H), 7.73-7.75 (d, J=9.7 Hz, 1H), 7.88 (d, J=8.4 Hz, 1H), 8.23-8.25 (dd, J$_1$=8.4 Hz, J$_2$=2.0 Hz, 1H), 8.36 (s, 1H), 8.48 (br s., 2H), 9.62 (br s., 1H).

Example 73

Synthesis of 4-[4-({5-[4-chloro-3-(trifluoromethyl)phenyl]-4H-1,2,4-triazol-3-yl}amino)phenoxy]-N-methylpyridine-2-carboxamide trifluoroacetate salt

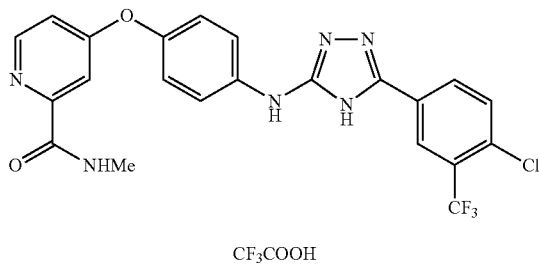

CF$_3$COOH

4-[5-(4-chloro-3-(trifluoromethyl)-phenyl)-4H-1,2,4-triazol-3-ylamino]phenol (100 mg, 0.282 mmol) was dissolved in 2 mL of anhydrous DMF. Solid potassium bis(trimethylsilyl)amide (140.6 mg, 0.705 mmol) was added and the resulting solution was heated at 80° C. for 15 min. Then solid K$_2$CO$_3$ (20 mg, 0.141 mmol) was added, followed by 4-chloro-2-pyridine-carboxamide (71.9 mg, 0.421 mmol). The reaction mixture was microwaved at 220° C. for 20 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected; solvent was removed in vacuo to give trifluoroacetate salt of the product as yellow solid (25.4 mg).

ESI-MS: [M+H]$^+$ 489, 490. $^1$H NMR (DMSO-d$_6$): δ 2.77-2.78 (d, J=4.8 Hz, 3H), 7.14-7.15 (dd, J$_1$=5.6 Hz, J$_2$=2.5 Hz, 1H), 7.15-7.17 (d, J=9.0 Hz, 2H), 7.40 (d, J=2.5 Hz, 1H), 7.68-7.71 (d, J=9.0 Hz, 2H), 7.87-7.89 (d, J=8.4 Hz, 1H), 8.23-8.25 (dd, J$_1$=8.4 Hz, J$_2$=2.0 Hz, 1H), 8.37 (s, 1H), 8.49-8.50 (d, J=5.6 Hz, 1H), 8.75-8.78 (q, J=4.8 Hz, 1H), 9.65 (br s., 1H).

Example 74

Synthesis of 5-[4-chloro-3-(trifluoromethyl)phenyl]-N-[4-(pyridine-3-yloxy)phenyl]-4H-1,2,4-triazol-3-amine trifluoroacetate salt

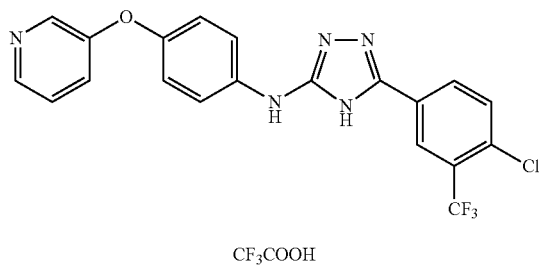

CF$_3$COOH

4-[5-(4-chloro-3-(trifluoromethyl)-phenyl)-4H-1,2,4-triazol-3-ylamino]phenol (200 mg, 0.562 mmol) was dissolved in 2 mL of anhydrous DMF. Solid potassium bis(trimethylsilyl)amide (280.3 mg, 1.405 mmol) was added and the resulting solution was heated at 80° C. for 15 min. Then solid K$_2$CO$_3$ (40 mg, 0.282 mmol) was added, followed by 3-bromopyridine (177.6 mg, 1.12 mmol). The reaction mixture was microwaved at 250° C. for 20 min. Then it was diluted with 1 mL of MeOH, filtered through 0.22 um syringe filter and purified by preparative reverse-phase chromatography using acetonitrile/water gradient with 0.1% TFA. The major peak having the mass of the product was collected, solvent was removed in vacuo to give trifluoroacetate salt of the product as a yellow solid (17.0 mg).

ESI-MS: [M+H]$^+$ 432, 433. $^1$H NMR (DMSO-d$_6$): δ 7.09-7.11 (d, J=9.0 Hz, 2H), 7.50-7.52 (m, 2H), 7.63-7.66 (d, J=9.0 Hz, 2H), 7.87-7.89 (d, J=8.4 Hz, 1H), 8.22-8.25 (dd, J$_1$=8.4 Hz, J$_2$=2.0 Hz, 1H), 8.37-8.38 (m, 2H), 8.43 (min, 1H), 9.56 (br s., 1H).

Example 75

Synthesis of 4-(5-{[3-Trifluoromethyl)phenyl]amino}-1,3,4-oxadiazol-2-yl)phenol

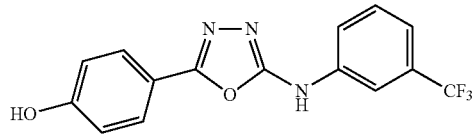

Mercury (II) oxide yellow (5.33 g, 24.60 mmol) was suspended in ca. 70 mL of anhydrous methanol, 4-Hydroxybenzoic acid hydrazide (3.74 g, 24.60 nm mmol) was added to this bright-orange suspension, followed by 3-trifluoromethylphenylisothiocyanate (5.0 g, 24.60 mmol). The reaction mixture was brought to reflux and refluxed for 2 hours. The reaction mixture turned pitch-black in color and formed black precipitate. Then it was cooled down to ambient temperature and filtered through a short pad of Celite, then through a short pad of silica gel. Then methanol was removed in vacuo and the resulting grey precipitate was re-crystallized from ca. 100 mL of EtOAc. The formed white crystalline solid was filtered, washed with a small amount of EtOAc and dried in vacuo to give the title product as white crystals (7.182 g). Yield 71.3%.

ESI-MS: [M+H]$^+$ 322.0. $^1$H NMR (DMSO-d$_6$): δ 6.92-6.95 (d, J=8.7 Hz, 2H), 7.33-7.35 (d, J=: 8.3 Hz, 1H), 7.57-7.60 (t, J=8.0 Hz, 1H), 7.72-7.75 (d, J=8.7 Hz, 2H), 7.80-7.82 (dd, J$_1$=8.0 Hz, J$_2$=1.8 Hz, 1H), 8.06 (s, 1H), 10.21 (s, 1H), 10.99 (br s., 1H). $^{13}$C NMR (DMSO-d6) 112.9, 114.5, 116.1, 117.9, 120.6, 127.6, 129.7, 130.0, 130.3, 139.6, 158.3, 158.9, 160.1.

Example 76

Synthesis of 6-[4-(5-{[3-(trifluoromethyl)phenyl]amino}-1,3,4-oxadiazol-2-yl)phenoxy}pyrimidine-2,4-diamine

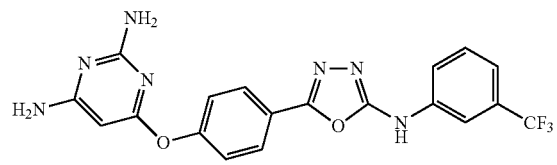 [SMILES: Nc1cc(Oc2ccc(-c3nnc(Nc4cccc(C(F)(F)F)c4)o3)cc2)nc(N)n1]

4-(5-{[3-(trifluoromethyl)-phenyl]amino}-1,3,4-oxadiazol-2-yl)phenol (160.6 mg, 0.5 mmol) was dissolved in 3 mL of anhydrous DMF in a 2-5 mL microwave vial (Personal Chemistry). Solid potassium bis(trimethylsilyl)amide (119.7 mg, 0.6 mmol) was added and the reaction mixture was stirred with heating at 80° C. for 10 min, then 6-chloro-2,4-diaminopyrimidine (86.7 mg, 0.6 mmol) was added, followed by anhydrous K$_2$CO$_3$ (69.1 mg, 0.5 mmol). Then the vial was capped and microwaved at 200° C. for 20 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 40 mL of EtOAc and ca. 40 mL of saturated NaHCO$_3$. EtOAc layer was washed with brine, dried over anhydrous Na$_2$SO$_4$ and filtered. Solvent was removed in vacuo to give the title product as a beige solid (81.0 mg). Yield 37.7%.

ESI-MS: [M+H]$^+$ 430.29. $^1$H NMR (DMSO-d$_6$): δ 5.19 (s, 1H), 6.04 (s, 2H), 6.33 (s, 2H), 7.27-7.30 (d, J=8.7 Hz, 2H), 7.36-7.37 (d, J=7.9 Hz, 1H), 7.59-7.63 (t, J=8.0 Hz, 1H), 7.82-7.83 (dd, J$_1$=8.0 Hz, J$_2$=1.8 Hz, 1H), 7.89-7.92 (d, J=8.7 Hz, 2H), 8.08 (s, 1H). 11.11 (s, 1H).

Example 77

Synthesis of 5-[4-(Pyrimidin-5-yloxy)phenyl]-N-[3-(trifluoromethyl)phenyl]-1,3,4-oxadiazol-2-amine

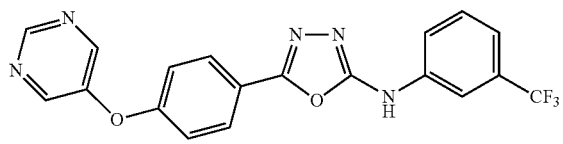 [SMILES: FC(F)(F)c1cccc(Nc2nnc(-c3ccc(Oc4cncnc4)cc3)o2)c1]

4-(5-{[3-(trifluoromethyl)-phenyl]amino}-1,3,4-oxadiazol-2-yl)phenol (160.6 mg, 0.5 mmol) was dissolved in 3 mL of anhydrous DMF in a 2-5 mL microwave vial (Personal Chemistry). Solid potassium bis(trimethylsilylsilyl)amide (149.6 mg, 0.75 mmol) was added and the reaction mixture was stirred with heating at 80° C. for 10 min, then 5-bromopyrimidine (119.2 mg, 0.75 mmol) was added, followed by anhydrous K$_2$CO$_3$ (69.1 mg, 0.5 mmol). Then the vial was capped and microwaved at 200° C. for 20 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca, 40 mL of EtOAc and ca. 40 mL of saturated NaHCO$_3$. EtOAc layer was washed with brine, dried over anhydrous Na$_2$SO$_4$ and filtered. Solvent was removed in vacuo to give the title product as a beige solid (87.0 mg). Yield 43.5%.

ESI-MS: [M+H]$^+$ 400.16. $^1$H NMR (DMSO-d$_6$): δ 7.31-7.33 (d, J=8.7 Hz, 2H), 7.35-7.37 (d, J=7.9 Hz, 1H), 7.59-7.62 (t, J=8.0 Hz, 1H), 7.81-7.83 (dd, J$_1$=8.0 Hz, J$_2$=1.8 Hz, 1H), 7.93-7.95 (d, J=8.7 Hz, 2H), 8.07 (s, 1H), 8.76 (s, 2H), 9.08 (s, 1H), 11.11 (s, 1H).

Example 78

Synthesis of 4-{5-[(4-chlorophenyl)amino]-1,3,4-oxadiazol-2-yl}phenol

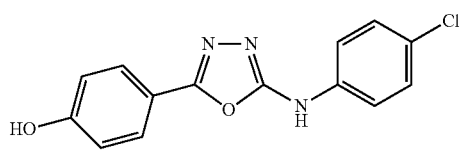 [SMILES: Oc1ccc(-c2nnc(Nc3ccc(Cl)cc3)o2)cc1]

Mercury (II) oxide yellow (6.38 g, 29.47 mmol) was suspended in ca. 70 mL of anhydrous methanol. 4-Hydroxybenzoic acid hydrazide (4.48 g, 29.47 mmol) was added to this bright-orange suspension, followed by 4-chlorophenylisothiocyanate (5.0 g, 29.47 mmol). The reaction mixture was brought to reflux and refluxed for 2 hours. The reaction mixture turned pitch-black in color and formed black precipitate. Then it was cooled down to ambient temperature and filtered through a short pad of Celite, then through a short pad of silica gel. Then methanol was removed in vacuo and the resulting grey precipitate was re-crystallized from ca. 40 mL of EtOAc. The formed white precipitate was filtered, washed with a small amount of EtOAc and dried in vacuo to give the title product as a white powder.

ESI-MS: [M–H]$^+$ 287.94. $^1$H NMR (DMSO-d$_6$): δ 6.91-6.94 (d, J=8.7 Hz, 2H), 7.39-7.41 (d, J=8.9 Hz, 2H), 7.61-7.63 (d, J=8.9 Hz, 2H), 7.71-7.74 (d, J=8.7 Hz, 2H), 10.19 (s, 1H), 10.73 (s, 1H). $^{13}$C NMR (DMSO-d6) 114.6, 116.1, 118.5, 125.3, 127.5, 128.9, 137.8, 158.1, 159.1, 160.0.

Example 79

Synthesis of 6-(4-{5-[(4-chlorophenyl)amino]-1,3,4-oxadiazol-2-yl}phenoxy) pyrimidine-2,4-diamine

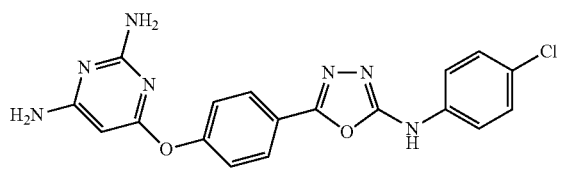 [SMILES: Nc1cc(Oc2ccc(-c3nnc(Nc4ccc(Cl)cc4)o3)cc2)nc(N)n1]

4-{5-[(4-chlorophenyl)amino]-1,3,4-oxadiazol-2-yl}phenol (144.0 mg, 0.5 mmol) was dissolved in 3 mL of anhydrous DMF in a 2-5 mL microwave vial (Personal Chemistry). Solid potassium bis(trimethylsilyl)amide (100.0 mg, 0.5 mmol) was added and the reaction mixture was stirred with heating at 80° C. for 10 min, then 6-chloro-2,4-diaminopyrimidine (72.3 mg, 0.5 mmol) was added, followed by anhydrous K$_2$CO$_3$ (34.5 mg, 0.25 mmol). Then the vial was capped and microwaved at 200° C. for 15 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 40 mL of EtOAc and ca. 40 mL of saturated NaHCO$_3$. EtOAc layer was washed with brine, dried over anhydrous Na₂SO₄ and filtered. Solvent was removed in vacuo to give the title product as a beige solid (24.5 mg).

ESI-MS: [M+H]⁺ 396.25. ¹H NMR (DMSO-d₆): δ 5.19 (s, 1H), 6.04 (s, 2H), 6.33 (s, 2H), 7.26-7.29 (d, J=8.7 Hz, 2H), 7.41-7.43 (d, J=8.9 Hz, 2H), 7.63-7.65 (d, J=8.9 Hz, 2H), 7.88-7.90 (d, J=8.7 Hz, 2H), 10.85 (s, 1.1).

Example 80

Synthesis of 5-[4-(Pyrimidin-5-yloxy)phenyl]-N-[4-chloro-phenyl]-1,3,4-oxadiazol-2-amine

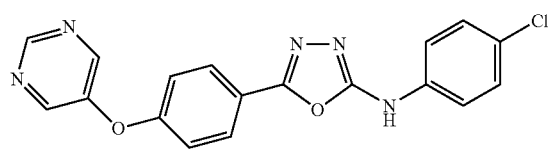 [SMILES: Clc1ccc(Nc2nnc(-c3ccc(Oc4cncnc4)cc3)o2)cc1]

4-{5-[(4-chlorophenyl)amino]-1,3,4-oxadiazol-2-yl}phenol (144.0 mg, 0.5 mmol) was dissolved in 3 mL of anhydrous DMF in a 2-5 mL microwave vial (Personal Chemistry). Solid potassium bis(trimethylsilyl)amide (100.0 mg, 0.5 mmol) was added and the reaction mixture was stirred with heating at 80° C. for 10 min, then 5-bromopyrimidine (79.5 mg, 0.5 mmol) was added, followed by anhydrous K₂CO₃ (34.5 mg, 0.25 mmol). Then the vial was capped and microwaved at 200° C. for 15 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 40 mL of EtOAc and ca. 40 mL of saturated NaHCO₃. EtOAc layer was washed with brine, dried over anhydrous Na₂SO₄ and filtered. Solvent was removed in vacuo to give the title product as a beige solid (61.6 mg).

ESI-MS: [M+H]⁺ 366.24. ¹H NMR (DMSO-d₆): δ 7.30-7.32 (d, J=8.7 Hz, 2H), 7.41-7.43 (d, J=8.9 Hz, 2H), 7.63-7.65 (d, J=8.9 Hz, 2H), 7.92-7.94 (d, J=8.7 Hz, 2H), 8.76 (s, 2H), 9.08 (s, 1H), 10.85 (s, 1H).

Example 81

Synthesis of 4-(5-{[2-chloro-5-(trifluoromethyl)phenyl]amino}-1,3,4-oxadiazol-2-yl)phenol

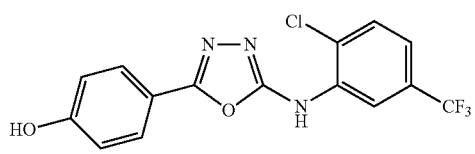 [SMILES: Oc1ccc(-c2nnc(Nc3cc(C(F)(F)F)ccc3Cl)o2)cc1]

Mercury (II) oxide yellow (1.82 g, 8.41 mmol) was suspended in ca. 50 mL of anhydrous methanol. 4-Hydroxybenzoic acid hydrazide (1.28 g, 8.41 mmol) was added to this bright-orange suspension, followed by 2-chloro-5-trifluoromethyl-phenylisothiocyanate (2.0 g, 8.41 mmol). The reaction mixture was brought to reflux and refluxed for 2 hours. The reaction mixture turned pitch-black in color and formed black precipitate. Then it was cooled down to ambient temperature and filtered through a short pad of Celite, then through a short pad of silica gel. Then methanol was removed in vacuo and the resulting grey solid was re-crystallized from ca. 20 mL of EtOAc. The formed white precipitate was filtered, washed with anhydrous Et₂O and dried in vacuo to give the title product as a white solid (2.638 g). Yield 88.1%

ESI-MS: [M+H]⁺ 356.22. ¹H NMR (DMSO-d₆): δ 6.93-6.96 (d, J=8.7 Hz, 2H), 7.41-7.43 (dd, J₁=8.3 Hz, J₂=1.7 Hz, 1H), 7.72-7.75 (m, 3H), 8.61 (s, 1H), 10.23 (s, 1H), 10.30 (s, 1H).

Example 82

Synthesis of 6-(4-{5-[(2-chloro-5-trifluoromethyl-phenyl)amino]-1,3,4-oxadiazol-2-yl}phenoxy)pyrimidine-2,4-diamine

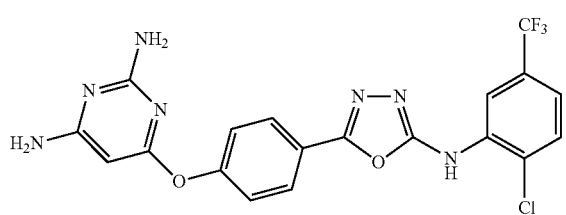 [SMILES: Nc1cc(Oc2ccc(-c3nnc(Nc4cc(C(F)(F)F)ccc4Cl)o3)cc2)nc(N)n1]

4-(5-{[2-chloro-5-(trifluoromethyl)phenyl]amino}-1,3,4-oxadiazol-2-yl)phenol (177.85 mg, 0.5 mmol) was dissolved in 3 mL of anhydrous DMF in a 2-5 mL microwave vial (Personal Chemistry). Solid potassium bis(trimethylsilyl)amide (200.0 mg, 1.0 mmol) was added and the reaction mixture was stirred with heating at 80° C. for 10 min, then 6-chloro-2,4-diamino-pyrimidine (86.7 mg, 0.6 mmol) was added, followed by anhydrous K₂CO₃ (69.1 mg, 0.5 mmol). Then the vial was capped and microwaved at 180° C. for 30 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 50 mL of EtOAc and ca. 50 mL of saturated aqueous NaHCO₃. EtOAc layer was washed with brine, dried over anhydrous Na₂SO₄ and filtered. Solvent was removed in vacuo to give the title product as an off-white solid (131.1 mg). Yield 56.5%.

ESI-MS: [M+H]⁺ 464.21. ¹H NMR (DMSO-d₆): δ 5.20 (s, 1H), 6.05 (s, 2H), 6.34 (s, 2H), 7.28-7.31 (d, J=8.7 Hz, 2H), 7.46-7.48 (dd, J₁=8.3 Hz, J₂=1.8 Hz, 1H), 7.76-7.78 (d, J=8.3 Hz, 1H), 7.90-7.92 (d, J=8.7 Hz, 2H), 8.62 (s, 1H), 10.47 (s, 1H).

Example 83

Synthesis of 5-[4-(Pyrimidin-5-yloxy)phenyl]-N-[2-chloro-5-(trifluoromethyl)-phenyl]-1,3,4-oxadiazol-2-amine

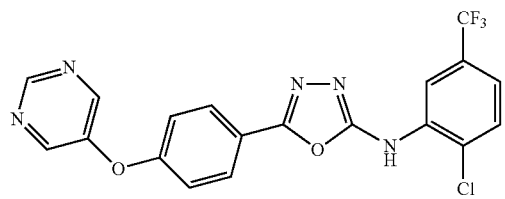 [SMILES: FC(F)(F)c1ccc(Cl)c(Nc2nnc(-c3ccc(Oc4cncnc4)cc3)o2)c1]

4-(5-{[2-chloro-5-(trifluoromethyl)phenyl]amino}-1,3,4-oxadiazol-2-yl)phenol (177.85 mg, 0.5 mmol) was dissolved in 3 mL of anhydrous DMF in a 2-5 mL microwave vial (Personal Chemistry). Solid potassium bis(trimethylsilyl)amide (200.0 mg, 1.0 mmol) was added and the reaction mixture was stirred with heating at 80° C. for 10 min, then 5-bromopyrimidine (95.4 mg, 0.6 mmol) was added, followed by anhydrous $K_2CO_3$ (69.1 mg, 0.5 mmol). Then the vial was capped and microwaved at 180° C. for 40 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 50 mL of EtOAc and ca. 50 mL of saturated aqueous $NaHCO_3$. EtOAc layer was washed with brine, dried over anhydrous $Na_2SO_4$ and filtered. Solvent was removed in vacuo to give the title product as a beige solid (129.1 mg). Yield 59.5%.

ESI-MS: $[M+H]^+$ 434.20. $^1$H NMR (DMSO-$d_6$): δ 7.32-7.35 (d, J=8.7 Hz, 2H), 7.46-7.48 (dd, $J_1$=8.3 Hz, $J_2$=1.8 Hz, 1H), 7.76-7.78 (d, J=8.3 Hz, 1H), 7.94-7.96 (d, J=8.7 Hz, 2H), 8.61 (s, 1H), 8.77 (s, 2H), 9.09 (s, 1H), 10.47 (s, 1H).

Example 84

Synthesis of 4-{5-[(3-chlorophenyl)amino]-1,3,4-oxadiazol-2-yl}-phenol

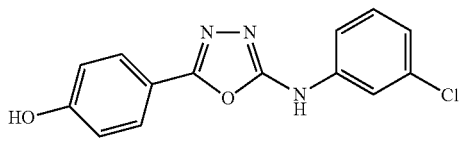 [SMILES: Oc1ccc(-c2nnc(Nc3cccc(Cl)c3)o2)cc1]

Mercury (II) oxide yellow (6.38 g, 29.47 mmol) was suspended in ca. 100 mL of anhydrous methanol. 4-Hydroxybenzoic acid hydrazide (4.48 g, 29.47 mmol) was added to this bright-orange suspension, followed by 3-chlorophenylisothiocyanate (5.0 g, 29.47 mmol). The reaction mixture was brought to reflux and refluxed for 2 hours. The reaction mixture turned pitch-black in color and formed black precipitate. Then it was cooled down to ambient temperature and filtered through a short pad of Celite. Then it was purified by silica gel chromatography using 0% to 20% methanol gradient in EtOAc. Solvent was removed in vacuo and the resulting grey precipitate was re-crystallized from ca. 50 mL of EtOAc. The formed white crystalline solid was filtered, washed with a small amount of EtOAc, anhydrous $Et_2O$ and dried in vacuo to give the title product as a white powder (7.606 g). Yield 89.7%.

ESI-MS: $[M+H]^+$ 288.26. $^1$H NMR (DMSO-$d_6$): δ 6.92-6.94 (d, J=8.7 Hz, 2H), 7.00-7.02 (dd, $J_1$=7.9 Hz, $J_2$=1.8 Hz, 1H), 7.33-7.36 (t, J=8.1 Hz, 1H), 7.47-7.49 (dd, $J_1$=8.1 Hz, $J_2$=1.8 Hz, 1H), 7.72-7.74 (d, J=8.7 Hz, 2H), 7.76-7.78 (t, J=2.1 Hz, 1H), 10.19 (s, 1H), 10.81 (s, 1H). $^{13}$C NMR (DMSO-d6) 114.6, 115.5, 116.1, 116.4, 121.3, 127.6, 130.6, 133.5, 140.3, 158.3, 159.0, 160.1.

Example 85

Synthesis of 6-(4-{5-[(3-chlorophenyl)amino]-1,3,4-oxadiazol-2-yl}phenoxy) pyrimidine-2,4-diamine

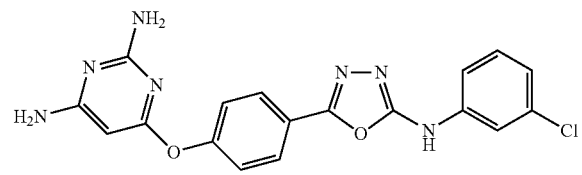 [SMILES: Nc1cc(Oc2ccc(-c3nnc(Nc4cccc(Cl)c4)o3)cc2)nc(N)n1]

4-{5-[(3-chlorophenyl)amino]-1,3,4-oxadiazol-2-yl}phenol (143.8 mg, 0.5 mmol) was dissolved in 3 mL of anhydrous DMF in a 2-5 mL microwave vial (Personal Chemistry). Solid potassium bis(trimethylsilyl)amide (200.0 mg, 1.0 mmol) was added and the reaction mixture was stirred with heating at 80° C. for 10 min, then 6-chloro-2,4-diaminopyrimidine (86.7 mg, 0.6 mmol) was added, followed by anhydrous $K_2CO_3$ (69.1 mg, 0.5 mmol). Then the vial was capped and microwaved at 180° C. for 40 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 50 nm, of EtOAc and ca. 50 mL of saturated aqueous $NaHCO_3$. EtOAc layer was washed with brine, dried over anhydrous $Na_2SO_4$ and filtered. Solvent was removed in vacuo to give the title product as a light-yellow solid (62.0 mg). Yield 31.3%.

ESI-MS: $[M+H]^+$ 396.22. $^1$H NMR (DMSO-$d_6$): δ 5.19 (s, 1H), 6.04 (s, 2H), 6.33 (s, 2H), 7.06-7.08 (m, 1H), 7.27-7.29 (d, J=8.7 Hz, 2H), 7.37-7.41 (t, J=8.1 Hz, 1H), 7.50-7.52 (dd, $J_1$=8.1 Hz, $J_2$=1.8 Hz, 1H), 7.78-7.79 (t, J=2.1 Hz, 1H), 7.89-7.90 (d, J=8.7 Hz, 2H), 10.95 (s, 1H).

Example 86

Synthesis of 5-[4-(Pyrimidin-5-yloxy)phenyl]-N-[3-chloro-phenyl]-1,3,4-oxadiazol-2-amine

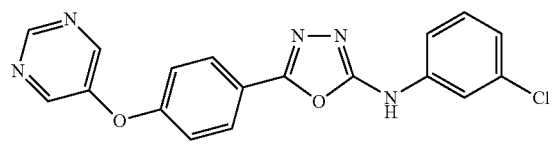 [SMILES: Clc1cccc(Nc2nnc(-c3ccc(Oc4cncnc4)cc3)o2)c1]

4-{5-[(3-chlorophenyl)amino]-1,3,4-oxadiazol-2-yl}phenol (143.8 mg, 0.5 mmol) was dissolved in 3 mL of anhydrous DMF in a 2-5 mL microwave vial (Personal Chemistry). Solid potassium bis(trimethylsilyl)amide (200.0 mg, 1.0 mmol) was added and the reaction mixture was stirred with heating at 80° C. for 10 min, then 5-bromopyrimidine (95.4 mg, 0.6 mmol) was added, followed by anhydrous $K_2CO_3$ (69.1 mg, 0.5 mmol). Then the vial was capped and microwaved at 180° C. for 30 min. Then the reaction mixture was diluted with ca. 1 mL of MeOH, filtered through 0.22 um syringe filter and purified by reverse-phase preparative HPLC in acetonitrile/water system with 0.01% TFA. Fractions, containing the product, were partitioned between ca. 50 mL of EtOAc and ca. 50 mL of saturated aqueous NaHCO$_3$. EtOAc layer was washed with brine, dried over anhydrous Na$_2$SO$_4$ and filtered. Solvent was removed in vacuo to give the title product as a light-yellow solid (74.7 mg). Yield 40.8%.

ESI-MS: [M+H]$^+$ 366.23. $^1$H NMR (DMSO-d$_6$): δ 7.06-7.08 (m, 1H), 7.31-7.33 (d, J=8.7 Hz, 2H), 7.37-7.41 (t, J=8.1 Hz, 1H), 7.50-7.52 (dd, J$_1$=8.1 Hz, J$_2$=1.8 Hz, 1H), 7.77-7.79 (t, J=2.0 Hz, 1H), 7.93-7.94 (d, J=8.7 Hz, 2H), 8.77 (s, 2H), 9.09 (s, 1H), 10.96 (s, 1H).

Example 87

Synthesis of 5-[4-(Pyridin-3-yloxy)phenyl]-1,3,4-oxadiazol-2-amine hydrobromide salt

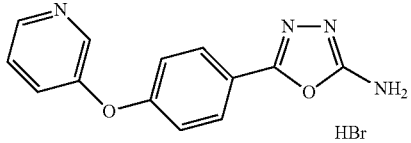 [SMILES: Nc1nnc(-c2ccc(Oc3cccnc3)cc2)o1 ; Br]

HBr 4-(pyridine-3-yloxy)benzohydrazide (3.7 g, 16.14 mmol) was dissolved in 100 mL of anhydrous THF and 3.0 M solution of cyanogen bromide (5.38 mL, 16.14 mmol) was added via syringe. Within 5-10 min of stirring an orange precipitate started to form. The reaction mixture was brought to reflux and refluxed for 1 hr. Then it was cooled down to ambient temperature and filtered. The collected orange precipitate was washed with ca. 100 mL of THF, ca. 100 mL of EtOAc, anhydrous Et2O and dried in vacuo to give the title product as an orange solid (4.40 g). Yield 81.4%.

ESI-MS: [M+H]$^+$ 255.05. $^1$H NMR (DMSO-d$_6$): δ 7.27-7.29 (d, J=8.8 Hz, 2H), 7.75-7.78 (dd, J$_1$=8.5 Hz, J$_2$=5.0 Hz, 1H), 7.85-7.87 (d, J=8.8 Hz, 2H), 7.92-7.94 (m, 1H), 8.59-8.60 (dd, J$_1$=5.0 Hz, J$_2$=1.0 Hz, 1H), 8.69-8.70 (d, J=2.7 Hz, 1H).

Example 88

Synthesis of N-{5-[4-(pyridine-3-yloxy)phenyl]-1,3,4-oxadiazol-2-yl}-4-(trifluoromethoxy)benzamide

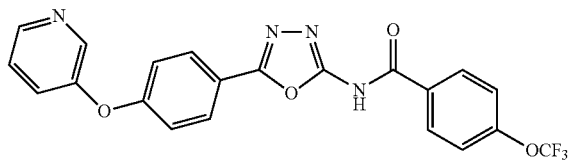 [SMILES: O=C(Nc1nnc(-c2ccc(Oc3cccnc3)cc2)o1)c1ccc(OC(F)(F)F)cc1]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. 4-Trifluoromethoxybenzoyl chloride (167.2 mg, 117 uL, 0.75 mmol) was added directly into the solution. The reaction mixture formed an orange-red solution with a small amount of precipitate. It was left to stir for 6 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a yellow solid (89.0 mg). Yield 40.2%.

ESI-MS: [M+H]$^+$ 442.82. $^1$H NMR (DMSO-d$_6$): δ 7.20-7.22 (d, J=8.8 Hz, 2H), 7.44-7.46 (d, J=8.6 Hz, 2H), 7.48-7.51 (dd, J=8.4 Hz, J$_2$=4.6 Hz, 1H), 7.59-7.62 (ddd, J$_1$=8.4 Hz, J$_2$=2.8 Hz, J$_3$=1.2 Hz, 1H), 7.94-7.96 (d, J=8.8 Hz, 2H), 8.17-8.19 (d, J=8.6 Hz, 2H), 8.45-8.46 (dd, J$_1$=4.6 Hz, J$_2$=1.2 Hz, 1H), 8.48-8.49 (d, J=2.8 Hz, 1H).

Example 89

Synthesis of N-{5-[4-(pyridin-3-yloxy)phenyl]-1,3,4-oxadiazol-2-yl}-3-(trifluoromethyl)benzamide

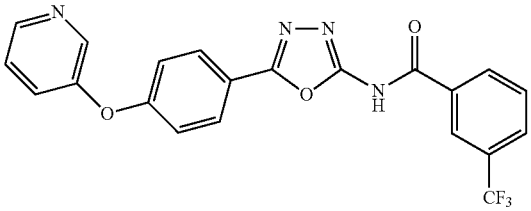 [SMILES: O=C(Nc1nnc(-c2ccc(Oc3cccnc3)cc2)o1)c1cccc(C(F)(F)F)c1]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. 3-Trifluoromethylbenzoyl chloride (156.4 mg, 0.75 mmol) was added to the solution. The reaction mixture formed an orange-red solution with a small amount of white precipitate. It was left to stir for 3 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a yellow solid (50.0 mg). Yield 23.4%.

ESI-MS: [M+H]$^+$ 426.94. $^1$H NMR (DMSO-d$_6$): δ 7.21-7.23 (d, J=8.8 Hz, 2H), 7.49-7.51 (dd, J$_1$=8.4 Hz, J$_2$=4.6 Hz, 1H), 7.60-7.62 (ddd, J$_1$=8.4 Hz, J$_2$=2.8 Hz, J$_3$=1.2 Hz, 1H), 7.75-7.76 (t, J=7.7 Hz, 1H), 7.95-7.98 (m, 3H), 8.33-8.34 (d, J=7.7 Hz, 1H), 8.39 (s, 1H), 8.46-8.47 (dd, J$_1$=4.6 Hz, J$_2$=1.2 Hz, 1H), 8.48-8.49 (d, J=2.8 Hz, 1H).

Example 90

Synthesis of 4-Bromo-N-{5-[4-(pyridin-3-yloxy)phenyl]-1,3,4-oxadiazol-2-yl}-benzamide

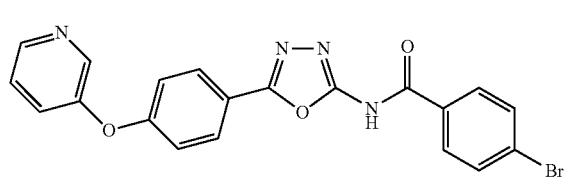 [SMILES: O=C(Nc1nnc(-c2ccc(Oc3cccnc3)cc2)o1)c1ccc(Br)cc1]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. 4-Bromobenzoyl chloride (164.6 mg, 0.75 mmol) was added to the solution. The reaction mixture formed an orange-red solution with a small amount of white precipitate. It was left to stir for 3 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a yellow solid (46.5 mg). Yield 21.2%.

ESI-MS: [M+H]⁺ 438.84. ¹H NMR (DMSO-d₆): δ 7.20-7.22 (d, J=8.8 Hz, 2H), 7.49-7.51 (dd, $J_1$=8.4 Hz, $J_2$=4.6 Hz, 1H), 7.60-7.62 (ddd, J=8.4 Hz, $J_2$=2.8 Hz, $J_3$=1.2 Hz, 1H), 7.68-7.70 (d, J=8.4 Hz, 2H), 7.95-7.97 (d, J=8.8 Hz, 2H), 8.00-8.02 (d, J=8.4 Hz, 2H), 8.45-8.46 (dd, $J_1$=4.6 Hz, $J_2$=1.2 Hz, 1H), 8.48-8.49 (d, J=2.8 Hz, 1H).

Example 91

Synthesis of N-{5-[4-(pyridin-3-yloxy)phenyl]-1,3,4-oxadiazol-2-yl}-3-(trifluoromethoxy)-benzamide

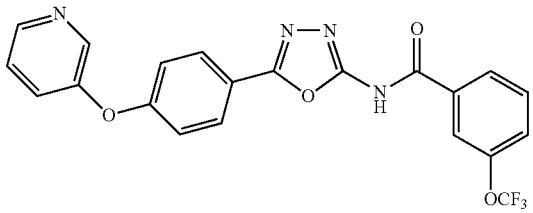

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 3-trifluoromethoxybenzoyl chloride (117 uL) was added directly into the solution. The reaction mixture formed an orange-red solution with a small amount of white precipitate. It was left to stir for 3 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a yellow solid (38.8 mg). Yield 17.5%.

ESI-MS: [M+H]⁺ 442.85. ¹H NMR (DMSO-d₆): δ 7.22-7.24 (d, J=8.8 Hz, 2H), 7.49-7.51 (dd, $J_1$=8.4 Hz, $J_2$=4.6 Hz, 1H), 7.60-7.62 (ddd, $J_1$=8.4 Hz, $J_2$=2.8 Hz, $J_3$=1.2 Hz, 1H), 7.61-7.63 (m, 1H), 7.68-7.71 (t, J=7.7 Hz, 1H), 7.97-7.98 (m, 3H), 8.08-8.10 (d, J=7.7 Hz, 1H), 8.46-8.47 (dd, $J_1$=4.6 Hz, $J_2$=1.2 Hz, 1H), 8.48-8.49 (d, J=2.8 Hz, 1H).

Example 92

Synthesis of 4-methoxy-N-{5-[4-(pyridin-3-yloxy) phenyl]-1,3,4-oxadiazol-2-yl}-3-(trifluoromethyl)-benzamide

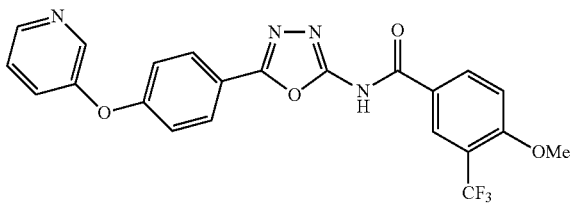 [SMILES: COc1ccc(C(=O)Nc2nnc(-c3ccc(Oc4cccnc4)cc3)o2)cc1C(F)(F)F]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 4-methoxy-3-trifluoromethylbenzoyl chloride (179.0 mg, 0.75 mmol) was added directly into the solution. The reaction mixture formed an orange-red solution with a small amount of white precipitate. It was left to stir for 3 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO₃. The EtOAc layer was washed with brine, dried over anhydrous sodium sulfate and filtered. Solvent was removed in vacuo to give the title product as a yellow solid (37.0 mg). Yield 16.2%.

ESI-MS: [M+H]⁺ 456.85. ¹H NMR (DMSO-d₆): δ 3.97 (s, 3H), 7.21-7.23 (d, J=8.8 Hz, 2H), 7.38-7.40 (d, J=9.1 Hz, 1H), 7.49-7.51 (dd, $J_1$=8.4 Hz, $J_2$=4.6 Hz, 1H), 7.60-7.62 (ddd, $J_1$=8.4 Hz, $J_2$=2.8 Hz, $J_3$=1.2 Hz, 1H), 7.95-7.97 (d, J=8.8 Hz, 2H), 8.34-8.35 (m, 2H), 8.46-8.47 (dd, $J_1$=4.6 Hz, $J_2$=1.2 Hz, 1H), 8.48-8.49 (d, J=2.8 Hz, 1H).

Example 93

Synthesis of 2,2-Difluoro-N-{5-[4-(pyridin-3-yloxy) phenyl]-1,3,4-oxadiazol-2-yl}-1,3-benzodioxole-5-carboxamide

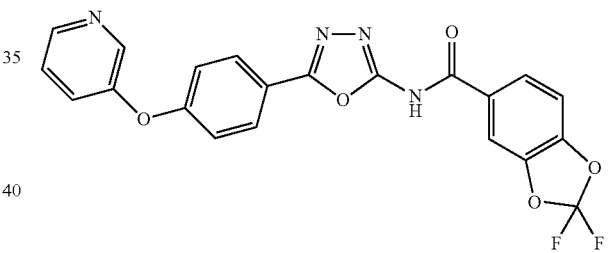

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 2,2-difluoro-1,3-benzodioxole-5-carbonyl chloride (165.4 mg, 0.75 mmol) was added directly into the solution. The reaction mixture formed an orange-red solution with a small amount of white precipitate. It was left to stir for 3 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO₃. The EtOAc layer was washed with brine, dried over anhydrous sodium sulfate and filtered. Solvent was removed in vacuo to give the title product as a yellow solid (27.0 mg). Yield 12.3%.

ESI-MS: [M+H]⁺ 456.85. ¹H NMR (DMSO-d₆): δ 7.19-7.21 (d, J=8.8 Hz, 2H), 7.47-7.51 (m, 2H), 7.58-7.60 (ddd, $J_1$=8.4 Hz, $J_2$=2.8 Hz, $J_3$=1.2 Hz, 1H), 7.93-7.95 (d, J=8.8 Hz, 2H), 7.99-8.01 (m, 2H), 8.45-8.46 (dd, J$_1$=4.6 Hz, J$_2$=1.2 Hz, 1H), 8.48-8.49 (d, J=2.8 Hz, 1H).

Example 94

Synthesis of 3-Chloro-2-fluoro-N-{5-[4-pyridin-3-yloxy)phenyl]-1,3,4-oxadiazol-2-yl}-5-trifluoromethyl)-benzamide

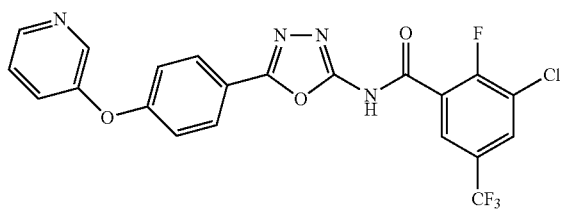 [SMILES: O=C(Nc1nnc(-c2ccc(Oc3cccnc3)cc2)o1)c1cc(C(F)(F)F)cc(Cl)c1F]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 3-chloro-2-fluoro-5-trifluoromethylbenzoyl chloride (250 uL) was added directly into the solution. The reaction mixture formed a red solution with a small amount of white precipitate. It was left to stir for 18 hours. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO$_3$. The EtOAc layer was washed with brine, dried over anhydrous sodium sulfate and filtered. Solvent was removed in vacuo to give the title product as a yellow solid (83.4 mg). Yield 34.8%.

ESI-MS: [M+H]$^+$ 480.71. $^1$H NMR (DMSO-d$_6$): δ 7.18-7.20 (d, J=8.8 Hz, 2H), 7.47-7.50 (dd, J$_1$=8.4 Hz, J$_2$=4.6 Hz, 1H), 7.58-7.60 (ddd, J$_1$=8.4 Hz, J$_2$=2.8 Hz, J$_3$=1.2 Hz, 1H), 7.92-7.94 (d, J=8.8 Hz, 2H), 8.13-8.16 (m, 2H), 8.44-8.45 (dd, J=4.6 Hz, J$_2$=1.2 Hz, 1H), 8.47-8.48 (d, J=2.8 Hz, 1H).

Example 95

Synthesis of 4-Fluoro-N-{5-[4-(pyridin-3-yloxy)phenyl]-1,3,4-oxadiazol-2-yl}-3-(trifluoromethyl)-benzamide

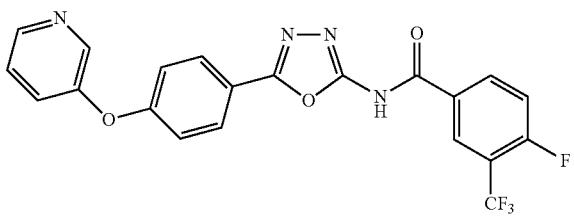 [SMILES: O=C(Nc1nnc(-c2ccc(Oc3cccnc3)cc2)o1)c1ccc(F)c(C(F)(F)F)c1]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 4-fluoro-3-trifluoromethylbenzoyl chloride (200 uL) was added directly into the solution. It was left to stir for 18 hours. The reaction mixture formed a red solution with a yellow precipitate. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a yellow solid (105.1 mg). Yield 47.3%.

ESI-MS: [M+H]$^+$ 444.79. $^1$H NMR (DMSO-d$_6$): δ 7.18-7.20 (d, J=8.8 Hz, 2H), 7.47-7.50 (dd, J$_1$=8.4 Hz, J$_2$=4.6 Hz, 1H), 7.53-7.60 (m, 2H), 7.93-7.94 (d, J=8.8 Hz, 2H), 8.40-8.43 (m, 1H), 8.43-8.45 (dd, J$_1$=4.6 Hz, J$_2$=1.2 Hz, 1H), 8.47-8.48 (d, J=2.8 Hz, 1H).

Example 96

Synthesis of N-{5-[4-(pyridin-3-yloxy)phenyl]-1,3,4-oxadiazol-2-yl}-2-(trifluoromethoxy)-benzamide

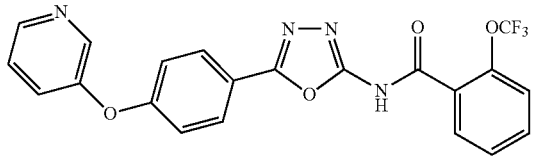 [SMILES: O=C(Nc1nnc(-c2ccc(Oc3cccnc3)cc2)o1)c1ccccc1OC(F)(F)F]

5-[4-(Pyridin-3-yloxy)phenyl]-1,3,4-oxadiazol-2-amine hydrobromide salt (167.5 mg, 0.5 mmol) was suspended in 2 mL of anhydrous pyridine. Neat 2-trifluoromethoxybenzoyl chloride (100 uL) was added directly into the solution. It was left to stir for 18 hours. The reaction mixture formed an orange solution with a yellow precipitate. Then it was diluted with ca. 1 mL of MeOH, filtered through 0.22 u syringe filter and purified by reverse phase preparative HPLC using acetonitrile/water mixture containing 0.01% of TFA. Fractions, containing the product, were combined and partitioned between ca. 40 mL of EtOAc and ca. 40 mL of saturated aqueous NaHCO3. The EtOAc layer was washed with brine, dried over anhydrous sodium sulfate and filtered. Solvent was removed in vacuo to give the title product as a bright-yellow solid (20.2 mg). Yield 9.1%.

ESI-MS: [M+H]$^+$ 443.04. $^1$H NMR (DMSO-d$_6$): δ 7.22-7.24 (d, J=8.8 Hz, 2H), 7.48-7.54 (m, 4H), 7.60-7.63 (ddd, J$_1$=8.4 Hz, J$_2$=2.8 Hz, J$_3$=1.2 Hz, 1H), 7.69-7.71 (t, J=7.8 Hz, 1H), 7.80-7.81 (d, J=7.5 Hz, 1H), 7.94-7.96 (d, J=8.8 Hz, 2H), 8.47-8.49 (m, 2H).

Example 97

Synthesis of N-amino-N'-(4-chloro-3-trifluoromethyl-phenyl-guanidine hydroiodide

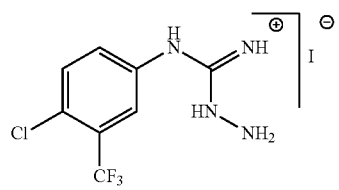

A mixture of 2.54 g 4-chloro-3-trifluoromethyl-phenylthiourea, 0.62 ml of iodomethane in 50 mL of anhydrous EtOH was refluxed for 1 hr to give 1-[4-chloro-3-(trifluoromethyl)

phenyl]-S-methylisothiourea hydroiodide. Then it was cooled down to ambient temperature and treated with 0.35 g of 98% hydrazine, heated gently with stirring until the initial vigorous evolution of MeSH subsided and then refluxed for additional 1 hour.

Example 98

Synthesis of 4-(3-{[4-chloro-3-(trifluoromethyl)phenyl]amino}-1,2,4-triazin-5-yl)phenol

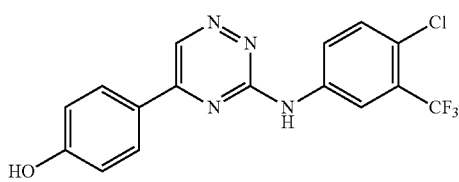 [SMILES: Oc1ccc(-c2cnnc(Nc3ccc(Cl)c(C(F)(F)F)c3)n2)cc1]

N-amino-N'-[4-chloro-3-(trifluoromethyl)phenyl]-guanidine hydroiodide can be reacted with about 1.0-1.5 equivalents of 4-hydroxy-phenylglyoxale in 1:1 mixture of methanol/water to yield the title product. The product can be isolated by precipitation or by extraction with a number of solvents, such as ethyl acetate, methylene chloride or diethyl ether or by silica gel column chromatography.

Example 99

Synthesis of 4-[4-(3-{[4-chloro-3-(trifluoromethyl)phenyl]amino}-[1,2,4]triazin-5-yl)-phenoxy]-N-methylpyridine-2-carboxamide

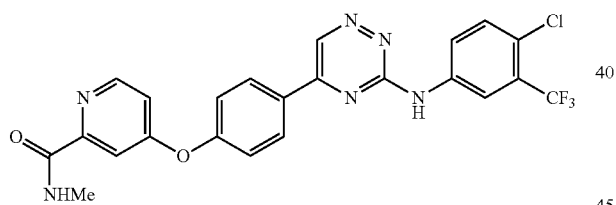

7.23 g (19.73 mmol) of 4-(3-{[4-chloro-3-(trifluoromethyl)phenyl]amino}-1,2,4-triazin-5-yl)phenol can be dissolved in 80 mL of anhydrous DMF under argon atmosphere. 2.44 g (21.71 mmol, 1.1 equivalent) of solid potassium tert-butoxide can be added to the solution. The resulting mixture can be heated to about 100° C. and stirred at that temperature for 15 min. Then a solution of 3.7 g (21.71 mmol, 1.1 equivalent) of 4-chloro-pyridine-2-carboxylic acid methylamide in 10 mL of anhydrous DMF can be added, followed by 3.28 g (23.68 mmol, 1.2 equivalent) of anhydrous $K_2CO_3$. The reaction mixture can be heated at 140° C. for 30 hrs. The progress of the reaction can be monitored by LC/MS. Then it can be allowed to cool down to ambient temperature. The resulting mixture can be poured into 500 mL of water and 100 mL of ethyl acetate. The aqueous layer can be extracted with a number of solvents, such as ethyl acetate, methylene chloride or ether. The combined extracts can be washed 3 times with 100 mL of water, then with brine and dried over anhydrous sodium sulfate. Solvent can be removed in vacuum to yield crude 4-[4-(3-phenylamino-[1,2,4]triazin-6-yl)-phenoxy]-pyridine-2-carboxylic acid methylamide. The product can be than purified using silica gel column chromatography. Those having ordinary skill in the art can determine which solvent system can be used as an eluents in the chromatographic purification.

Example 100

Synthesis of 4-(3-ethylsulfanyl-[1,2,4]-triazin-5-yl-phenol

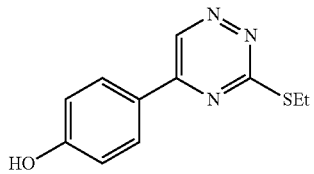

1.0-1.5 equivalent of 4-hydroxyphenylglyoxale can be reacted with 1-amino-S-ethylisothiourea hydrobromide in 1:1 mixture of methanol/water with 1.0-2.0 equivalent of $K_2CO_3$ to yield 4-(3-ethylsulfanyl-[1,2,4]triazin-5-yl)-phenol. The product can be isolated by a number of methods known to one skilled in the art, such as precipitation or by extraction with a number of solvents, such as ethyl acetate, methylene chloride or diethyl ether or by silica gel column chromatography.

Example 101

Synthesis of 4-(3-amino-[1,2,4]-triazin-5-yl-phenol

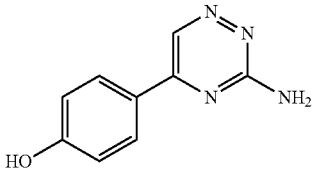 [SMILES: Nc1nncc(-c2ccc(O)cc2)n1]

1.0 equivalent of 4-(3-ethylsulfanyl-[1,2,4]triazin-6-yl)-phenol can be reacted with 1-5 equivalent of ammonia in dioxane to give 4-(3-amino-[1,2,4]triazin-5-yl)-phenol. The product can be isolated by a number of methods known to one skilled in the art, such as precipitation or by extraction with a number of solvents, such as ethyl acetate, methylene chloride or diethyl ether or by silica gel column chromatography.

Example 102

Synthesis of 4-[4-(3-amino-[1,2,4]triazin-5-yl)-phenoxy]-N-methylpyridine-2-carboxamide

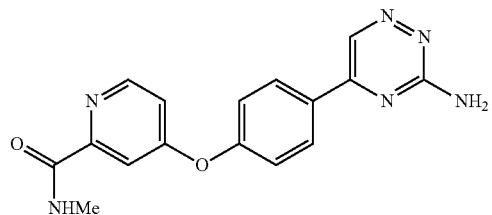 [SMILES: CNC(=O)c1cc(Oc2ccc(-c3cnnc(N)n3)cc2)ccn1]

3.71 g (19.73 mmol) of 4-(3-amino-[1,2,4]triazin-5-yl)-phenol can be dissolved in 80 mL of anhydrous DMF under argon atmosphere. 2.44 g (21.71 mmol, 1.1 equivalent) of solid potassium tert-butoxide can be added to the solution. The resulting mixture can be heated to about 100° C. and stirred at that temperature for 15 min. Then a solution of 3.7 g (21.71 mmol, 1.1 equivalent) of 4-chloro-pyridine-2-carboxylic acid methylamide in 10 mL of anhydrous DMF can be added, followed by 3.28 g (23.68 mmol, 1.2 eq.) of anhydrous $K_2CO_3$. The reaction mixture can be heated at 140° C. for 30 hrs. The progress of the reaction can be monitored by LC/MS. Then it can be allowed to cool down to ambient temperature. The resulting mixture can be poured into 500 mL of water and 100 mL of ethyl acetate. The aqueous layer can be extracted with a number of solvents, such as ethyl acetate, methylene chloride or ether. The combined extracts can be washed 3 times with 100 mL of water, then with brine and dried over anhydrous sodium sulfate. Solvent can be removed in vacuum to give crude 4-[4-(3-amino-[1,2,4]triazin-5-yl)-phenoxy]-N-methylpyridine-2-carboxamide. The product can be than purified using silica gel column chromatography. Those having ordinary skill in the art can determine which solvent system can be used as an eluents in the chromatographic purification.

Example 103

Synthesis of 4-[4-(3-{[4-chloro-3-(trifluoromethyl)benzoyl]amino}-[1,2,4]triazin-5-yl)-phenoxy]-N-methylpyridine-2-carboxamide

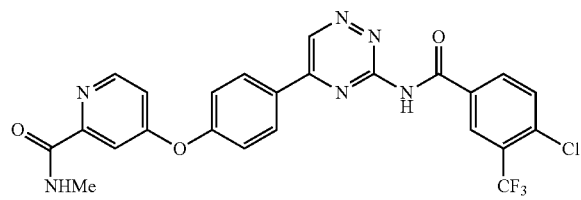 [SMILES: CNC(=O)c1cc(Oc2ccc(-c3cnnc(NC(=O)c4ccc(Cl)c(C(F)(F)F)c4)n3)cc2)ccn1]

108.6 mg (0.337 mmol, 1.0 eq) of 4-[4-(3-amino-[1,2,4]triazin-5-yl)-phenoxy]-N-methylpyridine-2-carboxamide can be dissolved in 2 mL of anhydrous DMF with heating to about 100° C. 45.4 mg (0.405 mmol, 1.2 equivalent) of solid t-BuOK can be added to the solution, followed by 0.405 mmol (1.2 equivalent) of 4-chloro-3-trifluoromethylbenzoyl chloride. It can be allowed to stir at ambient temperature for 1-2 hours. The product can be isolated by a number of methods known to those skilled in the art, such as precipitation or by extraction with a number of solvents, such as ethyl acetate, methylene chloride or diethyl ether or by silica gel column chromatography, or by reverse-phase prep-HPLC chromatography.

Example 104

Synthesis of 4-{4-[3-({[4-chloro-3-(trifluoromethyl)phenyl]sulfonyl}amino)-[1,2,4]triazin-5-yl)-phenoxy}-N-methylpyridine-2-carboxamide

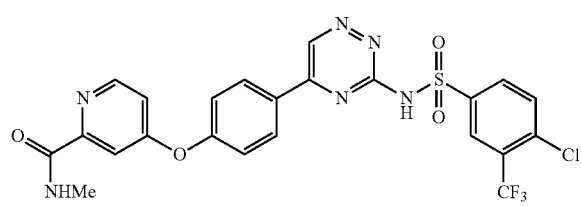 [SMILES: CNC(=O)c1cc(Oc2ccc(-c3cnnc(NS(=O)(=O)c4ccc(Cl)c(C(F)(F)F)c4)n3)cc2)ccn1]

108.6 mg (0.337 mmol, 1.0 equivalent) of 4-[4-(3-amino-[1,2,4]triazin-5-yl)-phenoxy]-N-methylpyridine-2-carboxamide can be dissolved in 2 mL of anhydrous pyridine with heating to about 100° C. 0.405 mmol (1.2 equivalent) of 4-chloro-3-trifluoromethyl-benzenesulfonyl chloride can be added. The reaction mixture can be allowed to stir at ambient temperature for 1-2 hours. The product can be isolated by a number of methods known to one skilled in the art, such as precipitation or by extraction with a number of solvents, such as ethyl acetate, methylene chloride or diethyl ether or by silica gel column chromatography, or by reverse-phase preparative HPLC.

Example 105

Testing of Inhibition of MAPK Pathway in Cellular Assay

Some compounds described by the general structure (B) were tested for inhibition of MAPK pathway in cellular assay. Western Blot: Early passage primary human umbilical vein endothelial cells (HUVECs) were maintained in EGM-2 containing SingleQuots (Cambrex, East Rutherford, N.J.), 10% FBS, 10 mM HEPES, and 50 μg/ml gentamicin. Prior to treatment of the cells with inhibitor, the HUVECs were starved for 18 h by replacing serum-containing complete media with serum-free and SingleQuot-free media. The starved cells were pre-treated with inhibitors for 60 min at various concentrations (0-20 μM). Next the HUVECs were treated with 50 ng/ml VEGF or FGF (Peprotech, Rocky Hill, N.J.) for 6 min and the cells were immediately washed with ice-cold PBS. Cells were lysed with ice-cold RIPA buffer containing 100 mM Tris pH 7.5, 150 mM NaCl, 1 mM EDTA, 1% deoxycholate, 1% Triton X-100, 0.1% SDS, 2 mM PMSF, one Complete-Mini protease inhibitor tablet (Roche, Indianapolis, Ind.; 1 tablet/7 ml of lysis buffer) and the phophatase inhibitors NaF (500 mM) and orthovanadate (1 mM). The cells were scraped and lysates transferred and centrifuged at 15,000 g for 10 main. Supernatants were transferred to new tubes and protein concentration was quantitated using the BCA protein reagent (Pierce, Rockford, Ill.). Cell lysates containing 20 μg of total protein were separated by 10% SDS-PAGE, transferred to nitrocellulose, and blocked in 5% milk in TBST. Anti phospho-ERK Thr 202/Tyr 204 (Cell Signaling, Beverly, Mass.), anti-phospho-MEK Ser217/221 (Cell Signaling), and c-Raf (BD Biosciences Pharmingen, San Diego, Calif.) used as primary antibodies were detected with horseradish peroxidase-conjugated goat anti-mouse or rabbit secondary antibodies and bands were visualized using the SuperSignal West Pico chemiluminescence reagent system (Pierce) and Kodak X-ray film (Rochester, N.Y.).

Bay 43-9006 (Raf/FGF inhibitor) showed reduction of expression of p-MEK and p-ERK with IC50 between 200 and 300 nM when tested in this assay. U0126 (MEK inhibitor) showed reduction in p-Erk levels with $IC_{50}$ between 200 and 300 nM, while p-MEK levels were unaffected. The results are shown in Table 1. As can be seen, compounds of the invention showed reduction in p-MEK and p-ERK levels with $IC_{50}$ between 400 nM and 20 μM.

Example 106

Cell Viability Assay

Some compounds described by the general structure (B) were tested for cell viability. XTT assay: HUVECs were seeded at 10,000 cells/well of a tissue culture treated 96-well plate treated with collagen type I and grown overnight in the complete EGM-2 media as described above. The following morning, the inhibitors were serial diluted with DMSO and added to the cells with a final DMSO concentration of 1%. After 72 hours cell viability was measured with an XTT assay (Sigma, St. Louis, Mo.). The cells were also photographed to compare morphological differences to the XTT trends observed. Determination of the $IC_{50}$ values was performed with quantitative software (Prism software package, Graph-Pad Software, San Diego Calif.). Several inhibitors blocked cell proliferation and induced apoptosis at concentrations below 1 μM and experiments were repeated three times to confirm the observations. The compounds of the invention displayed $IC_{50}$ between 100 nM and 40 uM in this assay (Table 2).

TABLE 2

Test Results for Examples 105 and 106

| Examples | Western Blot | Inhibition of HUVEC cell prolifiration (IC50) |
| --- | --- | --- |
| 4-{4-[5-(4-chloro-3-trifluoromethyl-phenylamino)-4H-[1,2,4]triazol-3-yl]-phenoxy}-pyridine-2-carboxylic acid methylamide | active at 10 uM | 2.85 uM |
| 4-[4-[5-(4-trifluoromethoxy-phenyl)-4H-[1,2,4]triazol-3-ylamino]-phenoxy}-pyridine-2-carboxylic acid methylamide | not active | 2.2 uM |
| (4-chloro-3-trifluoromethyl-phenyl)-{5-[4-(pyridine-3-yloxy)-phenyl]-4H-[1,2,4]triazol-3-yl}-amine | active at 5 uM | 1.81 uM |
| 4-{4-[5-(4-trifluoromethoxy-phenylamino)-4H-[1,2,4]triazol-3-yl]-phenoxy}-pyridine-2-carboxylic acid methylamide | not active | >40 uM |
| {5-[4-(pyridine-4-yloxy)-phenyl]-4H-[1,2,4]triazol-3-yl}-(4-trifluoromethoxy-phenyl)amine | not active | >40 uM |
| 6-{4-[5-(4-trifluoromethoxy-phenylamino)-4H-[1,2,4]triazol-3-yl]-phenoxy}-pyridazin-3-ylamine | not active | >20 uM |
| 6-{4-[5-(4-trifluoromethoxy-phenylamino)-4H-[1,2,4]triazol-3-yl]-phenoxy}-pyrimidine-2,4-diamine | not active | 6.0 uM |
| 6-[4-({5-[4-(trifluoromethoxy)-phenyl-4H-1,2,4-triazol-3-yl}amino)phenoxy]pyrimidine-2,4-diamine | not active | 6.58 uM |
| 6-{4-[5-(4-chloro-3-trifluoromethyl-phenylamino)-4H-[1,2,4]triazol-3-yl]-phenoxy}-pyrimidine-2,4-diamine | active at 5 uM | 0.089 uM |
| 6-{4-[5-(4-chloro-3-trifluoromethyl-phenylamino)-4H-[1,2,4]triazol-3-yl]-phenoxy}-pyridazin-3-ylamine | not active | 1.79 uM |
| 4-{3-[5-(4-chloro-3-trifluoromethyl-phenylamino)-4H-[1,2,4]triazol-3-yl]-phenoxy}-pyridine-2-carboxylic acid methylamide | not active | >20 uM |
| 6-{3-[5-(4-chloro-3-trifluoromethyl-phenylamino)-4H-[1,2,4]triazol-3-yl]-phenoxy}-pyrimidine-2,4-diamine | active at 5 uM | 0.404 uM |
| (4-chloro-3-trifluoromethyl-phenyl)-{5-[3-(pyridin-3-yloxy)-phenyl]-4H-[1,2,4]triazol-3-yl}-amine | active at 5 uM | 1.79 uM |
| 6-{3-[5-(4-chloro-3-trifluoromethyl-phenylamino)-4H-[1,2,4]triazol-3-yl]-phenoxy}-pyridazin-3-ylamine | not active | >10 uM |
| 6-[4-(5-{[4-Chloro-3-trifluoromethyl-phenyl]amino}-1,3,4-oxadiazol-2-yl)-phenoxy]-pyrimidine-2,4-diamine | active at 5 uM | 1.57 uM |
| N-[4-chloro-3-(trifluoromethyl)phenyl]-5-[4-(pyridin-3-yloxy)phenyl]-1,3,4-oxadiazol-2-amine | active at 5 uM | 1.72 uM |
| N-[4-chloro-3-(trifluoromethyl)phenyl]-5-[4-(pyridin-4-yloxy)phenyl]-1,3,4-oxadiazol-2-amine | active at 5 uM | 8.6 uM |
| N-[4-chloro-3-(trifluoromethyl)phenyl]-5-[4-(pyrimidin-5-yloxy)phenyl]-1,3,4-oxadiazol-2-amine | active at 5 uM | 9.65 uM |
| 4-[4-(5-{[4-chloro-3-(trifluoromethyl)phenyl]amino}-1,3,4-oxadiazol-2-yl)phenoxy]-N-methylpyridine-2-carboxamide | active at 5 uM | 5.6 uM |
| 6-[4-({5-[4-chloro-3-(trifluoromethyl)phenyl-4H-1,2,4-triazol-3-yl}amino)phenoxy]pyrimidine-2,4-diamine | active at 5 uM | 9.57 uM |
| 5-[4-chloro-3-(trifluoromethyl)phenyl]-N-[4-(pyridine-4-yloxy)phenyl]-4H-1,2,4-triazol-3-amine | not active | >40 uM |
| 5-[4-chloro-3-(trifluoromethyl)phenyl]-N-[4-(pyrimidin-5-yloxy)phenyl]-4H-1,2,4-triazol-3-amine | active at 5 uM | >10 uM |
| 6-[4-({5-[4-chloro-3-(trifluoromethyl)phenyl]-4H-1,2,4-triazol-3-yl}amino)phenoxy]pyridazin-3-amine | active at 5 uM | >40 uM |
| 4-[4-({5-[4-chloro-3-(trifluoromethyl)phenyl]-4H-1,2,4-triazol-3-yl}amino)phenoxy]-N-methylpyridine-2-carboxamide | not active | >40 uM |
| 5-[4-chloro-3-(trifluoromethyl)phenyl]-N-[4-(pyridine-3-yloxy)phenyl]-4H-1,2,4-triazol-3-amine | active at 5 uM | >40 uM |
| 6-[4-(5-{[3-(Trifluoromethyl)phenyl]amino}-1,3,4-oxadiazol-2-yl)phenoxy]pyrimidine-2,4-diamine | active at 5 uM | >10 uM |
| 5-[4-(Pyrimidin-5-yloxy)phenyl]-N-[3-(trifluoromethyl)phenyl]-1,3,4-oxadiazol-2-amine | active at 5 uM | >10 uM |
| 6-(4-{5-[(4-chlorophenyl)amino]-1,3,4-oxadiazol-2-yl}phenoxy)pyrimidine-2,4-diamine | active at 5 uM | 2.6 uM |
| 5-[4-(Pyrimidin-5-yloxy)phenyl]-N-[4-chloro-phenyl]-1,3,4-oxadiazol-2 amine | active at 5 uM | >20 uM |
| 6-(4-{5-[(2-chloro-5-trifluoromethyl-phenyl)amino]-1,3,4-oxadiazol-2-yl}phenoxy) pyrimidine-2,4-diamine | not active | ~20 uM |

TABLE 2-continued

Test Results for Examples 105 and 106

| Examples | Western Blot | Inhibition of HUVEC cell prolifiration (IC50) |
|---|---|---|
| 5-[4-(Pyrimidin-5-yloxy)phenyl]-N-[2-chloro-5-(trifluoromethyl)-phenyl]-1,3,4-oxadiazol-2-amine | not active | ~20 uM |
| 6-(4-{5-[(3-chlorophenyl)amino]-1,3,4-oxadiazol-2-yl}phenoxy)pyrimidine-2,4-diamine | active at 5 uM | ~20 uM |
| 5-[4-(Pyrimidin-5-yloxy)phenyl]-N-[2-chloro-phenyl]-1,3,4-oxadiazol-2-amine | active at 5 uM | ~20 uM |
| 5-[4-(Pyridin-3-yloxy)phenyl]-N-[4-chloro-phenyl]-1,3,4-oxadiazol-2-amine | active at 10 uM | 9.6 uM |
| 5-[4-(Pyridin-3-yloxy)phenyl]-N-[3-trifluoromethyl-phenyl]-1,3,4-oxadiazol-2-amine | active at 10 uM | >20 uM |
| 5-[4-(Pyridin-3-yloxy)phenyl]-1,3,4-oxadiazol-2-amine | not active at 10 uM | >40 uM |
| N-{5-[4-(pyridin-3-yloxy)phenyl]-1,3,4-oxadiazol-2-yl}-4-(trifluoromethoxy)benzamide | not active at 10 uM | >40 uM |
| N-{5-[4-(pyridin-3-yloxy)phenyl]-1,3,4-oxadiazol-2-yl}-3-(trifluoromethoxy)benzamide | active at 10 uM | >40 uM |
| 4-Bromo-N-{5-[4-(pyridin-3-yloxy)phenyl]-1,3,4-oxadiazol-2-yl}-benzamide | not active at 10 uM | >40 uM |
| N-{5-[4-(pyridin-3-yloxy)phenyl]-1,3,4-oxadiazol-2-yl}-3-(trifluoromethoxy)-benzamide | not active at 10 uM | >40 uM |
| 4-Methoxy-N-{5-[4-(pyridin-3-yloxy)phenyl]-1,3,4-oxadiazol-2-yl}-3-(trifluoromethoxy)-benzamide | active at 10 uM | >40 uM |
| 2,2-Difluoro-N-{5-[4-(pyridin-3-yloxy)phenyl]-1,3,4-oxadiazol-2-yl}-1,3-benzodioxole-5-carboxamide | not active at 10 uM | >40 uM |
| 3-Chloro-2-fluoro-N-{5-[4-(pyridin-3-yloxy)phenyl]-1,3,4-oxadiazol-2-yl}-5-(trifluoromethoxy)-benzamide | not active at 10 uM | >40 uM |
| 4-Fluoro-N-{5-[4-(pyridin-3-yloxy)phenyl]-1,3,4-oxadiazol-2-yl}-3-(trifluoromethoxy)-benzamide | active at 10 uM | ~20 uM |
| N-{5-[4-(pyridin-3-yloxy)phenyl]-1,3,4-oxadiazol-2-yl}-2-(trifluoromethoxy)-benzamide | not active at 10 uM | ~20 uM |

Although the invention has been described with reference to the above examples, it will be understood that modifications and variations are encompassed within the spirit and scope of the invention. Accordingly, the invention is limited only by the following claims.

What is claimed is:

1. A compound having the structure (A) or an N-oxide, N,N'-dioxide, N,N',N''-trioxide, or a pharmaceutically acceptable salt thereof:

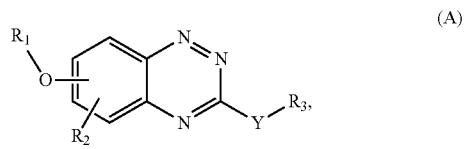

wherein:

Y is absent or is a moiety selected from a group consisting of:

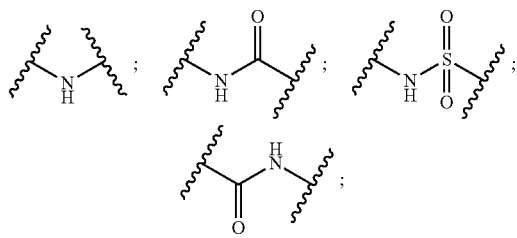

$R_1$ is a substituent selected from a group consisting of an aryl, a substituted aryl, a heterocycle, a heteroaryl, a substituted heterocycle, and a substituted heteroaryl;

$R_2$ is a substituent selected from a group consisting of hydrogen, hydroxyl, $C_1$-$C_6$ alkyl, $C_1$-$C_6$ alkylamino, halogen, $C_1$-$C_6$ alkoxy, —$NO_2$, —$NH_2$, and —C≡N; and $R_3$ is a substituent selected from a group consisting of an aryl, a substituted aryl, a heterocycle, a heteroaryl, a substituted heterocycle, and a substituted heteroaryl.

2. The compound of claim 1, wherein:

$R_1$ is selected from a group consisting of $C_6$-$C_{12}$ aryl; $C_3$-$C_{12}$ heteroaryl having 1-3 heteroatoms selected from N, S and O, substituted $C_3$-$C_{10}$ cycloalkyl having 0-3 heteroatoms selected from N, S, and O, substituted $C_6$-$C_{12}$ aryl, substituted $C_3$-$C_{12}$ heteroaryl having 1-3 heteroatoms selected from N, S and O, $C_7$-$C_{24}$ aralkyl; $C_7$-$C_{24}$ alkylaryl; substituted $C_7$-$C_{24}$ aralkyl; and substituted $C_7$-$C_{24}$ alkaryl;

$R_3$ is selected from a group consisting of $C_6$-$C_{12}$ aryl; $C_3$-$C_{12}$ heteroaryl having 1-3 heteroatoms selected from N, S and O, substituted $C_3$-$C_{10}$ cycloalkyl having 0-3 heteroatoms selected from N, S, and O, substituted $C_6$-$C_{12}$ aryl, substituted $C_3$-$C_{12}$ heteroaryl having 1-3 heteroatoms selected from N, S and O, $C_7$-$C_{24}$ aralkyl; $C_7$-$C_{24}$ alkylaryl; substituted $C_7$-$C_{24}$ aralkyl; and substituted $C_7$-$C_{24}$ alkaryl.

3. The compound of claim 1, wherein the compound having the structure (A) is selected from the group of compounds having the structures (A1), (A2), (A3), and (A4):

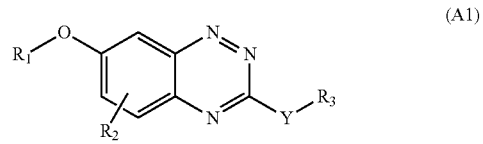

-continued
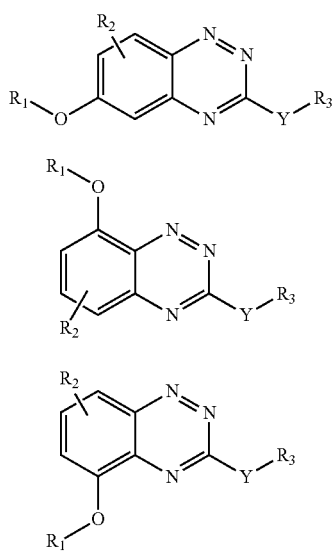
(A2)
(A3)
(A4)
4. The compound of claim 3, wherein the compound has the structure (A1) and wherein:
R₁ is selected from a group consisting of
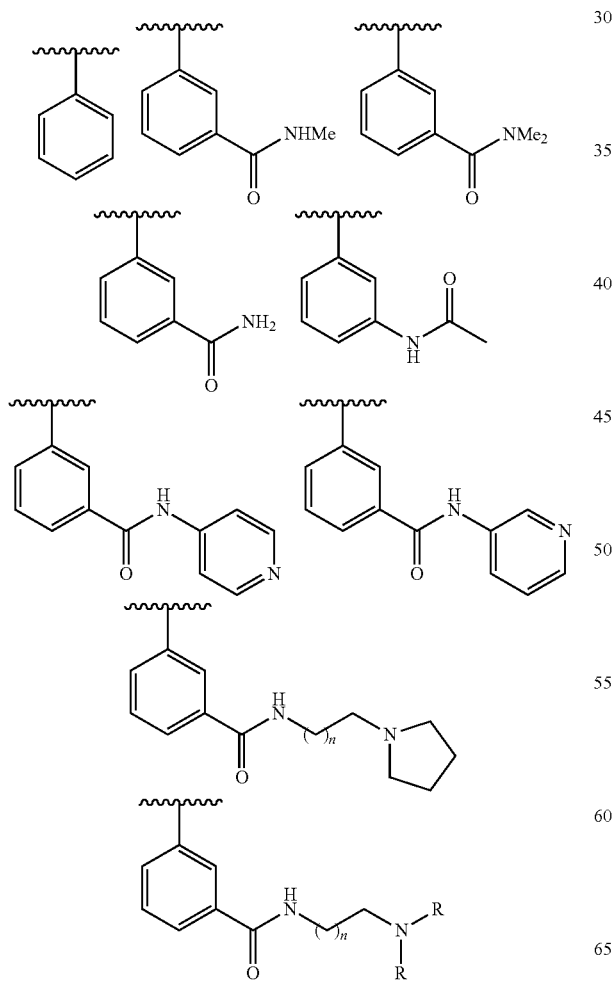
-continued
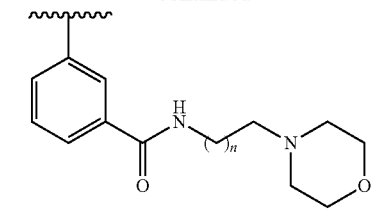
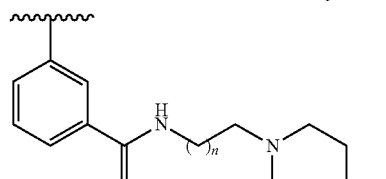
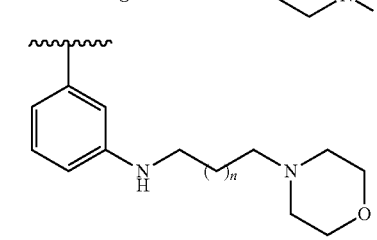
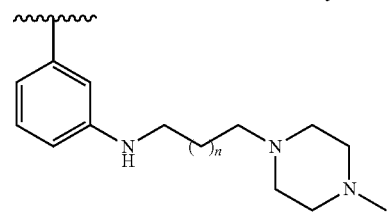
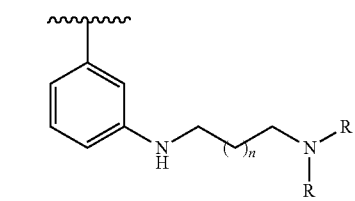
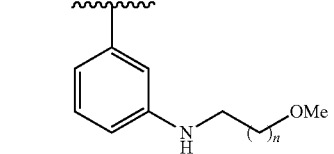
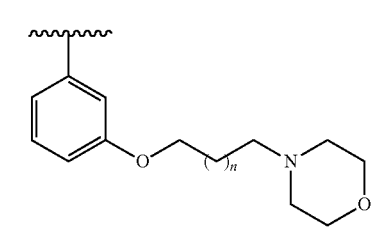
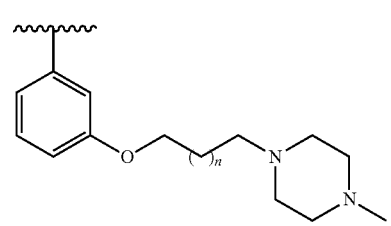

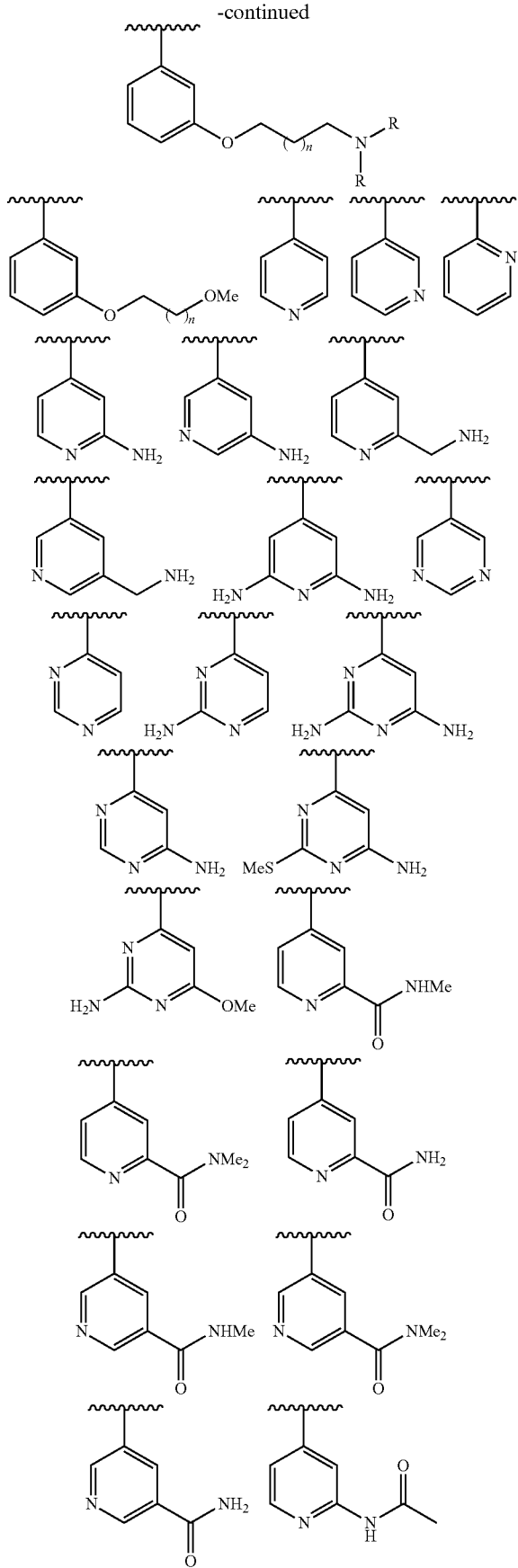
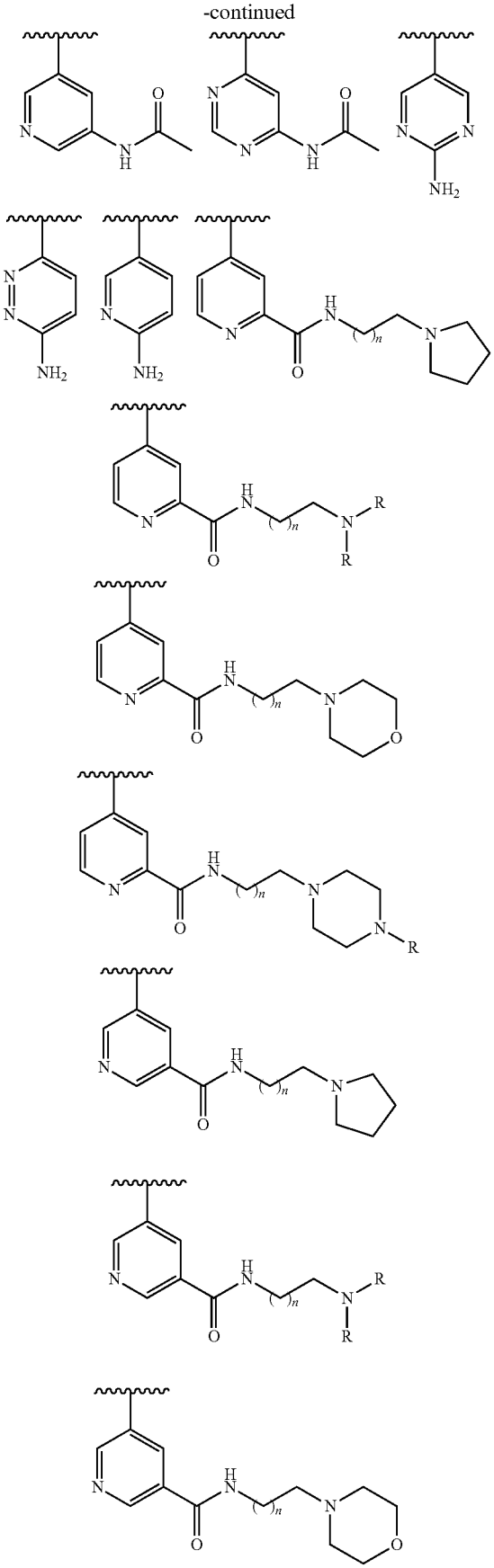

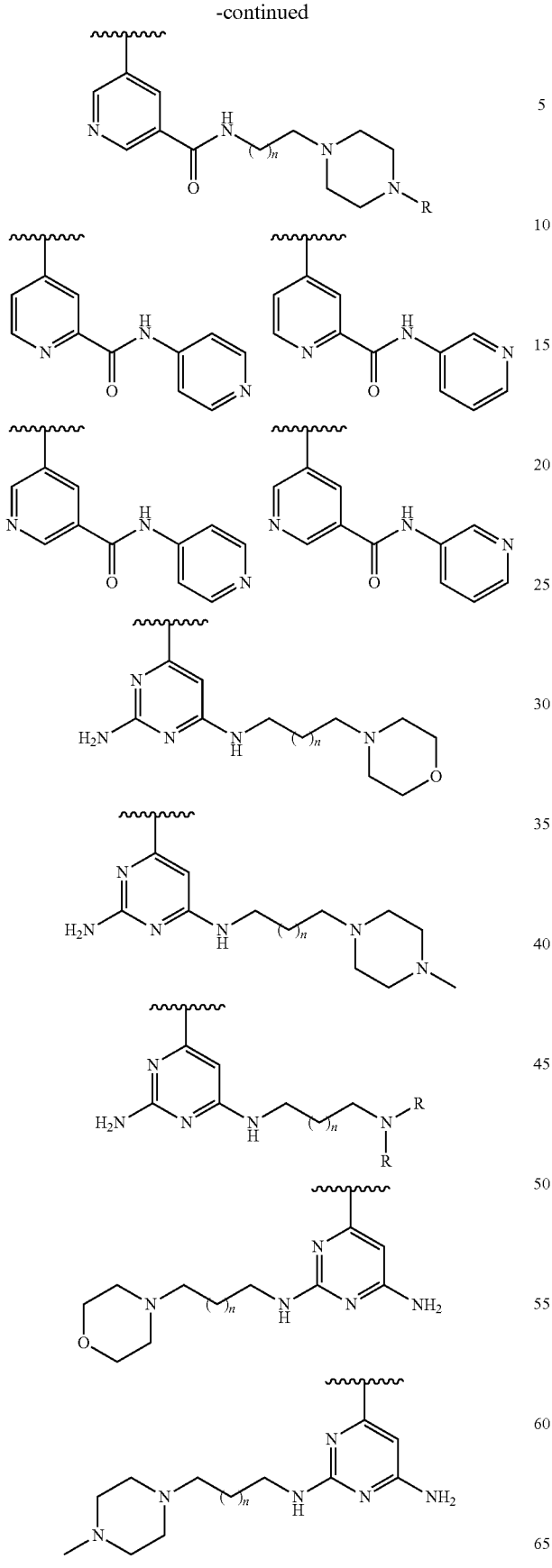
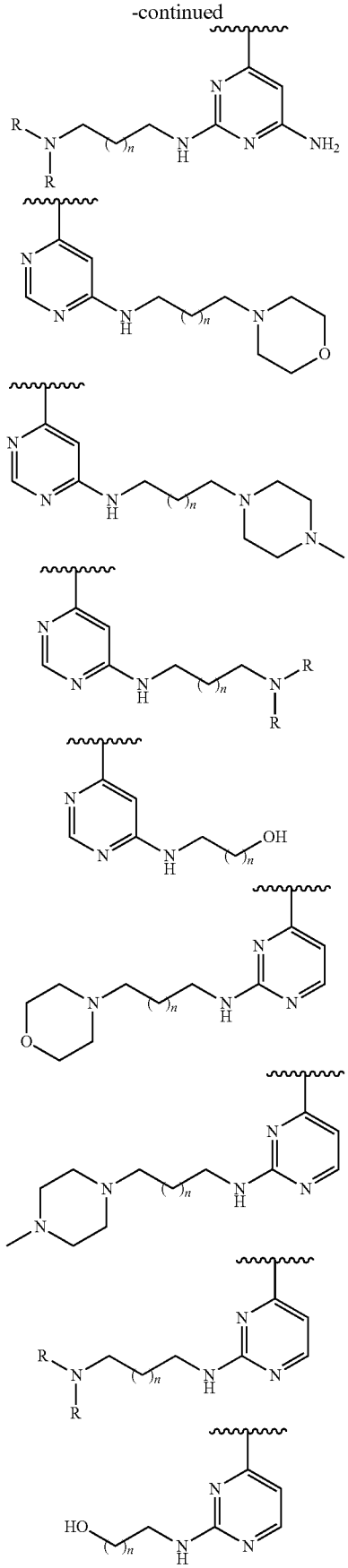

179
-continued
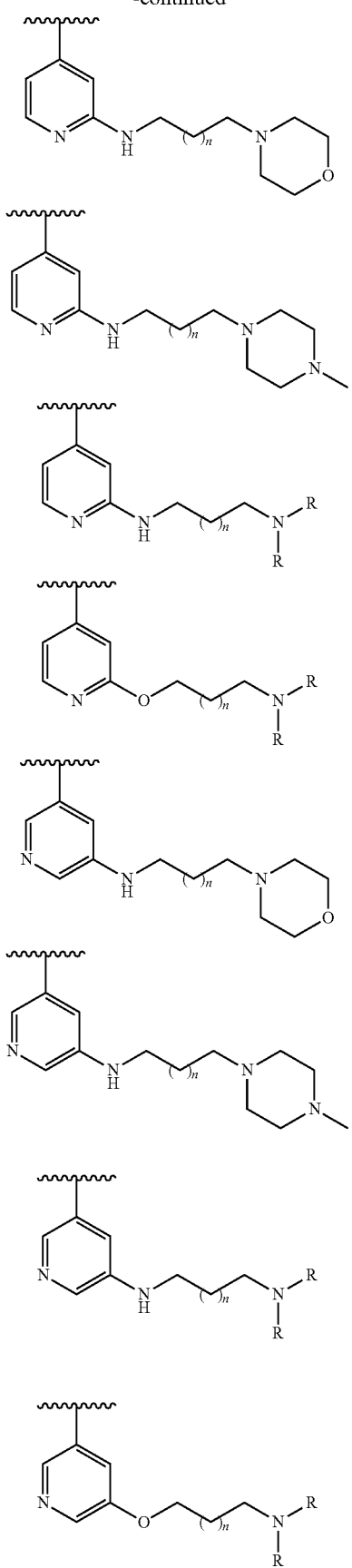
180
-continued
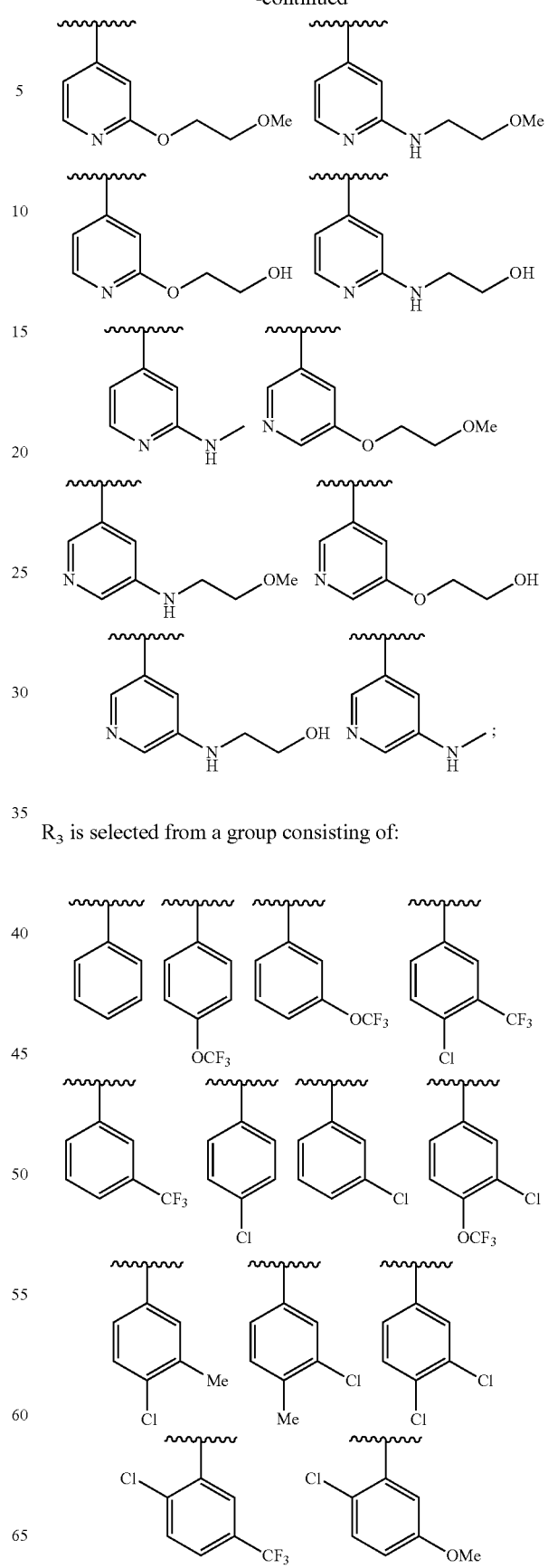
R₃ is selected from a group consisting of:

-continued
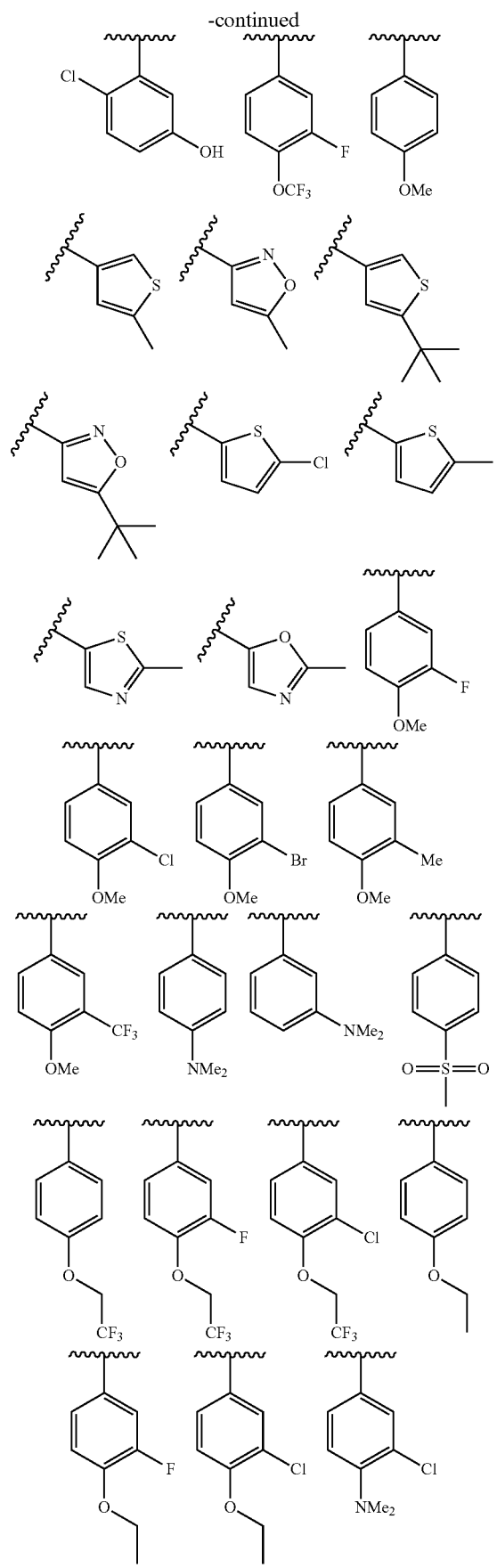
-continued
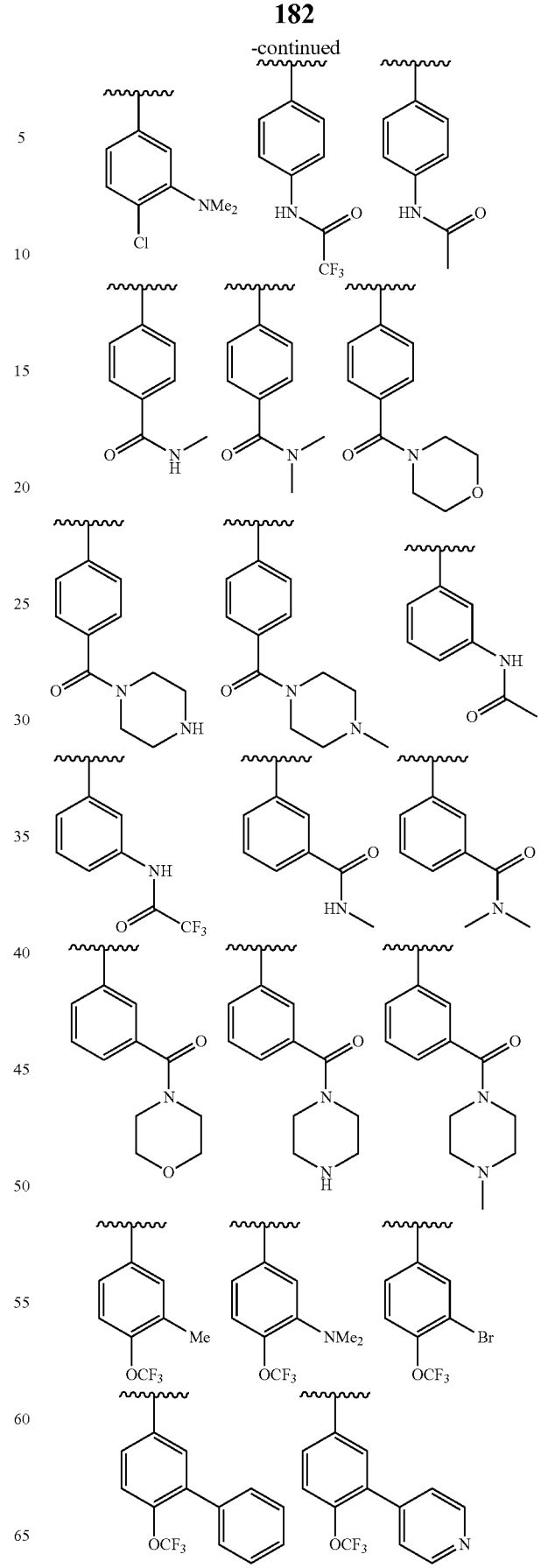

183
-continued
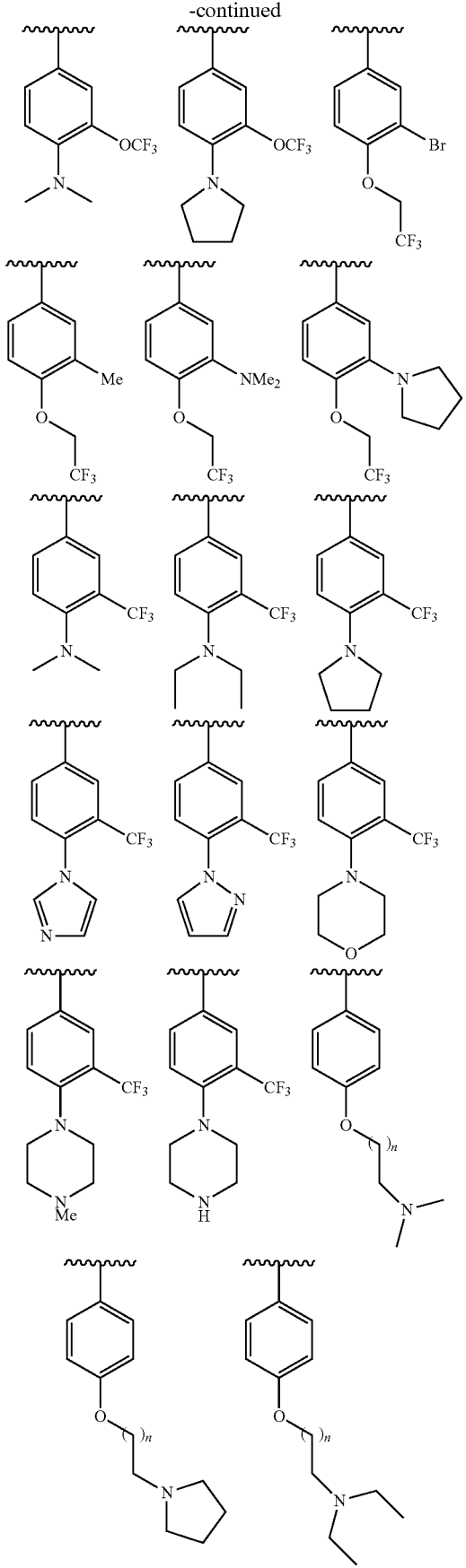
184
-continued
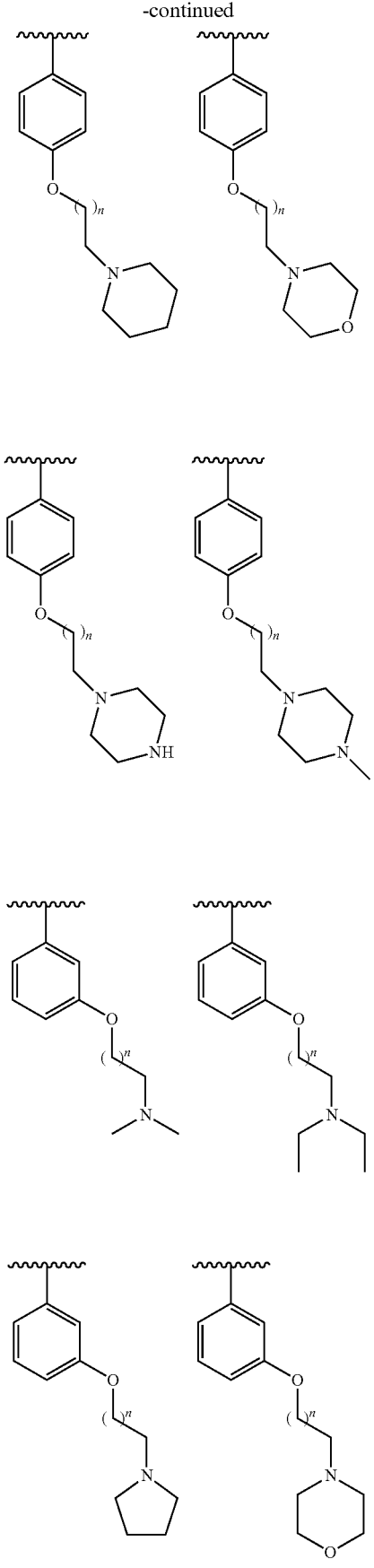

185
-continued
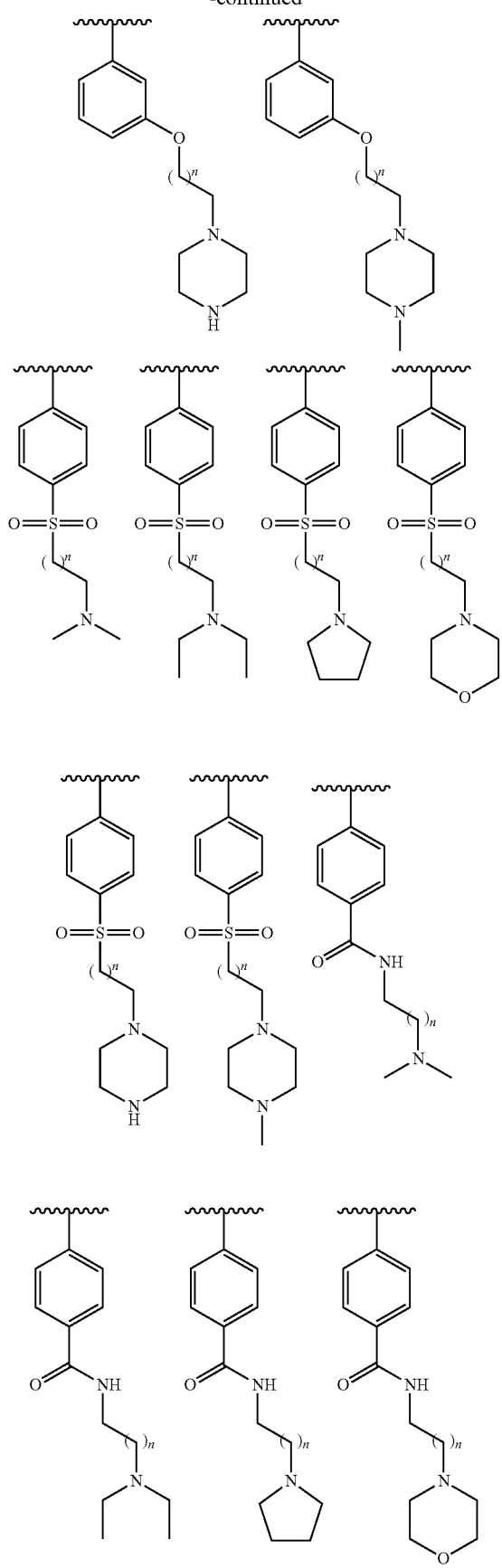
186
-continued
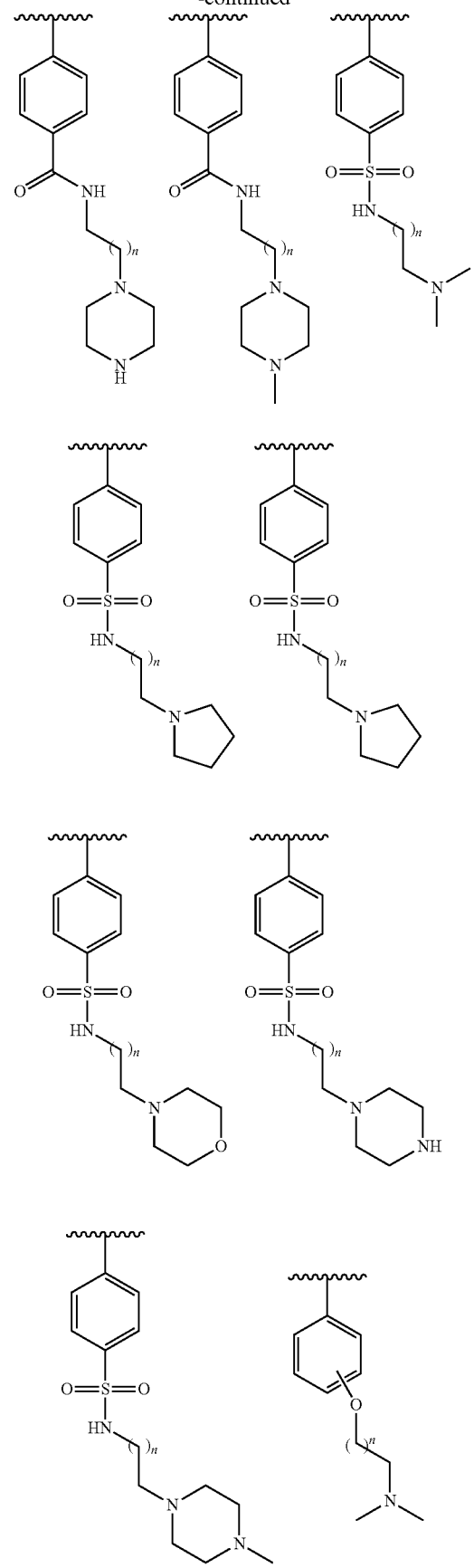

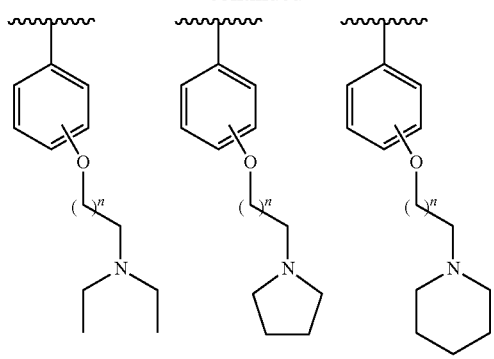
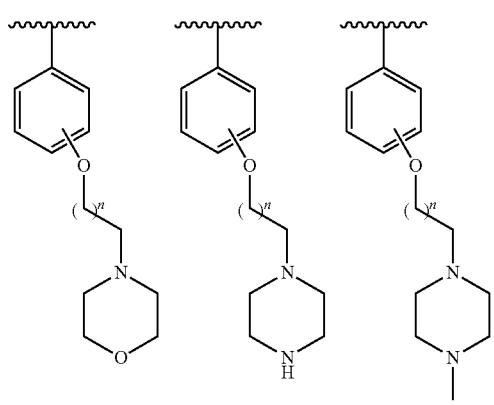
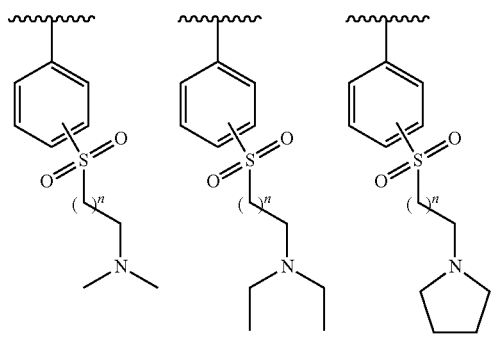
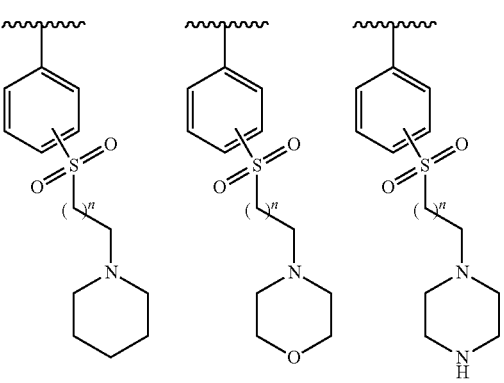
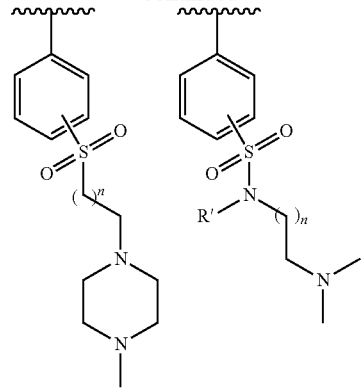
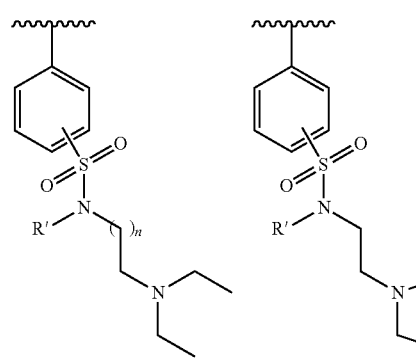
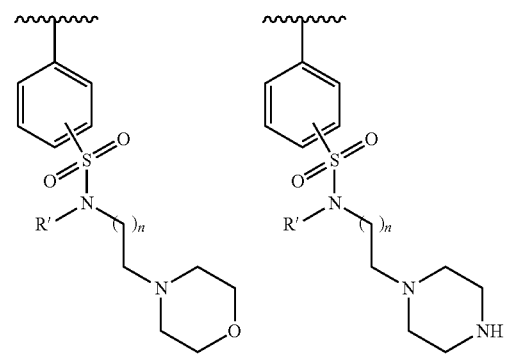
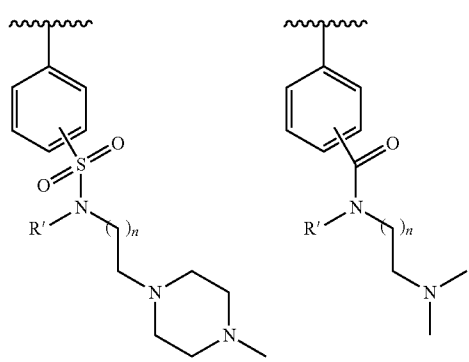

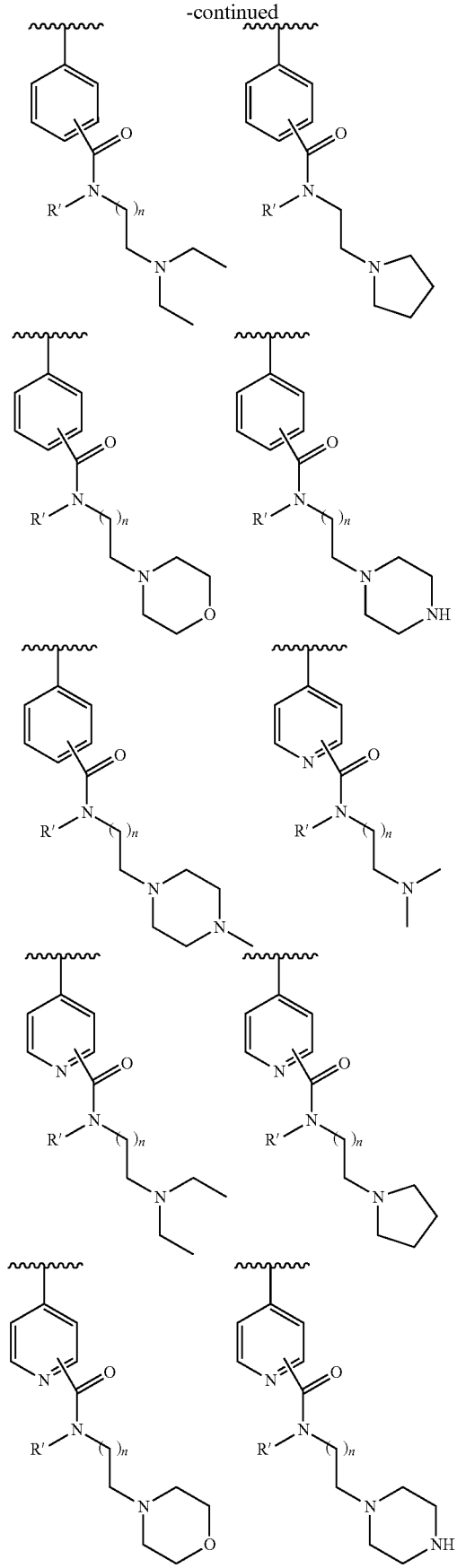
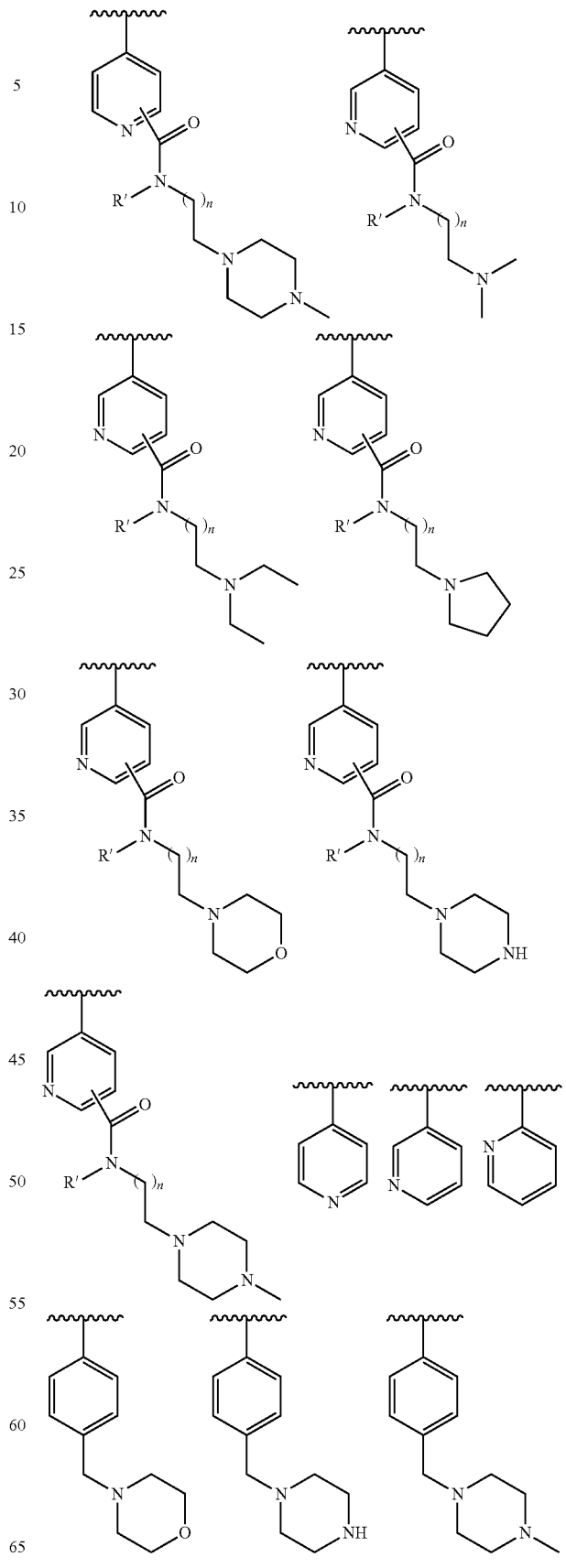

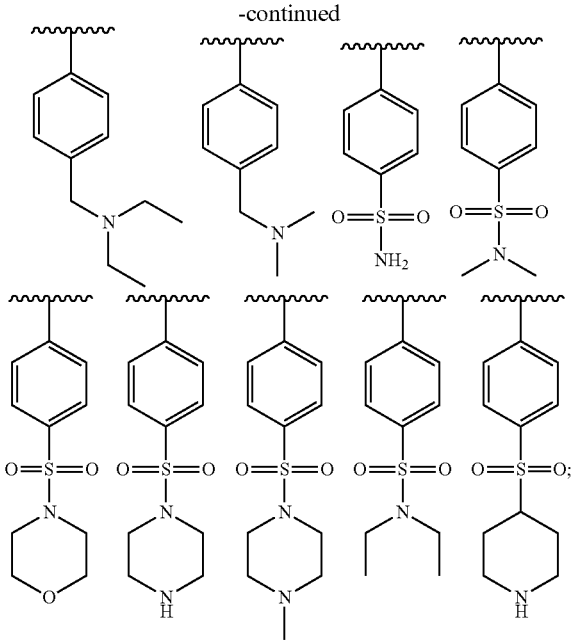

and n is an integer selected from a group consisting of 0, 1, 2, and 3.

5. The compound of claim 3, wherein the compound having the structure (A1) is selected from a group consisting of compounds having structures (1) and (2):

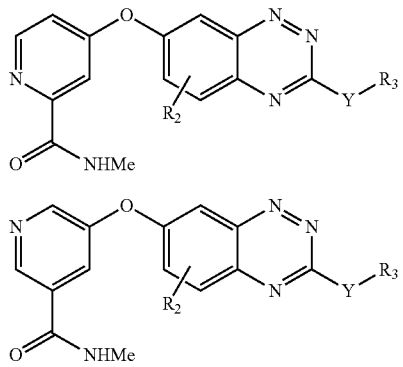

6. The compound of claim 3, wherein the compound having structure (A1) is selected from a group consisting of compounds having the structures (3), (4), (5) and (6):

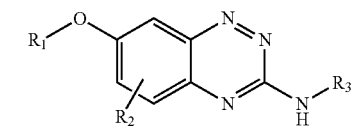

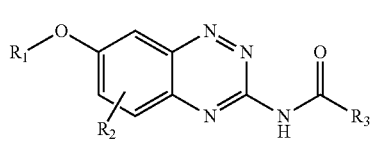

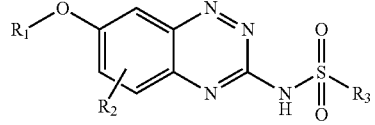

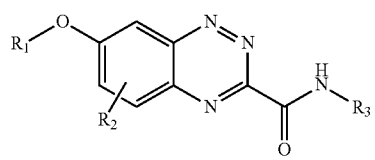

7. The compound of claim 3, wherein the compound having structure (A1) is selected from a group consisting of compounds having the structures (7)-(16):

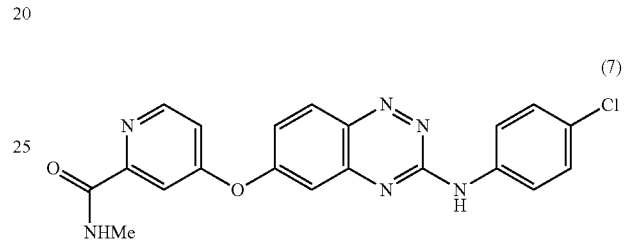

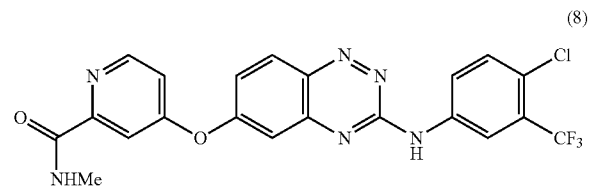

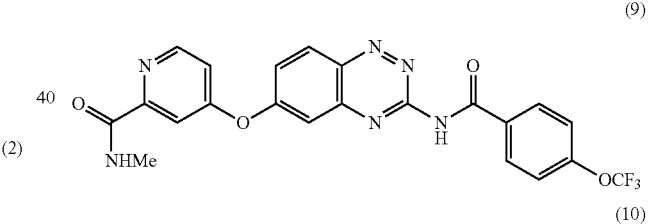

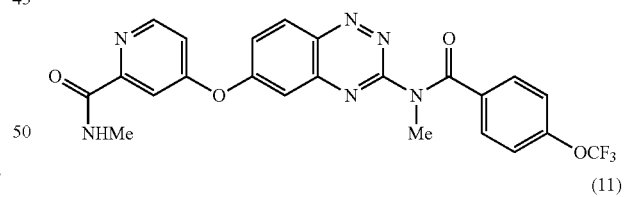

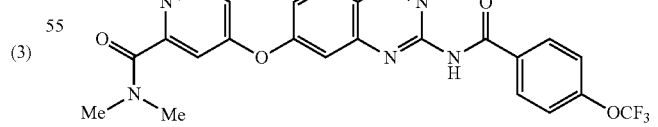

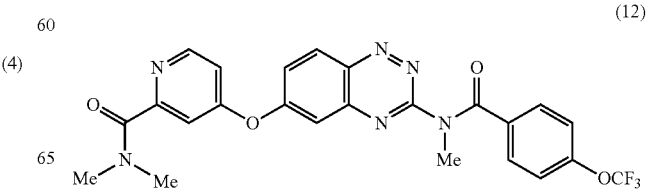

-continued

(13)
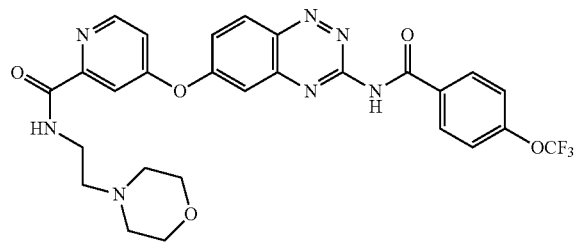 [SMILES: O=C(Nc1nnc2ccc(Oc3ccnc(C(=O)NCCN4CCOCC4)c3)cc2n1)c1ccc(OC(F)(F)F)cc1]

(14)
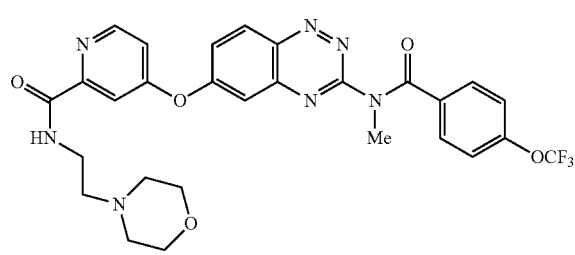 [SMILES: CN(C(=O)c1ccc(OC(F)(F)F)cc1)c1nnc2ccc(Oc3ccnc(C(=O)NCCN4CCOCC4)c3)cc2n1]

(15)
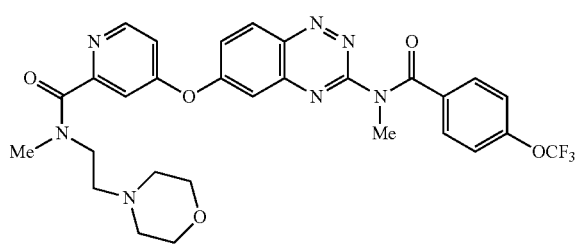 [SMILES: CN(CCN1CCOCC1)C(=O)c1cc(Oc2ccc3nnc(N(C)C(=O)c4ccc(OC(F)(F)F)cc4)nc3c2)ccn1]

(16)
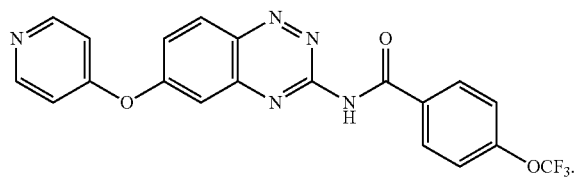 [SMILES: O=C(Nc1nnc2ccc(Oc3ccncc3)cc2n1)c1ccc(OC(F)(F)F)cc1]

8. The compound of claim 7, wherein the compound has the formula:

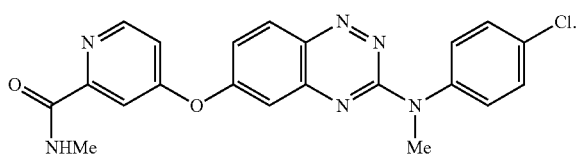

9. The compound of claim 7, wherein the compound has the formula:

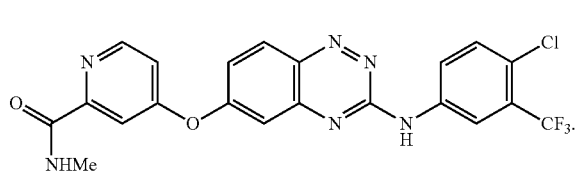

10. The compound of claim 7, wherein the compound has the formula:

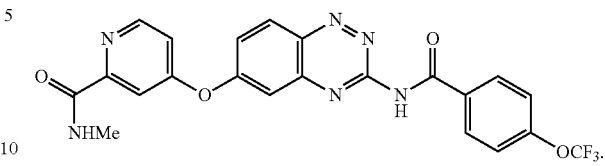

11. The compound of claim 7, wherein the compound has the formula:

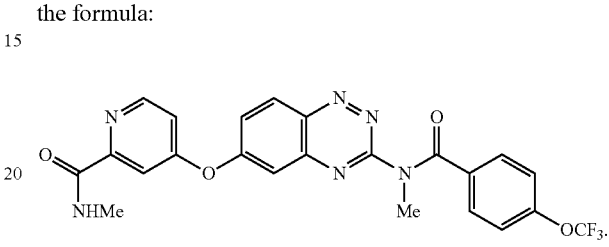

12. The compound of claim 7, wherein the compound has the formula:

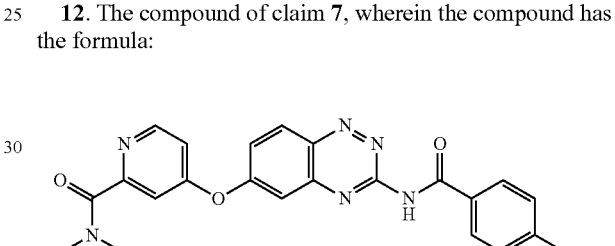

13. The compound of claim 7, wherein the compound has the formula:

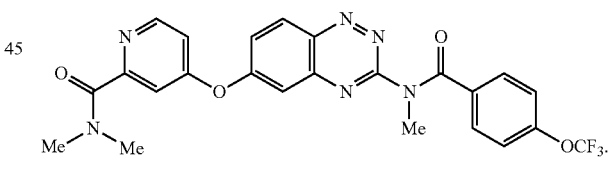

14. The compound of claim 7, wherein the compound has the formula:

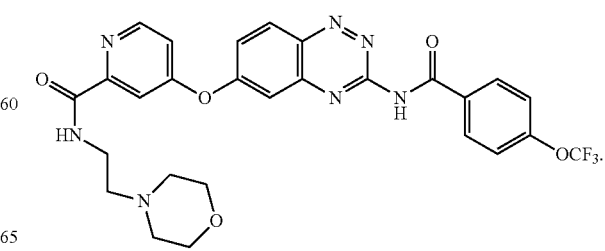

15. The compound of claim 7, wherein the compound has the formula:

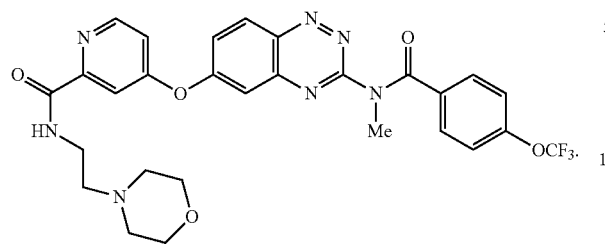

16. The compound of claim 7, wherein the compound has the formula:

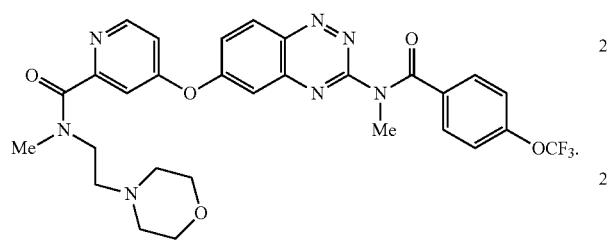

17. The compound of claim 7, wherein the compound has the formula:

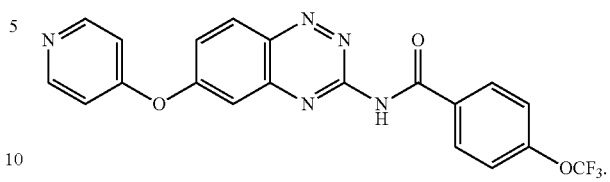

18. A pharmaceutical composition comprising a compound set forth in claim 1 and a pharmaceutically acceptable carrier.

19. A pharmaceutical composition comprising a compound as set forth in claim 3, wherein the compound is of Structure (A1), and a pharmaceutically acceptable carrier.

20. A pharmaceutical composition comprising a compound as set forth in claim 3, wherein the compound is of Structure (A2), and a pharmaceutically acceptable carrier.

21. A pharmaceutical composition comprising a compound as set forth in claim 3, wherein the compound is of Structure (A3), and a pharmaceutically acceptable carrier.

22. A pharmaceutical composition comprising a compound as set forth in claim 3, wherein the compound is of Structure (A4), and a pharmaceutically acceptable carrier.

* * * * *